United States Patent
Johnston et al.

(10) Patent No.: US 12,018,252 B2
(45) Date of Patent: Jun. 25, 2024

(54) METHODS AND COMPOSITIONS FOR IDENTIFYING NEOANTIGENS FOR USE IN TREATING CANCER

(71) Applicant: Arizona Board of Regents on Behalf of Arizona State University, Scottsdale, AZ (US)

(72) Inventors: Stephen Albert Johnston, Tempe, AZ (US); Luhui Shen, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/711,849

(22) Filed: Apr. 1, 2022

(65) Prior Publication Data

US 2022/0257701 A1    Aug. 18, 2022

Related U.S. Application Data

(63) Continuation of application No. PCT/US2020/053728, filed on Oct. 1, 2020.

(60) Provisional application No. 62/909,748, filed on Oct. 2, 2019.

(51) Int. Cl.
| | |
|---|---|
| *C12N 15/10* | (2006.01) |
| *A61K 38/08* | (2019.01) |
| *A61K 38/10* | (2006.01) |
| *A61K 38/16* | (2006.01) |
| *A61K 39/00* | (2006.01) |
| *A61P 35/00* | (2006.01) |
| *G01N 33/574* | (2006.01) |

(52) U.S. Cl.
CPC .......... *C12N 15/1062* (2013.01); *A61K 38/08* (2013.01); *A61K 38/10* (2013.01); *A61K 38/16* (2013.01); *A61K 39/0011* (2013.01); *A61P 35/00* (2018.01); *C12N 15/1093* (2013.01); *G01N 33/57484* (2013.01); *G01N 33/57488* (2013.01)

(58) Field of Classification Search
CPC .............. C40B 40/10; G01N 33/57488; G01N 33/57484
See application file for complete search history.

(56) References Cited

U.S. PATENT DOCUMENTS

| | | |
|---|---|---|
| 4,342,566 A | 8/1982 | Theofilopoulos et al. |
| 4,444,487 A | 4/1984 | Miller et al. |
| 4,683,195 A | 7/1987 | Mullis et al. |
| 4,704,692 A | 11/1987 | Ladner |
| 4,745,055 A | 5/1988 | Schenk et al. |
| 4,816,567 A | 3/1989 | Cabilly et al. |
| 4,863,457 A | 9/1989 | Lee |
| 4,868,116 A | 9/1989 | Morgan et al. |
| 4,897,355 A | 1/1990 | Eppstein et al. |
| 4,980,286 A | 12/1990 | Morgan et al. |
| 5,084,824 A | 1/1992 | Lam et al. |
| 5,143,854 A | 9/1992 | Pirrung et al. |
| 5,288,514 A | 2/1994 | Ellman |
| 5,378,475 A | 1/1995 | Smith et al. |
| 5,424,186 A | 6/1995 | Fodor et al. |
| 5,443,505 A | 8/1995 | Wong et al. |
| 5,449,754 A | 9/1995 | Nishioka |
| 5,506,337 A | 4/1996 | Summerton et al. |
| 5,539,083 A | 7/1996 | Cook et al. |
| 5,545,568 A | 8/1996 | Ellman |
| 5,556,762 A | 9/1996 | Pinilla et al. |
| 5,565,324 A | 10/1996 | Still et al. |
| 5,565,332 A | 10/1996 | Hoogenboom et al. |
| 5,571,639 A | 11/1996 | Hubbell et al. |
| 5,573,905 A | 11/1996 | Lerner et al. |
| 5,593,839 A | 1/1997 | Hubbell et al. |
| 5,595,915 A | 1/1997 | Geysen |
| 5,596,079 A | 1/1997 | Smith et al. |
| 5,599,695 A | 2/1997 | Pease et al. |
| 5,601,989 A | 2/1997 | Cheever et al. |
| 5,618,825 A | 4/1997 | Baldwin et al. |
| 5,619,680 A | 4/1997 | Berkovich et al. |
| 5,627,210 A | 5/1997 | Valerio et al. |
| 5,646,285 A | 7/1997 | Baindur et al. |
| 5,663,046 A | 9/1997 | Baldwin et al. |
| 5,670,326 A | 9/1997 | Beutel |
| 5,677,195 A | 10/1997 | Winkler et al. |
| 5,683,899 A | 11/1997 | Stuart |
| 5,686,247 A | 11/1997 | Holland et al. |
| 5,688,696 A | 11/1997 | Lebl |
| 5,688,997 A | 11/1997 | Baldwin et al. |
| 5,698,685 A | 12/1997 | Summerton et al. |

(Continued)

FOREIGN PATENT DOCUMENTS

| | | |
|---|---|---|
| CA | 2486738 | 12/2003 |
| CN | 1438324 A | 8/2003 |

(Continued)

OTHER PUBLICATIONS

Balboni et al., Annual Review of Immunology, 24, 391-418, 2006. (Year: 2006).*
Legutki et al., Vaccine, 28, 4529-4537, 2010. (Year: 2010).*
Gao et al., Molecular Diversity, 8, 177-187, 2004. (Year: 2004).*
PCT Search Report and Written Opinion in PCT/US2020/053728, mailed Mar. 18, 2021.
Abrahmsén et al., Engineering Subtilisin and Its Substrates for Efficient Ligation of Peptide Bonds in Aqueous Solution. Biochem. Apr. 1991;30(17): 4151-4159.

(Continued)

*Primary Examiner* — Elly-Gerald Stoica
(74) *Attorney, Agent, or Firm* — Knobbe, Martens, Olson & Bear, LLP

(57) ABSTRACT

Provided herein, are methods of identifying neoantigens for treating and preventing cancer. Also disclosed are methods and compositions for administering identified neoantigens for the treatment and prevention of cancer.

16 Claims, 27 Drawing Sheets
Specification includes a Sequence Listing.

(56) References Cited

U.S. PATENT DOCUMENTS

| | | |
|---|---|---|
| 5,712,146 A | 1/1998 | Khosla et al. |
| 5,721,099 A | 2/1998 | Still et al. |
| 5,721,367 A | 2/1998 | Kay et al. |
| 5,723,598 A | 3/1998 | Lerner et al. |
| 5,741,713 A | 4/1998 | Brown et al. |
| 5,759,774 A | 6/1998 | Hackett et al. |
| 5,792,431 A | 8/1998 | Moore et al. |
| 5,804,440 A | 9/1998 | Burton et al. |
| 5,807,683 A | 9/1998 | Brenner |
| 5,807,754 A | 9/1998 | Zambias et al. |
| 5,821,130 A | 10/1998 | Baldwin et al. |
| 5,824,520 A | 10/1998 | Mulligan-Kehoe |
| 5,831,014 A | 11/1998 | Cook et al. |
| 5,834,195 A | 11/1998 | Benkovic et al. |
| 5,834,318 A | 11/1998 | Buettner |
| 5,834,588 A | 11/1998 | Wasserman et al. |
| 5,837,243 A | 11/1998 | Deo et al. |
| 5,840,500 A | 11/1998 | Pei et al. |
| 5,840,839 A | 11/1998 | Wang et al. |
| 5,847,150 A | 12/1998 | Dorwald |
| 5,856,107 A | 1/1999 | Ostresh et al. |
| 5,856,496 A | 1/1999 | Fagnola et al. |
| 5,859,190 A | 1/1999 | Meyer et al. |
| 5,864,010 A | 1/1999 | Cook et al. |
| 5,874,443 A | 2/1999 | Kiely et al. |
| 5,877,214 A | 3/1999 | Kim |
| 5,880,972 A | 3/1999 | Horlbeck |
| 5,886,126 A | 3/1999 | Newkome et al. |
| 5,886,127 A | 3/1999 | Newkome et al. |
| 5,891,737 A | 4/1999 | Baindur et al. |
| 5,916,899 A | 6/1999 | Kiely et al. |
| 5,919,523 A | 7/1999 | Sundberg et al. |
| 5,919,955 A | 7/1999 | Fancelli et al. |
| 5,925,527 A | 7/1999 | Hayes et al. |
| 5,939,268 A | 8/1999 | Boger |
| 5,939,598 A | 8/1999 | Kucherlapati et al. |
| 5,942,387 A | 8/1999 | Hollinshead |
| 5,945,070 A | 8/1999 | Kath et al. |
| 5,948,696 A | 9/1999 | Dolle, III et al. |
| 5,958,702 A | 9/1999 | Benner |
| 5,958,792 A | 9/1999 | Desai et al. |
| 5,961,978 A | 10/1999 | Gaudernack et al. |
| 5,962,337 A | 10/1999 | Ohlmeyer |
| 5,965,719 A | 10/1999 | Hindsgaul |
| 5,972,719 A | 10/1999 | Dolle, III et al. |
| 5,976,894 A | 11/1999 | Dolle, III et al. |
| 5,980,704 A | 11/1999 | Cherukuri et al. |
| 5,985,356 A | 11/1999 | Shultz et al. |
| 5,999,086 A | 12/1999 | Ecker |
| 6,001,579 A | 12/1999 | Still et al. |
| 6,004,617 A | 12/1999 | Schultz et al. |
| 6,008,321 A | 12/1999 | Li et al. |
| 6,017,768 A | 1/2000 | Baldwin et al. |
| 6,025,371 A | 2/2000 | Gordeev et al. |
| 6,030,917 A | 2/2000 | Weinberg et al. |
| 6,031,071 A | 2/2000 | Mandeville et al. |
| 6,040,193 A | 3/2000 | Winkler et al. |
| 6,045,671 A | 4/2000 | Wu et al. |
| 6,045,755 A | 4/2000 | Lebl et al. |
| 6,060,596 A | 5/2000 | Lerner et al. |
| 6,061,636 A | 5/2000 | Horlbeck |
| 6,083,763 A | 7/2000 | Balch et al. |
| 6,096,551 A | 8/2000 | Barbas et al. |
| 6,130,364 A | 10/2000 | Jakobovits et al. |
| 6,180,377 B1 | 1/2001 | Morgan et al. |
| 6,261,834 B1 | 7/2001 | Srivastava |
| 6,309,831 B1 | 10/2001 | Goldberg et al. |
| 6,329,209 B1 | 12/2001 | Wagner et al. |
| 6,346,413 B1 | 2/2002 | Fodor et al. |
| 6,346,423 B1 | 2/2002 | Schembri |
| 6,359,125 B1 | 3/2002 | Kim et al. |
| 6,387,631 B1 | 3/2002 | Arnold et al. |
| 6,365,418 B1 | 4/2002 | Wagner et al. |
| 6,399,365 B2 | 6/2002 | Besemer et al. |
| 6,465,183 B2 | 10/2002 | Wolber |
| 6,475,808 B1 | 11/2002 | Wagner et al. |
| 6,475,809 B1 | 11/2002 | Wagner et al. |
| 6,489,159 B1 | 12/2002 | Chenchik et al. |
| 6,496,309 B1 | 12/2002 | Bliton et al. |
| 6,506,558 B1 | 1/2003 | Fodor et al. |
| 6,511,277 B1 | 1/2003 | Norris et al. |
| 6,545,748 B1 | 4/2003 | Trozera |
| 6,567,163 B1 | 5/2003 | Sandstrom |
| 6,569,671 B1 | 5/2003 | Okamoto et al. |
| 6,573,369 B2 | 6/2003 | Henderson et al. |
| 6,604,902 B2 | 8/2003 | Norris et al. |
| 6,620,584 B1 | 9/2003 | Chee et al. |
| 6,630,358 B1 | 10/2003 | Wagner et al. |
| 6,660,479 B2 | 12/2003 | Kim et al. |
| 6,706,875 B1 | 3/2004 | Goldberg et al. |
| 6,723,517 B1 | 4/2004 | Bamdad et al. |
| 6,733,977 B2 | 5/2004 | Besemer et al. |
| 6,759,046 B1 | 7/2004 | Gaudernack et al. |
| 6,780,582 B1 | 8/2004 | Wagner et al. |
| 6,806,954 B2 | 10/2004 | Sandstrom |
| 6,824,669 B2 | 11/2004 | Li et al. |
| 6,861,057 B2 | 3/2005 | Gaudernack et al. |
| 6,877,665 B2 | 4/2005 | Challa et al. |
| 6,890,760 B1 | 5/2005 | Webb |
| 6,897,073 B2 | 5/2005 | Wagner et al. |
| 6,919,181 B2 | 7/2005 | Hargreaves |
| 6,989,267 B2 | 1/2006 | Kim et al. |
| 6,989,276 B2 | 1/2006 | Thompson et al. |
| 7,006,680 B2 | 2/2006 | Gulati |
| 7,078,416 B2 | 7/2006 | Gaudernack et al. |
| 7,081,954 B2 | 7/2006 | Sandstrom |
| 7,108,472 B2 | 9/2006 | Norris et al. |
| 7,130,458 B2 | 10/2006 | Bartell |
| 7,148,058 B2 | 12/2006 | Charych et al. |
| 7,192,927 B2 | 3/2007 | Gaudernack et al. |
| 7,247,469 B2 | 7/2007 | Wagner et al. |
| 7,250,252 B2 | 7/2007 | Katz et al. |
| 7,354,721 B2 | 4/2008 | Tchaga |
| 7,375,117 B2 | 5/2008 | Gaudernack et al. |
| 7,466,851 B2 | 12/2008 | Gulati |
| 7,522,271 B2 | 4/2009 | Sandstrom |
| 7,534,563 B2 | 5/2009 | Hargreaves |
| 7,569,343 B2 | 8/2009 | Marton et al. |
| 7,588,906 B2 | 9/2009 | Brueggemeier et al. |
| 7,622,295 B2 | 11/2009 | Cabezas |
| 7,682,797 B2 | 3/2010 | Thompson et al. |
| 7,682,798 B2 | 3/2010 | Thompson et al. |
| 7,695,919 B2 | 4/2010 | Apel et al. |
| 7,723,125 B2 | 5/2010 | Tchaga |
| 7,794,723 B2 | 9/2010 | Gaudernack et al. |
| 7,863,244 B2 | 1/2011 | Gaudernack et al. |
| 7,993,583 B2 | 8/2011 | Dugan et al. |
| 8,053,552 B2 | 11/2011 | von Knebel-Doeberitz et al. |
| 8,073,626 B2 | 12/2011 | Troup et al. |
| 8,148,141 B2 | 4/2012 | Nokihara et al. |
| 8,193,326 B2 | 6/2012 | Gaudernack et al. |
| 8,242,058 B2 | 8/2012 | Raines et al. |
| RE44,031 E | 2/2013 | Apel et al. |
| 8,481,679 B2 | 7/2013 | Johnston et al. |
| RE44,539 E | 10/2013 | Thompson et al. |
| 8,614,177 B2 | 12/2013 | Gaudernack et al. |
| 8,796,414 B2 | 8/2014 | Johnston et al. |
| 8,821,864 B2 | 9/2014 | von Knebel-Doeberitz et al. |
| 9,115,402 B2 | 8/2015 | Hacohen et al. |
| 9,205,140 B2 | 12/2015 | Kloor et al. |
| 9,254,311 B2 | 2/2016 | Bancel et al. |
| 9,265,816 B2 | 2/2016 | Scheinberg et al. |
| 9,284,349 B2 | 3/2016 | Tsunoda et al. |
| 9,309,298 B2 | 4/2016 | Johnston et al. |
| 9,340,830 B2 | 5/2016 | Downing et al. |
| 9,482,666 B2 | 11/2016 | Domenyuk et al. |
| 9,709,558 B2 | 7/2017 | Johnston et al. |
| 9,732,131 B2 | 8/2017 | Johnston |
| 9,757,472 B2 | 9/2017 | Diehnelt et al. |
| 9,766,239 B2 | 9/2017 | Gupta et al. |
| 9,863,938 B2 | 1/2018 | Johnston et al. |
| 9,970,932 B2 | 5/2018 | Woodbury et al. |
| 10,006,919 B2 | 6/2018 | Woodbury et al. |
| 10,011,649 B2 | 7/2018 | Diehnelt et al. |

(56) References Cited

U.S. PATENT DOCUMENTS

| | | |
|---|---|---|
| 10,046,293 B2 | 8/2018 | Woodbury et al. |
| 10,125,167 B2 | 11/2018 | Diehnelt et al. |
| 10,126,300 B2 | 11/2018 | Johnston et al. |
| 10,416,174 B1 | 9/2019 | Johnston et al. |
| 10,578,623 B2 | 3/2020 | Woodbury et al. |
| 10,712,342 B2 | 7/2020 | Johnston et al. |
| 10,900,975 B2 | 1/2021 | Johnston et al. |
| 11,168,121 B2 | 11/2021 | Johnston et al. |
| 11,484,581 B2 | 11/2022 | Johnston et al. |
| 2002/0052308 A1 | 5/2002 | Rosen et al. |
| 2003/0082579 A1 | 5/2003 | Felgner et al. |
| 2003/0207467 A1 | 11/2003 | Snyder et al. |
| 2004/0038307 A1 | 2/2004 | Lee et al. |
| 2004/0038556 A1 | 2/2004 | French et al. |
| 2004/0048311 A1 | 3/2004 | Ault-Riche et al. |
| 2004/0063902 A1 | 4/2004 | Miranda |
| 2004/0071705 A1 | 4/2004 | Sato et al. |
| 2004/0265803 A1 | 12/2004 | von Knebel-Doeberitz et al. |
| 2005/0009204 A1 | 1/2005 | Fang et al. |
| 2005/0048566 A1 | 3/2005 | Delisi et al. |
| 2005/0064395 A1 | 3/2005 | Israel et al. |
| 2005/0239070 A1 | 10/2005 | von Knebel-Doeberitz |
| 2005/0244421 A1 | 11/2005 | Strittmatter et al. |
| 2005/0255491 A1 | 11/2005 | Lee et al. |
| 2006/0052948 A1 | 3/2006 | Gorlach |
| 2007/0003954 A1 | 1/2007 | Kodadek |
| 2007/0015172 A1 | 1/2007 | Zhang et al. |
| 2007/0020678 A1 | 1/2007 | Ault-Riche et al. |
| 2007/0099256 A1 | 5/2007 | Sundararajan et al. |
| 2007/0122841 A1 | 5/2007 | Rajasekaran et al. |
| 2007/0248985 A1 | 10/2007 | Dutta et al. |
| 2008/0026485 A1 | 1/2008 | Hueber et al. |
| 2008/0124719 A1 | 5/2008 | Chung et al. |
| 2008/0188618 A1 | 8/2008 | Greving et al. |
| 2008/0193965 A1 | 8/2008 | Zeng et al. |
| 2008/0207483 A1 | 8/2008 | Volinia |
| 2009/0062148 A1 | 3/2009 | Goldberg et al. |
| 2009/0075828 A1 | 3/2009 | Fisher et al. |
| 2009/0131278 A1 | 5/2009 | Wagner et al. |
| 2009/0176664 A1 | 7/2009 | Chu |
| 2009/0186042 A1 | 7/2009 | Johnston et al. |
| 2009/0270480 A1 | 10/2009 | Amegadzie et al. |
| 2010/0034807 A1 | 2/2010 | Moyle |
| 2010/0035765 A1 | 2/2010 | Kodadek |
| 2010/0093554 A1 | 4/2010 | Chu |
| 2010/0111993 A1 | 5/2010 | Tuereci et al. |
| 2010/0210478 A1 | 8/2010 | Gao et al. |
| 2010/0261205 A1 | 10/2010 | Kakuta et al. |
| 2011/0046015 A1 | 2/2011 | Honda et al. |
| 2011/0065594 A1 | 3/2011 | Thompson et al. |
| 2011/0071043 A1 | 3/2011 | Sampson et al. |
| 2011/0105366 A1 | 5/2011 | Lebl et al. |
| 2011/0105721 A1 | 5/2011 | Gaudernack et al. |
| 2011/0143953 A1 | 6/2011 | Johnston et al. |
| 2011/0159530 A1 | 6/2011 | Pass et al. |
| 2011/0189082 A1 | 8/2011 | Kirchner et al. |
| 2011/0190149 A1 | 8/2011 | Tainsky et al. |
| 2011/0229448 A1 | 9/2011 | Kelleher et al. |
| 2011/0263459 A1 | 10/2011 | Borer et al. |
| 2011/0275537 A1 | 11/2011 | Rychlewski et al. |
| 2011/0301057 A1 | 12/2011 | Propheter et al. |
| 2011/0301058 A1 | 12/2011 | Cheng et al. |
| 2011/0318380 A1 | 12/2011 | Brix et al. |
| 2012/0021967 A1 | 1/2012 | Johnston et al. |
| 2012/0052066 A1 | 3/2012 | Calderon et al. |
| 2012/0065123 A1 | 3/2012 | Johnston et al. |
| 2012/0094271 A1 | 4/2012 | Fu et al. |
| 2012/0189702 A1 | 7/2012 | Gupta et al. |
| 2012/0190574 A1 | 7/2012 | Johnston et al. |
| 2012/0238477 A1 | 9/2012 | Albert et al. |
| 2013/0164856 A1 | 6/2013 | Jebrail et al. |
| 2013/0224730 A1 | 8/2013 | Johnston et al. |
| 2013/0236490 A1 | 9/2013 | Kalyanasundaram |
| 2013/0273002 A1 | 10/2013 | Tuohy |
| 2014/0087963 A1 | 3/2014 | Johnston et al. |
| 2014/0113286 A1 | 4/2014 | Chan et al. |
| 2014/0128280 A1 | 5/2014 | Johnston et al. |
| 2014/0170178 A1 | 6/2014 | Kloor et al. |
| 2015/0079119 A1 | 3/2015 | Johnston |
| 2015/0217258 A1 | 8/2015 | Woodbury et al. |
| 2015/0241420 A1 | 8/2015 | Johnston et al. |
| 2015/0352201 A1 | 12/2015 | Scheinberg et al. |
| 2016/0038579 A1 | 2/2016 | Kloor et al. |
| 2016/0041158 A1 | 2/2016 | Woodbury et al. |
| 2016/0051654 A1 | 2/2016 | Singh et al. |
| 2016/0051657 A1 | 2/2016 | Varga et al. |
| 2016/0069895 A1 | 3/2016 | Delamarre et al. |
| 2016/0101170 A1 | 4/2016 | Hacohen et al. |
| 2017/0088844 A1 | 3/2017 | Williams |
| 2017/0121776 A1 | 5/2017 | Soliman et al. |
| 2017/0212101 A1 | 7/2017 | Zhu et al. |
| 2018/0259510 A1 | 9/2018 | Woodbury et al. |
| 2018/0273641 A1 | 9/2018 | Babb et al. |
| 2018/0284114 A1 | 10/2018 | Johnston |
| 2018/0340944 A1 | 11/2018 | Han et al. |
| 2019/0134593 A1 | 5/2019 | Hall et al. |
| 2019/0194358 A1 | 6/2019 | Johnston et al. |
| 2019/0271692 A1 | 9/2019 | Johnston et al. |
| 2019/0307868 A1 | 10/2019 | Rooney |
| 2020/0188496 A1 | 6/2020 | Johnston et al. |
| 2020/0209241 A1 | 7/2020 | Johnston |
| 2020/0256861 A1 | 8/2020 | Johnston et al. |
| 2020/0276285 A1 | 9/2020 | Johnston et al. |
| 2021/0011024 A1 | 1/2021 | Johnston et al. |
| 2021/0223257 A1 | 7/2021 | Johnston et al. |
| 2022/0008525 A1 | 1/2022 | Johnston |
| 2022/0162276 A1 | 5/2022 | Johnston |
| 2022/0170935 A1 | 6/2022 | Johnston |
| 2022/0251544 A1 | 8/2022 | Johnston et al. |
| 2023/0181645 A1 | 6/2023 | Johnston |
| 2023/0338486 A1 | 10/2023 | Johnston et al. |
| 2023/0338490 A1 | 10/2023 | Johnston |

FOREIGN PATENT DOCUMENTS

| | | |
|---|---|---|
| CN | 102099372 A | 6/2011 |
| CN | 104853764 A | 8/2015 |
| EP | 0125023 B1 | 6/1991 |
| EP | 0120694 B1 | 7/1993 |
| EP | 0256654 B1 | 9/1996 |
| EP | 1354895 | 10/2003 |
| EP | 1369126 | 12/2003 |
| EP | 1785726 A1 | 5/2007 |
| EP | 2572725 A1 | 3/2013 |
| WO | WO 1988/003565 | 5/1988 |
| WO | WO 1989/007136 | 8/1989 |
| WO | WO 1990/002806 | 3/1990 |
| WO | WO 1990/015070 | 12/1990 |
| WO | WO 1991/018980 | 12/1991 |
| WO | WO 1993/006121 | 4/1993 |
| WO | WO 1994/029348 | 12/1994 |
| WO | WO 1995/012608 | 5/1995 |
| WO | WO 1995/030642 | 11/1995 |
| WO | WO 1995/032731 | 12/1995 |
| WO | WO 1995/035503 | 12/1995 |
| WO | WO 1997/027329 | 7/1997 |
| WO | WO 1999/058552 | 11/1999 |
| WO | WO 2001/056691 | 8/2001 |
| WO | WO 2002/097051 | 12/2002 |
| WO | WO 2003/019192 | 3/2003 |
| WO | WO 2003/084467 | 10/2003 |
| WO | WO 2003/087162 | 10/2003 |
| WO | WO 2003/087766 | 10/2003 |
| WO | WO 2004/111075 | 12/2004 |
| WO | WO 2005/076009 | 8/2005 |
| WO | WO 2007/068240 | 6/2007 |
| WO | WO 2007/101227 | 9/2007 |
| WO | WO2007/147141 | 12/2007 |
| WO | WO 2008/048970 | 4/2008 |
| WO | WO 2009/126718 | 10/2009 |
| WO | WO 2010/037395 | 4/2010 |
| WO | WO 2010/043668 | 4/2010 |
| WO | WO 2010/059958 | 5/2010 |
| WO | WO 2010/111299 | 9/2010 |

(56) References Cited

FOREIGN PATENT DOCUMENTS

| WO | WO 2010/148365 | 12/2010 | | |
|---|---|---|---|---|
| WO | WO 2011/109440 | 9/2011 | | |
| WO | WO 2011/150168 | 12/2011 | | |
| WO | WO 2012/055069 | 5/2012 | | |
| WO | WO 2014/154905 | 10/2014 | | |
| WO | WO 2015/103037 | 7/2015 | | |
| WO | WO 2015/171747 | 11/2015 | | |
| WO | WO 2016/073299 | 5/2016 | | |
| WO | WO 2018/222917 | 12/2018 | | |
| WO | WO 2018/223092 | 12/2018 | | |
| WO | WO 2018/223093 | 12/2018 | | |
| WO | WO 2018/223094 | 12/2018 | | |
| WO | WO 2019/055618 | 3/2019 | | |
| WO | WO2019046815 | * | 3/2019 | ............ C12N 15/90 |
| WO | WO 2019/143712 | 7/2019 | | |
| WO | WO 2020/068896 | 4/2020 | | |
| WO | WO 2020/132275 | 6/2020 | | |
| WO | WO 2020/163802 | 8/2020 | | |
| WO | WO 2021/046466 | 3/2021 | | |

OTHER PUBLICATIONS

ACS, Cancer Facts and Figures 2016 Special Section: Cancer in Asian Americans, Native Hawaiians, and Pacific Islanders. American Cancer Society pp. 1-72.
Acsadi et al., Human Dystrophin Expression in MDX Mice After Intramuscular Injection of DNA Constructs. Nature Aug. 1991;352(6338): 815-818.
Agarwal et al., Disregulated Expression of the Th2 Cytokine Gene in Patients With Intraoral Squamous Cell Carcinoma. Immunol Invest. Jan. 1, 2003;32(1-2): 17-30.
Almquist et al., Synthesis and Biological Activity of a Ketomethylene Analogue of a Tripeptide Inhibitor of Angiotensin Converting Enzyme. J Med Chem. 1980;23:1392-1398.
Alpert et al., A clinically meaningful metric of immune age derived from high-dimensional longitudinal monitoring. Nature Med. Mar. 2019;25(3):487-495.
Altschul et al., Basic Local Alignment Search Tool. J. Mol. Biol. Oct. 5, 1990;215(3): 403-410.
Altschul et al., Issues in Searching Molecular Sequence Databases. Nature Genet. Feb. 1994;6(2): 119-129.
Anderson et al., The Human Plasma Proteome: History, Character, and Diagnostic Prospects. Mol Cell Proteo. Nov. 1, 2002;1(11): 845-867; and Additions & Corrections (1 page).
Andresen et al., Deciphering the Antibodyome—Peptide Arrays for Serum Antibody Biomarker Diagnostics. Curr Proteo. Apr. 1, 2009;6(1): 1-12.
Anonymous, NSB9; NSB Postech, Inc., 2007, in 4 pages.
Anonymous, Affymetrix; GeneChip Human Genome Arrays Data Sheet, 2003, in 4 pages.
Anthony-Cahill et al., Site-Specific Mutagenesis With Unnatural Amino Acids. Trends Biochem Sciences. Oct. 1, 1989;14(10): 400-403.
Arivazhagan et al., MicroRNA-340 Inhibits the Proliferation and Promotes the Apoptosis of Colon Cancer Cells by Modulating REV3L. Oncotarget Dec. 2017;9(4): 5155-5168.
Bae et al., Microsatellite Instability Status is Critical to Analysis of Survival in Stage II Colon Cancer. J Clin Oncol. Feb. 20, 2012;30(6): 675-676.
Baggiolini et al., Interleukin-8, A Chemotactic and Inflammatory Cytokine. FEBS Lett. Jul. 27, 1992;307:97-101.
Bagshawe et al., A Cytotoxic Agent can be Generated Selectively at Cancer Sites. Br J Cancer. Dec. 1988;58(6): 700-703.
Bagshawe K.D., The First Bagshawe Lecture. Towards Generating Cytotoxic Agents at Cancer Sites. Br J Cancer Sep. 1989;60(3): 275-281.
Bailey, Meme: Discovering and analyzing DNA and Protein Sequence Motifs. Nucl Acids Res. Jul. 1, 2006;34(suppl_2): W369-W373.
Banerji et al., A Lymphocyte-Specific Cellular Enhancer is Located Downstream of the Joining Region in Immunoglobulin Heavy Chain Genes. Cell. Jul. 1, 1983;33(3): 729-740.

Bartolomé et al., Activated Gα13 Impairs Cell Invasiveness Through p190RhoGAP-mediated Inhibition of RhoA Activity. Cancer Res. Oct. 15, 2008;68(20): 8221-8230.
Bauer et al., Identification and Quantification of a New Family of Peptide Endocannabinoids (Pepcans) Showing Negative Allosteric Modulation at CB1 Receptors. J Biol Chem. Oct. 26, 2012;287(44): 36944-36967.
Bauer et al., T Celll Responses Against Microsatellite Instability-Induced Frameshift Peptides and Influence of Regulatory T Cells in Colorectal Cancer. Cancer Immunol Immunother. Jan. 2013;62(1): 27-37.
Bellone et al., Relevance of the Tumor Antigen in the Validation of Three Vaccination Strategies for Melanoma. J Immunol, (2002) 165 (5), 2651-2656.
Benner S.A., Expanding the Genetic Lexicon: Incorporating Non-Standard Amino Acids Into Proteins by Ribosome-Based Synthesis. Trends Biotech. May 1, 1994;12(5): 158-163.
Berglund et al., A Genecentric Human Protein Atlas for Express Profiles Based on Antibodies. Mol Cell Proteo. Oct. 1, 2008;7(10): 2019-2027.
Berkner et al., Abundant Expression of Polyomavirus Middle T Antigen and Dihydrofolate Reductase in an Adenovirus Recombinant. J Virol. Apr. 1987;61(4): 1213-1220.
Berzofsky, J., et al. Progress on new vaccine strategies for the immunotherapy and prevention of cancer. J Clin Invest. (Jun. 2004) 113(11): 1515-1525.
Betanzos et al., Bacterial Glycoprofiling by Using Random Sequence Peptide Microarrays. ChemBioChem. Mar. 23, 2009;10(5): 877-888.
Bitter et al., Expression and Secretion Vectors for Yeast. Methods Enzymol. 1987;153: 516-544.
Bock et al., Selection of Single-Stranded DNA Molecules That Bind and Inhibit Human Thrombin. Nature Feb. 1992;355(6360): 564-566.
Boerner et al., Production of Antigen-Specific Human Monoclonal Antibodies from In Vitro-Primed Human Splenocytes. J Immunol., Jul. 1, 1991;147(1): 86-95.
Boltz et al., Peptide Microarrays for Carbohydrate Recognition. Analyst. 2009;134(4): 650-652.
Bonneville et al., Landscape of Microsatellite Instability Across 39 Cancer Types. JCO Precis Oncol. Sep. 2017;1: 1-5.
Borovkov et al., New Classes of Orthopoxvirus Vaccine Candidates by Functionally Screening a Synthetic Library for Protective Antigens. Virol. Dec. 5, 2009;395(1): 97-113.
Borrebaeck C.A.K., Antibodies in Diagnostics—From Immunoassays to Protein Chips. Immun Today. Aug. 1, 2000;21(8): 379-382.
Bout et al., Lung Gene Therapy: In Vivo Adenovirus-Mediated Gene Transfer to Rhesus Monkey Airway Epithelium. Hum Gene Thera. 1994;5: 3-10.
Bradner et al., Transcriptional Addiction in Cancer. Cell Feb. 9, 2017;168(4): 629-643.
Breitling, High-Density Peptide Arrays. Mol BioSys. 2009;5(3): 224-234.
Brown et al., Penetration of Host Cell Membranes by Adenovirus 2. J Virol. Aug. 1973; 12(2): 386-396.
Brown et al., Molecular and Cellular Mechanisms of Receptor-Mediated Endocytosis. DNA Cell Biol. Jul. 1991;10(6): 399-409.
Brown et al., The Preclinical Natural History of Serous Ovarian Cancer: Defining the Target for Early Detection. PLoS Med. Jul. 2009;6(7): e1000114; 14 pages.
Brown et al., Statistical Methods for Analyzing Immunosignatures. BMC Bioinfo. Dec. 2011;12(1): 1-5.
Brüggermann et al., Designer Mice: The Production of Human Antibody Repertoires in Transgenic Animals. Year Immunol. 1993;7: 33-40.
Brusic et al., Information Technologies for Vaccine Research. Expert Rev Vaccines. Jun. 2005;4(3): 407-417.
Butler et al., The Immunochemistry of Sandwich ELISAs-VI. Greater Than 90% of Monoclonal and 75% of Polyclonal Anti-Fluorescyl Capture Antibodies (CAbs) are Denatured by Passive Adsorption. Mol Immunol. Sep. 1, 1993;30(13): 1165-1175.

(56) References Cited

OTHER PUBLICATIONS

Butler J.E., Solid Supports in Enzyme-Linked Immunosorbent Assay and Other Solid-Phase Immunoassays. Methods. Sep. 2000;22(1): 4-23.

Caillaud et al., Adenoviral Vector As a Gene DElivery System Into Cultured Rat Neuronal and Glial Cells. Eu J Neurosci. Oct. 1993;5(10): 1287-1291.

Casey et al., Phage Display of Peptides in Ligand Selection for Use in Affinity Chromatography. Methods Mol Biol. 2008;421: 111-124.

Cenci et al., Managing and Exploiting Stress in the Antibody Factory. FEBS Lttrs. Jul. 31, 2007;581(19): 3652-3657.

Cerecedo et al., Mapping of the IgE and IgG4 Sequential Epitopes of Milk Allergens with a Peptide Microarray-Based Immunoassay. J All Clin Immunol. Sep. 1, 2008;122(3): 589-594.

Chalmers et al., Analysis of 100,000 Human Cancer Genomes Reveals the Landscape of Tumor Mutational Burden. Genome Med. Dec. 2017;9(1): 34 (14 pages).

Chambers et al., High-Level Generation of Polyclonal Antibodies by Genetic Immunization. Nat Biotechnol. Sep. 2003;21(9): 1088-1092.

Chan et al., 5-day dosing schedule of temozolomide in relapsed sensitive or refractory small cell lung cancer (SCLC) and methylguanine-DNA methyltransferase (MGMT) analysis in a phase II trial. Journal of Clinical Oncology, 2012 ASCO Annual Meeting Abstracts. (May 20, 2012) 30(15 Suppl) Abstract No. 7052.

Chang et al., Identifying Recurrent Mutations in Cancer Reveals Widespread Lineage Diversity and Mutational Specificity. Nature Biotech. Feb. 2016;34(2): 155-165.

Chase et al., Evaluation of Biological Sample Preparation for Immunosignature-Based Diagnostics. Clin Vac Immunol. Mar. 2012; 19(3): 352-358.

Chen et al., Identification of Multiple Cancer/Testis Antigens by Allogeneic Antibody Screening of a Melanoma Cell Line Library. PNAS Jun. 9, 1998;95(12): 6919-6923.

Chen, W. et al. Modification of Cysteine Residues In Vitro and In Vivo Affects the Immunogenicity and Antigenicity of Major Histocompatibility Complex Class I restricted Viral Determinants. J Exp Med., Jun. 7, 1999;189(11): 1757-1764.

Chen et al., Autoantibody Profiles Reveal Ubiquilin 1 as a Humoral Immune Response Target in Lung Adenocarcinoma. Cancer Res. Apr. 1, 2007;67(7): 3461-3467.

Chéne P., Challenges in Design of Biochemical Assays for the Identification of Small Molecules to Target Multiple Conformations of Prein Kinases. Drug Discover Today. Jun. 1, 2008;13(11-12): 522-529.

Christian et al., Simplified Methods for Construction, Assessment and Rapid Screening of Peptide Libraries in Bacteriophage. J Mol Biol. Oct. 5, 1992;227(3): 711-718.

Clark-Lewis et al., Chemical Synthesis, Purification, and Characterization of Two Inflammatory Proteins, Neutrophil Activating Peptide 1 (Interleukin-8) and Neutrophil Activating Peptide. Biochem. Mar. 26, 1991;30(12): 3128-3135.

Clark-Lewis et al., Structural Requirements for Interleukin-8 Function Identified by Design of Analogs and CXC Chemokine Hybrids. J Biol Chem. 1994;269: 16075-16081.

ClinicalTrials.gov; Identifier NCT02563002; Study of Pembrolizumab (MK-3475) vs Standard Therapy in Participants with Microsatellite Instability-High (MSI-H) or Mismatch Repair Deficient (dMMR) Stage IV Colorectal Carcinoma (MK-3475-177/KEYNOTE-177), published Sep. 29, 2015; 13 pages.

Cohen et al., An Artificial Cell-Cycle Inhibitor Isolated From a Combinatorial Library. PNAS U.S.A. Nov. 24, 1998;95(24): 14272-14277.

Collura et al., Patients With Colorectal Tumors with Microsatellite Instability and Large Deletions in HSP110 T17 Have Improved Response to 5-Fluorauracil-Based Chemotherapy. Gastroenter. Feb. 1, 2014;146(2): 401-411.

Cooperman et al., Cell Division Rates of Primary Human Precursor B Cells in Culture Reflect in vivo Rates. Stem cells. Nov. 2004;22(6): 1111-1120.

Corpet F., Multiple Sequence Alignment with Hierarchical Clustering. Nucl Acids Res. Nov. 25, 1988;16(22): 10881-10890.

Cotter et al., Molecular Genetic Analysis of Herpesviruses and Their Potential Use as Vectors for Gene Therapy Applications. Curr Opin Mol Thera. Oct. 1, 1999;1(5): 633-644.

Cramer et al., Conditions Associated With Antibodies Against the Tumor-Associated Antigen MUC1 and Their Relationship to Risk for Ovarian Cancer. Cancer Epidem Biomark Prevent. May 2005;14(5): 1125-1131.

Cretich, Protein and Peptide Arrays: Recent Trends and New Directions. Biomol Eng. Jun. 1, 2006;23(2-3): 77-88.

Cretich et al., Epitope Mapping of Human Chromogranin A by Peptide Microarrays. Chapter 10; Pept Micro. Jan. 1, 2009;570: 221-232.

Daver et al., The Usefulness of Prostate-Specific Antigen and Prostatic Acid Phosphatase in Clinical Practice. Am J Clin Oncol. Jan. 1988;11 (Suppl 2): S53-S60.

Davidson et al., Overproduction of Polyomavirus Middle T Antigen in Mammalian Cells Through the Use of an Adenovirus Vector. J Virol. Apr. 1987;61(4): 1226-1239.

Dawson et al. Synthesis of Proteins by Native Chemical Ligation. Science, Nov. 4, 1994;266: 776-779.

DeNiro et al., Zinc Transporter 8 (ZnT8) Expression is Reduced by Ischemic Insults: A Potential Therapeutic Target to Prevent Ischemic Retinopathy. PloS One. Nov. 27, 2012;7(11): e50360.

Derda et al., Diversity of Phage-Displayed Libraries of Peptides During Panning and Amplification. Mol. Feb. 21, 2011;16(2): 1776-1803.

de Vegvar et al., Microarray Profiling of Antiviral Antibodies for the Development of Diagnostics, Vaccines, and Therapeutics. Clin Immunol. May 1, 2004;111(2): 196-201.

Diehnelt et al., Discovery of High-Affinity Protein Binding Ligands-Backwards. PloS One. May 19, 2010;5(5): e10728.

Disis et al., HER-2/neu Oncogenic Protein: Issues in Vaccine Development. Crit Rev Immunol., (1998);18(1-2): 37-45.

Donnelly et al., Technical and Regulatory Hurdles for DNA Vaccines. Int J Parasitol. (2003) 33(5-6): 457-467.

Draghici S., Statistics and Data Analysis for Microarrays Using R and Bioconductor. Chapman & Hall/CRC Press. 2nd Edition; Apr. 18, 2016; TOC in 33 pages.

Duan H., Early Detection and Treatment of Breast Cancer by Random Peptide Array in neuN Transgenic Mouse Model. Doctoral Thesis; Arizona State University Jun. 30, 2015, 168 pages.

Dudley et al., Microsatellite Instability as a Biomarker for PD-1 Blockade. Clin Cancer Res. Feb. 15, 2016;22(4): 813-820.

Dunn et al., Cancer Immunoediting: From Immunosurveillance to Tumor Escape. Nature Immunol. Nov. 2002;3(11): 991-998.

Ellington et al., In Vitro Selection of RNA Molecules That Bind Specific Ligands. Nature. Aug. 1990;346(6287): 818-822.

Ellington et al., Selection In Vitro of Single-Stranded DNA Molecules That Fold Into Specific Ligand-Binding Structures. Nature Feb. 1992;355(6363): 850-852.

Emens et al., Toward a Breast Cancer Vaccine: Work in Progress. Oncol. Sep. 1, 2003;17(9): 1217.

Englehard V.H., Structure of Peptides Associated with Class I and Class II MHC Molecules. Annu Rev Immunol. Apr. 1994;12: 181-207.

Engvall et al., Enzyme-Linked Immunosorbent Assay (ELISA). Quantitative Assay of Immunoglobulin G. Immunochem. Sep. 1971;8(9): 871-874.

Falkner et al., Expression of Mouse Immunoglobulin Genes in Monkey Cells. Nature Jul. 15, 1982;298(5871): 286-288.

Falsey et al., Peptide and Small Molecule Microarray for High Throughput Cell Adhesion and Functional Assays. Bioconj Chem. May 16, 2001;12(3): 346-353.

Felgner et al., Lipofection: A Highly Efficient, Lipid-Mediated DNA-Transfection Procedure. PNAS U.S.A. Nov. 1987;84(21): 7413-7417.

Fidler I.J., Selection of Successive Tumour Lines for Metastasis. Nature New Biol. Apr. 1973;242(118): 148-149.

Fields et al., A novel genetic system to detect protein-protein interactions. Nature Jul. 20, 1989;340(6230): 245-246.

(56) References Cited

OTHER PUBLICATIONS

Filley et al., Recurrent Glioma Clinical Trial; CheckMate-143: The Game is not over yet. Oncotarget Oct. 10, 2017;8(53): 91779-91794.
Finn O.J., Cancer Vaccines: Between the Idea and the Reality. Nat Rev Immunol., Aug. 2003;3(8): 630-641.
Finn O.J., Premalignant Lesions as Targets for Cancer Vaccines. J Exp Med. Dec. 1, 2003;198(11): 1623-1626.
Fodor et al., Light-directed, spatially addressable parallel—Chemical Synthesis. Science Feb. 1991. 15;251(4995):767-773.
Fodor et al., Multiplexed Biochemical Assays with Biological Chips. Nature. Aug. 5, 1993;364(6437): 555-556.
Folgori et al., A General Strategy to Identify Mimotopes of Pathological Antigens Using Only Random Peptide Libraries and Human Sera. Embo J. May 1994;13(9): 2236-2243.
Food & Drug Administration (FDA), News Release. FDA Approves first Cancer Treatment for Any Solid Tumor With a Specific Genetic Feature; published online on May 23, 2017; 3 pages.
Food & Drug Administration (FDA), FDA Grants Accelerated Approval to Ipilimumab for MSI-H or dMMR Metastatic Colorectal Cancer. Published Jul. 10, 2018; 2 pages.
Food & Drug Administration (FDA), FDA Grants Nivolumab Accelerated Approval for MSI-H or dMMR Colorectal Cancer. Published Jul. 31, 2017; 2 pages.
Foong et al., Current Advances in Peptide and Small Molecule Microarray Technologies. Curr Opin Chem Biol. Apr. 1, 2012;16(1-2): 234-242.
Forsstrom et al., Proteome-Wide Epitope Mapping of Antibodies Using Ultra-Dense Peptide Arrays. Mol Cell Proteomics 2014; 13:; 1585-1597.
Förster et al., The Bulk of the Peripheral B-Cell Pool in Mice is Stable and not Rapidly Renewed from the Bone Marrow. PNAS Jun. 1990;87(12): 4781-4784.
Frith. Discovering Sequence Motifs With Arbitrary Insertions and Deletions. PLoS Comp Biol. May 9, 2008:4(5): e1000071.
Fu et al., Exploring Peptide Space for Enzyme Modulators. J Am Chem Soc. May 12, 2010;132(18): 6419-6424.
Fu et al., Peptide-Modified Surfaces for Enzyme Immobilization. PLoS One Apr. 8, 2011;6(4): e18692.
Gallina et al., Prediction of Pathological Stage is Inaccurate in Men with BSA Values above 20 ng/mL. Eur Urol. Nov. 2007;52(5): 1374-1380. Epub Dec. 11, 2006.
Garon et al., Pembrolizumab for the Treatment of Non-Small-Cell Lung Cancer. N Engl J Med. May 21, 2015;372(21): 2018-2028.
Georgiadis et al., Non-Invasive Detection of Microsatellite Instability and High Tumor Mutation Burden in Cancer Patients Treated with PD-1 Blockade. Clin Cancer Res. Dec. 1, 2019;25(23): 7024-7034.
Geysen et al., Use of Peptide Synthesis to Prove Viral Antigens for Epitopes to a Resolution of a Single Amino Acid. PNAS Jul. 1984;81(13): 3998-4002.
Gite et al. A High-throughput Nonisotopic Protein Truncation Test. Nat Biotech., Feb. 2003;21(2): 194-197.
Gnjatic et al., Identifying Baseline Immune-related Biomarkers to Predict Clinical Outcome of Immunotherapy. J Immunother Cancer 2017 12;5(1): 1-8.
Goldman et al., The UCSC Cancer Genomics Browser: Update 2015. Nucleic Acids Res. Jan. 28, 2015;43(D1): D812-D817.
Gómez-Foix et al., Adenovirus-Mediated Transfer of the Muscle Glycogen Phosphorylase Gene Into Hepatocytes Confers Altered Regulation of Glycogen Metabolism. J Biol Chem. Dec. 15, 1992;267(35): 25129-25134.
Goodman et al., Tumor Mutational Burden as an Independent Predictor of Response to Immunotherapy in Diverse Cancers. Mo. Cancer Ther. Nov. 1, 2017;16(11): 2598-2608.
Gout et al., Large-Scale Detection of in vivo Transcription Errors. PNAS U S A. Nov. 12, 2013;110(46): 18584-18589.
Gout et al., The Landscape of Transcriptioin Errors in Eukaryotic Cells. Science Adv. Oct. 20, 2017;3(10): e1701484.
Greving et al., Thermodynamic Additivity of Sequence Variations: An Algorithm for Creating High Affinity Peptides without Large Libraries or Structural Information. PLoS One. Nov. 2010;5(11): e15432.
Greving et al., High-Throughput Screening in Two Dimensions: Binding Intesity and Off-rate on a Peptide Microarray. Anal Biochem. Jul. 1, 2010;402(1): 93-95.
Guo et al., Therapeutic Cancer Vaccines: Past, Present and Future. Adv Cancer Res. Jan. 1, 2013;119: 421-475.
Gupta et al., Engineering a Synthetic Ligand for Tumor Necrosis Factor-α. Bioconj Chem. Aug. 17, 2011;22(8): 1473-1478; Epub Nov. 9, 2010.
Halperin et al., Exploring Antibody Recognition of Sequence Space Through Random-Sequence Peptide Microarrays. Mol Cell Proteo. Nov. 1, 2010;10(3): 10 pages.
Halperin R., Characterization and Analysis of a Novel Platform for Profiling the Antibody Response. Doctoral Dissertation, Arizona State University 2011, in 272 pages.
Halperin et al., GuiTope: An Application for Mapping Random-Sequence Peptides to protein Sequences. BMC Bioinfo. Dec. 2012;13(1): 1-8.
Hampe C.S., B Cells in Autoimmune Diseases. Scientifica Oct. 2012; Article ID 215308, in 18 pages.
Hanahan et al., Hallmarks of Cancer: The Next Generation. Cell Mar. 4, 2011;144(5): 646-674.
Hanash S., Disease Proteomics. Nature Mar. 2003;422(6928): 226-232.
Hann et al., On the Double Bond Isostere of the Peptide Bond: Preparation of an Enkephalin Analogue. J Chem Soc Perkin Transl I. 1982; 307-314.
Hansen et al., Polyclonal Antibody Production for Membrane Proteins via Genetic Immunization. Sci Rep. Feb. 24, 2016;6(1): 227 (13 pages).
Hansen et al., Combination of RNA- and Exome Sequencing: Increasing Specificity for Identification of Somatic Point Mutations and Indels in Acute Leukaemia. Leuk Res. Dec. 2016;51: 27-31.
Hao et al., Homeostasis of Peripheral B Cells in the Absence of B Cell Influx from the Bone Marrow. J Exp Med. Oct. 15, 2001;194(8): 1151-1164.
Hause et al., Classification and Characterization of Microsatellite Instability Across 18 Cancer Types. Nat Med Nov. 2016;22(11): 1342-1350.
Hecker et al., Computational Analysis of High-density Peptide Microarray Data with Application from Systemic Sclerosis to Multiple Sclerosis. Autoimmun Rev. Jan. 1, 2012;11(3): 180-190.
Hellmann et al. Genomic Profile, Smoking, and Response to Anti-PD-1 Therapy in Nonsmall Cell Lung Carcinoma. Mol Cell Oncol. 20163(1):e1048929 (3 pages) (2016).
Higgins et al., CLUSTAL: A Package for Performing Multiple Sequence Alignment on a Microcomputer. Gene. Dec. 15, 1988;73(1): 237-244.
Higgins et al., Fast and Sensitive Multiple Sequence Alignments on a Microcomputer. Comput Appl Biosci. Apr. 1989;5(2): 151-153.
Hilpert et al., Cellulose-bound Peptide Arrays: Preparation and Applications. Biotech Gen Engin Rev. Jan. 1, 2007;24(1): 31-106.
Hirayama et al., The Present Status and Future Prospects of Peptide-based Cancer Vaccines. Int Immunol. Jul. 1, 2016;28(7): 319-328.
Hodges et al., Mutational Burden, Immune Checkpoint Expression, and Mismatch Repair in Glioma: Implications for Immune Checkpoint Immunotherapy. Neuro Oncol. Aug. 1, 2017;19(8): 1047-1057.
Holladay et al., Synthesis of Hydroxyethylene and Ketomethylene Dipeptide Isosteres. Tetrahedron Lett. Jan. 1, 1983;24(41): 4401-4404.
Hollingsworth et al., Turning the Corner on Therapeutic Cancer Vaccines. NPJ Vac. Feb. 8, 2019:4(1): 10 pages.
Hoogenboom et al., By-Passing Immunisation: Human Antibodies from Synthetic Repertoires of Germline VH Gene Segments Rearranged In Vitro. J Mol Biol. 1991;227:381-388.
Hori et al., Mathematical Model Identifies Blood Biomarker-Based Early Cancer Detection Strategies and Limitations. Sci Transl Med. Nov. 16, 2011;3(109): 109-116.

(56) References Cited

OTHER PUBLICATIONS

Hruby V.J., Conformational Restrictions of Biologically Active Peptides Via Amino Acid Side Chain Groups. Life Sci. Jul. 19, 1982;31(3): 189-199.

Huang et al., MIMOX: A Web Tool for Phage Display Based Epitope Mapping. BMC Bioinformatics. Oct. 12, 2006;7: 451 in 10 pages.

Hughes et al., Monoclonal Antibody Targeting of Liposomes to Mouse Lung In Vivo. Cancer Res. Nov. 15, 1989;49(22): 6214-6220.

Hughes et al., Immunosignaturing Can Detect Products from Molecular Markers in Brain Cancer. PLoS One. Jul. 16, 2012;7(7): e40201.

Ibba et al., Towards Engineering Proteins by Site-Directed Incorporation In Vivo of Non-Natural Amino Acids. Bio/Tech. Jul. 1994;12(7): 678-682.

Itakura et al., Synthesis and Use of Synthetic Oligonucleotides. Ann Rev Biochem. 1984;53: 323-356.

Imashimizu et al., Direct Assessment of Transcription Fidelity by High-Resolution RNA Sequencing. Nucleic Acids Res. Oct. 1, 2013;41(19): 9090-9104.

Jaeger et al. Improved Predictions of Secondary Structures for RNA. PNAS U.S.A. Oct. 1989;86(20): 7706-7710.

Jaeger et al., Predicting Optimal and Suboptimal Secondary Structure for RNA. Meth Enzymol. 1990;183: 281-306.

Jaffe S., Vax Facts. The Scientist. Mar. 2004; 2 pages.

Jagger et al., An Overlapping Protein-Coding Region in Influenza A Virus Segment 3 Modulates the Host Response. Science. Jul. 13, 2012;337(6091): 199-204.

Jakobovits et al., Analysis of Homozygous Mutant Chimeric Mice: Deletion of the Immunoglobulin Heavy-Chain Joining Region Blocks B-Cell Development and Antibody Production. PNAS U.S.A. Mar. 15, 1993; 90(6): 2551-2555.

Jakobovits et al., Germ-Line Transmission and Expression of a Human-Derived Yeast Artificial Chromosome. Nature Mar. 18, 1993;362(6417): 255-258.

Jennings-White et al., Synthesis of Ketomethylene Analogs of Dipeptides. Tetra Ltt. Jan. 1, 1982;23(25): 2533-2534.

Jollymore M., Virus research aims to prevent or reverse immune-system aging. Nova Scotia Health Research Annual Report 2017, pub. Feb. 21, 2018, 2 pages. Retrieved from the internet: http://www.nshealth.ca/news/virus-research-aims-prevent-orreverse-immune-system-aging; Oct. 15, 2019.

Jonassen I., Efficient Discovery of Conserved Patterns Using a Pattern Graph. Comp Appl Biosci. Oct. 1, 1997;13(5): 509-522.

Jones et al., Replacing the Complementarity-Determining Regions in a Human Antibody With Those From a Mouse. Nature 1986;321(6069): 522-525.

Kahles et al., Comprehensive Analysis of Alternative Splicing Across Tumors from 8,705 Patients. Cancer Cell Aug. 13, 2018;34(2): 211-224.

Kandoth et al., Mutational Landscape and Significance Across 12 Major Cancer Types. Nature Oct. 2013;502(7471): 333-339.

Kerr C., Huntington's disease provides cancer clues. The Lancet Oncol. Sep. 1, 2002;3(9): 518.

Keskin et al., Neoantigen Vaccine Generates Intratumoral T Cell Responses in Phase Ib Glioblastoma Trial. Nature Jan. 2019;565(7738): 234-239.

Kimura et al., MUC1 Vaccine for Individuals with Advanced Adenoma of the Colon: A Cancer Immunoprevention Feasibility StudyMUC1 Vaccine Clinical Trial for Colon Cancer Prevention. Cancer Prevent Res. Jan. 1, 2013;6(1): 18-26.

Kirovski, D. et al. Combinatorics of the Vaccine Design Problem: Definition and an Algorithm.Technical Report MSR-TR-2007-148. Microsoft Research (http://research.microsoft.com); Nov. 2007; 11 pages.

Kirshenbaum et al., Highly Efficient Gene Transfer Into Adult Ventricular Myocytes by Recombinant Adenovirus. J Clin Invest. Jul. 1, 1993;92(1): 381-387.

Kloor et al., The Immune Biology of Microsatellite-Unstable Cancer. CellPress Trends in Cancer Mar. 2016;2(3): 121-133.

Köhler et al., Continuous Cultures of Fused Cells Secreting Antibody of Predefined Specificity. Nature, Aug. 7, 1975;256(5517): 495-497.

König R., Interactions Between MHC Molecules and Co-Receptors of the TCR. Curr Opin Immunol. Feb. 1, 2002;14(1): 75-83.

Korber et al., Immunoinformatics Comes of Age. PLoS Compu Biol. Jun. 2006;2(6):e71 (0484-0492).

Kreiter et al., Mutant MHC Class II Epitopes Drive Therapeutic Immune Responses to Cancer. Nature Apr. 2015;520(7549): 692-696.

Krieg A.M., CpG Motifs: The Active Ingredient in Bacterial Extracts? Nat Med. Jul. 2003;9(7): 831-835.

Kroening et al., Autoreactive Antibodies Rased by Self-derived de novo Peptides Can Identify Unrelated Antigens on Protein Microarrays. Are Autoantibodies Really Autoantibodies? Exp Mol Pathol. Jun. 1, 2012;92(3): 304-311.

Kukreja et al., Immunosignaturing Microarrays Distinguish Antibody Profiles of Related Pancreatic Diseases. J Proteo Bioinfo. 2012;S6(001): 5 pages.

Kukreja et al., Comparative Study of Classification Algorithms for Immunosignaturing Data. BMC Bioinfo. Dec. 2012; 13(1): 1-25.

Larkin et al., Combined Nivolumab and Ipilimumab or Monotheraby in Untreated Melanoma. New Engl J Med. Jul. 2, 2015;373(1): 23-34.

La Salle et al., An Adenovirus Vector For Gene Transfer Into Neurons and Glia in the Brain. Science Feb. 12, 1993;259(5097): 988-990.

Le et al., PD-1 Blockade in Tumors with Mismatch-Repair Deficiency. N Engl J Med Jun. 25, 2015;372(26): 2509-250.

Le et al., Mismatch Repair Deficiency Predicts Response of Solid Tumors to PD-1 Blockade. Science Jul. 28, 2017;357(6349): 409-413.

Leaf C., Why We're Losing the War on Cancer. Fortune. Mar. 22, 2004;149(6): 76-79.

Lee H., Identification of Neo-antigens for a Cancer Vaccine by Transcriptome Analysis. Doctoral Dissertation, Arizona State University, (May 2012), 168 pages.

Lee et al., Transcriptional Regulation and Its Misregulation in Disease. Cell Mar. 14, 2013;152(6): 1237-1251.

Lee et al., Therapeutic Targeting of Splicing in Cancer. Nat Med. Sep. 2016;22(9): 976-986.

Legutki et al., Scalable high-density peptide arrays for comprehensive health monitoring. Nature Commun. Sep. 3, 2014;5(1):4785 in 7 pages.

Lennerz et al., The Response of Autologous T Cells to a Human Melanoma is Dominated by Mutated Neoantigens. PNAS. Nov. 1, 2005;102(44): 16013-16018.

Letsinger et al., Cholesteryl-Conjugated Oligonucleotides: Synthesis, Properties, and Activity as Inhibitors of Replication of Human Immunodeficiency Virus in Cell Culture. PNAS U.S.A. Sep. 1989; 86(17): 6553-6556.

Lewis J.J., Therapeutic cancer vaccines: using unique antigens. PNAS: (2004) 101 Supplement 2:14653-14656.

Leyssen et al., Prospects for Antiviral Therapy. Adv Virus Res. 61, 511-53 (2003).

Lewczuk et al., Amyloid β Peptides in Plasma in Early Diagnosis of Alzheimer's Disease: A Multicenter Study with Multiplexing. Exp Neurol. Jun. 1, 2010;223(2): 366-370.

Li et al., Preclinical and Clinical Development of Neoantigen Vaccines. Ann Oncol. Dec. 28, 2017;28(12 Suppl): xii11-17.

Lin et al., Evaluation of MHC Class I Peptide Binding Prediction Servers: Application for Vaccine Research. BMC Immunol. Dec. 2008; 9(1): 1-3.

Lin et al., Development of a Novel Peptide Microarray for Large-Scale Epitope Mapping of Food Allergens. J Allergy Clin Immunol. Aug. 1, 2009;124(2): 315-322.

Lin et al., Transcriptional Amplification in Tumor Cells with Elevated c-Myc. Cell Sep. 2012;151(1): 56-67.

Lin et al., DNA Mismatch Repair and p53 Function are Major Determinants of the Rate of Development of Cisplatin Resistance. Mol Cancer Thera. May 2006;5(5): 1239-1247.

Lindahl T., DNA Repair: DNA Surveillance Defect in Cancer Cells. Curr Biol. Mar. 1, 1994;4(3): 249-251.

(56) References Cited

OTHER PUBLICATIONS

Linnebacher, M. et al. Frameshift Peptide-Derived T-Cell Epitopes: A Source of Novel Tumor-Specific Antigens. Int J Cancer, Jul. 1, 2001;93(1): 6-11.

Linnemann et al., High-Throughput Epitope Discovery Reveals Frequent Recognition of Neo-Antigens by CD4+ T Cells in Human Melanoma. Nat Med. Jan. 2015;21(1): 81-85.

Liu et al., Towards Proteome-Wide Production of Monoclonal Antibody by Phage Display. J Mol Biol. Feb. 1, 2002;315(5): 1063-1073.

Liu et al., Combinatorial Peptide Library Methods for Immunobiology Research. Exp Hematol. Jan. 1, 2003;31(1): 11-30.

Lollini et al., Vaccines and Other Immunological Approaches for Cancer Immunoprevention. Curr Drug Targets Dec. 1, 2011;12(13): 1957-1973.

Lorenz et al., Probing the Epitope Signatures of igG Antibodies in Human Serum from Patients with Autoimmune disease. Chapter 18; Meth Mol Biol. 2009;524: 247-258.

Lusky et al., Bovine Papilloma Virus Contains an Activator of Gene Expression at the Distal End of the Early Transcription Unit. Mol Cell Biol. Jun. 1983;3(6): 1108-1122.

Lykke-Andersen et al., Nonsense-Mediated mRNA Decay: An Intricate Machinery that Shapes Transcriptomes. Nat Rev Mol Cell Biol. 2015;16: 665-677.

Macmillan Publishers Ltd., Misguided Cancer Goal. This Week—Nature Nov. 29, 2012;491: 637.

Mackey et al., Getting More From Less: Algorithms for Rapid Protein Identification with Multiple Short Peptide Sequences. Mol Cell Proteo. Feb. 1, 2002;1(2): 139-147.

Maher et al., Transcriptome Sequencing to Detect Gene Fusions in Cancer. Nature Mar. 2009;458(7234): 97-101.

Maher et al., Chimeric Transcript Discovery by Paired-End Transcriptome Sequencing. PNAS U S A. Jul. 28, 2009:106(30): 12353-12358.

Maletzki et al., Frameshift-derived Neoantigens Constitute Immunotherapeutic Targets for Patients with Microsatellite-instable Haematological Malignancies: Frameshift Peptides for Treating MSI+ Blood Cancers. Eur J Cancer. Jul. 1, 2013;49(11): 2587-2595.

Marks et al., By-passing immunization. Human antibodies from V-gene libraries displayed on phage. J Mol Biol. Dec. 5, 1991;222(3): 581-597.

Martin et al., Low Mutation Burden in Ovarian Cancer May Limit the Utility of Neoantigen-Targeted Vaccines. Plos One. May 18, 2016;11(5): e0155189 (15 pages).

Massie et al., Construction of a Helper-Free Recombinant Adenovirus That Expresses Polyomavirus Large T Antigen. Mol Cell Biol. Aug. 1986;6(8): 2872-2883.

Matsui et al., Hepatitis C Virus Infection Suppresses GLUT2 Gene Expression via Downregulation of Hepatocyte Nuclear Factor 1α. J Virol. Dec. 1, 2012;86(23): 12903-12911.

McDade et al., What a Drop Can Do: Dried Blood Spots as a Minimally Invasive Method for Integrating Biomarkers Into Population-Based Research. Demography, 2007;44(4): 899-925.

Merbl et al., A Systems Immunology Approach to the Host-Tumor Interation: Large-Scale Patterns of Natural Autoantibodies Distinguish Healthy and Tumor-Bearing Mice. Plos One. Jun. 25, 2009;4(6): e6053.

Merriam-Webster Dictionary, "Putative" Definition 2020, 1-2; online from https://www.merriam-webster.com/dictionary/putative#learn-more on Mar. 24, 2020.

Merriam-Webster Dictionary, "Putative" Definition 2020, 1-5; online from https://www.merriam-webster.com/dictionary/putative on Jan. 2, 2020.

Mestas et al., Of Mice and Not Men: Differences Between Mouse and Human Immunology. J Immunol. Mar. 1, 2004;172(5): 2731-2738.

Miller et al., Basic Concepts of Microarrays and Potential Applications in Clinical Microbiology. Clin Microbiol Rev. Oct. 2009;22(4): 611-633.

Min et al., Peptide Arrays: Towards Routine Implementation. Curr Opin Chem Biol. Oct. 1, 2004;8(5): 554-558.

Minev B.R., Melanoma Vaccines. Semin Oncol. Oct. 1, 2002; 29 (5): 479-493.

Miseta et al., Relationship Between the Occurrence of Cysteine in Proteins and the Complexity of Organisms. Mol Biol Evol. Aug. 1, 2000;17(8): 1232-1239.

Mohan et al., Association Energetics of Cross-Reactive and Specific Antibodies. Biochem. Feb. 17, 2009;48(6): 1390-1398.

Möller et al., DNA Probes on Chip Surfaces Studied by Scanning Force Microscopy Using Specific Binding of Colloidal Gold. Nucleic Acids Res. Oct. 15, 2000:28(20): e91 in 5 pages.

Moreau et al., Discontinuous Epitope Prediction Based on Mimotope Analysis. Bioinform. May 1, 2006;22(9): 1088-1095; Epub Jan. 24, 2006.

Morrison S.L., Sequentially Derived Mutants of the Constant Region of the Heavy Chain of Murine Immunoglobulins. J Immunol. Aug. 1979;123(2): 793-800.

Morrison et al., Chimeric Human Antibody Molecules: Mouse Antigen-binding Domains with Human Constant Region Domains. Proc Natl Acad Sci USA. Nov. 1984;81(21):6851-6855.

Morsy et al., Efficient Adenoviral-Mediated Ornithine Transcarbamylase Expression in Deficient Mouse and Human Hepatocytes. J Clin Invest. Sep. 1, 1993;92(3): 1580-1586.

Motzer et al., Nivolumab Versus Everolimus in Advanced Renal-Cell Carcinoma. N Engl J Med. Nov. 5, 2015;373(19): 1803-1813.

Moudgil et al., Cytokines in autoimmunity: Role in induction, regulation, and treatment. J Interferon & Cyto Res., Oct. 2, 2011;31(1):695-703.

Moullier et al., Adenoviral-Mediated Gene Transfer to Renal Tubular Cells In Vivo. Kidney Internat. Apr. 1, 1994;45(4): 1220-1225.

Mulligan R.C., The Basic Science of Gene Therapy. Science. May 14, 1993;260(5110): 926-932.

Navalkar et al., Peptide Based Diagnostics: Are Random-Sequence Peptides More Useful Than Tiling Proteome Sequences? J Immunol Meth. Feb. 1, 2015;417: 10-21.

Needleman et al., A General Method Applicable to the Search for Similarities in the Amino Acid Sequence of Two Proteins. J Mol Biol. Mar. 1970;48(3): 443-453.

Negrini et al., Genomic Instability—An Evolving Hallmark of Cancer. Nat Rev Mol Cell Biol. Mar. 2010;11(3): 220-228.

Nestle F.O., Vaccines and Melanoma. Clin Exper Dermatol. 27: 597-601 (2002).

Nielsen et al., Peptide Nucleic Acid (PNA). A DNA Mimic With a Peptide Backbone. Biocon Chem. Jan. 1, 1994;5(1): 3-7.

Nobrega et al., Functional Diversity and Clonal Frequencies of Reactivity in the Available Antibody Repertoire. Eu J Immunol Apr. 199;28(4): 1204-1215.

O'Leary et al., Reference Sequence (RefSeq) Database at NCBI: Current Status, Taxonomic Expansion, and Functional Annotation. Nucleic Acids Res. Jan. 4, 2016;44(D1): D733-D745.

Oltean et al., Hallmarks of Alternative Splicing in Cancer. Oncogene Nov. 2014;33(46): 5311-5318.

Osborne et al., Transcription Control Region Within the Protein-Coding Portion of Adenovirus E1A Genes. Mol Cell Biol. Jul. 1984;4(7): 1293-1305.

Ott et al., An Immunogenic Personal Neoantigen Vaccine for Patients with Melanoma. Nature. Jul. 2017;547(7662): 217-221.

Oxford University, Combination Vaccines and Multiple Vaccinations; (http://vk.ovg.ox.ac.uk/combination-vaccines-and-multiple-vaccinations) Website Accessed Oct. 4, 2013, 1 page.

Panicker et al., Recent Advances in Peptide-Based Microarray Technologies. Comb Chem High Throughput Screen. Sep. 1, 2004;7(6): 547-556.

Pawlik et al., Malignant Melanoma: Current State of Primary and Adjuvant Treatment. Crit Rev Oncol Hematol. Mar. 1, 2003; 45(3): 245-264.

Pearson et al., Improved Tools for Biological Sequence Comparison. PNAS U.S.A. Apr. 1988;85(8): 2444-2448.

Perez-Gordo et al., Epitope Mapping of Atlantic Salmon Major Allergen by Peptide Microarray Immunoassay. Int Arch Allergy Immunol. 2012;157(1): 31-40.

(56) References Cited

OTHER PUBLICATIONS

Pietanza et al., Phase II Trial of Temozolomide in Patients with Relapsed Sensitive or Refractory Small Cell Lung Cancer, with Assessment of Methylguanine-DNA Methyltransferase as a Potential Biomarker. Clin Cancer Res., (Feb. 15, 2012) 18(4): 1138-1145.
Pietersz et al., Antibody Conjugates for the Treatment of Cancer. Immunol Rev. Oct. 1992; 129(1): 57-80.
Presta L.G., Antibody Engineering. Curr Opin Struct Biol. Aug. 1, 1992;2(4): 593-596.
Price et al., On Silico Peptide Microarrays for High-Resolution Mapping of Antibody Epitopes and Diverse Protein-Protein Interactions. Nat Med. Sep. 2012; 18(9): 1434-1440.
Pruitt et al., The Consensus Coding Sequence (CCDS) Project: Identifying a Common Protein-Coding Gene Set for the Human and Mouse Genomes. Genome Res. Jul. 1, 2009;19(7): 1316-1323.
Quackenbush J., Computational Analysis of Microarray Data. Nature Rev. Jun. 2001;2(6): 418-427.
Quintana et al., Antigen-Chip Technology for Accessing Global Information About the State of the Body. Lupus Jul. 2006; 15(7): 428-430.
Quintana et al., The Natural Autoantibody Repertoire and Autoimmune Disease. Biomed Pharmaco. Jun. 1, 2004;58(5): 276-281.
Ragot et al., Replication-Defective Recombinant Adenovirus Expressing the Epstein-Barr Virus (EBV) Envelope Glycoprotein gp340/220 Induces Protective Immunity Against EBV-Induced Lymphomas in the Cottontop Tamarin. J Gen Virol. Mar. 1, 1993;74(3): 501-507.
Rajarathnam et al., 1H NMR studies of interleukin 8 analogs: characterization of the domains essential for function. Biochem. May 31, 1994;33(21): 6623-6630.
Ram et al. In Situ Retroviral-Mediated Gene Transfer for the Treatment of Brain Tumors in Rats. Cancer Res. Jan. 1, 1993;53(1): 83-88.
Rammensee et al., Peptides Naturally Presented by MHC Class I Molecules. Immunol Rev. Apr. 1993; 11(1):213-244.
Rammensee et al., Towards Patient-specific Tumor Antigen Selection for Vaccination. Immunol Rev. Oct. 2002; 188(1): 164-176.
Rappuoli et al. [Eds.], New Approaches to Vaccine Design, from Vaccine Design Innovative Approaches and Novel Strategedies; (2011) Caister Academic Press; 12 pages.
Reddy et al., Protein "Fingerprinting" in Complex Mixtures With Peptoid Microarrays. PNAS Sep. 6, 2005;102(36): 12672-12677.
Reddy et al., Identification of Candidate IgG Biomarkers for Alzheimer's Disease via Combinatorial Library Screening. Cell Jan. 7, 2011;144(1): 132-142.
Reineke et al., Identification of Distinct Antibody Epitopes and Mimotopes From a Peptide Array of 5520 Randomly Generated Sequences. J Immunol Meth. Sep. 1, 2002;267(1): 37-51.
Reineke et al., Epitope Mapping Protocols. Meth Mol Biol. 524, 2nd Edition, Humana Press. 2009; 1-447.
Renno et al., What's new in the field of cancer vaccines? Cell Mol Life Sci. CMLS Jul. 2003;60(7): 1296-1310.
Restrepo et al., Application of Immunosignatures to the Assessment of Alzheimer's Disease. Annlas Neurol. Aug. 2011;70(2): 286-295.
Reuschenbach et al., Serum Antibodies Against Frameshift Peptides in Microsatellite Unstable Colorectal Cancer Patients with Lynch Syndrome. Fam Cancer Jun. 2010;9(2): 173-179.
Reuschenbach et al., A Multiplex Method for the Detection of Serum Antibodies Against in Silico-Predicted Tumor Antigens. Cancer Immunol Immunother. Dec. 2014;63(12): 1251-1259.
Riechmann et al., Reshaping Human Antibodies for Therapy. Nature Mar. 24, 1988;332(6162): 323-327.
Riess et al., Theory Meets Practice for Immune Checkpoint Blockade in Small-Cell Lung Cancer. J Clin Oncol. Nov. 11, 2016;34(31): 3717-3720.
Rigoutsos. Combinatorial Pattern Discovery in Biological Sequences: The Teiresias Algorithm. BioInform. (Oxford, England) Jan. 1, 1989;14(1): 55-67.
Rigoutsos. In Silico Pattern-Based Analysis of the Human Cytomegalovirus Genome. J Virol. Apr. 1, 2003;77(7): 4326-4344.
Rizo et al., Constrained Peptides: Models of Bioactive Peptides and Protein Substructures. Ann Rev Biochem. Jul. 1992;61(1): 387-416.
Rizvi et al., Mutational Landscape Determines Sensitivity to PD-1 Blockade in Non-Small Cell Lung Cancer. Science. Apr. 3, 2015;348(6230): 124-128.
Roberts et al., RNA-Peptide Fusions For The In Vitro Selection of Peptides and Proteins. PNAS U.S.A. Nov. 11, 1997;94(23): 12297-12302.
Roessler et al., Adenoviral-Mediated Gene Transfer to Rabbit Synovium In Vivo. J Clin Invest. J Clin Invest. Aug. 1, 1993;92(2): 1085-1092.
Roobol M.J., Contemporary Role of Prostate Cancer Gene 3 in the Management of Prostate Cancer. Curr Opin Urol. May 1, 2011;21(3): 225-229.
Ruggiano et al., ER-Associated Degradation: Protein Quality Control and Beyond. J Cell Biol. Mar. 17, 2014;204(6): 869-879.
Ryan et al., The Current Value of Determining the Mismatch Repair Status of Colorectal Cancer: A Rationale for Routine Testing. Crit Rev. Oncol/Hemat. Aug. 1, 2017;116: 38-57.
Sade-Feldman et al., Resistance to Checkpoint Blockade Therapy Through Inactivation of Antigen Presentation. Nat Commun. Oct. 26, 2017;8(1): 1136 (in 11 pages).
Sæterdal et al., Frameshift-mutation-derived Peptides as Tumor-Specific Antigens in Inherited and Spontaneous Colorectal Cancer. PNAS USA , Nov. 6, 2001;98(23): 13255-13260.
Sahin et al., Personalized RNA Mutanome Vaccines Mobilize Poly-Specific Therapeutic Immunity Against Cancer. Nature Jul. 2017;547(7662): 222-226.
Salipante et al., Microsatellite Instability Detection by Next Generation Sequencing. Clin Chem. Sep. 1, 2014;60(9): 1192-1199.
Schadendorf et al., Pooled Analysis of Long-Term Survival Data from Phase II and Phase III Trials of Ipilimumab in Unresectable or Metastatic Melanoma. J Clin Oncol. Jun. 6, 2015;33(17): 1889-1894.
Schiffman et al., Comparative Oncology: What Dogs and Other Species Can Teach Us About Humans with Cancer. Philos Trans R Soc. London B Biol Sci. Jul. 19, 2015;370(1673): 1-13.
Schnölzer et al., Constructing Proteins by Dovetailing Unprotected Synthetic Peptides: Backbone-Engineered HIV Protease. Science. Apr. 10, 1992;256(5054): 221-225.
Schultze et al., From Cancer Genomics to Cancer Immunotherapy: Toward Second-generation Tumor Antigens. Trends Immunol. Sep. 1, 2001;22(9): 516-553.
Schumacher et al., Neoantigens in Cancer Immunotherapy. Science Apr. 3, 2015;348(6230): 67-74.
Schwanhäusser et al., Global Quantification of Mammalian Gene Expression Control. Nature. May 2011;473(7347): 337-342.
Seth et al., Role of a Low-pH Environment in Adenovirus Enhancement of the Toxicity of a Pseudomonas Exotoxin-Epidermal Growth Factor Conjugate. J Virol. Sep. 1984;51(3): 650-655.
Seth et al., Evidence That the Penton Base of Adenovirus is Involved in Potentiation of Toxicity of Pseudomonas exotoxin Conjugated to Epidermal Growth Factor. Mol Cell Biol. Aug. 1984;4(8): 1528-1533.
Sette et al., The Relationship Between Class I Binding Affinity and Immunogenicity of Potential Cytotoxic T Cell Epitopes. J Immunol. Dec. 15, 1994;153(12): 5586-5592.
Shen L., Investigation of Tumor Frame Shift Antigens for Prophylactic Cancer Vaccine, Cancer Detection and Tumorigenicity. Doctoral Thesis; Arizona State University. Dec. 2012, 256 pages.
Shen et al., RNA Transcription and Splicing Errors as a Source of Cancer Frameshift Neoantigens for Vaccines. Scientific Rep. Oct. 2, 2019:9(1): 13 pages.
Shi et al., Application of High-throughput Protein Array in Clinical Screening for Tumor Markers. Int J Clin Exp Med. Jan. 1, 2016;9(5): 8529-8535.
Shin et al., Automated maskless photolithography system for peptide microarray synthesis on a chip. J Comb Chem. 2010;12(4):463-471.
Shreffler et al., IgE and IgG4 Epitope Mapping by Microarray Immunoassay Reveals the Diversity of Immune Response to the Peanut Allergen. Ara h2. J All Clin Immunol. Oct. 1, 2005;116(4): 893-899.

(56) References Cited

OTHER PUBLICATIONS

Silvera et al., Translational Control in Cancer. Nat Rev Cancer Apr. 2010; 10(4): 254-266.
Silverman G., Regulatory Natural Antibodies to Apoptotic Cells: Pallbearers and Protectors. Arth Rheum. Mar. 2011;63(3): 597-602.
Smart et al., Intron Retention is a Source of Neoepitopes in Cancer. Nat Biotechnol. Nov. 2018;36(11): 1056-1058.
Smith et al., Comparison of Biosequences. Adv Appl Math Dec. 1, 1981;2(4): 482-489.
Snyder et al., Genetics and Immunology: Reinvigorated. OncoImmunology, Oct. 3, 2015;4(10): e1029705 (2 pages).
Sørensen et al., Significantly Lower Incidence of Cancer Among Patients with Huntington Disease. J Am Cancer Soc. Oct. 1, 1999;86(7): 355-359.
Spatola A.F., Peptide Backbone Modifications: A Structure-Activity Analysis of Peptides Containing Amide Bond Surrogates, Conformational Constraints, and Related Backbone Replacements. Marcel Dekker, New York (Mar. 1983), Chapter 5; in 91 pages.
Spatola et al., Structure-Activity Relationships of Enkephalins Containing Serially Replaced Thiomethylene Amide Bond Surrogates. Life Sci. Apr. 7, 1986;38(14): 1243-1249.
Stafford et al., Microarray technology displays the complexities of the humoral immune response. Exp Rev Mol Diagn. Jan. 1, 2011;11(1): 5-8.
Stafford et al., Physical Characterization of the "Immunosignaturing Effect". Mol Cell Proteo. Apr. 1, 2012;11(4):M111.011593-1 (14 pages).
Stafford et al., Immunosignature system for diagnosis of cancer. PNAS Jul. 29, 2014;111(3):e3072-e3080.
Stafford et al., Use of Random Peptide Array to Discover Cancer Neo-Antigens for Vaccines and Diagnostics. Cancer Immunol Res. 2015;3(10 Suppl), Abstract PR10.
Sugden et al., A Vector That Replicates as a Plasmid and Can Be Efficiently Selected in B-Lymphoblasts Transformed by Epstein-Barr Virus. Mol Cell Biol. Feb. 1985;5(2): 410-413.
Sulzer et al., Memory in Idiotypic Networks Due to Competition Between Proliferation and Differentiation. Bull Math Biol. Nov. 1, 1993;55(6): 1133-1182.
Sussman H.E., Personalized Cancer Vaccine Promises Remission. Drug Discov Today. 2003;8(15): 657-658.
Svarovsky et al., Self-Assembled Micronanoplexes for Improved Biolistic Delivery of Nucleic Acids. Mo Pharm. Dec. 7, 2009;6(6): 1927-1933.
Svensson U., Role of Vesicles During Adenovirus 2 Internalization Into HeLa Cells. J Virol. Aug. 1985;55(2): 442-449.
Sykes et al., Genetic Live Vaccines Mimic the Antigenicity But Not Pathogenicity of Live Viruses. DNA Cell Biol. Jul. 1, 1999;18(7): 521-531.
Sykes et al., Linear Expression Elements: A Rapid, in vivo, Method to Screen for Gene Functions. Nat Biotech. Apr. 1999;17(4): 355-359.
Szardenings M., Phage Display of Random Peptide Libraries: Applicationis, Limits, and Potential. J Recept Sig Transd. Jan. 1, 2003;23(4): 307-349.
Tang et al., Genetic Immunization Is a Simple Method for Eliciting an Immune Response. Nature Mar. 1992;356(6365): 152-154.
Tang et al., Current Developments in SELDI Affinity Technology. Mass Spectrom. Rev. 2004;23: 34-44.
Tedesco et al., A New Strategy for the Early Diagnosis of Rheumatoid Arthritis: A Combined Approach. Autoimmun Review. Jan. 1, 2009;8(3): 233-237.
Thompson et al., Prostate-Specific Antigen in the Early Detection of Prostate Cancer. CMAJ Jun. 19, 2007;176(13): 1853-1858.
Thorpe et al., Molecular Evolution of Affinity and Flexibility in the Immune System. PNAS May 22, 2007; 104(21): 8821-8826.
Timares et al., Quantitative Analysis of the Immunopotency of Genetically Transfected Dendritic Cells. PNAS Oct. 27, 1998;95(22): 13147-13152.
Tolonen et al., Optimized in situ construction of oligomers on an array surface. Nucl Acids Res. Oct. 15, 2002;30(20):e107 in 5 pages.
Turajlic et al., Insertion-and-Deletion-derived Tumour-specific Neoantigens and the Immunogenic Phenotype: A Pan-Cancer Analysis. Lancet Oncol. Aug. 1, 2017;18(8): 1009-1021.
Uhlén et al., Generation and Validation of Affinity Reagensts on a Proteome-Wide Level. J Mol Recogn. Mar. 2009;22(2): 57-64.
UniPROTKB R5P615_9BACT, Mar. 15, 2017 [online]. Retrieved on Jan. 24, 2020] from the Internet <URL:https://linkprotect.cudasvc.com/url?a=https%3a%2f%2fwww.uniprot.org%2funiprot%2fR5P616.AYCY%3fversion%3d10&c=E, 1,vujsqy5TRr_U35_1YBVS1rbhV WSGyEB12uM3LhAfKr4IROEfYIVBtGvz5bc2mP7vR9wt8iNvSt ZXhd2PDIN4sjP6hdPbd6ZZbEJfLarPtZj5DoMeYtDzis0,&typo=0> Amino Acids 121-135, 66.3% identity to Seq ID No. 3 (2 pages).
UniPROTKB A9V5X0_MONBE, Mar. 28, 2018 [online]. Retrieved on Jan. 24, 2020 from the internet ,URL:https://linkprotect.cudascv.com/url?a=https%3a%2f%2fwww.uniprot.org%2funiprot%2fA9V5X0.txt%3fversion%3d40&c=E, 1, YC45ztA63iYZyJnWnuFaCIKCemM4Eo-Fv_wh2OzFlqCMoXYkdK0UF77xKX4L8rbQO1n-X7JYz72WUvE23ETf_BkC_T7mkMT6zkmfFFuoqNFAti6ZawzDw,,&typo+0> Amino Acids 1262-1276, 67.4% identity to Seq ID No. 5 (3 pages).
UniPROTKB I1B218_9RHOB, Feb. 28, 2018 [online] retrieved on Jan. 24, 2020 from the internet <URL:https://linkprotect.cudasvc.com/url?a=https%3a%2%2fwww.uniprot.org%2funiprot%2fI1B218.txt%3fversion%3d15%c=E,1,zqlHjk#bx1fUnHj3nqLaZ_dpGmdYuOghUMJzIB-gxyg9cCdO40G3X0TRNn7-J-WNtYFhqW7BMHwzTxViFJAgD0JQuHgttbkXC2BrGvePf-oC8_1i9Bw,,&typo=0> Amino Acids 44-58, 67.4% identity to SEQID No. 8, (2 pages).
Untergasser et al., Primer3Plus, an Enhanced Web Interface to Primer3. Nucleic Acids Res. Jul. 1, 2007;35(suppl_2: W71-W74.
Usami et al., The Effect of pH, Hydrogen Peroxide and Temperature on the Stability of Human Monoclonal Antibody. J Pharm Biomed Anal. Jun. 1996;14(8-10): 1133-1140.
Usmani B.A., Genomic Instability and Metastatic Progression. Pathobiology 1993;61(2): 109-116.
Varga et al., Infectious Entry Pathway of Adenovirus Type 2. J Virol. Nov. 1991;65(11): 6061-6070.
Vella et al., Healthy Individuals Have T-Cell and Antibody Responses to the Tumor Antigen Cyclin B1 That When Elicited in Mice Protect from Cancer. PNAS U S A. Aug. 18, 2009;106(33): 14010-14015.
Verhoeyen et al., Reshaping Human Antibodies: Grafting an Antilysozyme Activity. Science 1988;239:1534-1536.
Vesely et al., Cancer Immunoediting: Antigens, Mechanisms, and Implications to Cancer Immunotherapy. Ann N Y Acad Sci. 2013;1284: 1-5.
Vitiello et al., Neoantigen Prediction and the Need for Validation. Nat Biotech. Sep. 2017;35(9): 815-817.
Vogelstein et al., Cancer Genome Landscapes. Science. Mar. 29, 2013;339(6127): 1546-1558.
Volk et al., The Accuracy of Primary Care Patients' Self-Reports of Prostate-Specific Antigen Testing. Am J Prev med. Jan. 2002;22(1): 56-58.
Vonderheide et al., Immunotherapy at Large: The Road to Personalized Cancer Vaccines. Nat Med Sep. 6, 2013;19(9): 1098-1100.
Vranic S., Microsatellite Instability Status Predicts Response to Anti-PD-1/PD-L1 Therapy Regardless the Histotype: A Comment on Recent Advances. Bosn J Basic Med Sci. Aug. 2017;17(3): 274-275.
Wang et al., Detection of Mammary Tumor Virus ENV Gene-Like Sequences in Human Breast Cancer. Nov. 15, 1995;55(22): 5173-5179.
Wang et al., Utilization of an Alternative Open Reading Frame of a Normal Gene in Generating a Novel Human Cancer Antigen. J Exper Med. Mar. 1, 1996;183(3): 1131-1140.
Wang et al., Differences in Microsatellite Instability Profiles Between Endometrioid and Colorectal Cancers: A Potential Cause for False-Negative Results? J Mol Diag. Jan. 1, 2017;19(1): 57-64.

(56) References Cited

OTHER PUBLICATIONS

Ward et al., Binding Activities of a Repertoure of Single Immunoglobulin Variable Domains Secreted from *Escherichia coli*. Nature Oct. 12, 1989;341(6242): 544-546.
Waterboer et al., Dried Blood Spot Samples for Seroepidemiology of Infections With Human Papillomaviruses. Cancer Epidem Biomarkers Prevent. Feb. 1, 2012;21(2): 287-293.
Weinschenk et al., Integrated Functional Genomics Approach for the Design of Patient-individual Antitumor Vaccines. Cancer Res. Oct. 15, 2002;62(20): 5818-5827.
Whitlock et al., Protective Antigens Against Glanders Identified by Expression Library Immunization. Front Microbiol. Nov. 21, 2011;2: 227 (14 pages).
Whittemore et al., A General Method to Discover Epitopes from Sera. PLoS One. Jun. 13, 2016;11(6): e157462, 13 pages.
Woerner et al. Systematic Identification of Genes With Coding Microsatellites Mutated in DNA Mismatch Repair-Deficient Cancer Cells. Int J Cancer, Jul. 1, 2001;93(1): 12-19.
Wolchok et al., Phase I Trial of High Dose Paracetamol and Carmustine in Patients With Metastatic Melanoma. Melanoma Res. Apr. 1, 2003;13(2): 189-196.
Wolff et al., Direct Gene Transfer Into Mouse Muscle In Vivo. Science Mar. 23, 1990;247(4949 Pt 1): 1465-1468.
Xu et al., Research Progress in Clinical Treatment of Tumor Immune Checkpoint Inhibitors. China Clinical Pharmacology and Therapeutics, Feb. 2016;21(2): 218-224.
Yang et al., Segmentation and Intensity Estimation for Microarray Images With Saturated Pixels. BMC Bioinfo. Dec. 2011;12(1): 462, 11 pages.
Yannelli et al., Development of an Autologous Canine Cancer Vaccine System for Resectable Malignant Tumors in dogs. Vet Immun Immunopath. Dec. 1, 2016;182: 95-100.
Zabner, Safety and Efficacy of Repetitive Adenovirus-Mediated Transfer of CFTR cDNA to Airway Epithelia of Primates and Cotton Rats. Nat Genet. Jan. 1994;6(1): 75-83.
Zaher et al., Fidelity at the Molecular Level: Lessons from Protein Synthesis. Cell Feb. 20, 2009;136(4): 746-762.
Zhang et al., Generation and Identification of Recombinant Adenovirus by Liposome-Mediated Transfection and PCR Analysis. BioTechniques Nov. 1, 1993;15(5): 868-872.
Zhang J., Frameshift Antigens for Cancer Vaccine Development. Doctoral Thesis; Arizona State University. May 31, 2018, 234 pages.
Zhang et al., Using Frameshift Peptide Arrays for Cancer Neo-Antigens Screening. Sci Reports. Nov. 26, 2018;8(1): 10 pages.
Zhou et al., Properties and Function of Polyreactive Antibodies and Polyreactive Antigen-Binding B Cells. Autoimmun. Dec. 1, 2007;29(4): 219-228.
Zöller M.J., New recombinant DNA methodology for protein engineering. Curr Opin. Biotech. Aug. 1, 1992;3(4): 348-354.
Zöller et al., Prophylactic Tumor Vaccination: Comparison of Effector Mechanisms Initiated by Protein Versus DNA Vaccination. J Immunol. Mar. 2001; 1;166(5): 3440-3450.
Zuker M., On Finding All Suboptimal Foldings of an RNA Molecule. Science Apr. 7, 1989;244(4900): 48-52.
Zundel et al., Development and Evaluation of an Enzyme-Linked Immunoassay for the Prostate: Specific Antigen Utilizing Two Monoclonal Antibodies. Urol Res. 1990;18(5): 327-330.
Johnston et al., A New Source of Neoantigens for Pediatric and Adult Brain Cancer Vaccines. Neuro-Oncology, Nov. 11, 2019, 21(6): Abstract ATIM-02, 1 page.
Mullis et al., Specific Enzymatic Amplification of DNA in vitro: The Polymerase Chain Reaction. Cold Spring Harbor Symp Quant Biol. 1987;51: 263-273.
Peterson et al., Comparison of Personal and Shared Frameshift Neoantigen Vaccines in a Mouse Mammary Cancer Model. BMC Immunol. Dec. 2020;21(1): 1-5.
Pimpin et al., Review on Micro- and Nanolithography Techniques and Their Applications. Engin J. Jan. 1, 2012;16(1): 37-55.
Szymczak et al., Peptide Arrays: Development and Application. Anal Chem. Jan. 1, 2018;90(1): 266-282.
Zhang et al., Peptide Arrays, Microarrays in Diagnostics and Biomarker Development, B. Jordan (Ed.), Springer-Verlag Berlin, Heidelberg; Chapter 7, 2012; pp. 81-112.
Amor et al., Senolytic CAR T-cells Reverse Senescence-associated Pathologies. Nature. Jul. 2, 2020;583(7814): 127-132.
Bartok et al., Anti-tumor Immunity Induces Aberrant Peptide Presentation in Melanoma. Nature. Feb. 11, 2021;590(7845): 332-337.
Chaib et al., Cellular Senescence and Senolytics: The Path to the Clinic. Nature Med. Aug. 2022;28(8): 1556-1568.
Furman et al., Chronic Inflammation in the Etilology of Disease Across the Life Span. Nature Med. Dec. 2019;25(12): 1822-1832.
Han S., Clinical Vaccine Development. Clinical and Experimental Vaccine Research. Jan. 1, 2015;4(1): 46-53.
Harries L.W., Dysregulated RNA Processing and Metabolism: A New Hallmark of Ageing and Provocation for Cellular Senescence. FEBS J. Mar. 2023;290(5): 1221-1234.
He et al., Senescence in Health and Disease. Cell. Jun. 1, 2017;169(6): 1000-1011.
Kim et al., Comparison of the effect of different immunological adjuvants on the antibody and T-cell response to immunization with MUC1-KLH and GD3-KLH conjugate cancer vaccines. Vaccine. Nov. 12, 1999;18(7-8): 597-603.
Kirkland et al., Cellular Senescence: A Translational Perspective. EBioMedicine. Jul. 1, 2017;21:21-28.
López-Otín et al. Hallmarks of Aging: An Expanding Universe. Cell Jan. 19, 2023;186: 36 pages.
Met et al., Principles of Adoptive T Cell Therapy in Cancer. Semin Immunopathol. Jan. 2019;41(1): 49-58.
Naqvi et al., Long-term Follow-up of Lower Dose Dasatinib (50 mg daily) as Frontline Thrapy in Newly Diagnosed Chronic-phase Chronic Myeloid Leukemia. Cancer. Jan. 1, 2020;126(1): 67-75.
National Institute of Health [NIH] MedlinePlus—"Vaccines", Definition 2022, in 8 pages.by MedlinePlus.
Pollack et al., Tetramer Guided, Cell Sorter Assisted Production of Clinical Grade Autologous NY-ESO-1 Specific CD8+ T cells. J Immunother Cancer. Dec. 2014;2: 1-0.
Rapoport et al., Combination Immunotherapy after ASCT for Multiple Myeloma Using MAGE-A3/Poly-ICLC Immunizations Followed by Adoptive Transfer of Vaccine-Primed and Costimulated Autologous T cells. Clin Cancer Res. Mar. 1, 2014;20(5): 1355-1365.
Shen et al., Production of High-complexity Frameshift Neoantigen Peptide Microarrays. RSC Advances. 2020;10(50): 29675-29681.
Shen et al., Predicting Response and Toxicity to Immune Checkpoint Inhibitors in Lung Cancer Using Antibodies to Frameshift Neoantigens. J Transl Med. May 22, 2023;21(1): 338 in 14 pages.
Suda et al., Senolytic Vaccination Improves Normal and Pathological Age-related Phenotypes and Increases Lifespan in Progeroid Mice. Nature Aging. Dec. 2021;1(12): 1117-1126.
Suvarna et al., Current Overview on the Clinical Update of Bcl-2 Anti-apoptotic Inhibitors for Cancer Therapy. Eur J Pharmacol. Nov. 5, 2019;862: 172655 in 20 pages.
Wang et al., Comprehensive Map of Age-associated Splicing Changes Across Human Tissues and Their Contributions to Age-associated Diseases. Sci Rep. Jul. 19, 2018;8(1): 10929 in 12 pages.
Yang et al., NKG2D-CAR T-cells Eliminate senescent Cells in Aged Mice and Nonhuman Primates. Scie Transl Med. Aug. 16, 2023;15(709): eadd1951 in 15 pages.
Zhong et al., Comparison of the Molecular and Cellular Phenotypes of Common Mouse syngeneic Models with Human Tumors. BMC Genom. Dec. 2020;21: 1-7.
Zhou et al., Translation of Noncoding RNAs and Cancer. Cancer Letts. Jan. 28, 2021;497: 89-99.
Zhu et al., The Achilles' Heel of Senescent Cells: From Transcriptome to Senolytic Drugs. Aging Cell. Aug. 2015;14(4): 644-658.
European Extended Search Report for Application No. EP 20871469. 1, dated Sep. 20, 2023 (9 pages).

\* cited by examiner

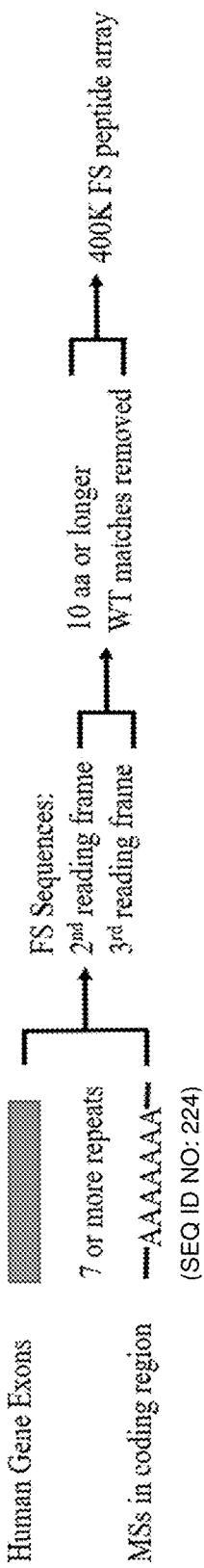
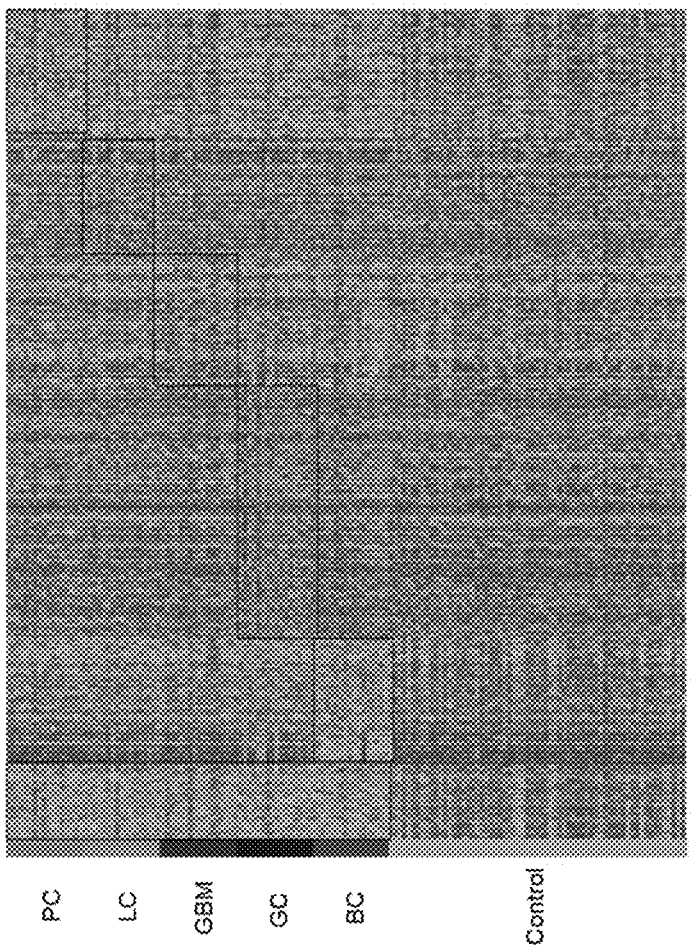
FIG. 3A
FIG. 3B

Human Exon Junction Frameshift Database

| ID | Gene | Frameshift Peptide | SEQ ID NO |
|---|---|---|---|
| NM_001204516.1_Exon1_2nd | KIFAP3 | CKGRTPDTSK | 231 |
| NM_001243136.1_Exon2_2nd | PELI3 | CTTSPRRSSP | 232 |
| NM_001301138.1_Exon1_2nd | VPS39 | CTTLSSQCRS | 233 |
| NM_001302453.1_Exon1_2nd | CCDC151 | CTLRLPPVRN | 234 |
| NM_001394441.1_Exon2_2nd | MMP8 | CNKYLKRSQL | 235 |
| NM_001308192.1_Exon2_2nd | CPEB4 | CTHWRVHSLT | 236 |
| NM_001308351.1_Exon4_2nd | ZNF433 | CKKPSGTWPL | 237 |
| NM_014350.3_Exon1_2nd | TNFAIP8 | CTPKQKNPRK | 238 |
| NM_139320.1_Exon3_2nd | CHRFAM7A | CKNIASTSIF | 239 |

METHODS AND COMPOSITIONS FOR IDENTIFYING NEOANTIGENS FOR USE IN TREATING CANCER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The present application is a continuation of PCT application PCT/US2020/053728, filed Oct. 1, 2020, which claims the benefit of U.S. Provisional patent application Ser. No. 62/909,748 entitled "Methods and Compositions for Identifying Neoantigens for Use in Treating and Preventing Cancer," filed Oct. 2, 2019, which are incorporated herein by reference in its entirety.

STATEMENT AS TO FEDERALLY SPONSORED RESEARCH

This invention was made with government support under W81XWH-07-1-0549 awarded by the Army Research office. The government has certain rights in the invention.

REFERENCE TO SEQUENCE LISTING

The present application is being filed along with a sequence listing in electronic format. The sequence listing is provided as a file entitled SequenceListingCALV007C2, created Apr. 28, 2022 which is 147 KB in size. The information in the electronic format of the sequence listing is incorporated herein by reference in its entirety.

BACKGROUND

Checkpoint inhibitor immunotherapeutics are revolutionizing cancer therapy. However, even in the most responsive cancers a substantial portion (50%-80%) of the patients have poor to no positive response (1-5). The evidence to date is that whether a patient has an effective response to the treatment depends on the nature of the immune response they have established against the tumor. More specifically, the level and quality of the immune response to neoantigens in the cancer seems to be most important.

SUMMARY

Provided herein, in certain aspects, are peptide arrays comprising a plurality of frameshift variant peptides. In some cases, the plurality of frameshift variant peptides comprise peptides encoded by genes having a variant in a microsatellite (MS) in a coding region of the gene. Alternatively or in combination, the plurality of frameshift variant peptides comprise peptides encoded by an mRNA having a splicing error. In some embodiments, the plurality of frameshift variant peptides comprise two or more pooled frameshift peptides. In some cases, the plurality of frameshift variant peptides comprise one or more peptides provided in any one of Tables 1 or 7. In some embodiments, the plurality of frameshift variant peptides are fixed on a substrate. In some embodiments, the substrate comprises glass, composite, resin, or combination thereof. In some embodiments, the peptide array is configured to detect binding by at least one of fluorescence, luminescence, calorimetry, chromatography, radioactivity, Bio-Layer Interferometry, and surface plasmon resonance. In some embodiments, the peptide array comprises at least about 25000, about 50000, about 75000, about 100000, about 125000, about 150000, about 175000, about 200000, about 225000, about 250000, about 275000, about 300000, about 325000, about 350000, about 375000, or about 400000 frameshift variant peptides.

In additional aspects, there are provided methods of measuring an immune response to a neoantigen peptide in a subject. In some cases, the method comprises: (a) contacting a biological sample obtained from a subject to a peptide array comprising a plurality of frameshift variant peptides. In some cases, the plurality of frameshift variant peptides comprise peptides encoded by genes having a variant in a microsatellite (MS) in a coding region of the gene. Alternatively or in combination, the plurality of frameshift variant peptides comprise peptides encoded by an mRNA having a splicing error. In some cases, the method further comprises detecting binding of the biological sample to at least one peptide in the peptide array. In some embodiments, the plurality of frameshift variant peptides comprise two or more pooled frameshift peptides. In some embodiments, the plurality of frameshift variant peptides comprise one or more peptides provided in any one of Tables 1 or 7. In some embodiments, the plurality of frameshift variant peptides are fixed on a substrate. In some embodiments, the substrate comprises glass, composite, resin, or combination thereof. In some embodiments, the peptide array is configured to detect binding by at least one of fluorescence, luminescence, calorimetry, chromatography, radioactivity, Bio-Layer Interferometry, and surface plasmon resonance. In some embodiments, the peptide array comprises at least about 25000, about 50000, about 75000, about 100000, about 125000, about 150000, about 175000, about 200000, about 225000, about 250000, about 275000, about 300000, about 325000, about 350000, about 375000, or about 400000 frameshift variant peptides. In some embodiments, the biological sample comprises blood, serum, plasma, cerebrospinal fluid, saliva, urine, or combinations thereof. In some embodiments, the biological sample comprises an antibody. In some embodiments, the subject is a mammal. In some embodiments, the subject is a human, a dog, a cat, a mouse, a rat, a rabbit, a horse, a cow, or a pig. In some embodiments, the subject is suspected of having a cancer. In some embodiments, the cancer is selected from the group consisting of Acute lymphoblastic leukemia, Acute monocytic leukemia, Acute myeloid leukemia, Acute promyelocytic leukemia, Adenocarcinoma, Adult T-cell leukemia, Astrocytoma, Bladder cancer, Bone Cancer, Brain Tumor, Breast Cancer, Burkitt's lymphoma, Carcinoma, Cervical Cancer, Chronic Lymphocytic Leukemia, Chronic myelogenous leukemia, Colon Cancer, Colorectal cancer, Endometrial cancer, Glioblastoma multiforme, Glioma, Hepatocellular carcinoma, Hodgkin's lymphoma, Inflammatory breast cancer, Kidney Cancer, Leukemia, Lung cancer, Lymphoma, Malignant Mesothelioma, Medulloblastoma, Melanoma, Multiple myeloma, Neuroblastoma, Non-Hodgkin Lymphoma, Non-Small Cell Lung Cancer, Ovarian Cancer, Pancreatic Cancer, Pituitary tumor, Prostate cancer, Retinoblastoma, Skin Cancer, Small Cell Lung Cancer, Squamous cell carcinoma, Stomach cancer, T-cell leukemia, T-cell lymphoma, Thyroid cancer, and Wilms' tumor.

In further aspects, there are provided methods of detecting a cancer in a subject. In some embodiments, the method comprises: (a) contacting a biological sample obtained from a subject to a peptide array comprising a plurality of frameshift variant peptides. In some embodiments, the plurality of frameshift variant peptides comprise peptides encoded by genes having a variant in a microsatellite (MS) in a coding region of the gene. Alternatively or in combination, the plurality of frameshift variant peptides comprise peptides encoded by an mRNA having a splicing error. In some embodiments, the method further comprises detecting binding of the biological sample to at least one peptide in the peptide array. In some embodiments, the plurality of frameshift variant peptides comprise one or more peptides provided in any one of Tables 1 or 7. In some embodiments, the plurality of frameshift variant peptides comprise two or more pooled frameshift peptides. In some embodiments, the plurality of frameshift variant peptides are fixed on a substrate. In some embodiments, the substrate comprises glass, composite, resin, or combination thereof. In some embodiments, the peptide array is configured to detect binding by at least one of fluorescence, luminescence, calorimetry, chromatography, radioactivity, Bio-Layer Interferometry, and surface plasmon resonance. In some embodiments, the peptide array comprises at least about 25000, about 50000, about 75000, about 100000, about 125000, about 150000, about 175000, about 200000, about 225000, about 250000, about 275000, about 300000, about 325000, about 350000, about 375000, or about 400000 frameshift variant peptides. In some embodiments, the biological sample comprises blood, serum, plasma, cerebrospinal fluid, saliva, urine, or combinations thereof. In some embodiments, the biological sample comprises an antibody. In some embodiments, the subject is a mammal. In some embodiments, the subject is a human, a dog, a cat, a mouse, a rat, a rabbit, a horse, a cow, or a pig. In some embodiments, the subject is suspected of having a cancer. In some embodiments, the cancer is selected from the group consisting of Acute lymphoblastic leukemia, Acute monocytic leukemia, Acute myeloid leukemia, Acute promyelocytic leukemia, Adenocarcinoma, Adult T-cell leukemia, Astrocytoma, Bladder cancer, Bone Cancer, Brain Tumor, Breast Cancer, Burkitt's lymphoma, Carcinoma, Cervical Cancer, Chronic Lymphocytic Leukemia, Chronic myelogenous leukemia, Colon Cancer, Colorectal cancer, Endometrial cancer, Glioblastoma multiforme, Glioma, Hepatocellular carcinoma, Hodgkin's lymphoma, Inflammatory breast cancer, Kidney Cancer, Leukemia, Lung cancer, Lymphoma, Malignant Mesothelioma, Medulloblastoma, Melanoma, Multiple myeloma, Neuroblastoma, Non-Hodgkin Lymphoma, Non-Small Cell Lung Cancer, Ovarian Cancer, Pancreatic Cancer, Pituitary tumor, Prostate cancer, Retinoblastoma, Skin Cancer, Small Cell Lung Cancer, Squamous cell carcinoma, Stomach cancer, T-cell leukemia, T-cell lymphoma, Thyroid cancer, and Wilms' tumor.

In further aspects, there are provided compositions comprising a plurality of frameshift variant peptides. In some cases, the plurality of frameshift variant peptides comprise peptides encoded by genes having a variant in a microsatellite (MS) in a coding region of the gene. Alternatively or in combination, wherein the plurality of frameshift variant peptides comprise peptides encoded by an mRNA having a splicing error. In some embodiments, the plurality of frameshift variant peptides comprise one or more peptides provided in any one of Tables 1 or 7. In some embodiments, the plurality of frameshift variant peptides comprise two or more pooled frameshift peptides. In some embodiments, the composition further comprises an adjuvant. In some embodiments, the adjuvant is selected from the group consisting of ABM2, AS01B, AS02, AS02A, Adjumer, Adjuvax, Algammulin, Alum, Aluminum phosphate, Aluminum potassium sulfate, *Bordetella pertussis*, Calcitriol, Chitosan, Cholera toxin, CpG, Dibutyl phthalate, Dimethyldiocta- decylammonium bromide (DDA), Freund's adjuvant, Freund's complete, Freund's incomplete (IFA), GM-CSF, GMDP, Gamma Inulin, Glycerol, HBSS (Hank's Balanced Salt Solution), IL-12, IL-2, Imiquimod, Interferon-Gamma, ISCOM, Lipid Core Peptide (LCP), Lipofectin, Lipopolysaccharide (LPS), Liposomes, MF59, MLP+TDM, Monophosphoryl lipid A, Montanide IMS-1313, Montanide ISA 206, Montanide ISA 720, Montanide ISA-51, Montanide ISA-50, nor-MDP, Oil-in-water emulsion, P1005 (non-ionic copolymer), Pam3Cys (lipoprotein), Pertussis toxin, Poloxamer, QS21, RaLPS, Ribi, Saponin, Seppic ISA 720, Soybean Oil, Squalene, Syntex Adjuvant Formulation (SAF), Synthetic polynucleotides (poly IC/poly AU), TiterMax Tomatine, Vaxfectin, XtendIII, and Zymosan.

In additional aspects, there are provided methods of treating or preventing cancer in a subject comprising administering a composition comprising any one of the frameshift variant peptides provided herein. In some embodiments, the subject is a mammal. In some embodiments, the subject is a human, a dog, a cat, a mouse, a rat, a rabbit, a horse, a cow, or a pig. In some embodiments, the cancer is selected from the group consisting of Acute lymphoblastic leukemia, Acute monocytic leukemia, Acute myeloid leukemia, Acute promyelocytic leukemia, Adenocarcinoma, Adult T-cell leukemia, Astrocytoma, Bladder cancer, Bone Cancer, Brain Tumor, Breast Cancer, Burkitt's lymphoma, Carcinoma, Cervical Cancer, Chronic Lymphocytic Leukemia, Chronic myelogenous leukemia, Colon Cancer, Colorectal cancer, Endometrial cancer, Glioblastoma multiforme, Glioma, Hepatocellular carcinoma, Hodgkin's lymphoma, Inflammatory breast cancer, Kidney Cancer, Leukemia, Lung cancer, Lymphoma, Malignant Mesothelioma, Medulloblastoma, Melanoma, Multiple myeloma, Neuroblastoma, Non-Hodgkin Lymphoma, Non-Small Cell Lung Cancer, Ovarian Cancer, Pancreatic Cancer, Pituitary tumor, Prostate cancer, Retinoblastoma, Skin Cancer, Small Cell Lung Cancer, Squamous cell carcinoma, Stomach cancer, T-cell leukemia, T-cell lymphoma, Thyroid cancer, and Wilms' tumor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1: shows a model for RNA based, frame-shift peptide production in tumor cells—normal cells. Errors in DNA replication are very rare and repaired. Transcription error rates are higher but also rare as are mis-splicing during intron excision. Additionally, the FS transcript with a premature termination may be degraded by Nonsense Mediated Decay (NMD). Aberrant proteins, including those with frameshifts are largely eliminated by the protein quality control system, Ubiquitin/Proteasome System (UPS). The net result is that very few frameshift peptides are presented on MHC I/II or escape the cell to be presented to the immune system. Cancer Cell: All levels of information transfer become more error prone. More errors are made in DNA replication, but only when cells divide. Most DNA mutations are point mutations and encode low or non-immunogenic epitopes. Global transcription is increased and is generally less accurate and even more so through MSs producing INDELs. Most transcribed genes with MSs in the coding region will have more FS transcripts. RNA splicing is also far less accurate, creating more FS transcripts from each out-of-frame splicing between exons from the same gene and different genes. The substantial increase of the FS transcripts from INDELs of MS and mis-splicing overwhelms the RNA quality control systems, such as NMD. Consequently, more truncated proteins with the FS peptide will be translated. These unfolded truncated proteins, combined with aberrant proteins from other mutations, overwhelms the protein quality control system, leading to more frameshift peptides being presented on MHC I/II and mis-secreted or released from the cancer cell which the immune system can respond to.

FIGS. 3A-3I: show detection of antibody response against FS in cancer patients.

FIG. 3A: shows a design of human FS array with microsatellite FS peptides from all coding MS regions and predicted mis-splicing FS peptides from every exon of human genes.

FIG. 3B: shows common reactivity and cancer-type reactivity against FS peptides were represented by ~7000 selected FS peptides. LC: lung cancer; BC: breast cancer; GBM: glioblastoma; GC: gastric cancer; and PC: pancreatic cancer (n=17/each cancer type) and a set of non-cancer samples (n=64), as control.

FIG. 3C: shows p-value and fold change volcano plot analysis of 5 cancer's IgG reactivity on the 400K FS array compared to normal. The horizontal line represents the significant p-value cut-off=1/392328 (the number of the array peptides).

FIG. 3D: shows a positive rate of all 400K FS peptides in each cancer type, overall cancer and normal group (calculated by counting samples with higher reactivity than AVG (Normal)+6*SD (Normal)), error bar represents Mean±SEM.

FIG. 3E: shows a distribution of personal anti-FS response and shared anti-FS response in all 5 cancer types.

FIG. 3F: shows the top 20 FS peptides for each GBM sample were selected for personal vaccines.

FIG. 3G: shows components of cancer-type specific FS vaccines, top 100 FS peptides for each cancer type were selected with highest positive rate in corresponding cancer type. Shading in normal represents negative sample; other shading is indicative of a positive sample.

FIG. 3H: shows components of a general FS vaccine, top 100 FS peptides were selected with highest positive rate in cancer group. Shading in normal represents negative sample; other shading is indicative of a positive sample.

FIG. 3I: shows a heat map of the positive rate distribution of the FS peptides in Stage I and late stages pancreatic cancer.

FIG. 4A: shows tumor growth curve of mSMC1A-1ˆ4 immunization in the B16F10-C57BL6 tumor model compared to the control antigen, non-protective Cowpox viral antigen (CPV 172 (31)) immunization. Mice (n=10 per group) were genetically immunized at 8 weeks of age and challenged with 1×10W B16-F10 cells 4 weeks later.

FIG. 4B: shows tumor growth curve after mSMC1A-1ˆ4 immunization in the 4T1-BALB/c tumor model. Mice (n=10 per group) were prophylactically immunized and challenged 2.5 weeks after the last immunization by 5×10³ 4T1 cells. The CD8 and CD4 T cell depletion started 2 weeks after the last immunization. The control groups were genetically immunized with empty vectors and boosted with the KLH protein.

FIG. 4C: shows tumor growth curve after FS neo-antigen immunization in the 4T1-BALB/c tumor model. Mice (n=4 per group) were genetic immunized with SLAIN2 FS, ZDHHC17 FS and mock control three times in two week intervals and challenged 2 weeks after the last immunization by subcutaneous injection of 2×10³ 4T1 cells.

FIG. 4D: shows three MS FS antigens were selected based on the best predicted H2D binding epitopes for BALB/C mice. The tumor growth curve is after three MS FS antigen immunizations in the 4T1-BALB/c tumor model. Mice (n=10 per group) were prophylactically immunized with the different FS antigens or control antigen and challenged 2 weeks later with 5×10³ 4T1 cells.

FIG. 4E: shows ELISPOT analysis of the three MS FS neo-antigens immunizations. 3 mice were genetically immunized with a pool of the three MS FS neo-antigens and challenged with 5×10³ 4T1 cells. Splenocytes were collected 19 days after tumor challenge and a pool of three splenocytes were used in the assay. Error bars represent SD of triplicates.

FIG. 4F: shows three FS antigens were selected and immunized individually or pooled in the BALB-NeuT mouse breast tumor model. A tumor free curve is presented of BALB-NeuT mice immunized with individual FS neo-antigens (SMC1A-1ˆ4, n=32; RBM FS, n=22; and SLAIN2 FS, n=14) (total n=68), pool of these three FS neo-antigens (n=37) and control group (total n=44), including untreated (n=14) and immunized with control antigens (n=30). Control vs individual or 3 FS pool, p≤0.0001; individual vs 3FS pool, p=0.005. Error bars in all mouse growth curves represent SEM, *, p<0.05 and **, p<0.005 by two tailed t-test. Statistical analysis of the tumor free curve was with Mantal-Cox test.

FIG. 5A: is a schematic of exon mis-splicing of mSMC1A. The asterisk indicates the stop codon that is generated by a shift in reading frame upon joining exon 1 with exon 4.

FIG. 5B: is a schematic of exon mis-splicing of ZDHHC17. The asterisk indicates the stop codon that is generated by a shift in reading frame upon joining exon 15 with exon 17.

FIG. 5C: is a schematic of exon mis-splicing of SLAIN2 by splicing exon 6 with exon 8.

FIG. 5D: is a schematic of exon mis-splicing of RBM by splicing RBM14 exon 1 with RBM4 exon 2.

FIG. 6A: is an example of INDEL Frameshift peptides from dog gene SEC62

FIG. 6B: shows examples of mis-splicing Frameshift peptides from $2^{nd}$ frame and $3^{rd}$ frame of human exons.

FIG. 6C: shows a distribution of MS FS peptides in human FS array with insertion or deletion events.

FIG. 6D: shows a distribution of MS FS peptide lengths in human FS array with corresponding FS antigen length.

FIG. 6E: shows a distribution of MS Type in human FS array.

FIG. 6F: shows a distribution of MS repeat length in human FS array.

FIG. 6G: shows a distribution of Mis-splicing FS antigen length in human FS array.

FIG. 6H: shows a distribution of Exon numbers of FS antigens in human FS array.

FIG. 7A: shows a hierarchical clustering of all 400K FS peptides in 17 GBM samples.

FIG. 7B: shows a personal anti-FS response in 17 GBM cancer patients.

FIG. 7C: shows a personal anti-FS response in 17 gastric cancer patients.

FIG. 7D: shows a personal anti-FS response in 17 breast cancer patients.

FIG. 7E: shows a personal anti-FS response in 17 pancreatic cancer patients.

FIG. 7F: shows a personal anti-FS response in 17 lung cancer patients.

FIG. 7G: shows a correlation matrix of anti-FS response in all cancer samples from 5 cancer types.

DETAILED DESCRIPTION

Figure 1:
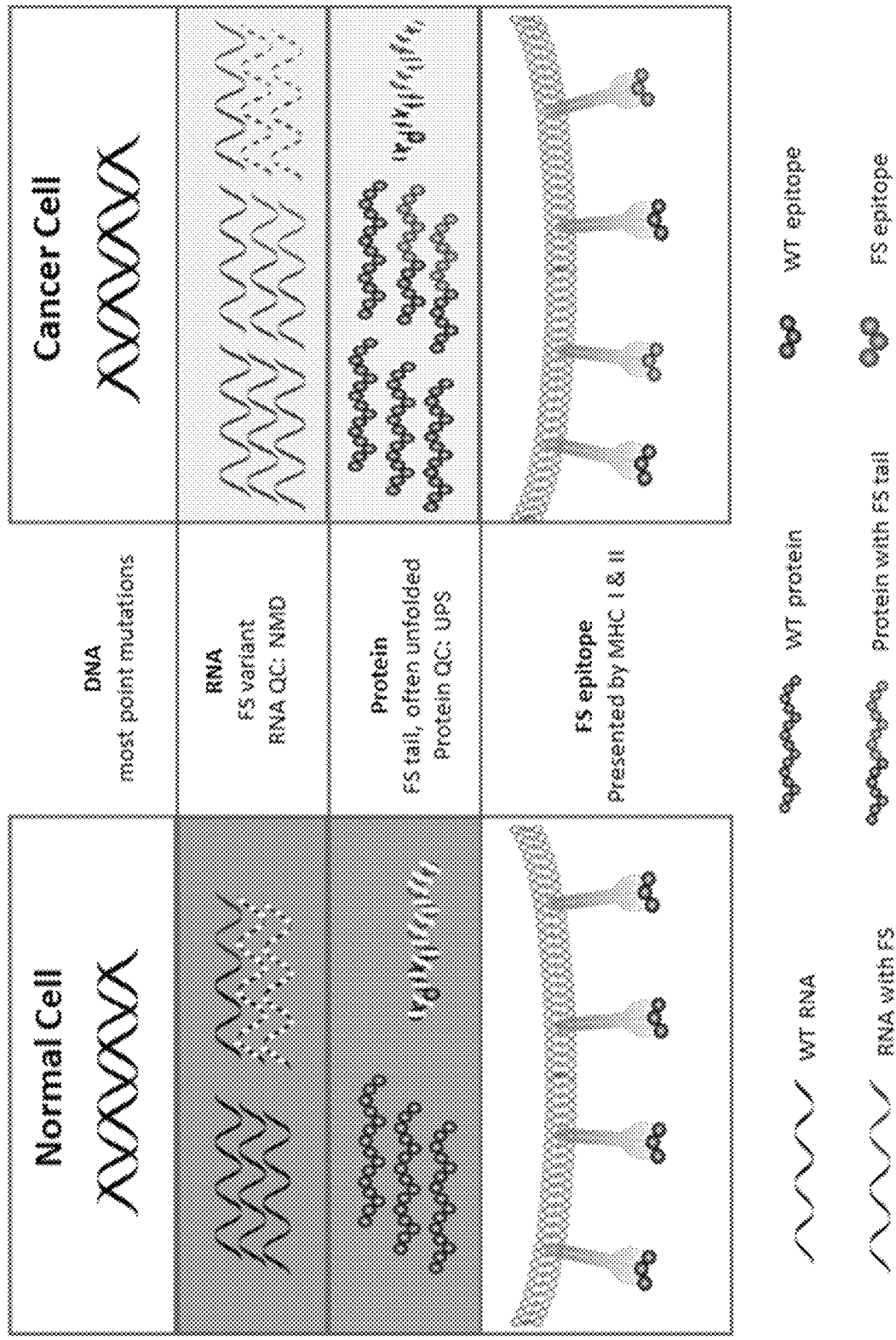

Provided herein are methods and compositions for preventing, treating, and diagnosing cancer comprising the use of neoantigens. Neoantigens herein comprise peptides encoded by nucleic acids having frameshift mutations, such as insertions or deletions, causing a frameshift in the mRNA and a long stretch of mutant amino acids that are, in some cases, recognized as a non-self peptide by the immune system.

The success of checkpoint inhibitors in cancer therapy is largely attributed to activating the patient's immune response to their tumor's neoantigens arising from DNA mutations. This realization has motivated the interest in personal cancer vaccines based on sequencing the patient's tumor DNA to discover neoantigens. Embodiments provided herein relate to an additional, unrecognized source of tumor neoantigens. In some embodiments, errors in transcription of microsatellites (MS) and mis-splicing of exons create highly immunogenic frameshift (FS) neoantigens in tumors. The sequence of these FS neoantigens are predictable, allowing creation of a peptide array representing all possible neoantigen FS peptides. This array can be used to detect the antibody response in a patient to the FS peptides. A survey of 5 types of cancers reveals peptides that are personally reactive for each patient. This source of neoantigens and the method to discover them may be useful in developing cancer vaccines.

Personal cancer vaccines are promising as a new therapeutic treatment. These vaccines are currently based on mutations in tumor DNA. In some embodiments, variants in RNA production create frameshift neoantigens that may be another source of neoantigens for personal vaccines. Because there are only ~220K of these antigens a simple peptide array can be used for their detection. Checkpoint inhibitor immunotherapeutics are revolutionizing cancer therapy. However, even in the most responsive cancers a substantial portion (50%-80%) of the patients have poor to no positive response (1-5). A surprising finding in the analysis of these patients was that one of the best correlates of response has been the total number of neoantigens in the tumor (6-8). This is also the case for patients with high microsatellite instability (MSI) where the production of FS neoantigens drives the effective anti-tumor immune responses (9-11). The realization of the immunological importance of these DNA mutations has spawned the effort to develop personal vaccines (12). As promising as early studies are of these vaccines, a major problem is that the majority of tumors will not have enough neoantigen-generating mutations to sustain development of a personal vaccine (13-15). For example, melanoma tumors have a high mutational level with an average of 200 neoepitope mutations. This provides a large number to algorithmically screen for optimal antigenic presentation. In recent reports of two Phase I clinical trials of personal melanoma vaccines, starting with 90-2,000 personal neoantigens, 10 or 20 were identified for the vaccine (16, 17). However, in glioblastoma multiforme (GBM) only 3.5% patients had a high tumor mutation load, and further analysis showed that only a very small subset of GBM patients would potentially benefit from checkpoint blockade treatment (18). This is also consistent with a lack of response in GBM patients to checkpoint inhibitors (19). Massive genomic sequencing results indicated that GBM, ovarian cancer, breast adenocarcinoma and many other cancer types had very low number non-synonymous mutations, which will make these cancers difficult targets for personalized cancer vaccines (14, 20).

To solve this problem, methods and compositions are provided herein related to an alternative source of neoantigens which expand the scope of the application and efficacy of the neoantigen based cancer vaccines. In the process of becoming a tumor, not only does the DNA mutation rate increase with faster cell divisions, but also there is a disruption of basic cellular functions, including RNA transcription, splicing and the quality control system on peptides (21). The disrupted RNA processes increase the FS transcripts generated by RNA splicing errors and the insertions and deletions (INDELs) of MSs (22). Both of these processes, combined with the disrupted quality control system in tumor cells, can lead to the production of FS peptides and exposure of the FS epitopes to the immune system. Embodiments provided herein relate to FS variants produced by errors in RNA processing as a source of cancer neoantigens and a simple system to detect them.

Disclosed herein are models for how errors in transcription microsatellites and mis-splicing of exons could create frameshift neoantigens. Embodiments provided herein include examples in the RNA of tumors for both mis-splicing and of mis-transcription of an INDEL where the errors are present at the RNA but not DNA level. Also provided are methods for analysis of the NCBI EST library to reveal other examples of FS variants. Using an array comprising all predicted FS peptides with specific qualifications, human sera from patients with 5 different cancers have higher antibody reactivity than people without cancer. Three different patterns of high antibody reactive can be determined—pan-cancer, cancer-type focused and personal. Several examples are presented demonstrating that the FS variants offer at least partial protection in mouse models and that the protection is additive for each FS antigen.

The methods and compositions provided herein indicates that variants produced at the RNA level in tumor cells may be a good source of neoantigens for vaccines for several reasons. First, these FS variants produce neoantigens which are more likely to be immunogenic than neo-epitopes encoded by single nucleotide mutations (7). Second, FS from MS INDELs would be particularly attractive sources. There are a limited number of possible variants (~8600 of homopolymers >=7 bp), which encode about 7,000 FS peptides longer than 10 aa, thus reducing the search space for neoantigens. Third, because of the predictable number of candidates it should be possible to use a peptide array to screen for immune reactive neoantigens. This approach would be much simpler than sequencing tumor DNA obtained from a biopsy. Fourth, because any expressed gene has the potential to produce neoantigens, it may not be necessary to limit the vaccine to oncological driver genes. Finally, it should be difficult for the tumor cells to evolve away from the vaccine since these FSs are variants, not heritable mutations. Particularly if the FS antigen was produced in RNA from an essential gene, the tumor cells would need to restrict MHC presentation (17, 52) or create an immune suppressive environment (53) to escape an immune response.

Elements of the model are supported by other published work. The immunological reactivity of FS neoantigens is the presumed basis of the effectiveness of PD-1 in most MSI-H cancers (54, 55). It also explains the responsiveness of renal cancer to CPI therapy—these cancers have low point mutation levels but high FS mutations (3, 7, 20). It has also been shown that cancer cells have much higher mis-splicing rates than normal cells (39, 41, 56). Recently, Andre et al. (56) showed informatically that cancer cells could make neofusion sites by mis-splicing. However, their analysis did not include fusions that created FS peptides. Also, Alicia et.al. (57) analyzed intron retention in tumor databases. This process can also create FS neoepitopes, though apparently much less frequently than mis-splicing of exons. The only aspects of the model not independently confirmed are 1) that the FS peptides potentially generated at the RNA level are made in tumors, 2) that the RNA-generated FSPs can generate immune responses, and 3) that these peptides can be protective against tumors. However, the methods provided herein support these 3 remaining aspects of the model.

Figure 3C:
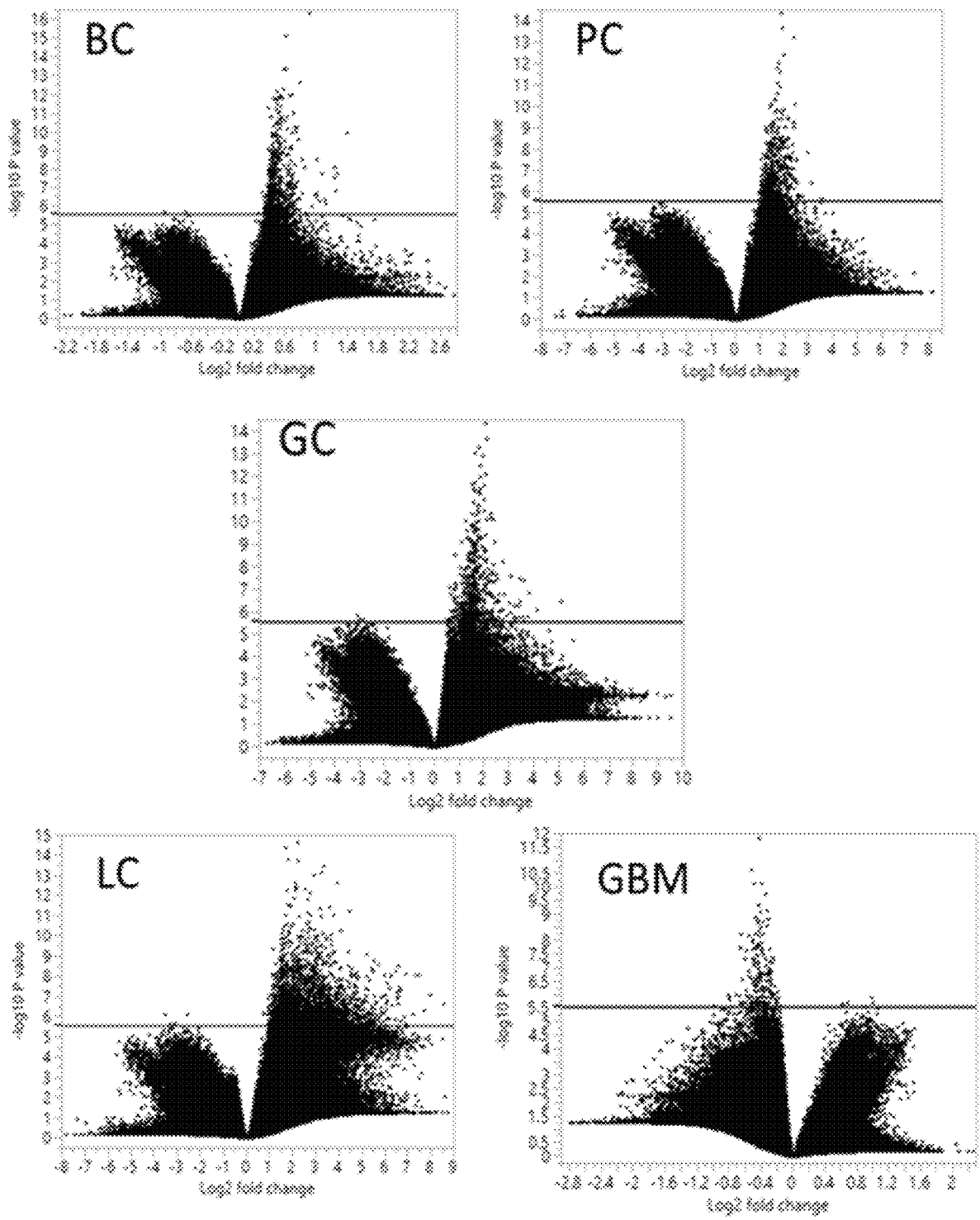

An important aspect of this source of neoantigens is that it may allow extending the personal vaccines to more patients and tumor types. Many tumors have relatively low numbers of DNA mutations and probably could not support constructing a vaccine (58). Estimates from published mutational surveys of various tumors(59) indicate that only 40% of patients could be treated with personal vaccines. However, the methods and compositions provided herein predicts that the RNA FS variants would be produced in any cancer type, even if the DNA mutation level is low. This is substantiated, for example, in GBM (FIGS. 3B and G), which is a low mutation rate cancer (14, 20), but elicits similar overall immune response to FS peptides as other high mutation cancers.

The model also predicts that there may be recurrent FSs produced in different tumors. This is substantiated, for example, at the RNA level for SMC1 FS in breast cancers (FIG. 2D), and also confirmed by antibody reactivity using the FS arrays. This data shows 4641 FS peptides that were positive in 10% or more of all the samples across all five tumor types.

Sets of FS peptides were found that had enriched activity in individual tumor types. A collection of a set of these peptides could potentially be used to constitute a general, therapeutic vaccine or one focused on a particular tumor or set of tumors. Such vaccines would have an advantage over a personal vaccine of being pre-made but would have fewer antigens in common with the tumor. Conceivably, pan-cancer peptides could be used to create a prophylactic cancer vaccine, as has been proposed for cancer associated antigens (60). However, as shown in comparing late and early stage pancreatic cancer profiles, a prophylactic vaccine from FS neoantigens would be best constituted from peptides reactive at early stages of cancer. Clinical trials in dogs were recently initiated of a prophylactic vaccine that is designed to be broadly protective (data not shown).

FIG. 3F and FIGS. 7A-7G show refinement of the collection of reactive peptides to the personal level. Using GBM as an example, a set of peptides that are personal for each patient are found. In the 17 patients analyzed there were 1316-8299 personal peptides which were reactive only in that individual. Approximately 70% of all cancer-specific reactivity on the arrays was personal. A set of 20 personal FS antigens for each GBM patient is presented in FIG. 3F. The high antibody reactive indicates the high expression and/or high immunogenic of the FS antigen in the patient, with potential reactive CD4+ T cell response.

Figure 3D:
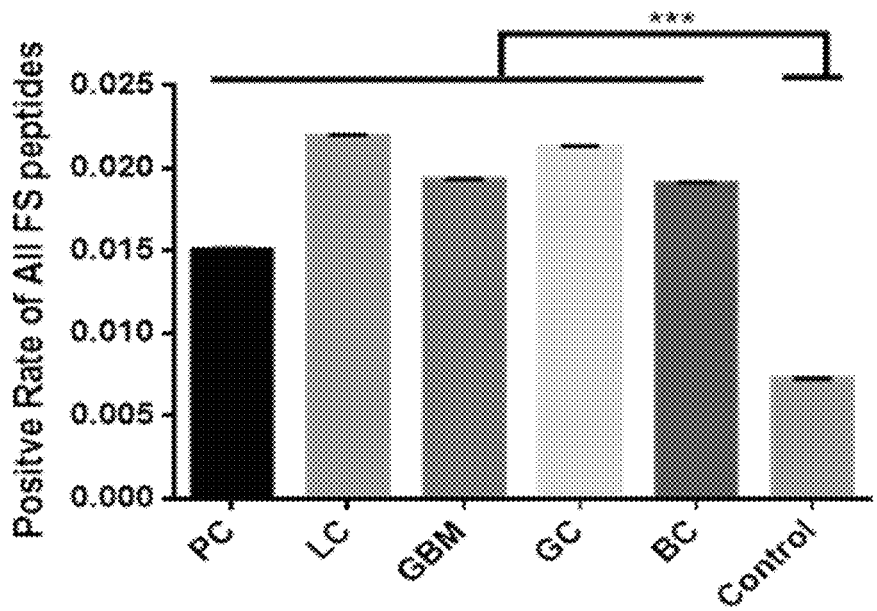
Figure 3E:
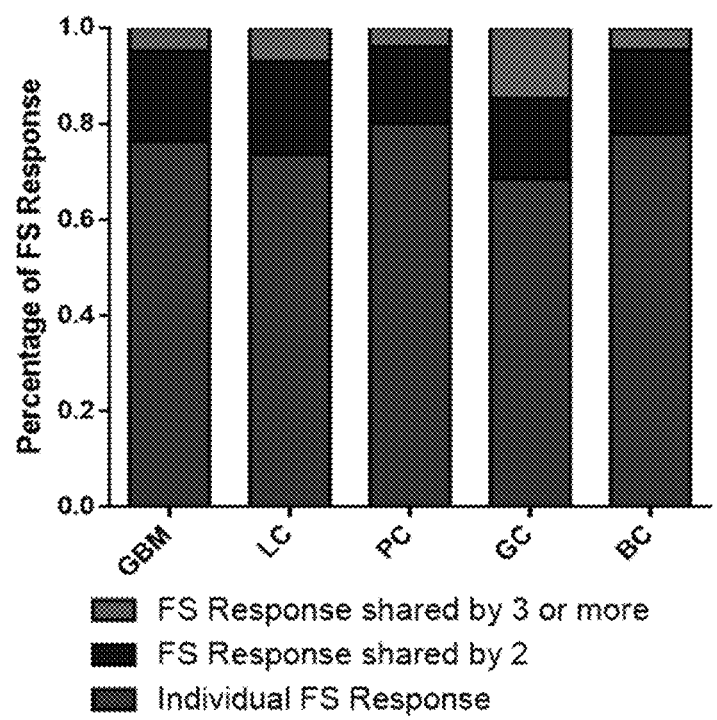
Figure 3F:
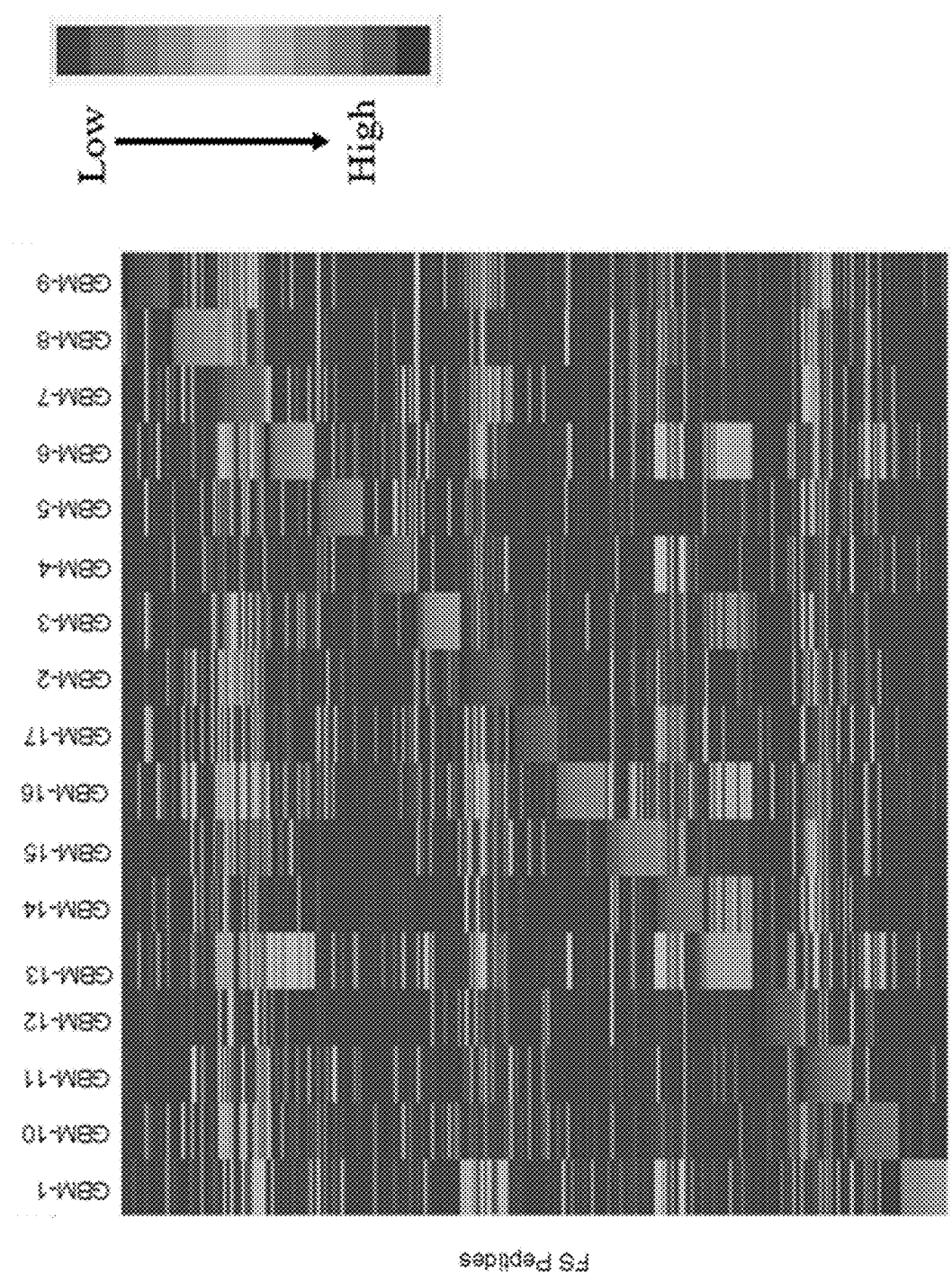
Figure 3G:
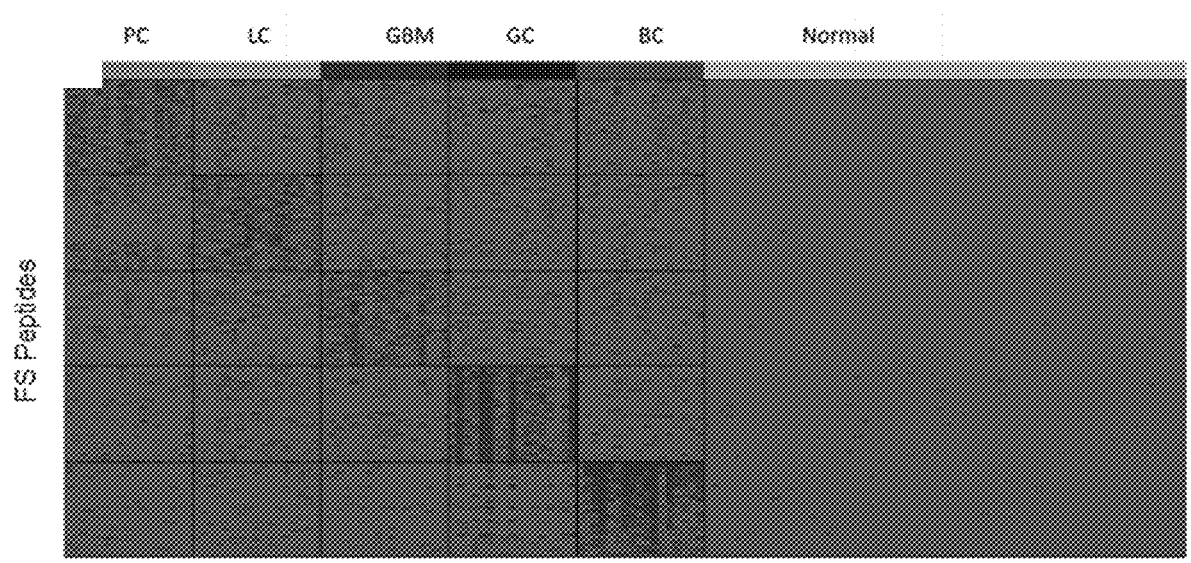
Figure 3H:
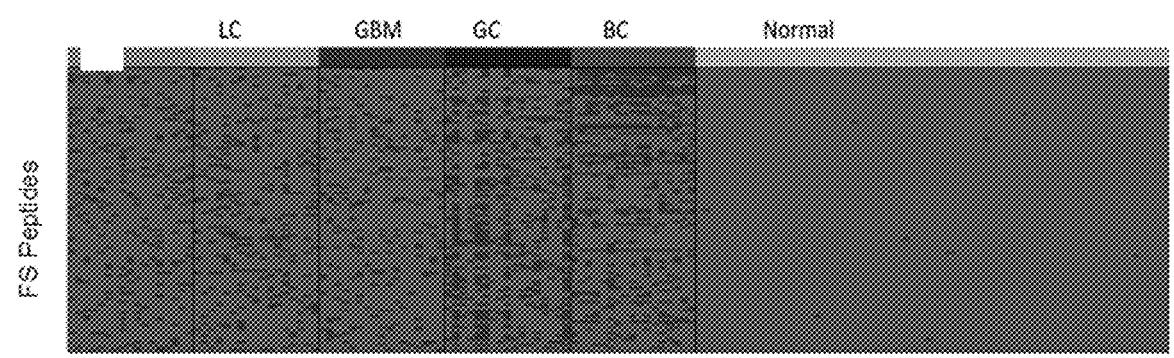

In FIGS. 3G and 3H, people without cancer have sporadic antibody reactivity to some of the peptides. This has also been noted that healthy individuals have antibody and T-cell responses to tumor associated antigens (61, 62). This could be due to random background cross-reactive IgG antibodies unrelated to cancer. It was previously shown that monoclonal antibodies are capable of binding random sequence peptides with high affinity, even though the peptides do not contain a sequence resembling the cognate site (63). Alternatively, this reactivity could be a manifestation of immune surveillance (64) eliminating potential tumor cells. Any cell that produced and presented FS antigens, whether tumor or not, could be susceptible to this elimination, effectively a "bad cell" response.

Figure 4A:
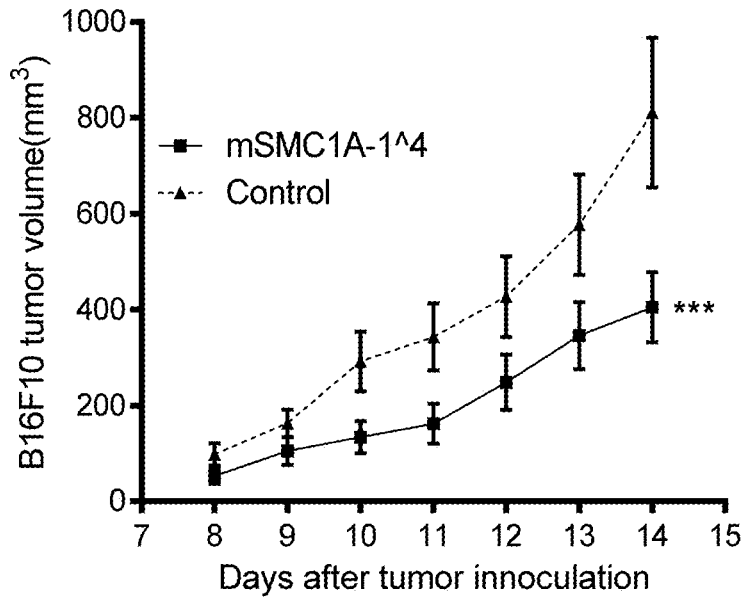
FIGS. 4A-4F: show protection of FS antigens as cancer vaccine candidates in different mouse tumor models.
Figure 4B:
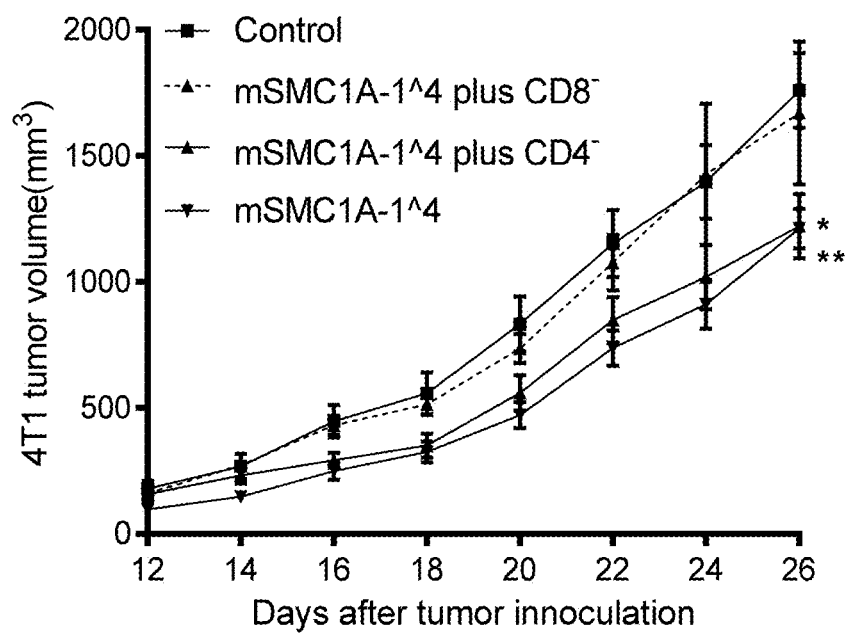
Figure 4C:
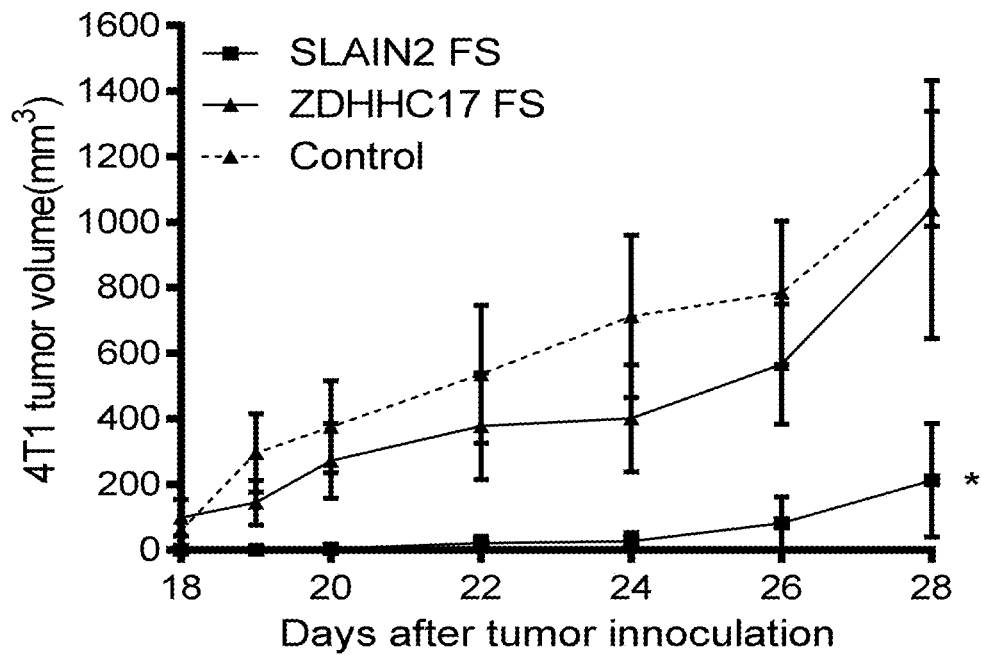
Figure 4D:
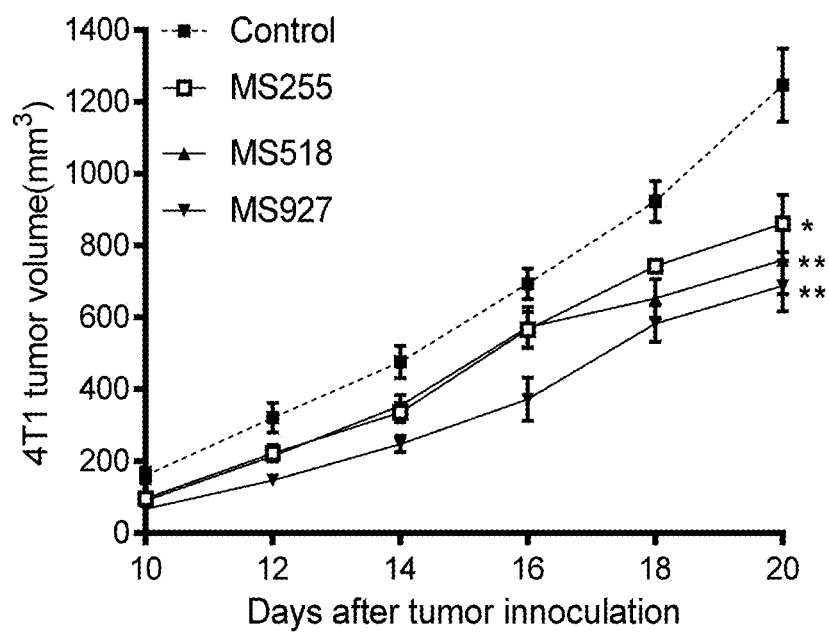
Figure 4E:
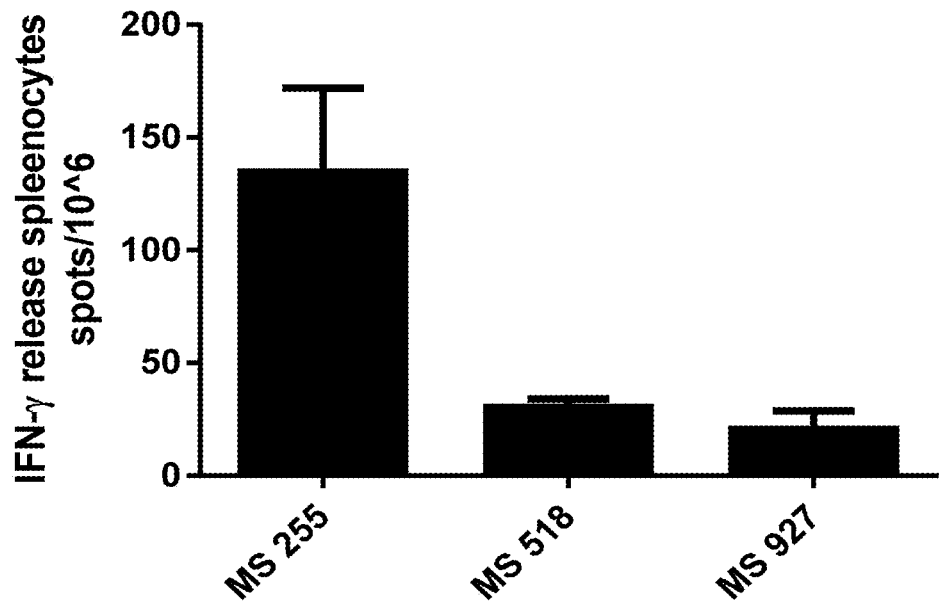
Figure 4F:
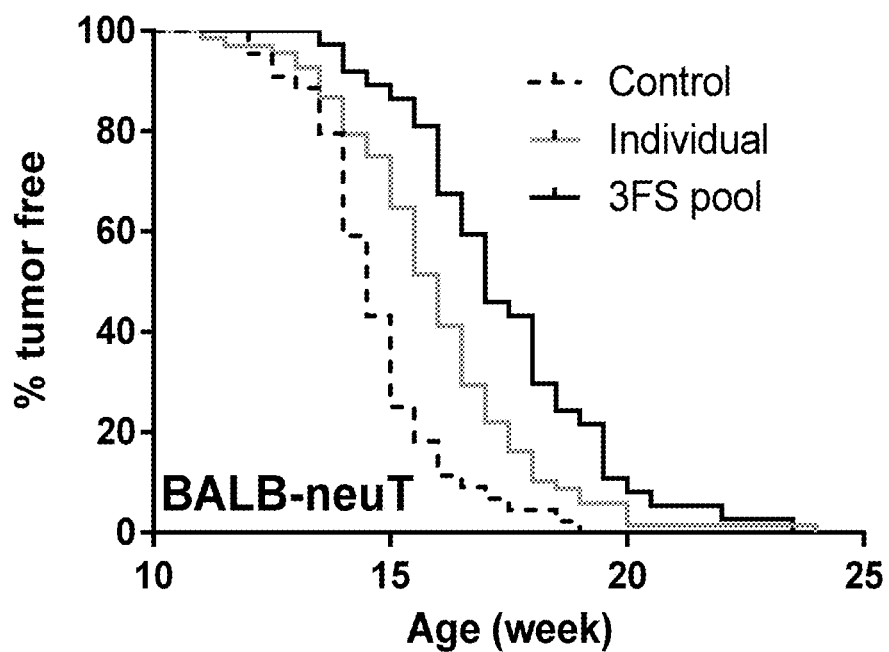

The vaccines tested did not produce complete protection by themselves in the models tested. However, it should be noted that both these models are very stringent and probably do not completely replicate natural tumors. One reason for this may be due to low level production of each FS neoantigen, consistent with the additive effects of the FS peptides in vaccines (FIG. 4F). Only occasional identification by mass spectrometry of FS peptide from MHC I elution of tumor cells is achieved, consistent with other reports (57). The quantitative analysis of transcription errors reported by Gout et al recently is consistent with this proposition (22, 32). However, this could also be due to the tumor cells deleting the antigen and evolving resistance, or that the T cell epitopes have low affinity, as is predicted for the mSMC1A FS peptide in the BALB/c mouse strain. Neoantigens produced by mutations in the DNA will produce 50-100% variant RNA and therefore potentially more presented antigen than would be expected for RNA based neoantigens. Pre-existing T-cell responses were not detected in mouse tumor models, even though vaccination with the FS is at least partially protective. The level of RNA-error-based FS production in the tumor is generally not enough to elicit a T-cell response, but is enough to elicit T-cells elicited by a vaccine to kill the tumor cell. This is consistent with analysis of three clinical trials of personal vaccines (16, 17, 65), where most of the antigens which produced a T-cell response had no pre-exiting T-cell response detectable. Recently, complete protection in the 4T1 model using pools of 10 selected FS antigens with both personal and cancer-type specific vaccines was shown (MTB, LS and SAJ, data not shown).

The arrays detect antibody responses to FS peptides. B-cell responses are not commonly considered important for an anti-tumor effect. It was recently shown that antibodies generated by dogs with cancer could be detected on an 800 FS peptide array. Peptides reactive on the dog array, whose homolog was also present in a mouse tumor line, were protective in the mouse models, while non-reactive peptides on the array did not confer protection. This study establishes that antibody response is an indicator of vaccine effectiveness. The level of antibody response correlated with protection in the mouse models. One explanation for this observation is that the IgG antibody response depends on CD4+ T-cell help. FS with good CD4+ T cell epitopes may also elicit tumor cell killing. It has been noted that CD4+ T cell responses to vaccines correlate with protection (66, 67).

In summary, the methods and compositions provided herein relate to another class of neoantigens that are useful in developing different types of cancer vaccines. Also provided herein are array formats for directly detecting immune responses to these tumor antigens. Dog and human clinical trials for use of the tumor antigens identified by the methods disclosed herein are underway.

As used herein, the term "detect," "detection," "detectable," or "detecting" is understood both on a quantitative and a qualitative level, as well as a combination thereof. It thus includes quantitative, semi-quantitative, and qualitative measurements of measuring a cancer in a subject, using the methods and compositions as disclosed herein.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. Cancer includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor). A cancer may include, for example, gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., Adult T-cell leukemia, Acute monocytic leukemia, Acute myeloid leukemia, Acute promyelocytic leukemia, myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, sarcoma, Adenocarcinoma, Astrocytoma, Bone Cancer, Brain Tumor, Burkitt's lymphoma, Carcinoma, Cervical Cancer, Chronic Lymphocytic Leukemia, Chronic myelogenous leukemia, Endometrial cancer, Glioblastoma multiforme, Glioma, Hepatocellular carcinoma, Hodgkin's lymphoma, Inflammatory breast cancer, Kidney Cancer, Leukemia, Lymphoma, Malignant Mesothelioma, Medulloblastoma, Melanoma, Multiple myeloma, Neuroblastoma, Non-Hodgkin Lymphoma, Non- Small Cell Lung Cancer, Pancreatic Cancer, Pituitary tumor, Retinoblastoma, Skin Cancer, Small Cell Lung Cancer, Squamous cell carcinoma, Stomach cancer, T-cell leukemia, T-cell lymphoma, and Wilms' tumor.

As used herein the term "frameshift mutation" is a mutation causing a change in the frame of the protein. Thus, a frameshift variant peptide is a peptide in which a frame has changed due to a frameshift mutation. In some embodiments provided herein, a frameshift includes two or more pooled frameshifts. As used herein, the term "pooled" refers to a plurality of frameshift samples that have been combined to create a new composition.

As used herein, the term "microsatellite instability," also known as "MSI" refers to the changes in microsatellite repeats in tumor cells or genetic hypermutability caused due to deficient DNA mismatch repair. Microsatellites, also known as simple sequence repeats, are repeated sequences of DNA comprising repeating units 1-6 base pairs in length. Although the length of microsatellites is highly variable from person to person and contributes to the DNA fingerprint, each individual has microsatellites of a set length. MSI results from the inability of the mismatch repair (MMR) proteins to fix a DNA replication error. MSI comprises DNA polymorphisms, wherein the replication errors vary in length instead of sequence. MSI comprises frame-shift mutations, either through insertions or deletions, or hypermethylation, leading to gene silencing. It is known in the art that microsatellite instability may result in colon cancer, gastric cancer, endometrium cancer, ovarian cancer, hepatobiliary tract cancer, urinary tract cancer, brain cancer, and skin cancers.

EXAMPLES

Example 1: Materials and Methods for Isolating Neoantigens

Cell Lines and Tissues

HEK293, B16-F10 and 4T1 cell lines were purchased from ATCC in 2006. Upon receipt, cells were cultured for three passages in RPMI medium (ATCC) with 10% FBS, 100 U/mL penicillin, and 100 mg/mL streptomycin and stored in aliquots under liquid nitrogen. Cells were maintained at 37° C. under humidified 5% $CO_2$, 95% air. Cells between 2 and 20 passages were used. Cell lines were not re-authenticated. Other cells lines are listed in Table 2 and were cultured in ATCC-recommended media.

Mice and Mouse Tumor Models

BALB/c and C57BL/6 mice were from Charles River Laboratories or Jackson Laboratories. For the tumor challenge, $5\times10^3$ 4T1 cells were injected in the mammary pad at the right flank of the mice, or $1\times10^5$ B16F10 cells were injected subcutaneously in the right flank of the mice. Tumor volumes were measured and calculated by ($Length^2 \times Width/2$) daily after the size was larger than 1 $mm^3$. Breeding pairs of BALB-neuT and FVB-neuN (FVB/N-Tg (MMTVneu) 202Mul) mice were obtained from Joseph Lustgarten, Mayo Clinic Arizona. Mice were monitored weekly for the tumor incidence after tumor size reached 1 $mm^3$. All experiments were performed in accordance with protocols approved by the Institutional Animal Care and Use Committee of Arizona State University.

Statistical significance of differences was analyzed by a Student t-test.

EST Analysis

To identify potential putative chimeric transcripts, that when translated would result in a frame-shifted neo-peptide, two publicly available datasets and applied an algorithm that was used to identify chimeric transcripts were used. Specifically, the sequences found within the Expressed Sequence Taq (EST) library and the Human RefSeq database (23) from the National Center for Biotechnology Information (NCBI) were used. Using the stand-alone BLAST program, all EST sequences were aligned to RefSeq. ESTs that aligned with 50-85 base pairs and had 95% homology to RefSeqs that have been previously annotated by National Center Institute (NCI) were selected. The alignment data was filtered by eliminating the EST sequences that did not align to multiple RefSeqs or were aligned in the 3'-5' orientation. Lastly, the sequences that aligned with non-coding sequence regions were eliminated. The remaining EST sequences were then used to identify the chimeric transcripts. Only the ESTs that aligned to two or more distinct RefSeq in consecutive positions were considered to be potential candidates. To be defined as a coding chimeric transcript, the EST sequences had to be at least 100 bp long with sequence similarity greater than or equal to 95% to the RefSeq. Also, the junction points between the two genes had to occur within the coding sequence of the upstream gene and orientation of the upstream gene alignment had to be in the positive (5'-3') orientation. To eliminate false calls, all potential chimeric EST sequences had to be either present in more than one cDNA library or supported by three or more independent EST sequences. In addition, chimeric transcripts were classified based on the relative position of two genes. Classification of types of chimeric transcript was based on relative position of two fusion genes on the chromosome. Specifically, genes found on different chromosomes resulted in inter-chromosomal fusion while genes found in same chromosome were intra-chromosomal or read-through chimeric transcripts. Read-through chimeric transcripts resulted from two neighboring genes on same strand, otherwise intra-chromosomal.

PCR Screen for EST FS Candidates

The 50 Human Breast cancer cell lines were obtained from the American Type Culture Collection (ATCC) and were grown according to recommendations. Human breast cancer tissue specimens were acquired from Mayo Clinic, and were informed consent and approval by the Mayo Clinic Institutional Review Board. All specimens were coded and anonymized. All experiments were performed in accordance with the approval protocol. Total RNA was extracted from breast cancer cell lines and primary breast tissues using the TRIzol LS reagent (Life Technologies, Carlsbad, CA) following the manufacturers protocol. RNA integrity was determined by gel electrophoresis and concentration was determined by measuring absorbance at 260/280 on the Nano-drop (NanoDrop Products, Wilmington, DE). cDNA was prepared by using the SuperScript™ III First-Strand Synthesis SuperMix (Life Technologies, Carlsbad, CA) that includes random hexamers and oligo dT's following the manufacturer's recommended protocol. cDNA integrity and quality were assessed by performing a β-actin control PCR. End Point PCR primers for each chimeric transcript were designed using Primer3 (24) so that the forward and reverse primers both bind 80 bp to 280 bp upstream/downstream from the junction point. End-point PCR reactions using approximately 25 ng of cDNA, reagents from (Life Technologies, Carlsbad, CA) and 35 cycles were performed using Mastercycler ep gradient S (Eppendorf, Hamburg, Germany). PCR products were analyzed on 1.5% agarose gels. PCR products were purified, and sequence confirmed by Applied Biosystems 3730 (Life Technologies, Carlsbad, CA) sequencing.

End-Point RT-PCR cDNAs from human primary breast tumors and normal mammary glands were from BioChain (Newark, CA). Total RNA from other sources was extracted with TRIzol (Life Technologies, Carlsbad, CA). cDNA was synthesized from total RNA using the SuperScript III First-Stand Synthesis SuperMix (Life Technologies). The primer sequences used for end-point RT-PCR were synthesized by Life Technologies or Sigma. End-point RT-PCR reactions (25 sL) used the GoTaq PCR kit (Promega, Madison, WI) and the following conditions: 95° C. for 2 min; 35 cycles of 95° C. for 30 secs, 60° C. for 30 sec (annealing), and 72° C. for 10 to 30 sec (extension); and 72° C. for 5 min. Exceptions were that mouse SMC1A primers used an annealing temperature of 55° C., and β-actin primers were done with 25 cycles and 30 sec of extension time. Sequence verification was performed on RT-PCR products in initial reactions and later during intermittent reactions. The following primers (from 5' to 3') for the PCR were used: SEC62 DNA human forward: TGCCATACCTGTTTTTTCCC (SEQ ID NO: 1); SEC62 human DNA reverse: AGTTATCTCAGGTAGGTGTTGC (SEQ ID NO: 2); SEC62 DNA dog forward: AAGG-GAGTCTGTGGTTGA (SEQ ID NO: 3); SEC62 DNA dog reverse: CAAAGAGGGAAGAGAGTGG (SEQ ID NO: 4); SEC62 cDNA human forward: AAAGGAAAAGCT-GAAAGTGGAA (SEQ ID NO: 5); SEC62 human cDNA reverse: GCAACAGCAAGGAGAAGAATAC (SEQ ID NO: 6); SEC62 cDNA dog forward: AAGG-GAGTCTGTGGTTGA (SEQ ID NO: 7); SEC62 cDNA dog reverse: CAAAGAGGGAAGAGAGTGG (SEQ ID NO: 8); SMC1A mouse forward: CTGTCATGGGTTTCCTG (SEQ ID NO: 9); SMC1A mouse reverse: GAGCTGTCCTCTCCTTG (SEQ ID NO: 10); SMC1A human forward: CCTGAAACTGATTGAGATTGAG (SEQ ID NO: 11); SMC1A human reverse: TCTTCAGCCTT-CACCATTTC (SEQ ID NO: 12); β-actin mouse forward: CCAACCGTGAAAAGATGACC (SEQ ID NO: 13); β-actin mouse reverse: TGCCAATAGTGATGACCTGG (SEQ ID NO: 14); β-actin human forward: CCAACCGCGAGAAGATGACC (SEQ ID NO: 15); β-actin human reverse: TGCCAATGGTGATGACCTGG (SEQ ID NO: 16); Rat Her-2 forward: ATCGGTGATGTCGGC-GATAT (SEQ ID NO: 17); Rat Her-2 reverse: GTAACACAGGCAGATGTAGGA (SEQ ID NO: 18).

Sec62 Transfection and Flow Analysis

HEK293 cell line were purchased from ATCC and cultured with standard protocols. Lipofectamine 2000 Transfection Reagent (Thermo Fisher Scientific, MA) was used to transfect plasmids into cell lines for overnight. Cells were then prepared in FACS buffer and quantified with flow cytometry. The three open reading frames (ORFs) were assembled by PCR and inserted into pCMVi vector at EcoR I MCS site. Detailed sequences of three ORFs were included in Table 6.

Gene Expression

Gene expression was measured with the TaqMan Gene Expression Assay (Life Technologies) according to the manufacturer's directions. The hSMC1A-specific labeled probe was 5'-CAATGGCTCTGGGTGCTGTGGAATC-3' (SEQ ID NO: 19). The unlabeled forward and reverse primers were 5'-GGGTCGACAGATTATCGGACC-3' (SEQ ID NO: 20) and 5'-GTCATACTCCTGCGCCAGCT-3 (SEQ ID NO: 21), respectively. Results were normalized by human GAPDH.

Example 2: Human Frameshift Peptide Array Synthesis and Analysis

Microsatellite Frameshift antigens: human mRNA sequences were acquired from NCBI CCDS databases (25). Microsatellite regions (homopolymers of 7 runs or more) were mapped to human coding genes, $2^{nd}$ and $3^{rd}$ reading frame peptide sequences after MS regions were predicted and stored in Microsatellite FS database, MS FS peptides 10 aa or longer were included in the human FS peptide array.

Mis-splicing Frameshift antigens: human mRNA sequences and exon coordinates were acquired from NCBI Refseq database (23). $2^{nd}$ and $3^{rd}$ reading frame FS peptide sequences were predicted from the start of every exon. Then all the FS peptides were aligned against the human proteome, FS peptides with higher than 98% homology to wild type proteome were removed. FS peptides 10 aa or longer were then included in the human FS peptide array. Table 7 depicts exemplary variant FS peptides.

A total number of 64 non-cancer control samples and 13 pancreatic stage 1 cancer samples, 85 late stage cancer samples from 5 cancer types were tested on the FS array, detailed information was summarized in Table 5. All samples were acquired from collaborators and were informed consent upon collection through the institute's own IRB. All samples were anonymized before receipt at Arizona State University (ASU) via Institutional Review Board (IRB) protocol No. STUDY00003722, 'Receipt of Deidentified Human Serum for Immunosignature Analysis' and protocol No. 0912004625, 'Profiling Biological Sera for Unique Antibody Signatures'. All experiments were performed in accordance with the approval protocol.

400K Frameshift Peptide Array Assay

Serum was diluted 1:100 in binding buffer (0.01M Tris-HCl, pH 7.4, 1% alkali-soluble casein, 0.05% Tween-20) and 150 µl diluted samples were loaded into each compartment of the 12-plex array and incubated overnight at room temperature or 4° C. After sample binding, the arrays were washed 3× in wash buffer (1×TBS, 0.05% Tween-20), 10 min per wash. Primary sample binding was detected via Alexa Fluor® 647-conjugated goat anti-human IgG secondary antibody (Jackson ImmunoResearch #109-605-098). The secondary antibody was diluted 1:10,000 (final concentration 0.15 ng/µl) in secondary binding buffer (Ix TBS, 1% alkali-soluble casein, 0.05% Tween-20). Arrays were incubated with secondary antibody for 3 h at room temperature, washed 3× in wash buffer (10 min per wash), 30 secs in reagent-grade water, and then dried by centrifuging at 690 RPM for 5 mins. All washes and centrifugations were done on a Little Dipper 650C Microarray Processor (SciGene) with preset programs. Fluorescent signal of the secondary antibody was detected by scanning at 635 nm at 2 µm resolution and 15% gain, using an MS200 microarray scanner (Roche NimbleGen).

Example 3: Genetic Immunization

Plasmids for Genetic Immunization

The DNA fragments encoding FS peptides were cloned as a C-terminal fusion into the genetic immunization vectors pCMVi-UB (26) and pCMVi-LSrCOMPTT (27, 28) with the Bgl II and Hind III and mixed with 1:1 ratio as the vaccine antigen. Three adjuvants were encoded by genetic immunization vectors. The pCMVi-mGM-CSF vector expresses the adjuvant mouse granulocyte/macrophage colony-stimulating factor (mGM-CSF) under control of the human cytomegalovirus (CMV) promoter (27). LTAB indicates immunization with 1:5 ratio by weight of two plasmids, pCMVi-LTA and pCMVi-LTB, expressing the heat-labile enterotoxins LTA and LTB from *Escherichia coli*. These plasmids express LTA and LTB as C terminal fusions to the secretion leader sequence from the human α1 antitrypsin gene (29). Vectors pCMVi-UB, pCMVi-LSr-COMPTT, pCMVi-LTA (also called pCMVi-LS-LTA-R192G) and pCMVi-LTB are available from the PSI: Biology-Materials Repository DNASU (dnasu.org) at Arizona State University. Additional adjuvants were the class A CpG 2216 single-stranded oligodeoxynucleotide obtained from Sigma and alum from Pierce.

Bullet Preparation for Genetic Immunization with Gene Gun

Bullets for biolistic genetic immunization used the gold micronanoplex approach and were prepared as described (30) with the following changes. Two grams of 1-micron gold was used. Prior to addition of N-hydroxysuccinimide and N-(3-dimethylaminopropyl)-N'-ethylcarbodiimide hydrochloride, the gold was resuspended in 20 mL of a 0.1 M solution of 2-(N-morpholino) ethanesulfonic acid (MES), pH 6.0. DNA-gold micronanoplexes were prepared by combining, per bullet, 57 μL of cysteamine-gold solution with precipitated DNA (≤10 μg) that had been resuspended in ≤15 μL of water, and then vortexing for 10 min. To the DNA-cysteamine-gold was added 6 L/bullet of a freshly made solution of PEI-micron gold (167 mg/mL in 0.1 M MES, pH 6, without NaCl). The pelleted micronanoplexes were washed with ethanol prior to resuspension in n-butanol (55 L/bullet), followed by bullet formation under nitrogen gas.

Immunization Dosage and Regime and Tumor Challenge

C57BUB16-F10 Mouse Melanoma Model

Six week old mice (n=10 per group) received one genetic immunization with the Gene Gun in the pinna of the ear (4 shots/mouse) with 20 ng of antigen (SMC1A-1^4 and non-protective Cowpox viral antigen CPV 172 (31)) in pCMVi vectors plus the adjuvants pCMVi-mGM-CSF (0.5 μg) and CpG 2216 (5 μg) for each shot. All of the mice were challenged with $1 \times 10^5$ B16-F10 cells 4 weeks after the immunization.

BALB/C-4T1 Mouse Breast Tumor Model

For the three MS FS experiments, all mice (n=10 per group) were genetically immunized in the ear by Gene Gun at 8 weeks of age (2 shots/mouse, 60 ng pooled antigens plus 0.25 μg LTAB and 2.5 μg CpG2216 as the adjuvant for each shot) and boosted twice (two days apart) in three weeks with 1 μg pooled antigens plus the same adjuvants dosage. All mice were boosted again in two weeks with 50 μg KLH conjugated MS FS peptides with 50 μg CpG 2216 and 50 ul alum in total 100 ul PBS. The negative groups were immunized with the empty vectors and KLH protein with the same dosage. All mice were challenged with $5 \times 10^3$ 4T1 cells two weeks after the last immunization.

For the mSMC1A-1^4 experiment, all mice were (n=10 per group) genetically immunized in the ear by Gene Gun at 8 weeks of age (2 shots/mouse, 1 μg antigen plus 0.25 μg LTAB and 2.5 μg CpG2216 as the adjuvant for each shot), and boosted in two weeks with KLH conjugated SMC1A-1^4 peptide plus 50 μg Poly:IC (Sigma) in 100 ul PBS. The same regime was repeated in two weeks. The negative groups were immunized with the empty vectors and KLH protein with the same dosage. All mice were challenged with $5 \times 10^3$ 4T1 cells 4 weeks after the last immunization. The CD8 and CD4 T cell depletion started 2 weeks after the last immunization by i.p injection of 100 μg antibody (anti CD8, clone 2.43; anti CD4, clone GK 1.5; BioXCell, West Lebanon, NH) every 3 days until the end of the experiment.

BALB-neuT Mice

Mice were genetically immunized by Gene Gun at 4-6 weeks with 100 ng of antigen(s) in pCMVi vectors, boosted twice (3-4 days apart) at 9-10 weeks with 1 μg of the same antigen(s), and boosted once at 13-14 weeks with protein. Genetic immunizations included adjuvants LTAB (0.5 μg) and CpG 2216 (5 μg). Protein boosts were 50 μg of KLH conjugated FS peptides (SMC1A-1^4, n=32; RBM FS, n=22; SLAIN2 FS, n=14 and pool of three FS neoantigens, n=37). The protein boost included 50 μg CpG 2216 and 50 μl alum in 100 μl PBS as the adjuvant. The negative groups (n=30) were immunized with the empty vectors and GST or KLH protein with the same adjuvants and dosage.

ELISPOT

Peptides used in the ELISPOT assays were synthesized in-house. The Mouse IFN-7 ELISPOT Set (BD Biosciences) was used according to the manufacturer's directions except that blocking was at 37° C. $10^6$ fresh mouse splenocytes were added to each well, followed by co-culturing for 48 hr with 20 μg of peptide in a volume of 200 μl RPMI medium. The plate was scanned and spots were analyzed by the AID EliSpot Reader System (Autoimmun Diagnostika GmbH, Germany).

Statistical Analysis

The statistical calculation software used was GraphPad Prism 7 (GraphPad Software, San Diego, CA) and JMP Pro (SAS Institute, NC). The data presentation and the statistical tests for each experiment are indicated in the legend of the corresponding figures, as well as the samples size and p-values.

Example 4: Model for the Production of RNA-Based Frameshift Variants

Mistakes in RNA mis-splicing and transcription, particularly of INDELs of MSs in coding regions, in cancer cells may also be a source of neoantigens. FIG. 1 depicts an exemplary model of some embodiments provided herein. As information flows from DNA to RNA to protein there is a general increase in error rates (22, 32-35). These errors include mis-splicing and INDELs of MSs. Both errors will produce a background level of FS transcripts, which encode truncated proteins with a FS peptide at the C-terminus. The level of the FS peptides in normal cells is managed by the quality control mechanisms, such as nonsense mediated decay (36) and ER-associated degradation (37), such that these FS peptides are not presented to the immune system. However, the initiation event of a potentially cancerous cell will destabilize basic cellular processes including transcription, RNA splicing and the quality control system (21, 38-41). These global errors can be augmented due to chromosomal instability (42) or key, broadly effective mutations (43, 44). Consequently, the number of FS peptides produced, combining with other aberrant proteins, exceeds the disrupted quality control system, allowing FS peptides to be presented in MHC IIMHC II complexes or externally to dendritic cells. The level of FS production may be sufficient to be presented in MHC complexes but not induce a T-cell response. In most cases the aberrant cells are killed due to inherent dysfunction or by the immune system. Those escaping to become cancer cells could do so by decreasing MHC expression and/or establishing an immune suppressive environment. An important aspect of the model is that because of the global increase in the errors of transcription and splicing, the FS neoantigens will be constantly produced. Thus, in contrast to the commonly held view (45), bystander FS neoantigens would be good immunological targets. The production of these variants is not dependent on DNA replication as is the case for DNA mutations nor are they heritable and subject to selection.

As seen in FIG. 1, errors in DNA replication are very rare and repaired. Transcription error rates are higher but also rare as are mis-splicing during intron excision. Additionally, the FS transcript with a premature termination may be degraded by Nonsense Mediated Decay (NMD). Aberrant proteins, including those with frameshifts are largely eliminated by the protein quality control system, Ubiquitin/Proteasome System (UPS). The net result is that very few frameshift peptides are presented on MHC I/II or escape the cell to be presented to the immune system. Cancer Cell: All levels of information transfer become more error prone. More errors are made in DNA replication, but only when cells divide. Most DNA mutations are point mutations and encode low or non-immunogenic epitopes. Global transcription is increased and is generally less accurate and even more so through MSs producing INDELs. Most transcribed genes with MSs in the coding region will have more FS transcripts. RNA splicing is also far less accurate, creating more FS transcripts from each out-of-frame splicing between exons from the same gene and different genes. The substantial increase of the FS transcripts from INDELs of MS and mis-splicing overwhelms the RNA quality control systems, such as NMD. Consequently, more truncated proteins with the FS peptide will be translated. These unfolded truncated proteins, combined with aberrant proteins from other mutations, overwhelms the protein quality control system, leading to more frameshift peptides being presented on MHC I/II and mis-secreted or released from the cancer cell which the immune system can respond to.

Example 5: Detection of Frameshift Transcripts

Figure 2A:
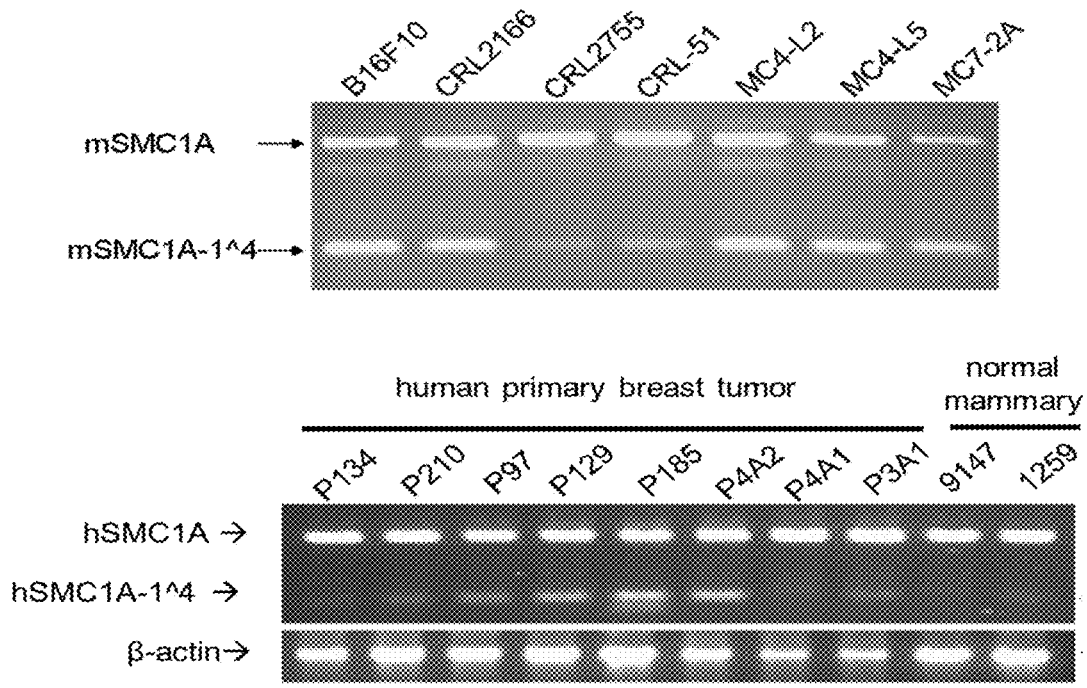
FIG. 2A: shows end-point RT-PCR analysis of the mSMC1A-1ˆ4 in mouse tumor cell lines and human hSMC1A-1ˆ4.
Figure 2B:
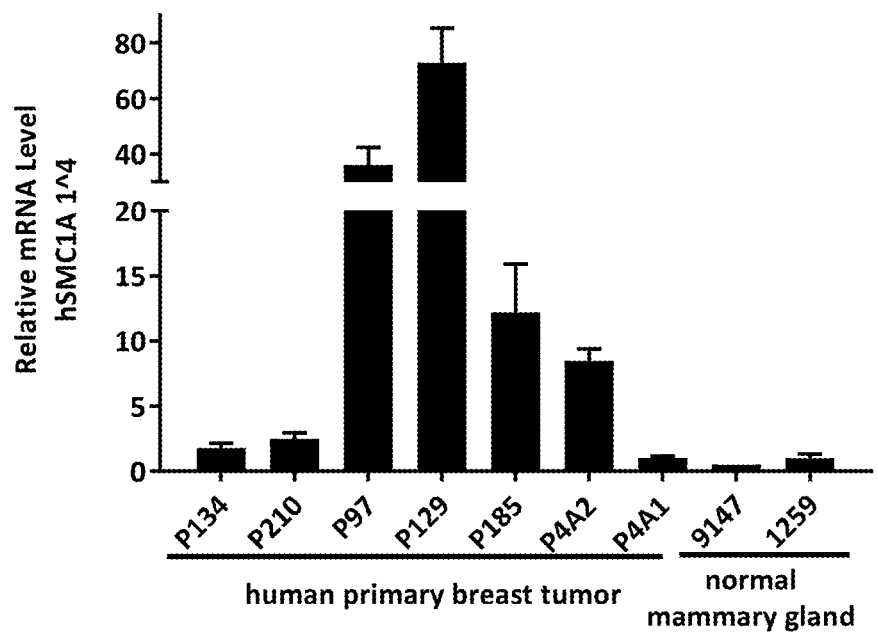
FIG. 2B: shows end-point RT-PCR analysis and RT-qPCR of the human hSMC1A-1ˆ4 expression in human primary breast tumor tissues and normal mammary tissues. All values are normalized relative to the expression levels in sample 1259 (set as 1). Data are mean 2-ΔΔC of triplicates with SD.
Figure 5A:
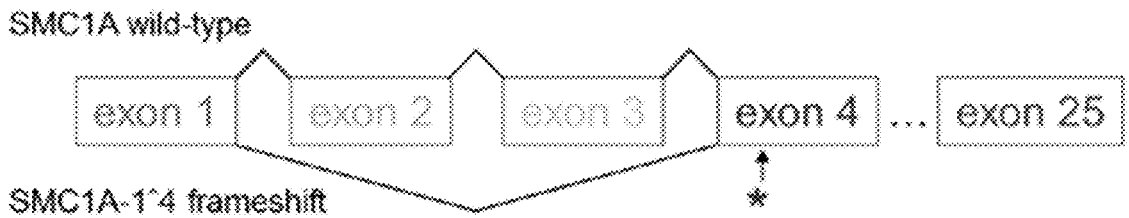
FIGS. 5A-5D: are a schematic of FS mis-splicing.
Figure 5B:
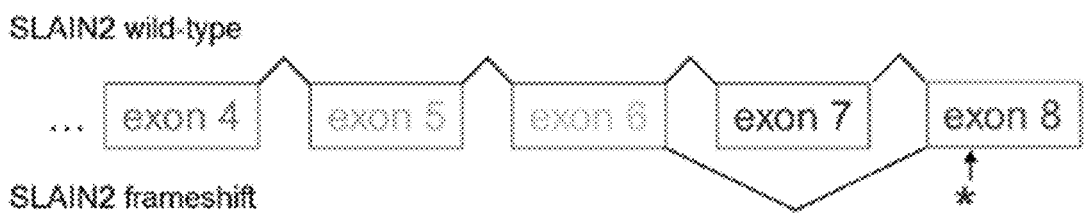
Figure 5C:
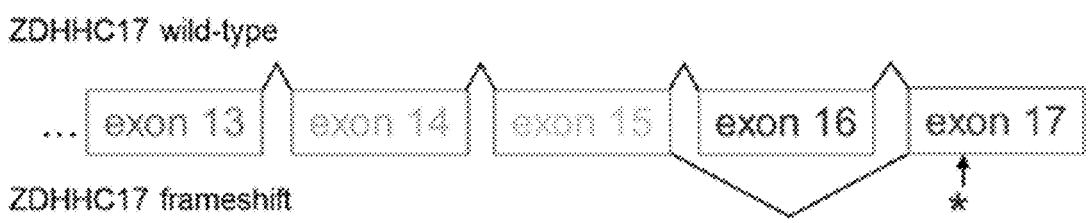
Figure 5D:
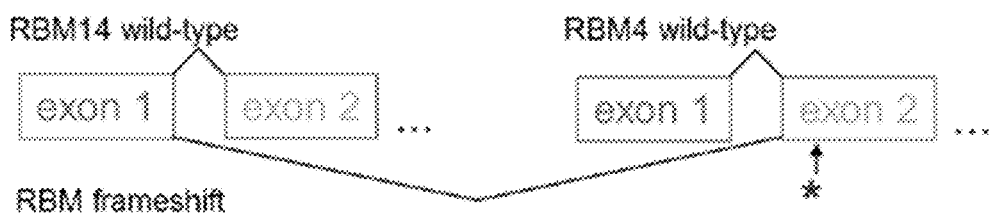
Figure 5E:
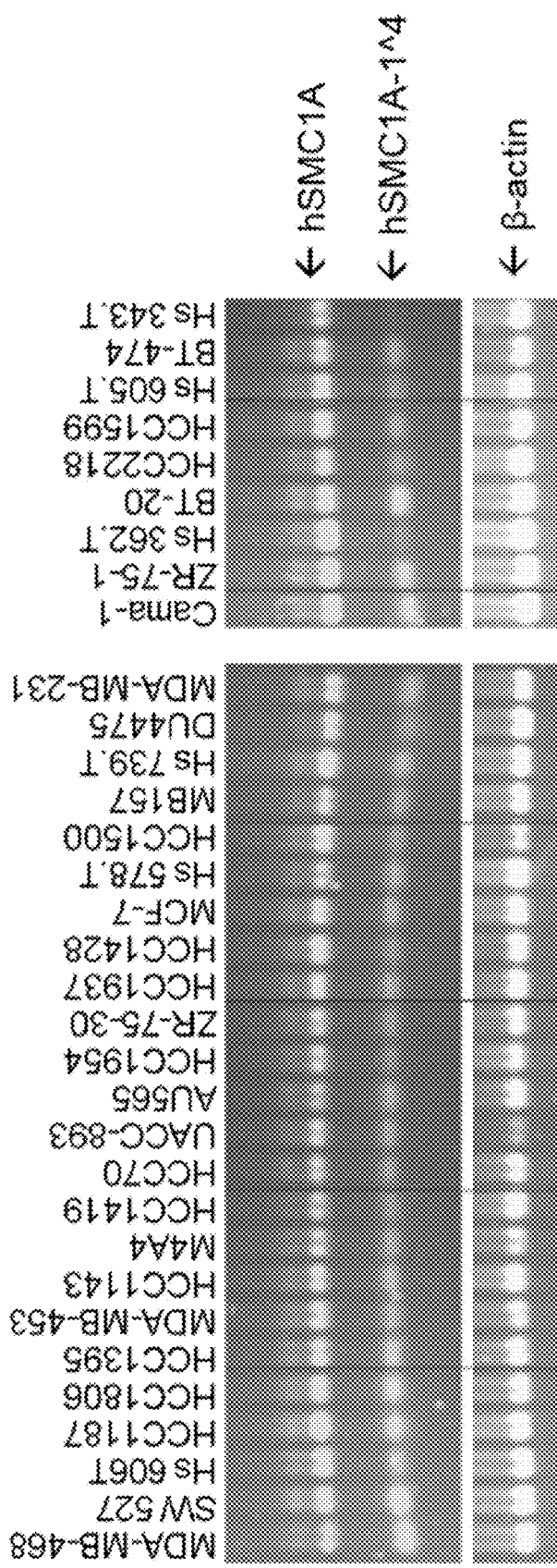
FIG. 5E: shows an RT-PCR of human SMC1A (hSMC1A), human SMC1A FS (hSMC1A-1^4) and β-actin in 33 human breast tumor cell lines.
Figure 5F:
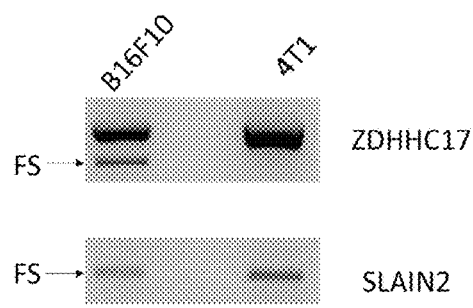
FIG. 5F: shows an RT-PCR analysis of the ZDHHC17_FS and SLAIN2_FS in B16F10 and 4T1 tumor cell cDNA.
Figure 5G:
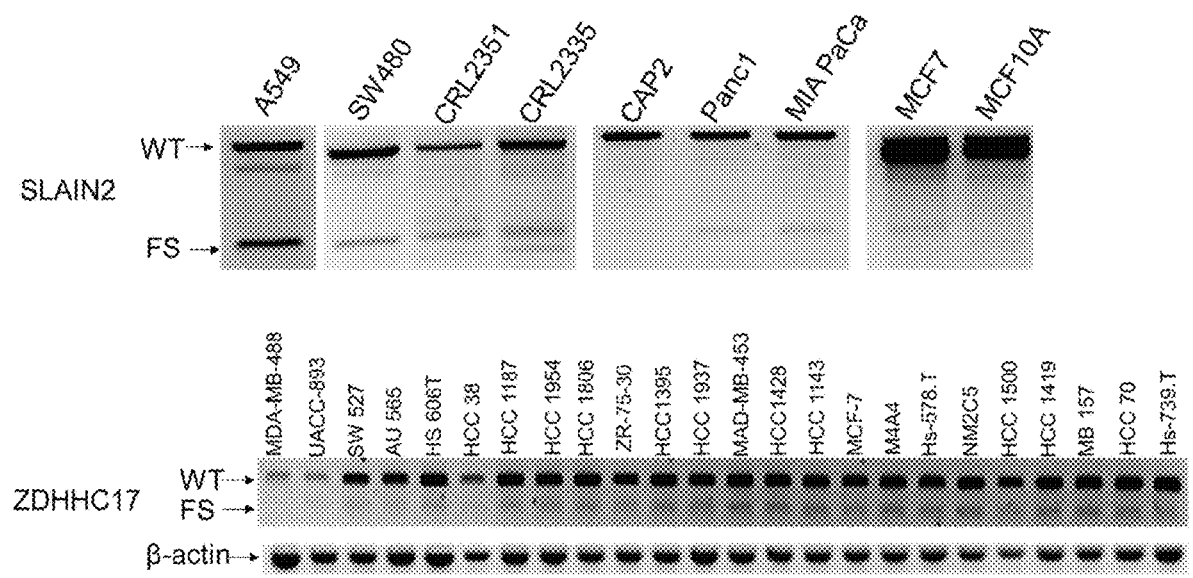
FIG. 5G: shows an RT-PCR analysis of SLAIN2_FS and ZDHHC17_FS in different human tumor cells.
Figure 5H:
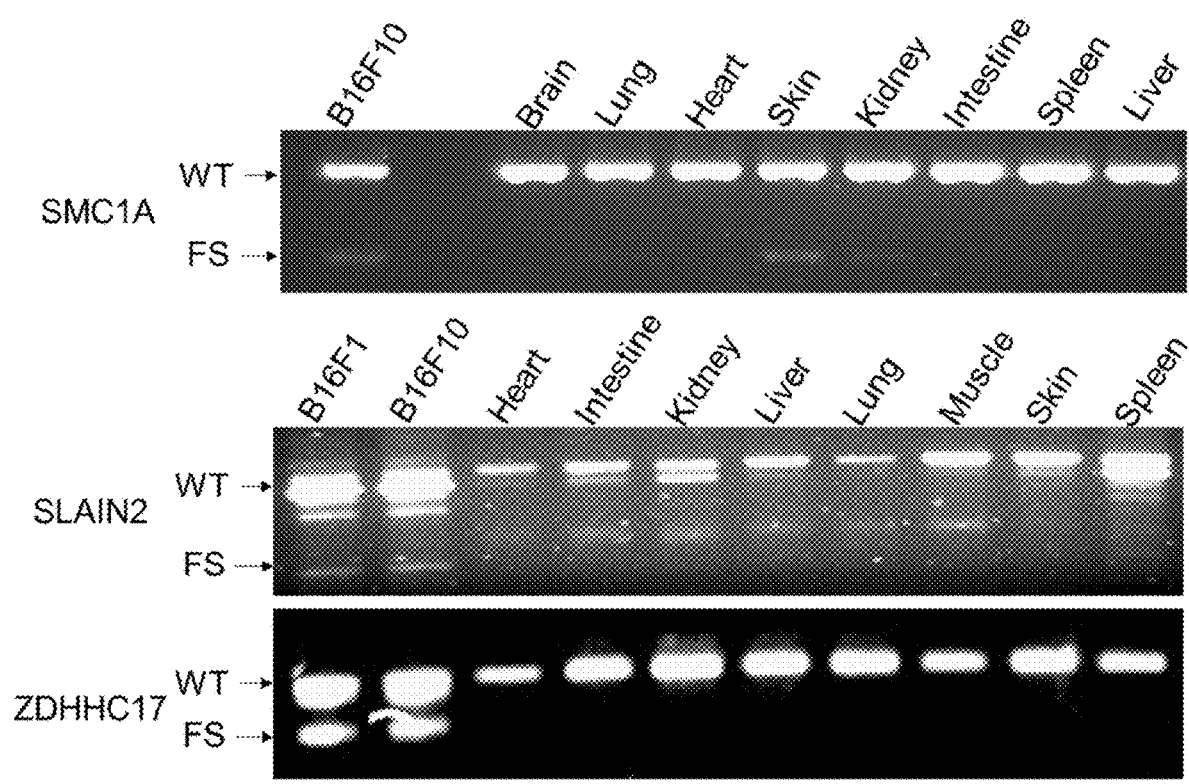
FIG. 5H: shows an RT-PCR analysis of SMC1A_FS, SLAIN_FS and ZDHHC17_FS variants in B16 melanoma cells and normal tissues from C57BL6 mouse.
Figure 6A:
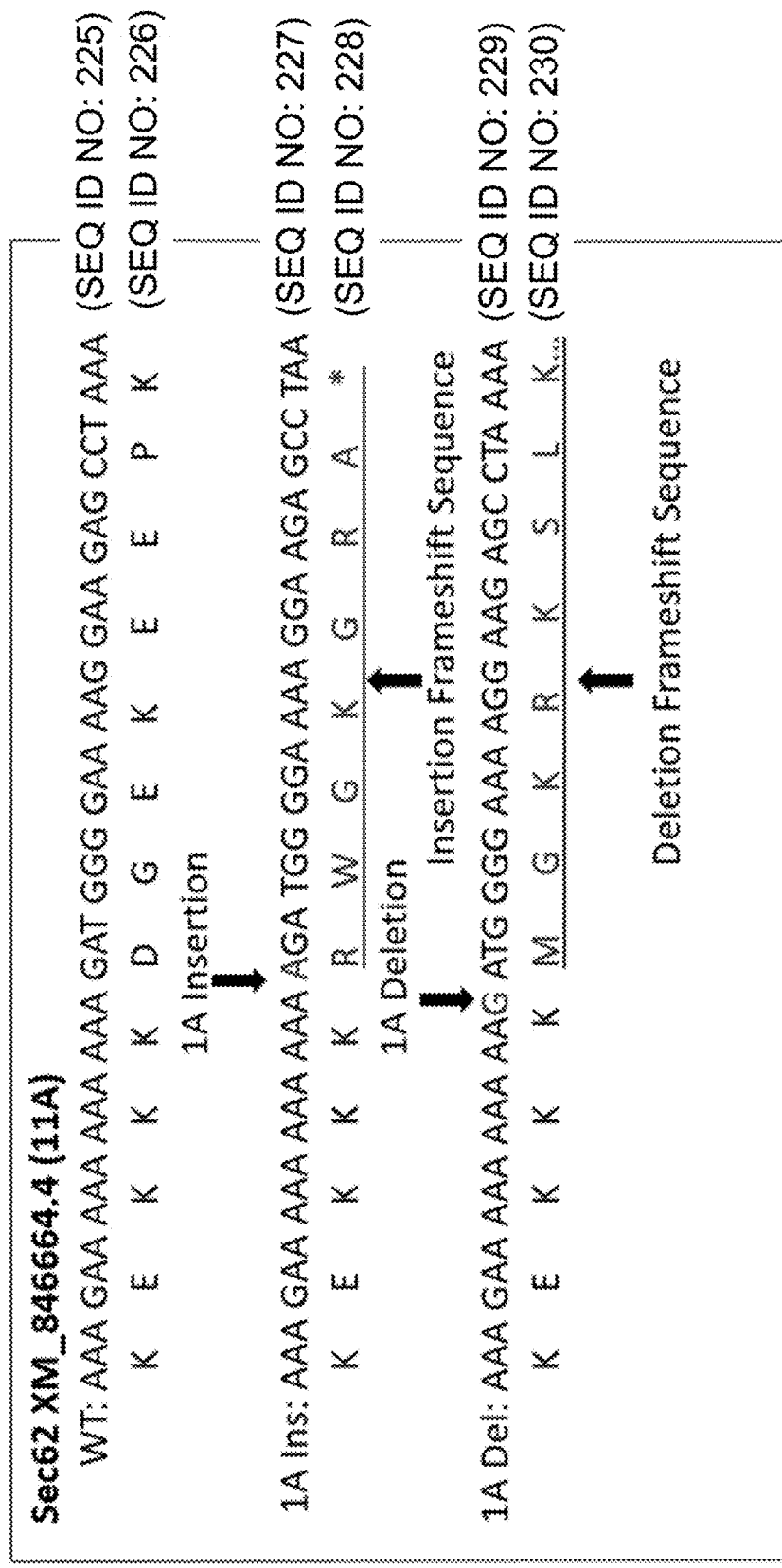
FIGS. 6A-6H: show components of frameshift peptide array and characteristics.
Figure 6B:
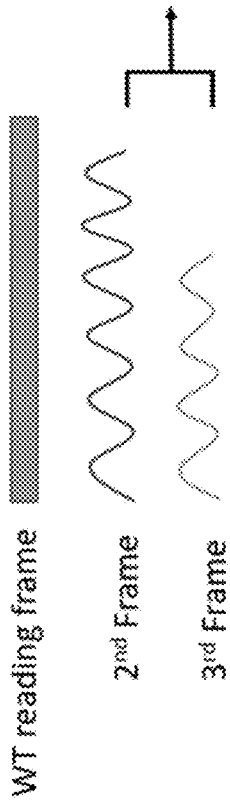
Figure 6C:
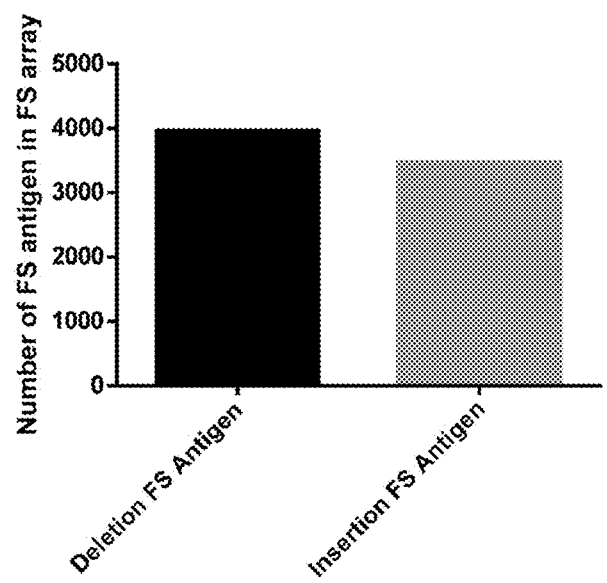
Figure 6D:
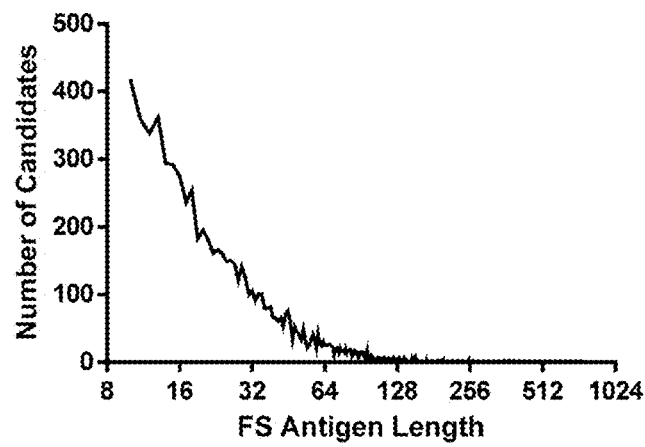
Figure 6E:
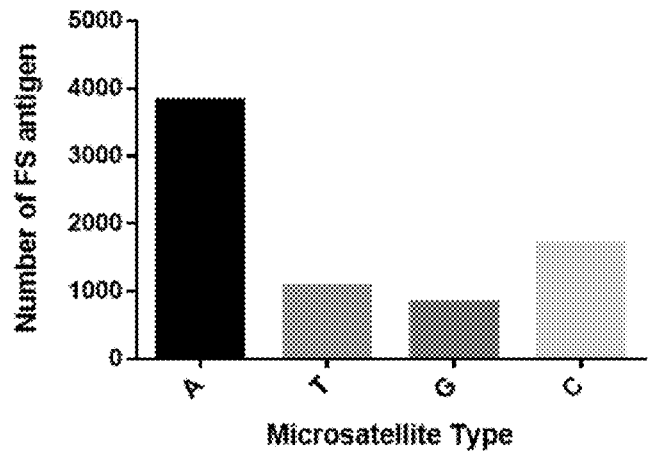
Figure 6F:
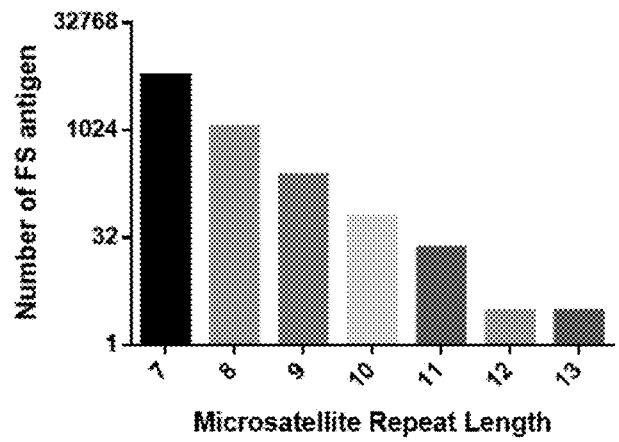
Figure 6G:
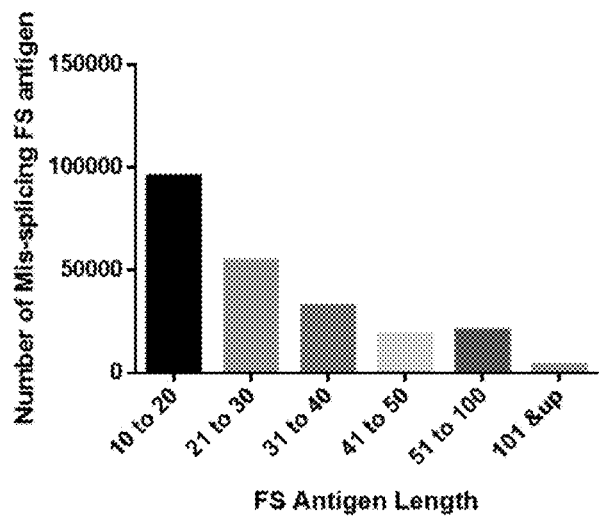
Figure 6H:
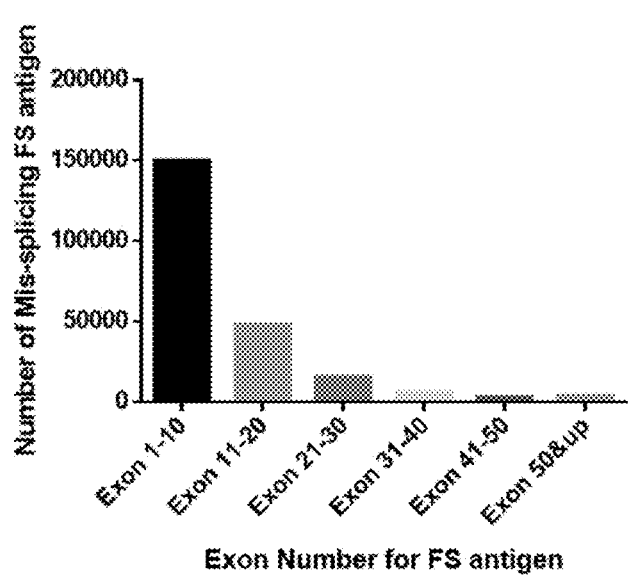

This model makes several specific predictions. First, frequent FS variants in different cancers will be produced by errors in RNA splicing and transcription, not as DNA mutations. As an example of errors in mis-splicing, substantial levels of a FS transcript, SMC1A1^4 (exon 1 to exon 4), from the gene SMC1A in different mouse and human tumors were found (FIGS. 2A, 5A, 5E and 5F). The SMC1A1^4 encodes a 17 amino acids (aa) FS peptide (FIG. 5A). Corresponding exon deletion in the DNA of mouse tumor cell lines was not detected, nor in the 12 TCGA cohorts (N=4730) via Cancer Genomics Browser analysis (data not shown) (46). Quantitative PCR demonstrates more expression of the SMC1A1^4 transcript in breast cancers than normal breast samples (FIG. 2B). To establish an estimate of the frequency of mis-splicing FS variants, 500 clones from a poly A-primed cDNA library of the mouse melanoma cell line, B16F10 were sequenced. Two FS variants SLAIN2_FS and ZDHHC17_FS were identified, which skip exon 7 and 16 respectively (FIGS. 5B and 5C). Table 3 depicts mouse mis-splicing FS antigens in the vaccine. Interestingly, only SLAIN2 was detected in 4T1, a mouse breast tumor cell line (FIG. 5G). The same conserved FS variants were also detected in different human cancers (FIG. 5H). While there were usually more (3-100-fold) frameshift transcripts in mis-splicing of these exons from tumor tissues or cancer cell lines, a low level of frameshift transcripts could be detected in some normal tissues (FIGS. 2B and 5H), which is consistent with the prediction of the model.

Figure 2C:
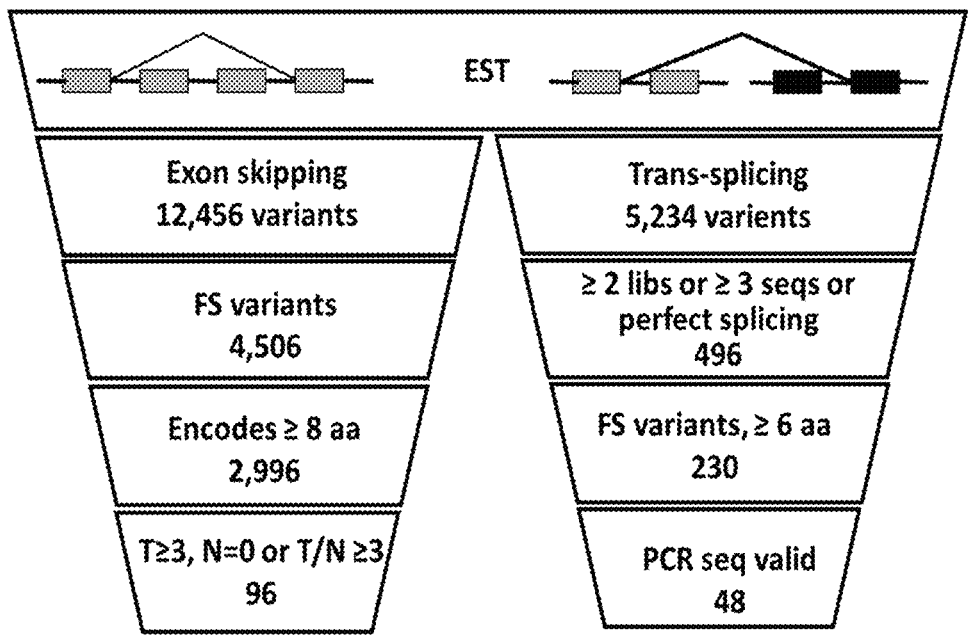
FIG. 2C: shows an analysis of the human EST database for FS variants by exon skipping and trans-splicing.
Figure 2D:
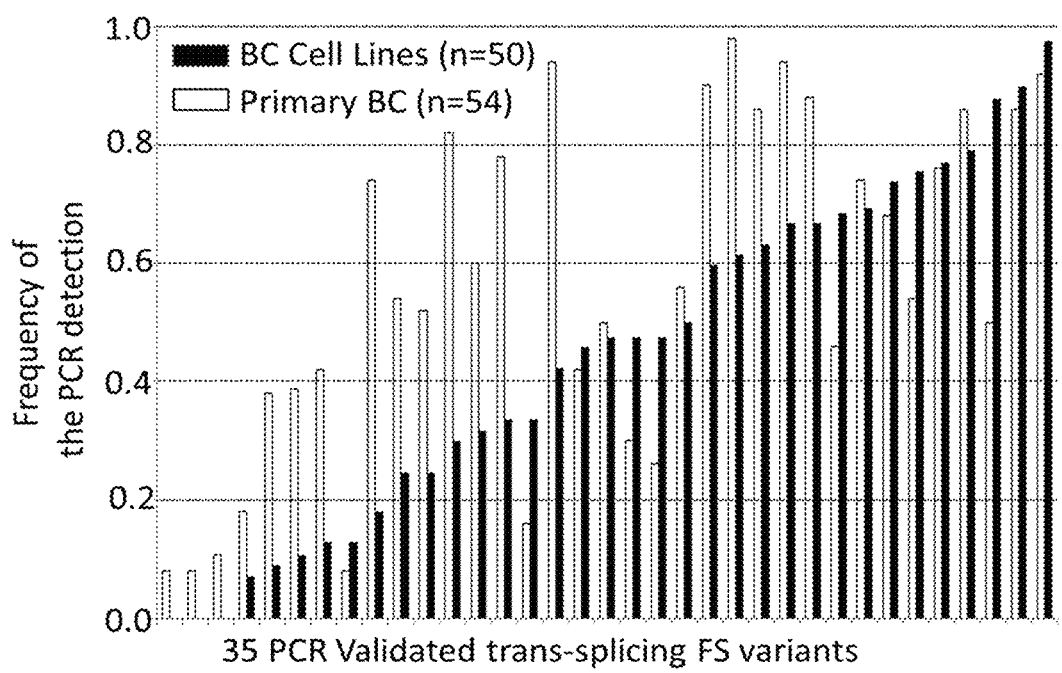
FIG. 2D: shows an analysis of the frequency of the expression of the 35 trans-splicing variants in 50 human breast cancer cell lines and 54 primary human breast tumors.

The analysis of RNA-generated FS variants was expanded by comparing NCBI tumor EST libraries to normal EST libraries. To simplify the analysis, FS variants caused by exon skipping or trans-splicing were focused on, i.e. splicing exons from different genes. A total of 12,456 exon skipping variants and 5,234 trans-splicing variants were found (FIG. 2C). 96 tumor associated FS variants from exon skipping passed the filters described in FIG. 2C, which also encode a FS peptide longer than 7 aa (Table 1). 230 FS trans-splicing variants that encode FS peptides longer than 6 aa were also identified. Primers were designed to screen 220 of these in different pools of cDNAs from 50 human breast cancer cell lines (Table 2) and 48 were successfully validated. Two of these 48 FS variants, BCAS4-BCAS3 and MDS1-EVI1, have been described elsewhere (47, 48). 35 of these 48 FS variants were also found in 54 human primary breast tumors. The frequency of FS variants detected in tumor cell lines or tumor tissue is summarized in FIG. 2D. The expression frequency of these 48 variants range from 2% to 98% in tumor cell lines and primary tumors. Overall, a total of 27 out of 35 variants were expressed in over 50% of 50 tumor cell lines or 54 primary tumors. 12 of 35 variants tested were not detected in three normal tissues.

Figure 2E:
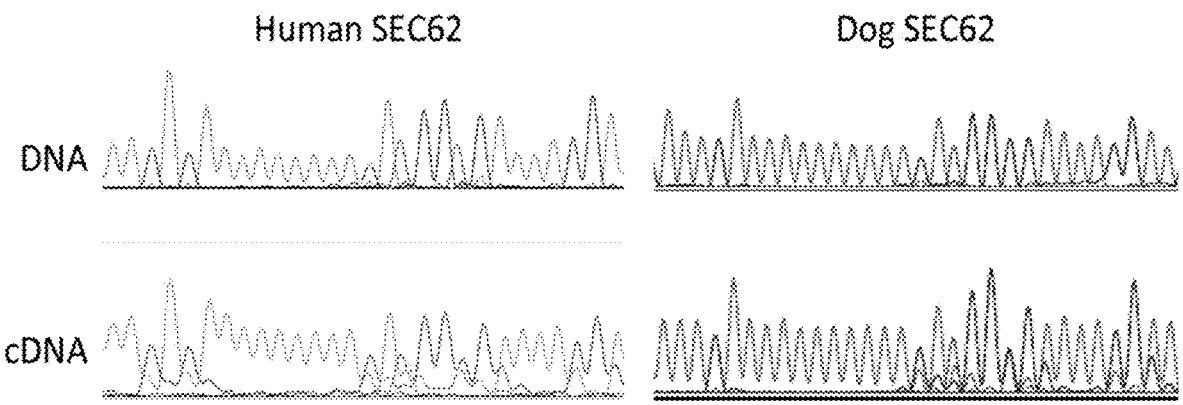
FIG. 2E: is an example of a sequence trace of the MS region in SEC62 dog and human genes in paired DNA/cDNA samples.
Figure 2F:
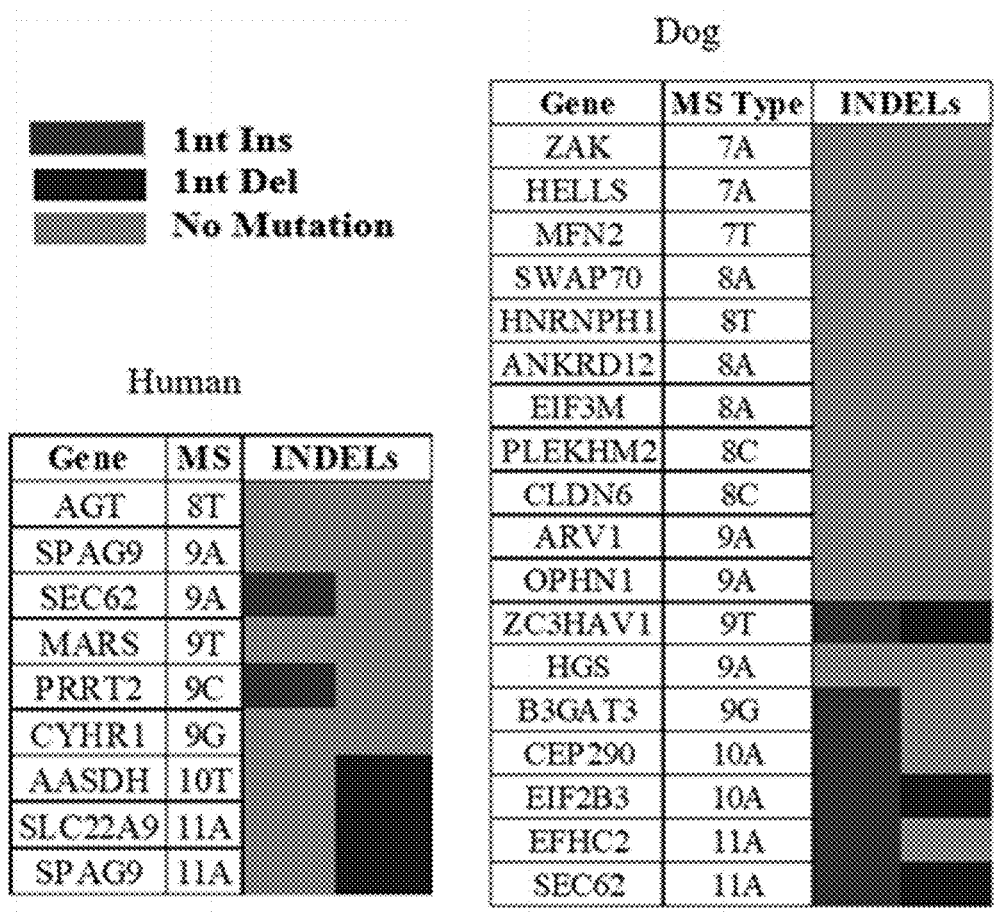
FIG. 2F: shows an ex vivo analysis of the MS INDEL in transcription and translation of the MS INDEL variants. eGFP was fused to the $3^{rd}$ reading frame after 11A MS of SEC62 or after 11 non-MS nucleotides. The eGFP directly fused to 12A MS was the positive control. The three different plasmids were transfected individually into 293T cells and GFP fluorescence was measured 24 hrs after transfection.

Another source of FS transcripts in tumors predicted by embodiments of the model provided herein is INDELs in MSs generated in transcription. As an example, the microsatellite region in the Sec62 gene contains 9 and 11 repeats of Adenine in human and dog, respectively. The sequence of Sec62 and the corresponding INDEL frameshift peptides are shown in FIG. 2A. Human breast cancer cell lines and dog primary tumor tissues from 7 different cancer types were used for sequencing. No INDELs were detected at the genomic level. However, there was a significant level of one A insertion in the cDNA samples from the same tumor for both MSs (FIG. 2E). Two clones with one A insertion and one clone with one A deletion were found in sequencing 15 PCR clones from dog Sec62 cDNA. The INDEL rate was similar as estimated from the PCR sequence trace. 9 human MS candidates and 18 dog MS candidates were further sequenced in cDNA samples from cancer cell lines or primary tumor tissues. INDELs were frequently detected in MS candidates with repeat length of 9 or longer (FIG. 2F). This is consistent with large scale sequencing results in yeast (22). The INDEL rate in transcription for MSs with repeat length of 7, 8 and 9 was very high compared to the genomic mutation rate but was not detected in the PCR sequencing trace due to low sensitivity of the assay. There is no evidence of INDELs in the MS in DNA in published reports except for Microsatellite Instability-High cancer patients with a defective mis-match repair system (15, 49, 50).

Figure 2G:
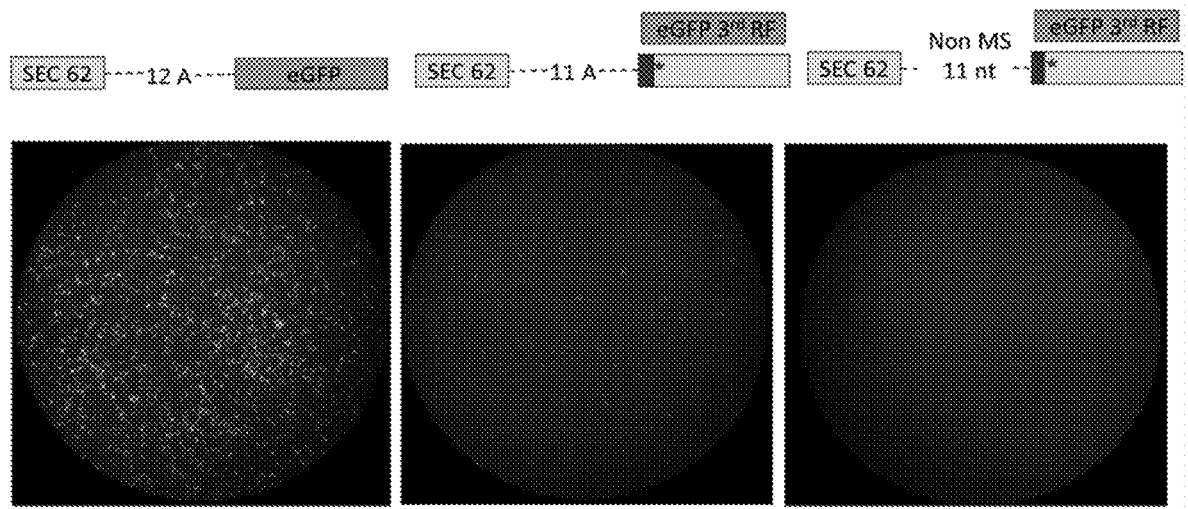
FIG. 2G: shows a FACS analysis of the GFP positive cells.
Figure 2H:
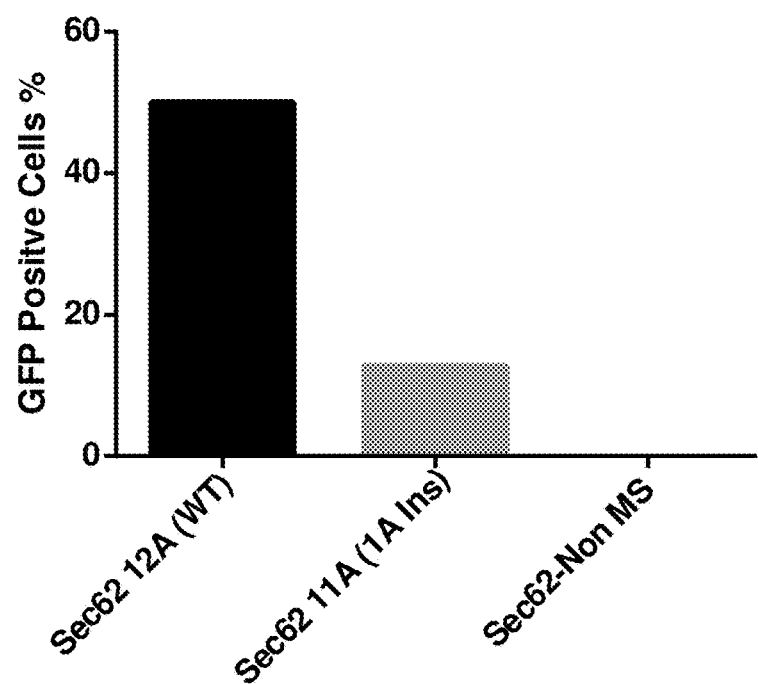
FIG. 2H: is a summary of sequencing results of microsatellite candidates in human (4 breast cancer cell lines) and dog (primary dog tumor tissues)

To further validate the INDELs in the transcription and the translation of the FS peptide, three plasmids based on the dog Sec62 gene were constructed. One has the eGFP fused in the 3$^{rd}$ reading frame to the MS region of 11 A in the dog Sec62 CDS. The eGFP protein will be correctly translated if there is one A insertion during the transcription. The 11 A with 11 nucleotides of non-MS sequence in another plasmid as the negative control was replaced, so there is no MS related INDEL in the transcription and no expression of eGFP. The 11 A with 12A as the positive control was also replaced, so the eGFP is in the 1st reading frame and would be translated with the upstream dog Sec62 gene. (FIG. 2G). Plasmids were transfected into 293T cells. 12.77% of the cells were GFP positive in the first construct which indicates this portion of the cells had 1A insertions at the mRNA level and then successfully translated the FS protein. In contrast, none of cells were GFP positive in the negative control which indicates the MS region was crucial for INDELs (FIG. 2H). This experiment not only shows that the transcription could induce translatable FS variants with the INDELs in the MS region, but also indicates that FS peptides could be globally expressed in cancer cells with the defects in the quality control system.

Example 6: Detection of Antibodies to Frameshift Peptides

The model also predicts that the increased expression of FS variants, combined with other aberrant proteins, would overwhelm the quality control system and could potentially elicit immune responses to these FS peptides. To test this, an array of all possible predicted RNA-defined frameshift peptides was designed, meeting specific qualifications that the tumor cell could produce from INDELs in coding MS and mis-splicing of exons.

There are over 8000 MS in the coding region of the human genome that are runs of 7 or more repeats of homopolymers. The majority of MS regions meeting selection criteria are A runs and the number of MS candidates decreases exponentially as the repeat length or frameshift peptide length criteria increases. Each MS could generate 2 predictable FS peptides depending on whether there was an insertion or deletion. In addition, there are ~200,000 possible FS peptides that could be generated by mis-splicing of exons in the human genome, such as the examples of mis-splicing FSs. Similar to MS FSs, the number of mis-splicing FSs decreases exponentially as the FS peptide length requirement increases. Most of mis-splicing FSs are generated from the first 10 exons of human genes. The restriction of the peptide being longer than 10 amino acids for both sources of FS was applied. By these criteria there are over 220,000 possible FS antigens. Each FS antigen that was longer than 15 aa was divided into 15 aa, non-overlapping peptides. This produced a total of ~400,000 peptides. Peptides that share more than 10 aa identical sequences with any human reference proteins were excluded. Finally, each FS array was designed to contain a total of 392,318 FS peptides (FIG. 3A).

NimbleGen (Roche, Madison, WI) synthesized the FS peptide array, processed the array assay and summarized the IgG signals of each array with their standard protocol (51). The specific IgG reactivities was analyzed to these FSPs in 64 non-cancer control samples and a total of 85 cancers from 5 different late stage cancer types with 17 samples each (LC: lung cancer, BC: breast cancer, GBM: glioblastoma, GC: gastric cancer, PC: pancreatic cancer) and 12 stage I pancreatic cancer samples.

Each array was normalized to its median florescence for analysis. Three patterns of FS feature reactivity that were higher in cancer than non-cancer were found: common reactivity against FS peptides across all 5 cancer types; cancer type specific reactivity and personal reactivity. Reactivity against ~7000 selected peptides are shown in FIG. 3B. Common reactivity and cancer type reactivity in 5 cancer types were marked with black squares. Non-cancer control samples had very low, sporadic reactivity in these FS peptides.

Total reactivity on the 400K arrays was evaluated in the 5 cancer types and non-cancer samples with two methods. The first method compares the number of significant peptides in the cancer and control samples using fold change and p-values. By this method, BC, GC, PC and LC cancer samples had significantly more FS peptides compared to control samples which met the fold change and p-value criteria described in FIG. 3C. The exception is GBM where the reactivity in the controls was higher than the GBM samples. The second method used a scoring method for each FS peptide. A peptide is scored as positive (red) if it is higher than six times the standard deviation (6SD) from the mean value of non-cancers for the peptide. All 5 cancer types had more positive FS peptides than the non-cancer controls (p-value<0.0001, FIG. 3D).

Figure 7A:
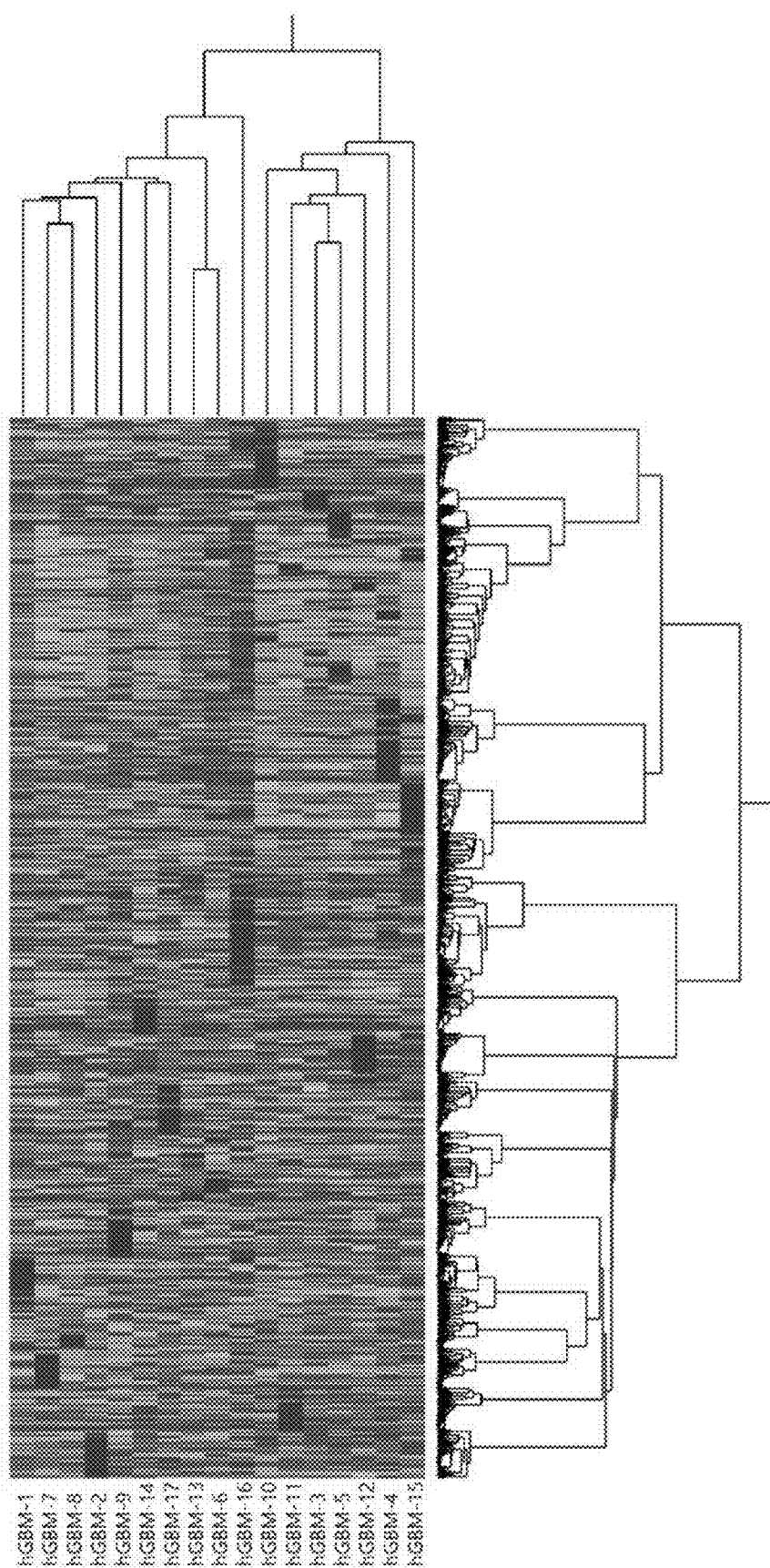
FIGS. 7A-7G: show a personal frameshift response in 4 cancer types.
Figure 7B:
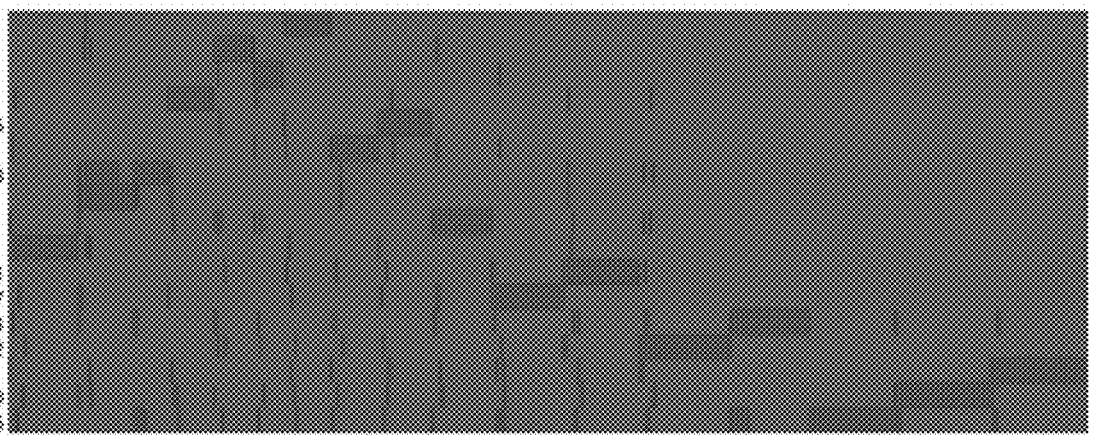
Figure 7C:
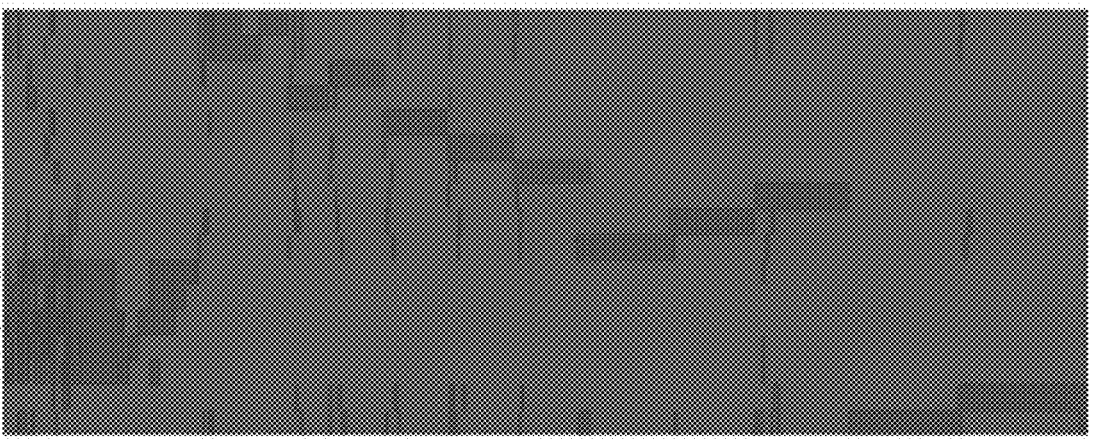
Figure 7D:
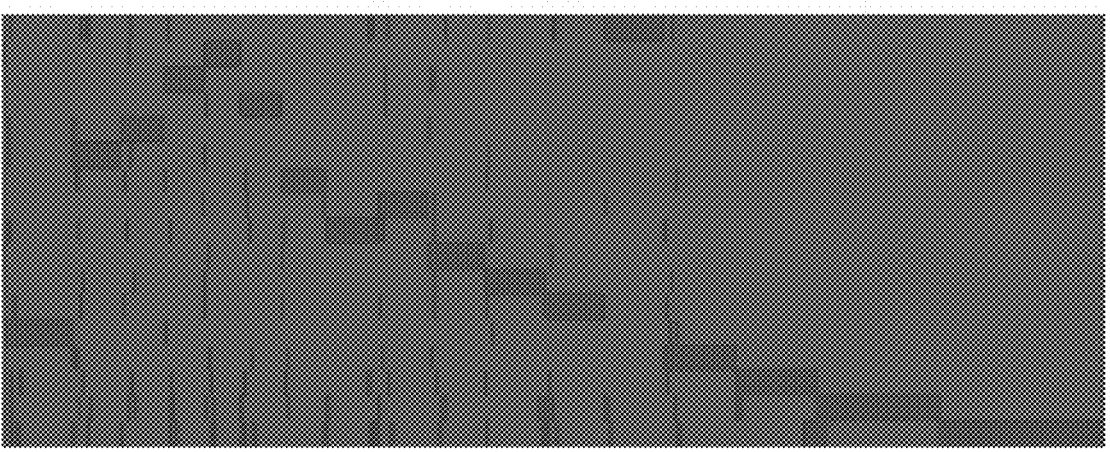
Figure 7E:
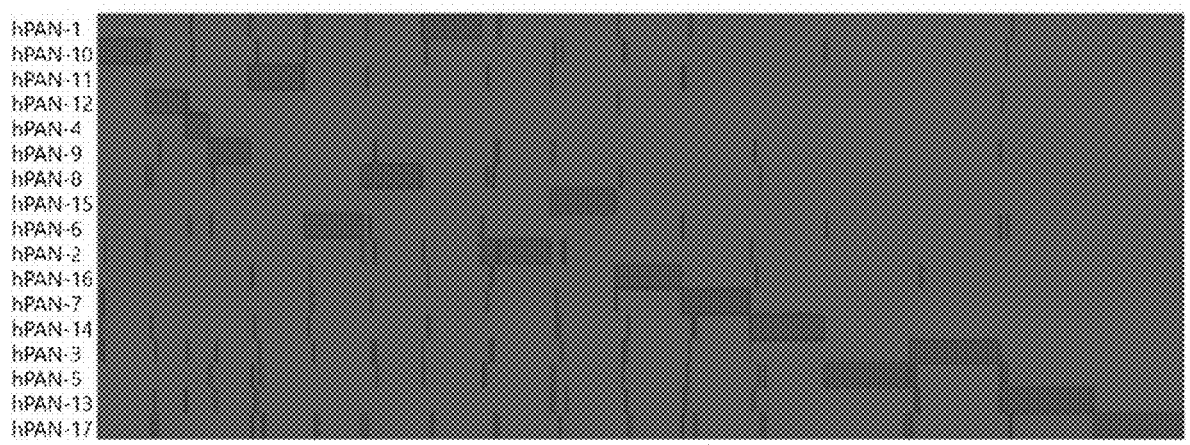
Figure 7F:
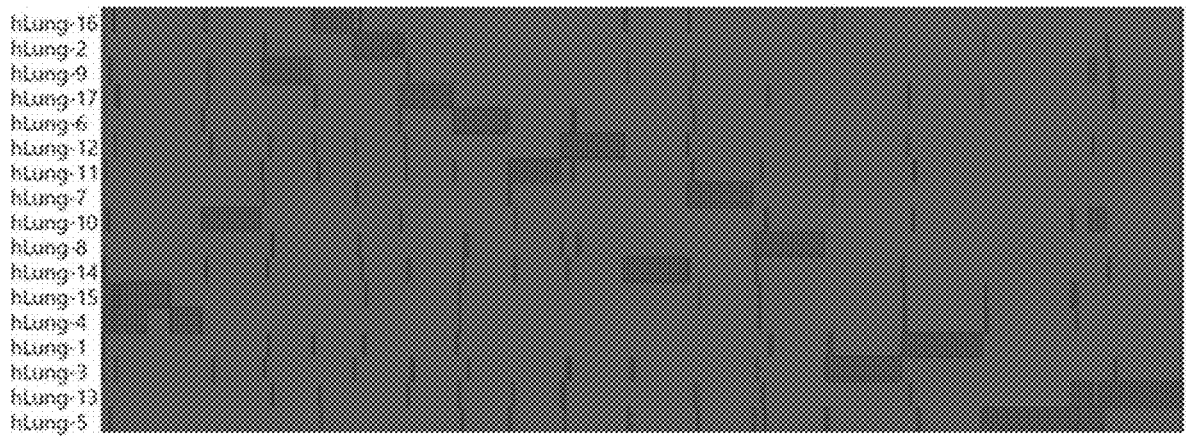
Figure 7G:
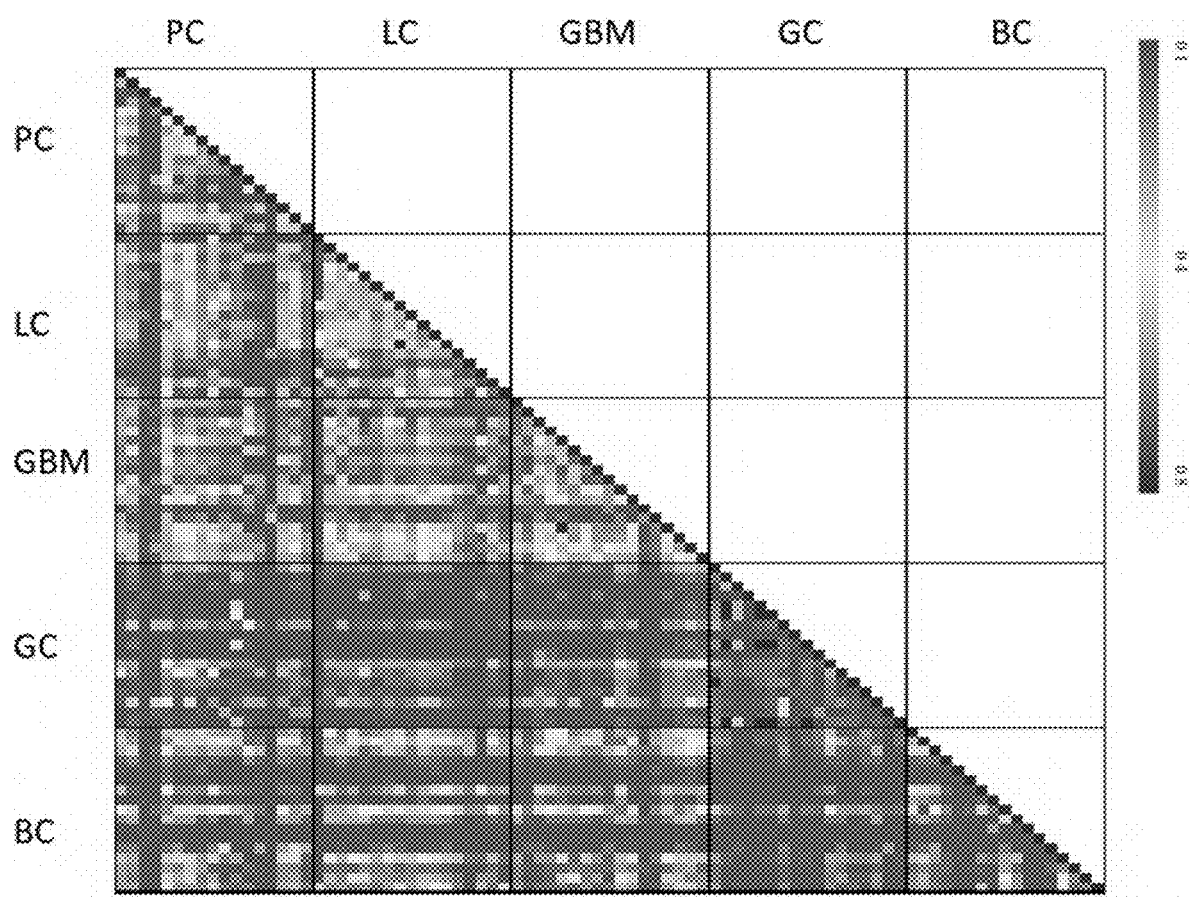

The analysis of individual cancer samples within the same cancer type using the scoring method showed that there were three patterns of reactivity. Most of the positive FS peptides (69%~80%) were personal for that individual. However, 16%~19% of the positive peptides were shared between two samples in that cancer type, with 1.5%~6.9% shared between 3 or more. The distribution of these classes is shown in FIG. 3E. Gastric cancer samples had the highest shared FS response (6.9% were shared in 3 or more). This is consistent with the very high correlation coefficients in several gastric cancer samples (FIG. 7F). Hierarchical clustering results of all positive FS peptides in the 5 cancer types are shown in FIGS. 7A-7G.

Embodiments of the model provided herein predicts that a FS peptide with high antibody reactivity is highly immunogenic and/or highly expressed in the tumor cells. These FS peptides could be cancer vaccine candidates. Analysis of the distribution of positive peptides allows the formulation 3 types of potential vaccines. One type is a personal vaccine. As an example, the personal vaccines for the 17 GBM patients are shown. Each patient had ~5800 positive FS peptides using the 6SD cut-off criterion and ~4500 positive FS peptides being unique for that patient (FIG. 7B). A filter for highest binding signals was applied to choose the 20 top peptides for each patient. These are depicted in FIG. 3F. This same system was applied to each of the other 4 cancer types with similar results (data not shown). It is noteworthy that even though GBM has been found to have a low DNA mutation rate (14), there appear to be an abundance of reactive RNA variant FS peptide for which to create a vaccine.

As noted in FIG. 3B, there were also peptides that were commonly reactive in a cancer type. Based on this analysis a set of peptides could be chosen to optimize the number in common for a particular cancer. This is depicted in FIG. 3G for the 5 tumor types. The top 100 peptides based on the maximum coverage for the particular cancer type were chosen. These vaccine compositions are referred to herein as "focused" vaccines, as it is clear from the FIG. 3G that many of the peptides optimal for a particular cancer are shared across other cancer types.

Finally, it was determined if there were FS peptides that were common across all 5 cancer types that met the p-value and frequency requirements. In FIG. 3H, exemplary 100 candidate FS peptides for a pan-cancer (at least for the 5 considered) vaccine are presented. It has been found that there are extremely few recurrent mutations in the DNA of certain tumors types (49) and with low chance of being immunogenic. In contrast common reactive FS variants can readily be identified.

Figure 3I:
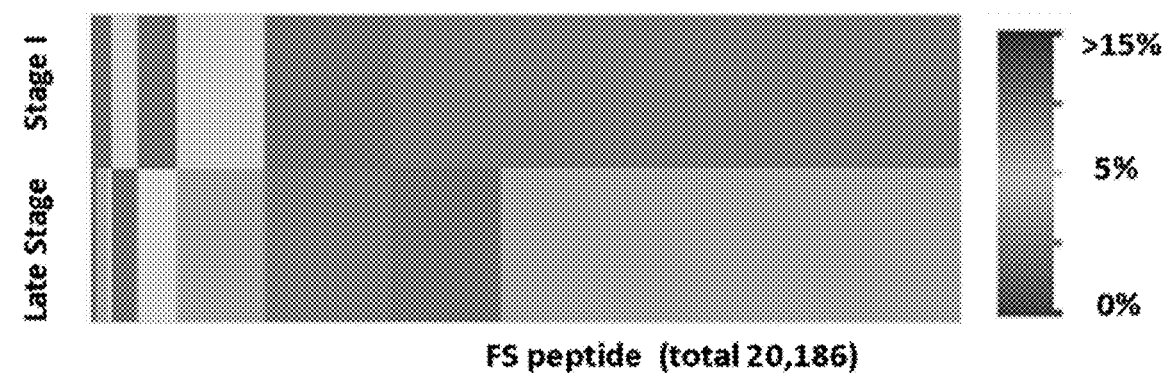

All of the samples used for this analysis were from patients with late stage cancer. Cancer vaccines could also potentially be used for treatment of early stage cancers, and it is unclear whether early and late stage cancer vaccines would require different components. 20,000 most reactive and recurrent peptides were compared to non-cancer for both the late stage and stage 1 pancreatic cancer. As evident in FIG. 3I, most of the peptides did not overlap between the late and early stages of pancreatic cancer. This implies that an early and late stage vaccine would require distinct peptide compositions.

Example 7: Frameshift Peptides Offer Partial Protection as Vaccines

The data presented herein shows that FS variants are present at the RNA level in tumors and that antibody responses to these FS peptides are present in cancer patients. However, the clinically relevant question is whether these FS variants can afford therapeutic value as vaccines, which is explored using mouse tumor models.

It was determined if the SMC1A 1^4 FS peptide confers protection in the B16F10 mouse melanoma cancer model and/or the 4T1 mouse breast cancer model. This FS variant was shown to be common in both human and these mouse tumors (FIGS. 2A, and 5E). The FS peptide was encoded on a plasmid in a standard genetic immunization vector and introduced with a gene gun. $1 \times 10^5$ B16F10 tumor cells were injected and the animals vaccinated 4 weeks later. The tumor volume was monitored and compared to control mice receiving a mock vaccination. As shown in FIG. 4A, the vaccine conferred significant retardation of tumor growth. The SMC1A 1^4 FS immunization also significantly retarded the 4T1 tumor growth in BALB/c mice (FIG. 4B). Depletion of CD8 or CD4 T-cells in the immunized mice indicates that this protection is CD8 T cell dependent (FIG. 4B).

It was tested whether the detection of FS variants in the RNA correlated with protection. The SLAIN2 and ZDHHC17 FSs had been identified in sequencing B16F10 cDNA. The SLAIN2 FS was present in the 4T1 mammary cancer cell line, but ZDHHC17 FS was not (FIG. 5F). When tested as gene vaccines in the mouse tumor injection model of 4T1, SLAIN2-FS conferred tumor retardation but ZDHHC17 did not (FIG. 4C).

The model (FIG. 1) implies that most transcribed genes with MSs in exons will produce FS peptides and these also may confer protection as vaccines. To test this prediction, three MS FSPs were selected based on the peptide size and best predicted H2-D binding epitopes in the mouse MS FS database (FIG. 4D and Table 4). As predicted, each FS neoantigen vaccination significantly retarded the tumor growth compared to the control group (FIG. 4D). Each FS antigen also elicited specific IFN γ releasing splenocytes (FIG. 4E).

Embodiments of the model provided herein also predicts that each tumor cell will present multiple FS neoantigens. These peptides could be presented at low levels as only a fraction of each RNA would be defective. Therefore, multiplexing neoantigens in a vaccine would be predicted to be more protective. To test this prediction, three FS neoantigens were tested individually and pooled together as vaccines in the BALB-NeuT transgenic mouse mammary cancer model. Each FS neoantigen-based vaccine individually showed similar protection by significantly delaying the tumor growth. As predicted, the pooled neoantigen vaccine produced a significant additive increase in delaying tumor initiation and growth (FIG. 4F). This suggests that pooling multiple FS neoantigens will increase efficacy.

Figure 8:
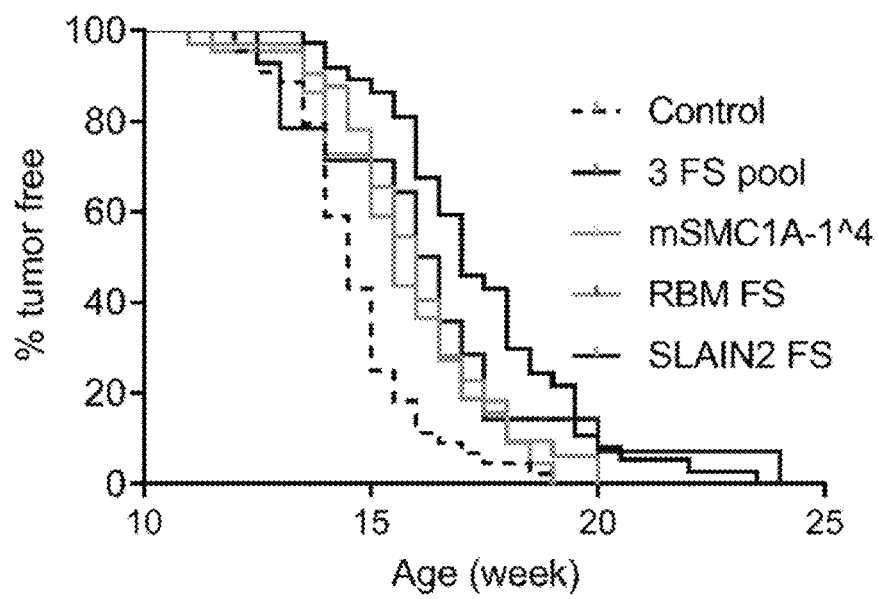
FIG. 8: shows tumor free curve of each FS neo-antigen immunized group in BALB-NeuN mice. BALB-NeuT mice were immunized with individual FS antigens (mSMC1A-1^4, n=32; RBM, n=22; and SLAIN2, n=14) (total n=68), pool of these three FS antigens (n=37) and control group (total n=44), including untreated (n=14) and immunized with control antigens (n=30). All of the mice were immunized with the same regime as in FIG. 4D. Detail immunization regime see the method. Control vs. each of individual FS group, p<0.05; 3FS pool vs. mSMC1A-1^4 or RBM FS, p 50.005; 3FS pool vs. SLAIN2, p=0.43. All statistical analysis were with Mantal-Cox test. Detail immunization regimes were described in the methods.
Figure 9:
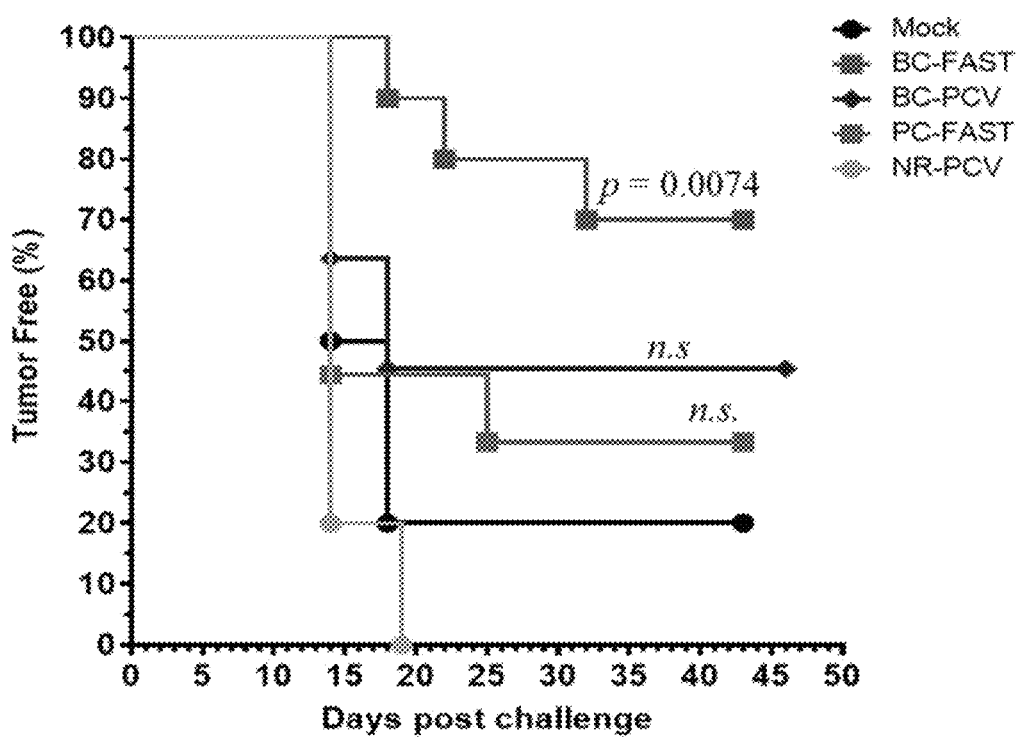
FIG. 9: shows pooled FS vaccines are more protective than personal vaccines. Mouse 4T1 model was used to test pooled FS peptides as vaccines relative to personal vaccines used in the field. Pooled vaccines were made to 4T1 based on screening 30 mice injected with 4T1 and assayed on the FS arrays (BC-FAST). Personal vaccines also made to each mouse injected with 4T1 (BC-PCV) or a pancreatic tumor line (PC-FAST). As shown the BC-FAST vaccine was more protective than the personal vaccines.
Figure 10:
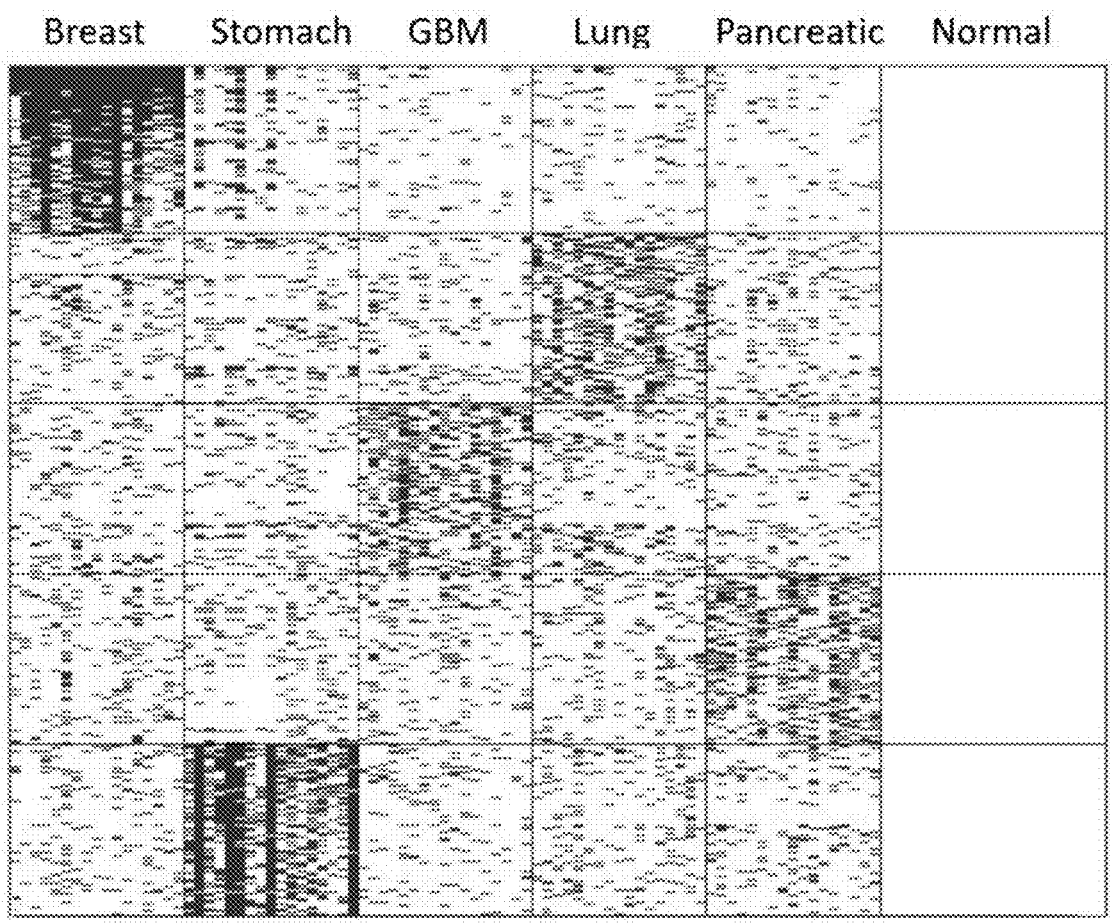
FIG. 10: shows pooled FSP vaccines can be constructed for any tumor in humans. The blood of 15 to 17 individuals with one of the 5 designated cancers, including breast, stomach, glioblastoma (GBM), lung, and pancreatic, were screened on FSP arrays to determine reactivity. High reactivity relative to non-cancer individuals is designated by a bars. The 100 most recurrently reactive peptides for each cancer are shown.

Furthermore, as shown in FIGS. 8 and 9, pooled FS vaccines have increased efficacy compared to personal vaccines. Specifically, a mouse 4T1 model was used to test pooled FS peptides as vaccines relative to personal vaccines used in the field. Pooled vaccines were made to 4T1 based on screening 30 mice injected with 4T1 and assayed on the FS arrays (BC-FAST). Personal vaccines also made to each mouse injected with 4T1 (BC-PCV) or a pancreatic tumor line (PC-FAST). As shown the BC-FAST vaccine was more protective than the personal vaccines (FIG. 9). In addition, pooled FS vaccines can be constructed for any tumor in humans (FIG. 10). The blood of 15 to 17 individuals with one of the 5 designated cancers, including breast, stomach, glioblastoma (GBM), lung, and pancreatic, were screened on FSP arrays to determine reactivity. High reactivity relative to non-cancer individuals is designated by a bars. The 100 most recurrently reactive peptides for each cancer are shown.

REFERENCES

1. J. W. Riess, P. N. Lara, Jr., D. R. Gandara, Theory Meets Practice for Immune Checkpoint Blockade in Small-Cell Lung Cancer. *J Clin Oncol*, (2016).
2. D. Schadendorf et al., Pooled Analysis of Long-Term Survival Data From Phase II and Phase III Trials of Ipilimumab in Unresectable or Metastatic Melanoma. *J Clin Oncol* 33, 1889-1894 (2015).
3. R. J. Motzer et al., Nivolumab versus Everolimus in Advanced Renal-Cell Carcinoma. *N Engl J Med* 373, 1803-1813 (2015).
4. E. B. Garon et al., Pembrolizumab for the treatment of non-small-cell lung cancer. *N Engl J Med* 372, 2018-2028 (2015).
5. J. Larkin et al., Combined Nivolumab and Ipilimumab or Monotherapy in Untreated Melanoma. *N Engl J Med* 373, 23-34 (2015).
6. A. M. Goodman et al., Tumor Mutational Burden as an Independent Predictor of Response to Immunotherapy in Diverse Cancers. *Mol Cancer Ther* 16, 2598-2608 (2017).
7. S. Turajlic et al., Insertion-and-deletion-derived tumour-specific neoantigens and the immunogenic phenotype: a pan-cancer analysis. *Lancet Oncol* 18, 1009-1021 (2017).
8. N. A. Rizvi et al., Cancer immunology. Mutational landscape determines sensitivity to PD-1 blockade in non-small cell lung cancer. *Science* 348, 124-128 (2015).
9. S. Bae, J. Tie, J. Desai, P. Gibbs, Microsatellite instability status is critical to analysis of survival in stage II colon cancer. *J Clin Oncol* 30, 675-676; author reply 676-677 (2012).
10. K. Bauer et al., T cell responses against microsatellite instability-induced frameshift peptides and influence of regulatory T cells in colorectal cancer. *Cancer Immunol Immunother* 62, 27-37 (2013).
11. J. C. Dudley, M. T. Lin, D. T. Le, J. R. Eshleman, Microsatellite Instability as a Biomarker for PD-1 Blockade. *Clin Cancer Res* 22, 813-820 (2016).
12. R. H. Vonderheide, K. L. Nathanson, Immunotherapy at large: the road to personalized cancer vaccines. *Nat Med* 19, 1098-1100 (2013).
13. A. Vitiello, M. Zanetti, Neoantigen prediction and the need for validation. *Nat Biotechnol* 35, 815-817 (2017).
14. Z. R. Chalmers et al., Analysis of 100,000 human cancer genomes reveals the landscape of tumor mutational burden. *Genome Med* 9, 34 (2017).
15. B. Vogelstein et al., Cancer genome landscapes. *Science* 339, 1546-1558 (2013).
16. P. A. Ott et al., An immunogenic personal neoantigen vaccine for patients with melanoma. *Nature* 547, 217-221 (2017).
17. U. Sahin et al., Personalized RNA mutanome vaccines mobilize poly-specific therapeutic immunity against cancer. *Nature* 547, 222-226 (2017).
18. T. R. Hodges et al., Mutational burden, immune checkpoint expression, and mismatch repair in glioma: implications for immune checkpoint immunotherapy. *Neuro Oncol* 19, 1047-1057 (2017).
19. A. C. Filley, M. Henriquez, M. Dey, Recurrent glioma clinical trial, CheckMate-143: the game is not over yet. *Oncotarget* 8, 91779-91794 (2017).
20. C. Kandoth et al., Mutational landscape and significance across 12 major cancer types. *Nature* 502, 333-339 (2013).
21. D. Hanahan, R. A. Weinberg, Hallmarks of cancer: the next generation. *Cell* 144, 646-674 (2011).

22. J. F. Gout et al., The landscape of transcription errors in eukaryotic cells. *Sci Adv* 3, e1701484 (2017).
23. N. A. O'Leary et al., Reference sequence (RefSeq) database at NCBI: current status, taxonomic expansion, and functional annotation. *Nucleic Acids Res* 44, D733-745 (2016).
24. A. Untergasser et al., Primer3Plus, an enhanced web interface to Primer3. *Nucleic Acids Res* 35, W71-74 (2007).
25. K. D. Pruitt et al., The consensus coding sequence (CCDS) project: Identifying a common protein-coding gene set for the human and mouse genomes. *Genome Res* 19, 1316-1323 (2009).
26. K. F. Sykes, S. A. Johnston, Genetic live vaccines mimic the antigenicity but not pathogenicity of live viruses. *DNA Cell Biol* 18, 521-531 (1999).
27. R. S. Chambers, S. A. Johnston, High-level generation of polyclonal antibodies by genetic immunization. *Nat Biotechnol* 21, 1088-1092 (2003).
28. D. T. Hansen et al., Polyclonal Antibody Production for Membrane Proteins via Genetic Immunization. *Sci Rep* 6, 21925 (2016).
29. G. C. Whitlock et al., Protective antigens against glanders identified by expression library immunization. *Front Microbiol* 2, 227 (2011).
30. S. A. Svarovsky, M. J. Gonzalez-Moa, M. D. Robida, A. Y. Borovkov, K. Sykes, Self-assembled micronanoplexes for improved biolistic delivery of nucleic acids. *Mol Pharm* 6, 1927-1933 (2009).
31. A. Borovkov et al., New classes of orthopoxvirus vaccine candidates by functionally screening a synthetic library for protective antigens. *Virology* 395, 97-113 (2009).
32. J. F. Gout, W. K. Thomas, Z. Smith, K. Okamoto, M. Lynch, Large-scale detection of in vivo transcription errors. *Proc Natl Acad Sci USA* 110, 18584-18589 (2013).
33. B. Schwanhausser et al., Global quantification of mammalian gene expression control. *Nature* 473, 337-342 (2011).
34. M. Imashimizu, T. Oshima, L. Lubkowska, M. Kashlev, Direct assessment of transcription fidelity by high-resolution RNA sequencing. *Nucleic Acids Res* 41, 9090-9104 (2013).
35. H. S. Zaher, R. Green, Fidelity at the molecular level: lessons from protein synthesis. *Cell* 136, 746-762 (2009).
36. S. Lykke-Andersen, T. H. Jensen, Nonsense-mediated mRNA decay: an intricate machinery that shapes transcriptomes. *Nat Rev Mol Cell Biol* 16, 665-677 (2015).
37. A. Ruggiano, O. Foresti, P. Carvalho, Quality control: ER-associated degradation: protein quality control and beyond. *J Cell Biol* 204, 869-879 (2014).
38. J. E. Bradner, D. Hnisz, R. A. Young, Transcriptional Addiction in Cancer. *Cell* 168, 629-643 (2017).
39. S. C. Lee, O. Abdel-Wahab, Therapeutic targeting of splicing in cancer. *Nat Med* 22, 976-986 (2016).
40. T. I. Lee, R. A. Young, Transcriptional regulation and its misregulation in disease. *Cell* 152, 1237-1251 (2013).
41. S. Oltean, D. O. Bates, Hallmarks of alternative splicing in cancer. *Oncogene* 33, 5311-5318 (2014).
42. S. Negrini, V. G. Gorgoulis, T. D. Halazonetis, Genomic instability—an evolving hallmark of cancer. *Nat Rev Mol Cell Biol* 11, 220-228 (2010).
43. C. Y. Lin et al., Transcriptional amplification in tumor cells with elevated c-Myc. *Cell* 151, 56-67 (2012).
44. D. Silvera, S. C. Formenti, R. J. Schneider, Translational control in cancer. *Nat Rev Cancer* 10, 254-266 (2010).
45. P. L. Lollini et al., Vaccines and other immunological approaches for cancer immunoprevention. *Curr Drug Targets* 12, 1957-1973 (2011).
46. M. Goldman et al., The UCSC Cancer Genomics Browser: update 2015. *Nucleic Acids Res* 43, D812-817 (2015).
47. C. A. Maher et al., Transcriptome sequencing to detect gene fusions in cancer. *Nature* 458, 97-101 (2009).
48. C. A. Maher et al., Chimeric transcript discovery by paired-end transcriptome sequencing. *Proc Natl Acad Sci USA* 106, 12353-12358 (2009).
49. M. T. Chang et al., Identifying recurrent mutations in cancer reveals widespread lineage diversity and mutational specificity. *Nat Biotechnol* 34, 155-163 (2016).
50. R. J. Hause, C. C. Pritchard, J. Shendure, S. J. Salipante, Classification and characterization of microsatellite instability across 18 cancer types. *Nat Med* 22, 1342-1350 (2016).
51. B. Forsstrom et al., Proteome-wide epitope mapping of antibodies using ultra-dense peptide arrays. *Mol Cell Proteomics* 13, 1585-1597 (2014).
52. M. Sade-Feldman et al., Resistance to checkpoint blockade therapy through inactivation of antigen presentation. *Nat Commun* 8, 1136 (2017).
53. M. D. Vesely, R. D. Schreiber, Cancer immunoediting: antigens, mechanisms, and implications to cancer immunotherapy. *Ann N Y Acad Sci* 1284, 1-5 (2013).
54. D. T. Le et al., Mismatch repair deficiency predicts response of solid tumors to PD-1 blockade. *Science* 357, 409-413 (2017).
55. D. T. Le et al., PD-1 Blockade in Tumors with Mismatch-Repair Deficiency. *N Engl J Med* 372, 2509-2520 (2015).
56. A. Kahles et al., Comprehensive Analysis of Alternative Splicing Across Tumors from 8,705 Patients. *Cancer Cell* 34, 211-224 e216 (2018).
57. A. C. Smart et al., Intron retention is a source of neoepitopes in cancer. *Nat Biotechnol* 36, 1056-1058 (2018).
58. S. D. Martin et al., Low Mutation Burden in Ovarian Cancer May Limit the Utility of Neoantigen-Targeted Vaccines. *PLoS One* 11, e0155189 (2016).
59. T. N. Schumacher, R. D. Schreiber, Neoantigens in cancer immunotherapy. *Science* 348, 69-74 (2015).
60. T. Kimura et al., MUC1 vaccine for individuals with advanced adenoma of the colon: a cancer immunoprevention feasibility study. *Cancer Prev Res (Phila)* 6, 18-26 (2013).
61. L. A. Vella et al., Healthy individuals have T-cell and antibody responses to the tumor antigen cyclin B1 that when elicited in mice protect from cancer. *Proc Natl Acad Sci USA* 106, 14010-14015 (2009).
62. D. W. Cramer et al., Conditions associated with antibodies against the tumor-associated antigen MUC1 and their relationship to risk for ovarian cancer. *Cancer Epidemiol Biomarkers Prev* 14, 1125-1131 (2005).
63. P. Stafford et al., Physical characterization of the "immunosignaturing effect". *Mol Cell Proteomics* 11, M111 011593 (2012).
64. G. P. Dunn, A. T. Bruce, H. Ikeda, L. J. Old, R. D. Schreiber, Cancer immunoediting: from immunosurveillance to tumor escape. *Nat Immunol* 3, 991-998 (2002).
65. D. B. Keskin et al., Neoantigen vaccine generates intratumoral T cell responses in phase Ib glioblastoma trial. *Nature* 565, 234-239 (2019).

66. S. Kreiter et al., Mutant MHC class II epitopes drive therapeutic immune responses to cancer. *Nature* 520, 692-696 (2015).

67. C. Linnemann et al., High-throughput epitope discovery reveals frequent recognition of neo-antigens by CD4+ T cells in human melanoma. *Nat Med* 21, 81-85 (2015).

TABLE 1

| RefSeq_ID | Encode FS peptides | Joint_pos | #Total_EST | EST_Ids | #Total_Lib | #Tumor_lib | #Normal_lib |
|---|---|---|---|---|---|---|---|
| NM_001640.3 | SPSQAMWATRM (SEQ ID NO: 22) | 1940-2047 | 7 | 14679393, 16524005, 18802412, 18807797, 19365353, 19366001, 33261912, | 3 | 3 | 0 |
| NM_199002.1 | GVGGGILPPETP PVSAWGELCPP AWLHL (SEQ ID NO: 23) | 2623-2788 | 3 | 10264060, 19733507, 23301501, | 3 | 3 | 0 |
| NM_014154.2 | RHEKCCNWKQ QAESQSHCFRS CSKIVVLASARN LKHRAEN (SEQ ID NO: 24) | 370-448 | 5 | 20492217, 22518928, 45367569, 146009855, 146104793, | 3 | 3 | 0 |
| NM_001686.3 | TTNPSRISLPSW VWMNFLRKTS (SEQ ID NO: 25) | 1183-1398 | 4 | 11106585, 12431398, 19143008, 20486863, | 4 | 3 | 1 |
| NM_004217.2 | DHGGVGRCSNV LPWEEGDSQRH KARKSALRAQG RAEDC (SEQ ID NO: 26) | 317-599 | 3 | 10342556, 14654109, 22671315, | 3 | 3 | 0 |
| NM_016561.2 | WSCSSITGAAG NLNTTSWSTRL WPNGRRKKLSS GWSSWALGHLF TGKGFYLNE (SEQ ID NO: 27) | 545-751 | 6 | 19376801, 28113628, 45652559, 47036548, 52114251, 52114353, | 4 | 3 | 1 |
| NM_024808.2 | FSLKMSSYPLLG LIMKGNSFHNVI PVNALT (SEQ ID NO: 28) | 379-426 | 4 | 9808442, 17166915, 146059308, 146063843, | 4 | 3 | 0 |
| NM_013265.2 | PCTGLSLHPMA PRIWSRWSFPA GRCQDRPNKHV WPPQKKKKKK KKKKK (SEQ ID NO: 29) | 2168-2397 | 4 | 4311385, 46230323, 46834109, 47020765, | 4 | 4 | 0 |
| NM_020314.5 | GSADRDDGKV (SEQ ID NO: 30) | 1339-1540 | 4 | 8407623, 9889142, 10213802, 80934926, | 4 | 3 | 1 |
| NM_018553.3 | CYQHPFPKKSQ FPGAYWTSFEG EEEGSGQLTLPGP (SEQ ID NO: 31) | 1845-2308 | 3 | 8618242, 14448310, 14469670, | 3 | 3 | 0 |
| NM_134447.1 | GFAASWLFKKP RPSECHTVIFKE ESYMN (SEQ ID NO: 32) | 1419-2068 | 20 | 2111082, 3151384, 3405187, 3801503, 5395116, 5446288, 5636075, 6451167, 7152982, 7319964, 8634237, | 18 | 12 | 4 |

TABLE 1-continued

| RefSeq_ID | Encode FS peptides | Joint_pos | #Total_EST | EST_Ids | #Total_Lib | #Tumor_lib | #Normal_lib |
|---|---|---|---|---|---|---|---|
| | | | | 8634238, 19587294, 19753219, 21251126, 23295375, 24791739, 24792974, 154727570, 154730372, | | | |
| NM_152266.3 | DAAFFMSPKLI WWQEMATERG LFGLEIPIILKEL (SEQ ID NO: 33) | 224-283 | 4 | 10744663, 11064241, 22668651, 32210516, | 4 | 3 | 1 |
| NM_080571.1 | CFTSSPLRW (SEQ ID NO: 34) | 241-360 | 7 | 12272400, 20501581, 22824741, 45697997, 46272730, 146043981, 146121376, | 7 | 4 | 0 |
| NM_178448.3 | RVQGTLVHCPT RHLSQRRGPGR QRGNSLPEPSS MLTCPQQPHRA TFPAAPGLQGCP RTGPSQPSMQL PSYPEDGSGLSR GHKDVRPGPPG QERVQVLRACA PQPQHQVDCSA VGGPVAAREKP PVSRLGSAHQG LPTSAFEGACH ALGDPGIFTGLE AGDRTVSVPG (SEQ ID NO: 35) | 2485-2522 | 4 | 10217199, 13329041, 14652514, 71054789, | 4 | 3 | 1 |
| NM_000070.2 | CLQKHLPVALS TSLC (SEQ ID NO: 36) | 2741-3083 | 3 | 2222976, 4124403, 7038190, | 3 | 3 | 0 |
| NM_032830.2 | MTSLLSSHHPLK RRNLEP (SEQ ID NO: 37) | 1977-2102 | 13 | 1720716, 2269339, 4332045, 5397085, 5638770, 5769282, 7317235, 11450365, 13719026, 13734654, 24787788, 24808260, 45860690, | 9 | 6 | 2 |
| NM_032830.2 | LLSSHHPLKRRN LEP (SEQ ID NO: 38) | 1986-2111 | 4 | 13908790, 18392074, 46257227, 92180377, | 4 | 3 | 0 |
| NM_001040648.1 | TSASQIQAILVP (SEQ ID NO: 39) | 1865-2258 | 3 | 4630123, 4899627, 5676137, | 3 | 3 | 0 |
| NM_001161452.1 | LLLQLRPGSRPF PVTYVSVTGRQ PYKSW (SEQ ID NO: 40) | 889-1669 | 4 | 1940552, 3933437, 13402321, 14509526, | 4 | 4 | 0 |
| NM_001039712.1 | AAAAAHHHSPR PAALRHPQEET GCVP (SEQ ID NO: 41) | 225-429 | 3 | 13914233, 21175318, 45699401, | 3 | 3 | 0 |

TABLE 1-continued

| RefSeq_ID | Encode FS peptides | Joint_pos | #Total_EST | EST_Ids | #Total_Lib | #Tumor_lib | #Normal_lib |
|---|---|---|---|---|---|---|---|
| NM_015954.2 | LLQPPFVFIPPGCVML (SEQ ID NO: 42) | 263-412 | 5 | 10202290, 11101998, 13284397, 15434305, 52108714, | 5 | 3 | 1 |
| NM_213566.1 | SPKLPLVRRWMQ (SEQ ID NO: 43) | 540-731 | 3 | 9183529, 10729953, 13583484, | 3 | 3 | 0 |
| NM_001384.4 | LPCSSLTSYWEMLWLWLHDWRRRQGQRCSFWVTQPTAAAAWMCWVLSKLELRLSYILALPA (SEQ ID NO: 44) | 292-345 | 9 | 9141503, 9341726, 9720673, 11614383, 12102395, 13326770, 22703054, 22813642, 56794883, | 7 | 6 | 1 |
| NM_130443.2 | HFPACQLLPLCDLISSALPYVE (SEQ ID NO: 45) | 2342-2439 | 4 | 6594041, 6974193, 24809933, 31153484, | 4 | 3 | 0 |
| NM_001402.5 | CLQNWWYWYCSCWPSGDWCSQTRYGGHLCSSQRYNGSKICRNAP (SEQ ID NO: 46) | 119-818 | 4 | 10201484, 16001157, 19093438, 19204512, | 3 | 3 | 0 |
| NM_014285.5 | GFWSRFPPPW (SEQ ID NO: 47) | 448-528 | 5 | 9137001, 46278258, 145993595, 146042851, 146123968, | 5 | 3 | 1 |
| NM_001113378.1 | VSPGVSELRRNSKKYGKAGEAVWFSSDPPVLFFHFLRTE (SEQ ID NO: 48) | 3439-3628 | 4 | 6444477, 6870295, 6870449, 83195477, | 3 | 3 | 0 |
| NM_001018078.1 | VLGSQRHPGQGSCGSCPWHLCSSPHPTCGSGFGTRSGRAGRRCCGAGPSPGTWTVRTPPAARRPACAGSARRCRAARGRAVAPRFESCSSMLPGTGTRRPC (SEQ ID NO: 49) | 860-1009 | 3 | 10218110, 19144710, 46186123, | 3 | 3 | 0 |
| NM_006098.4 | GWPGHVMGSQRRQTPLHARWWGHHQRPVLQP (SEQ ID NO: 50) | 637-748 | 8 | 2574599, 9807168, 13524413, 33203609, 52715305, 58413416, 58566171, 90906220, | 7 | 5 | 1 |
| NM_015666.3 | GPRGHAGEGGRQSCGRPVLRGR (SEQ ID NO: 51) | 390-507 | 4 | 13133604, 145997763, 146023828, 146095508, | 4 | 3 | 1 |
| NM_016426.6 | VQMKMMKSSSDPLDIKKDVLLPAWN (SEQ ID NO: 52) | 291-350 | 24 | 14072238, 14079103, 14080406, 14176079, 52197802, 52282171, | 15 | 9 | 3 |

TABLE 1-continued

| RefSeq_ID | Encode FS peptides | Joint_pos | #Total_EST | EST_Ids | #Total_Lib | #Tumor_lib | #Normal_lib |
|---|---|---|---|---|---|---|---|
| | | | | 52282469, 52282506, 52282657, 84914016, 145998391, 146023882, 146039486, 146039586, 146040214, 146050613, 146052038, 146057369, 146057491, 146062991, 146072037, 146080660, 146102605, 146107434, | | | |
| NM_031243.2 | EGVLLQVTNEE VVNHRVFKK (SEQ ID NO: 53) | 1300-3179 | 4 | 12422802, 13033025, 13047121, 24132471, | 4 | 3 | 1 |
| NM_031243.2 | KEGVLLQVTNE EVVNHRVFKK (SEQ ID NO: 54) | 2581-3176 | 3 | 2466855, 4569115, 5659331, | 3 | 3 | 0 |
| NM_006644.2 | DSCGIVNSY (SEQ ID NO: 55) | 2925-3176 | 6 | 2077398, 10153160, 10993881, 12672555, 13911640, 51668448, | 5 | 4 | 1 |
| NM_006644.2 | DSCGIVNSY (SEQ ID NO: 56) | 2924-3175 | 6 | 4074102, 10032700, 10153621, 19588875, 19608035, 45695863, | 4 | 3 | 1 |
| NM_024660.2 | NCPVWRHNPCL ASWMSWRCWKS (SEQ ID NO: 57) | 441-821 | 6 | 2033361, 9124825, 9141800, 9332671, 10216854, 23253517, | 6 | 4 | 1 |
| NM_014761.2 | IVGPGPKPEASA KLPSRPADNYD NFVLPELPSVPD TLPTASAGASTS ASEDIDFDDLSR RFEEL (SEQ ID NO: 58) | 916-955 | 5 | 19137983, 19193502, 28140121, 46922603, 283449919, | 5 | 3 | 1 |
| NM_001130089.1 | VGSMPKELLGE SSSSMIFEERG (SEQ ID NO: 59) | 450-617 | 7 | 9329185, 9335633, 9336682, 14810814, 22365213, 45711902, 45715554, | 5 | 4 | 1 |
| NM_199187.1 | HRDSRGSGRNG RHPEREGDHAK PERPPGLLPGQS EEPGDREPEAGE QNPGALGEEGT PGQRLEPLLQD HRGPEGSDLRK YCGQCPHRSAD (SEQ ID NO: 60) | 197-260 | 18 | 10141571, 10142544, 10402934, 10586887, 12758550, 14177331, 19893549, 21768308, 21774629, 21774763, 21777572, | 10 | 8 | 2 |

TABLE 1-continued

| RefSeq_ID | Encode FS peptides | Joint_pos | #Total_EST | EST_Ids | #Total_Lib | #Tumor_lib | #Normal_lib |
|---|---|---|---|---|---|---|---|
| | | | | 21811780, 21815923, 22682079, 22908399, 24042754, 24045349, 56795793, | | | |
| NM_002273.3 | LLRSRHSTRILP TAAGLRLRACT RSSMRSCRAWL GSTGMTCGAQR LRSLR (SEQ ID NO: 61) | 831-881 | 9 | 9340416, 9759824, 9759932, 9897110, 9897831, 10156714, 21813841, 21814354, 21816557, | 4 | 4 | 0 |
| NM_177433.1 | RCQPDRHSHIW ALRWPWWSWC QHQWQLWCLW FLLQV (SEQ ID NO: 62) | 1731-1809 | 6 | 2054843, 5511019, 5673765, 5853954, 20203884, 23531396, | 4 | 3 | 1 |
| NM_153450.1 | ETPSDSDHKKK KKKKEEDPERK RKKKEKKKKK VE (SEQ ID NO: 63) | 590-830 | 8 | 3151481, 3750732, 4223069, 6139460, 11444683, 11451179, 11452422, 18988750, | 5 | 3 | 1 |
| NM_015950.3 | AGNVRSNSRPSI QR (SEQ ID NO: 64) | 749-824 | 4 | 2252141, 3277351, 19588584, 23291327, | 4 | 3 | 1 |
| NM_032112.2 | PASGGSDLVNH SFLCKWHP (SEQ ID NO: 65) | 541-717 | 3 | 12308492, 12339978, 22813610, | 3 | 3 | 0 |
| NM_032112.2 | CLLLGAVTL (SEQ ID NO: 66) | 599-713 | 5 | 10154760, 13408766, 20201885, 20493143, 21494992, | 3 | 3 | 0 |
| NM_014018.2 | EIPERNQGPVAA IRS (SEQ ID NO: 67) | 237-420 | 5 | 1295506, 6898484, 10246880, 33209502, 34555226, | 5 | 4 | 1 |
| NM_001145839.1 | LHWGSTKVHLL LI (SEQ ID NO: 68) | 415-801 | 4 | 10738994, 80835964, 146091479, 146109603, | 4 | 3 | 1 |
| NM_001114185.1 | GGPRRIWS (SEQ ID NO: 69) | 410-712 | 8 | 10147163, 10989026, 16773154, 16776609, 16779119, 22853771, 22902798, 145986212, | 4 | 4 | 0 |
| NM_000431.2 | GGPRRIWS (SEQ ID NO: 70) | 419-721 | 5 | 16773347, 16777501, 28132078, 47402601, 146062357, | 4 | 3 | 1 |

TABLE 1-continued

| RefSeq_ID | Encode FS peptides | Joint_pos | #Total_EST | EST_Ids | #Total_Lib | #Tumor_lib | #Normal_lib |
|---|---|---|---|---|---|---|---|
| NM_003491.2 | RSVKWSPNTMQ MGRTPMP (SEQ ID NO: 71) | 452-499 | 5 | 9151226, 9345658, 19210146, 27947049, 126672362, | 5 | 4 | 0 |
| NM_024313.2 | VPTACCRCCFC WDV (SEQ ID NO: 72) | 788-2696 | 16 | 9141107, 9803380, 12427492, 13328739, 13908466, 14678515, 21780385, 21785028, 22345418, 22361309, 22361754, 46290768, 68292178, 82116561, 90837311, 92186397, | 12 | 9 | 1 |
| NM_016391.4 | SGKTSSILCRRG RWRWS (SEQ ID NO: 73) | 391-483 | 13 | 2054860, 2932939, 2942143, 3601044, 4535246, 5425877, 5438639, 5596079, 5659519, 7151152, 19723340, 19738445, 24795292, | 10 | 8 | 2 |
| NM_007243.1 | AGDAVLGAHTQ RPCVVGGSG (SEQ ID NO: 74) | 151-349 | 3 | 12766042, 46616730, 145998555, | 3 | 3 | 0 |
| NM_001042549.1 | GAKPGGLALGA V (SEQ ID NO: 75) | 533-12194 | 3 | 3887573, 4991027, 6451223, | 3 | 3 | 0 |
| NM_181843.1 | DEVFALPLAHL LQTQNQGYTHF CRGGHFRYTLP VFLHGPHRVWG LTAVITEFALQL LAPGTYQPRLA GLTCSGAEGLA RPKQPLASPCQ ASSTPGLNKGL (SEQ ID NO: 76) | 426-498 | 5 | 10326854, 11970552, 18510936, 19030548, 46555631, | 5 | 4 | 1 |
| NM_198887.1 | QENCSNPGGRG CSDPRSCHFTPA WAKEQNAISKN IHI (SEQ ID NO: 77) | 2448-3467 | 4 | 1192583, 3280105, 5636736, 24792671, | 4 | 3 | 0 |
| NM_007342.2 | AKFCPTFNKSM EEQGK (SEQ ID NO: 78) | 704-782 | 5 | 11617690, 52065044, 52097801, 52298172, 80768446, | 5 | 3 | 1 |
| NM_001199462.1 | GLWLFRPQNVL QMPQSILLQQG ASDPRLEIGT (SEQ ID NO: 79) | 257-383 | 9 | 3988478, 4076572, 4268320, 4268335, 6700534, 10373888, 10984780, | 5 | 4 | 0 |

TABLE 1-continued

| RefSeq_ID | Encode FS peptides | Joint_pos | #Total_EST | EST_Ids | #Total Lib | # Tumor lib | # Normal lib |
|---|---|---|---|---|---|---|---|
| | | | | 11512824, 11512860, | | | |
| NM_002618.3 | DYRRLPPGPAN FFCIFSRDGVSP CYPGWSPSPDL VMSPLRSPKVL GLQA (SEQ ID NO: 80) | 2760-3281 | 4 | 9808150, 11159219, 13459444, 22920343, | 4 | 3 | 1 |
| NM_031948.3 | PLRRPCTRSCW GQGS (SEQ ID NO: 81) | 465-629 | 3 | 14807581, 19210482, 146069312, | 3 | 3 | 0 |
| NM_004577.3 | CDLNSLCIFVAI FHTKCFKCGESI KHLYS (SEQ ID NO: 82) | 1630-1940 | 5 | 2159346, 13709277, 13742243, 14506129, 27939669, | 4 | 3 | 1 |
| NM_020387.2 | GTIVVQWGPSW CLT (SEQ ID NO: 83) | 269-466 | 18 | 2277936, 9146588, 10156678, 10742718, 14380528, 14511202, 19128358, 19180556, 19196633, 19199578, 19199919, 23272326, 24184393, 38619719, 52187412, 52187724, 52259400, 52288970, | 14 | 10 | 3 |
| NM_006743.4 | GLWMVVRSVW IMQASLLGEPEE VALGPMGVVA ATLEVVGTRAM GVAGIMTVDLE GMDMDMDVPE TIMAETRVVMT ATQEEITETIMTT (SEQ ID NO: 84) | 338-445 | 6 | 10885369, 12600212, 12600293, 13460579, 19132700, 21168881, | 4 | 3 | 1 |
| NM_016026.3 | SLPPNPSAARET KGISPIKDSKCV FPRTSPGKDPLP (SEQ ID NO: 85) | 165-546 | 3 | 1679208, 22269010, 80545142, | 3 | 3 | 0 |
| NM_152553.2 | GLFVFPIYCLC (SEQ ID NO: 86) | 1017-1133 | 5 | 10400124, 13908341, 14428408, 52261877, 83255255, | 5 | 3 | 1 |
| NM_198486.2 | EVWRHLLGRPH S (SEQ ID NO: 87) | 427-538 | 5 | 21985536, 21986341, 145986153, 145999838, 146106725, | 4 | 3 | 1 |
| NM_000973.3 | IRELCHRYLPQP (SEQ ID NO: 88) | 225-453 | 8 | 1154529, 6937038, 9128356, 19091430, 19200294, 20486488, 22907262, 24044064, | 6 | 5 | 1 |

TABLE 1-continued

| RefSeq_ID | Encode FS peptides | Joint_pos | #Total_EST | EST_Ids | #Total_Lib | #Tumor_lib | #Normal_lib |
|---|---|---|---|---|---|---|---|
| NM_001002.3 | GVRQWQHLQP (SEQ ID NO: 89) | 646-754 | 13 | 9124850, 10205674, 13031883, 13403621, 13466151, 13666955, 14173427, 14175419, 19817898, 19895213, 21816494, 22689525, 47384119, | 8 | 7 | 1 |
| NM_001005.3 | GLLWCAAVHH GEWGQRLRGC GVWETPRTEG (SEQ ID NO: 90) | 285-381 | 3 | 9125003, 9139471, 22695855, | 3 | 3 | 0 |
| NM_001006.3 | FGKAHGASW (SEQ ID NO: 91) | 614-725 | 6 | 10160942, 12602739, 19378611, 21773234, 22849872, 22908519, | 4 | 4 | 0 |
| NM_138421.2 | GDGGSGSKGRP VEQTEVFLCISK PSSFL (SEQ ID NO: 92) | 1088-1286 | 3 | 1801795, 7155873, 16771906, | 3 | 3 | 0 |
| NM_017827.3 | LHARAPGPRGP PLLCPCCLRVSH (SEQ ID NO: 93) | 1708-1833 | 4 | 4890586, 5746185, 13915028, 23284022, | 4 | 4 | 0 |
| NM_001005914.1 | LPQQDLWHLQF HQGLPRRCHPV CAEPPPHVQLCP AHWGAPSFPTS WSQLHLHSNCR GPGCSR (SEQ ID NO: 94) | 1164-1377 | 3 | 9896956, 52185731, 80585087, | 3 | 3 | 0 |
| NM_021627.2 | GIFELFIL (SEQ ID NO: 95) | 328-463 | 4 | 19184218, 52117054, 80576973, 82328796, | 4 | 3 | 1 |
| NM_001193342.1 | GIGAVCMDWW AAAPPGECAPR PGCAAHHCGHR LLH (SEQ ID NO: 96) | 1086-1200 | 4 | 19211503, 146039032, 146045087, 146056161, | 4 | 3 | 0 |
| NM_001532.2 | SPCPSSPPSQPW (SEQ ID NO: 97) | 1096-1137 | 4 | 21176693, 24044445, 28133989, 80539035, | 4 | 3 | 1 |
| NM_178148.2 | VLSDLGCAAGK SDDPQLWGHSH ITG (SEQ ID NO: 98) | 343-499 | 4 | 13997158, 46283786, 78233770, 80883909, | 4 | 3 | 1 |
| NM_006306.2 | CCGIYCHEEPQR EDSSI (SEQ ID NO: 99) | 179-482 | 6 | 10204155, 10350966, 20396212, 20413818, 52288176, 84940096, | 4 | 3 | 1 |
| NM_030918.5 | HFPDGEVTAER CGHLAFPYPLPF PSPPSSYSFHVP FQTE (SEQ ID | 1593-2370 | 10 | 1162267, 2324233, 2356934, 2552335, | 10 | 7 | 2 |

TABLE 1-continued

| RefSeq_ID | Encode FS peptides | Joint_pos | #Total_EST | EST_Ids | #Total_Lib | #Tumor_lib | #Normal_lib |
|---|---|---|---|---|---|---|---|
| | NO: 100) | | | 2557157, 3765160, 4328216, 12300356, 24781036, 24803854, | | | |
| NM_006461.3 | ISVSIMWTQRRKL (SEQ ID NO: 101) | 269-862 | 5 | 24952240, 45703140, 46182693, 46185076, 52109618, | 5 | 3 | 0 |
| NM_006925.3 | VKGVLHSLTAAGQTH (SEQ ID NO: 102) | 1055-1428 | 6 | 2952696, 4286279, 18979142, 21477426, 21982089, 24787231, | 6 | 5 | 1 |
| NM_006374.3 | KHQAMDHHGVPGRRLSTGLA (SEQ ID NO: 103) | 426-477 | 7 | 9183882, 11256565, 17161793, 17163262, 17174422, 22286625, 24120773, | 5 | 4 | 1 |
| NM_014760.3 | GDQQPDRTQAGLKSVSQVEDVFRELIGTQKTRTGCFPPSGS (SEQ ID NO: 104) | 2877-2907 | 8 | 6883317, 10991109, 12385448, 21770848, 46184886, 58050995, 82074179, 91879091, | 8 | 6 | 2 |
| NM_006521.4 | CSAQARNRSEDETQPLPLGTLLAF (SEQ ID NO: 105) | 2451-2492 | 8 | 9149080, 9330710, 9331155, 9336773, 9344551, 9344576, 10734097, 10734771, | 3 | 3 | 0 |
| NM_199293.2 | HQALGAVPSCEGV (SEQ ID NO: 106) | 112-370 | 6 | 16526130, 45700010, 45704764, 45705693, 45717940, 46847261, | 4 | 3 | 1 |
| NM_207379.1 | QFRTPGWPLKALAGRGWPEDASPGQEPSKGAGRGWA (SEQ ID NO: 107) | 543-1313 | 10 | 3933593, 3933605, 4111770, 4312229, 4684269, 6504772, 6838403, 10031991, 10940483, 11083896, | 4 | 3 | 0 |
| NM_006291.2 | PRAAVSGIQQWWNGRQNWKRKKEKMSSRLAGAFRVLWRAVSTASIRRHIQVAPRPLQAGPAMGP (SEQ ID NO: 108) | 2087-2545 | 11 | 9176343, 10210944, 11290536, 19369027, 22342759, 22374168, 22662093, 22852902, 22853464, 22853646, 2902765, | 5 | 4 | 1 |

TABLE 1-continued

| RefSeq_ID | Encode FS peptides | Joint_pos | #Total_EST | EST_Ids | #Total_Lib | # Tumor_lib | # Normal_lib |
|---|---|---|---|---|---|---|---|
| NM_015140.3 | LIVGGGAPDRKGFQ (SEQ ID NO: 109) | 2096-2811 | 10 | 21980643, 46551962, 46552370, 46845450, 46876330, 46920760, 46925643, 46929343, 46951310, 47021176, | 5 | 4 | 1 |
| NM_012473.3 | CQRCPLCWP (SEQ ID NO: 110) | 343-468 | 3 | 12687717, 21780390, 28088991, | 3 | 3 | 0 |
| NM_001184977.1 | GVRCLIHSIHGFL (SEQ ID NO: 111) | 308-382 | 6 | 11265100, 18775927, 19897757, 51485275, 81213059, 82161427, | 6 | 4 | 1 |
| NM_003370.3 | WPQLLLEPNSGKSASRRRPQGGPQPPKLRVVEAEVGDSWKR (SEQ ID NO: 112) | 567-1019 | 4 | 8608901, 14173570, 46181698, 46269629, | 3 | 3 | 0 |
| NM_052844.3 | VAARAWAQPPLPGAECGHRREGATLAGHRGRPAAAHRGLRPGHAAAATEHQAQEASPRGDRGGRHGSGLLQL (SEQ ID NO: 113) | 828-939 | 7 | 10145344, 10147104, 16526305, 21773170, 21777139, 31447502, 46265826, | 5 | 4 | 1 |
| NM_001033519.1 | RYGRCVHCREIVLQQPSGHRQP (SEQ ID NO: 114) | 290-374 | 5 | 10391746, 10393365, 12339226, 14653998, 78233952, | 4 | 3 | 1 |
| NM_152858.1 | GLMASDYSEEVATSEKFPF (SEQ ID NO: 115) | 674-895 | 3 | 11158199, 12338537, 21118493, | 3 | 3 | 0 |
| NM_182969.1 | DRKRGCCPTSSSLPISLRVRLS (SEQ ID NO: 116) | 1312-1480 | 4 | 22340486, 27841540, 27878857, 83526847, | 4 | 3 | 1 |
| NM_005741.4 | SHSQSGGPRHPGGTRRKAMGSQCPELQGGPEPQRPSSRRREI (SEQ ID NO: 117) | 722-1106 | 4 | 9155377, 16534738, 16535238, 22701945, | 3 | 3 | 0 |

TABLE 2

The 50 human breast cancer cell lines.

| No. | Cell Line | ATCC_Name | Tissue |
|---|---|---|---|
| 1 | MCF-10A | CRL-10317 | Breast |
| 2 | BT-474 | HTB-20 | Breast |
| 3 | Hs 319.T | CRL-7236 | Breast |
| 4 | HCC1428 | CRL-2327 | Breast |
| 5 | HCC1599 | CRL-2331 | Breast |
| 6 | Hs 605.T | CRL-7365 | Breast |
| 7 | Hs 362.T | CRL-7253 | Breast |
| 8 | ZR-75-1 | CRL-1500 | Breast |
| 9 | MCF-7 | HTB-22 | Breast |
| 10 | Hs 281.T | CRL-7227 | Breast |
| 11 | HCC1500 | CRL-2329 | breast |
| 12 | BT-20 | HTB-19 | breast |
| 13 | HCC1143 | CRL-2321 | breast |
| 14 | UACC-812 | CRL-1897 | breast |
| 15 | SW527 | CRL-7940 | breast |
| 16 | MDA-MB-453 | HTB-131 | breast |
| 17 | ZR-75-30 | CRL-1504 | breast |
| 18 | MDA-MB-468 | HTB-132 | breast |

TABLE 2-continued

The 50 human breast cancer cell lines.

| No. | Cell Line | ATCC_Name | Tissue |
|---|---|---|---|
| 19 | HCC1187 | CRL-2322 | breast |
| 20 | SK-BR-3 | HTB-30 | breast |
| 21 | MDA-MB-175-VII | HTB-25 | breast |
| 22 | Hs 574.T | CRL-7345 | breast |
| 23 | HCC 1008 | CRL-2320 | breast |
| 24 | Hs 742.T | CRL-7482 | breast |
| 25 | Hs 748.T | CRL-7486 | breast |
| 26 | BT-483 | HTB-121 | breast |
| 27 | HCC202 | CRL-2316 | breast |
| 28 | HCC 2157 | CRL-2340 | breast |
| 29 | BT-549 | HTB-122 | breast |
| 30 | MDA-MB-415 | HTB-128 | breast |
| 31 | HCC1395 | CRL-2324 | breast |
| 32 |  | HTB-127 | breast |
| 33 | MDA-MB-231 | HTB-26 | breast |
| 34 | CAMA-1 | HTB-21 | breast |
| 35 | MDA-MB-134-VI | HTB-23 | breast |
| 36 | Hs 606.T | CRL-7368 | breast |
| 37 | HCC1806 | CRL-2335 | breast |
| 38 | HCC1419 | CRL-2326 | breast |
| 39 | AU565 | CRL-2351 | breast |
| 40 | HCC1937 | CRL-2336 | breast |
| 41 | Hs 578T | HTB-126 | breast |
| 42 | Hs 739.T | CRL-7477 | breast |
| 43 | DU4475 | HTB-123 | breast |
| 44 | HCC70 | CRL-2315 | breast |
| 45 | HCC38 | CRL-2314 | breast |
| 46 | HCC1954 | CRL-2338 | breast |
| 47 | MB 157 | CRL-7721 | breast |
| 48 | HCC2218 | CRL-2343 | breast |
| 49 | Hs 343.T | CRL-7245 | breast |
| 50 | UACC-893 | CRL-1902 | breast |

TABLE 3

Mouse mis-splicing FS antigens in the vaccine

| Antigen Name | Peptide size | peptide sequence |
|---|---|---|
| ZDHHC17 FS | 21 | AVLLMCQLYQPWMCKEYYRLL (SEQ ID NO: 118) |
| SLAIN2 FS | 21 | IPRMQPQASANHCQLLKVMVA (SEQ ID NO: 119) |
| mSMC1A1^4 | 27 | TAIIGPNGSGCSGVYCHEEPQGEDSSV (SEQ ID NO: 120) |
| RBM FS | 45 | GRVIECDVVKGSCQDGEAVHWKSAPGGHRAGDPLTLRAVREGAGM (SEQ ID NO: 121) |

TABLE 4

Three mouse MS FS antigens with predicted H2-D epitope

| Antigen ID | MS Access # | MS type | INDEL | Peptide size | peptide sequence (Kd/Ld epitope score > 20) |
|---|---|---|---|---|---|
| MS927 | NM_053009.3 | 9_A | Del | 33 | ICMSPPLLWATLQAPE TTSAACKASYRPEGLYL (SEQ ID NO: 122) |
| MS255 | NM_010086.4 | 9_A | In | 24 | YFSCDKRCIKHYAGNK SLLTFSGY (SEQ ID NO: 123) |
| MS518 | NM_153511.3 | 10_A | Del | 59 | TLCMEVMLRWNTRELG YLYLQLCFLNTHFLHT SQEEKLLTLGRFLTWT SRCGSFVIRPL (SEQ ID NO: 124) |

TABLE 5

Samples tested on Human 400K FS array

| Sample Type | Number of Samples | Source |
|---|---|---|
| Breast Cancer | 17 | UT Southwestern |
| Lung Cancer | 17 | UT Southwestern |
| GBM | 17 | Barrows Neurological Institute |
| Pancreatic Cancer | 17 | TGEN |
| Pancreatic Cancer Stage 1 | 13 | TGEN |
| Gastric Cancer | 17 | Japan |
| Control | 64 | Varied Sources |

TABLE 6

Three ORFs of Sec62 gene

Sec62-12A:

(SEQ ID NO: 125)
atggcggagcgcaggagacacaagaagcggatccaggaagttggtgaacc
atctaaagaagagaaggctgtagccaagtatcttcgatttaactgtccaa
caaagtctaccaatatgatggggcaccgagagattatacattgcttcaaa
agcagtggattgccattggattcaaagtgggcaaaggccaagcaaaggaga
ggaagcattacaacaagggagtctgtggagactactgcaacaggcat
taaagaagcagattacaccgggcactaaaagtaatgaaaatgaagtatga
taaagacataaaaaaagaaaaagagaaaggaaaggccgaaagtggaaaag
aagaagataaaaagagcaggaaagaaaatctaaaggatgaaaagacgaaa
aaggagaaagaaaaaaaaaaaagatggggaaaaggaagaggattacaagg
acgacgacgaagtgaaattcatggtgagcaagggcgaggagctgacac
cggggtggtgcccatcctggtcgagctggacggcgactaaacggccaca
agacagcgtgtccggcgagggcgagggcgatgccacctacggcaagctga
ccctgaagacatctgcaccaccggcaagctgcccgtgccctggcccaccc
tcgtgaccaccctgacctacggcgtgcagtgcttcagccactaccccgac
cacatgaagcagcacgacttcttcaagtccgccatgcccgaaggctacgt
ccaggagcgcaccatcacttcaaggacgacggcaactacaagacccgcgc
cgaggtgaagttcgagggcgacaccctggtgaaccgcatcgagctgaagg
gcatcgacttcaaggaggacggcaacatcctggggcacaagctggagtac
aactacaacagccacaacgtctatatcatggccgacaagcagaagaacgg
catcaaggtgaacttcaagatccgccacaacatcgaggacggcagcgtgc
agctcgccgaccactaccagcagaacacccccatcggcgacggccccgtg
ctgctgcccgacaaccactacctgagcacccagtccgccctgagcaaaga
ccccaacgaagcgcgatcacatggtcctgctggagacgtgaccgccgc
cgggatcactctcggcatggacgagctgtacaagagatctggtaccacgc
gtatcgataagcttgcatgcctgcaggtcgactctagaggatcgtga;

Sec62-11A:

(SEQ ID NO: 126)
atggcggagcgcaggagacacaagaagcggatccaggaagaggtgaacca
tctaaagaagagaaggctgtagccaagtatcgatttaactgtccaaca
aagtctaccaatatgatggggcaccgagagattatacattgcttcaaaag
cagtggattgccattggattcaaagtgggcaaaggccaagaaaggagagg
aagattattacaacaagggagtctgtggagactactgcaacaggcatta
aagaagcagattacaccgggcactaaaagtaatgaaaatgaagtatgata
aagacataaaaaaagaaaaagagaaaggaaaggccgaaagtggaaaaga
agaagataaaaagagcaggaaagaaaatctaaaggatgaaaagacgaaaa
aggagaaagaaaaaaaaaaaagatggggaaaaggaagaggattacaaggac
gacgacgacaagtgaaattcatggtgagcaagggcgaggagctgacaccg
gggtggtgcccatcctggtcgagctggacggcgactaaacggccacaag TABLE 6-continued Three ORFs of Sec62 gene acagcgtgtccggcgagggcgagggcgatgccacctacggcaagctgacc
ctgaagacatctgcaccacctacggcaagctgcccgtgccctggccccctc
gtgaccaccctgacctacggcgtgcagtgcttcagccactaccccgacca
catgaagcagcacgacttcttcaagtccgccatgcccgaaggctacgtcc
aggagcgcaccatcttcttcaaggacgacggcaactacaagacccgcgcc
gaggtgaagttcgagggcgacaccctggtgaaccgcatcgagctgaaggg
catcgacttcaaggaggacggcaacatcctggggcacaagctggagtaca
actacaacagccacaacgtctatatcatggccgacaagcagaagaacggc
atcaaggtgaacttcaagatccgccacaacatcgaggacggcagcgtgca
gctgccgaccactaccagcagaacacccccatcggcgacggccccgtgc
tgctgcccgacaaccactacctgagcacccagtccgccctgagcaaagac
cccaacgagaagcgcgatcacatggtcctgctggagttcgtgaccgccgc
cgggatcactctcggcatggacgagctgtacaagagatctggtaccacgc
gtatcgataagcttgcatgcctgcaggtcgactctagaggatcgtga;

Sec62-Non MS:
(SEQ ID NO: 127)
atggcggagcgcaggagacacaagaagcggatccaggaagttggtgaacc
atctaaagaagaagaaggctgtagcaagtatcttcaagttttaactgtccaa
caaagtctaccaatatgatggggcaccgagttgattattttcattgcttca
aaagcagtggattgcctttggattcaaagtgggcaaaggccaagaaagg
agaggaagctttatttacaacaagggagtctgtggttgactactgcaaca ggcttttaaagaagcagttttttcacccgggcactaaaagtaatgaaatg
aagtatgataaagacataaaaaaagaaaaagagaaaggaaaggccgaaag
tggaaaagaagaagatataaaaagagcaggaaagaaaatctaaaggatgaaa
agacgaaaaaggagaaagagaggaagagagatggggaaaaggaagaggat
tacaaggacgacgacgacaagtgaaattcatggtgagcaagggcgaggag
ctgttcaccggggtggtgcccatcctggtcgagctggacggcgacgtaaa
cggccacaagttcagcgtgtccggcgagggcgagggcgatgccacctacg
gcaagctgaccctgaagttcatctgcaccaccggcaagctgcccgtgccc
tggcccaccctcgtgaccaccctgacctacggcgtgcagtgcttcagcca
ctaccccgaccacatgaagcagcacgacttcttcaagtccgccatgcccg
aaggctacgtccaggagcgcaccatcttcttcaaggacgacggcaactac
aagacccgcgccgaggtgaagttcgagggcgacaccctggtgaaccgcat
cgagctgaagggcatcgacttcaaggaggacggcaacatcctggggcaca
agctggagtacaactacaacagccacaacgtctatatcatggccgacaag
cagaagaacggcatcaaggtgaacttcaagatccgccacaacatcgagga
cggcagcgtgcagctgccgaccactaccagcagaacacccccatcggcg
acggccccgtgctgctgcccgacaaccactacctgagcacccagtccgcc
ctgagcaaagaccccaacgagaagcgcgatcacatggtcctgctggagtt
cgtgaccgccgcgggatcactctcggcatggacgagctgtacaagagat
ctggtaccacgcgtatcgataagcttgcatgcctgcaggtcgactctaga
ggatcgtga.

TABLE 7

| Trans-splicing ID | upstream gene ACC# | downstream gene ACC# | up WT sequence | down stream FS sequence |
|---|---|---|---|---|
| BOLA2_Exon_SMG1_Exon12 | NM_001031827.1 | NM_015092.3 | MASAKSLDRWKARLLEGGST ALTYALVRAEVSFPAEVAPV RQQGSVAGARAGVVSLLGCR SSWTAAMELSAEYLREKLQR DLEAEHVEVEDTTLNRCSCSF RVLVVSAKFEGKPLLQRHR (SEQ ID NO: 128) | LLNR (SEQ ID NO: 129) |
| GFOD1_Exon1_C6orf114_Exon2 | NM_018988.2 | NM_033069.2 | MLPGVGVFGTSLTARVIIPLL KDEGFAVKALWGRTQEEAEE LAKEMSVPFYTSRIDEVLLHQ DVDLVCINLPPPLTRQIAVKT L (SEQ ID NO: 130) | EPGHQRKKISRQKNTGEKKMP RGSVQLSFCSLQHPHMGHLFTP HDAALGESQGTGFKPLGMQPV (SEQ ID NO: 131) |
| MDS1_Exon2_EVI1_Exon4 | NM_004991.2 | NM_001105078.2 | MRSKGRARKLATNNECVYG NYPEIPLEEMPDADGVASTPS LNIQEPCSPATSSEAFTPKEGS PYKAPIYIPDDIPIPAEFELRES NMPGAGLGIWTKRKIEVGEK FGPYVGEQRSNLKDPSYGWE (SEQ ID NO: 132) | ILDEFYNVKFCIDASQPDVGSW LKYIRFAGCYDQHNLVACQIND QIFYRVVADIAPGEELLLFMKS EDYPHETMAPDIHEERQYRCED CDQLFESKAELADHQKFPCSTP HSAFSMVEEDFQQKLESENDLQ EIHTIQECKECDQVFPDLQSLEK HMLSHTEEREYKCDQCPKAFN WKSNLIRHQMSHDSGKHYECE NCAKVFTDPSNLQRHIRSQHVG ARAHACPECGKTFATSSGLKQ HKHIHSSVKPFICEV (SEQ ID NO: 133) |
| C11orf79_Exon3_C11orf66_Exon5 | NM_017841.1 | NM_145017.1 | MAVSTVFSTSSLMLALSRHSL LSPLLSVTSFRRFYRGDSPTDS QKDMIEIPLPPWQERTDESIET KRARLLYESRKRGMLENCILL SLFAKEHLQHMTEKQLNLYD RLINEPSNDWDIYYWAT (SEQ ID NO: 134) | GPEGPFRHPGARASGHHGAGA QGSASAPPAAGPGPAGAGELPT WPTLHDVGVQFQVSQGPSRPA RFLAEEIDRRKGGEWLHQTVPP EPHCLPTALTGPPWGPCPPPRPE CHQVRLPPQDSPTWR (SEQ ID NO: 135) |
| ABHD14A_Exon3_ACY1_Exon2 | NM_015407.3 | NM_000666.1 | MVGALCGCWFRLGGARPLIP LGPTVVQTSMSQSQVALLGL SLLLMLLLYVGLPGPPEQTSC LWGDPNVTVLAGLTPGNSPIF YREVLPLNQAHRVEVVLLHG KAFNSHTWEQLGTLQLLSQR GYRAVALDLP (SEQ ID NO: 136) | AHHAQRHDQQGSRGGAPIGDA LPPVPAYPHCPAQA (SEQ ID NO: 137) |

TABLE 7-continued

| Trans-splicing ID | up-stream gene ACC# | down-stream gene ACC# | up WT sequence | down stream FS sequence |
|---|---|---|---|---|
| RBM14_NA_RBM4_Exon2 | NM_006328.3 | NM_002896.2 | MKIFVGNVDGADTTPEELAA LFAPYGTVMSCAVMKQFAFV HMRENAGALRAIEALHGHEL RPGRALVVEMSRPRPLNTWK IFVGNVSAACTSQELRSLFER RGRVIECDVVK (SEQ ID NO: 138) | GSCQDGEAVHRKPAPGGYRAG DSLTLRAVWEGAGM (SEQ ID NO: 139) |
| C20orf29_Exon2_VISA_Exon2 | NM_018347.1 | NM_020746.3 | MVHAFLIHTLRAPNTEDTGLC RVLYSCVFGAEKSPDDPRPH GAERDRLLRKEQILAVA (SEQ ID NO: 140) | SLVSSQSIHPSWGQSPLSRI (SEQ ID NO: 141) |
| RRM2_Exon9_C2orf48_Exon2 | NM_001034.1 | NM_182626.1 | MLSLRVPLAPITDPQQLQLSP LKGLSLVDKENTPPALSGTRV LASKTARRIFQEPTEPKTKAA APGVEDEPLLRENPRRFVIFPI EYHDIWQMYKKAEASFWTA EEVDLSKDIQHWESLKPEERY FISHVLAFFAASDGIVNENLV ERFSQEVQITEARCFYGFQIA MENIHSEMYSLLIDTYIKDPK EREFLFNAIETMPCVKKKAD WALRWIGDKEATYGERVVA FAAVEGIFFSGSFASIFWLKKR GLMPGLTFSNELISRDEGLHC DFACLMFKHLVHKPSEERVR EIIINAVRIEQEFLTEALPVKLI GMNCTLMKQYIEFVADRLML ELGFSKV (SEQ ID NO: 142) | LGDREVQSRWSPGPRGDSTPVR EMETNHPPSVRG (SEQ ID NO: 143) |
| ELAC1_Exon2_SMAD4_Exon2 | NM_018696.2 | NM_005359.5 | MSMDVTFLGTGAAYPSPTRG ASAVVLRCEGECWLFDCGEG TQTQLMKSQLKAG (SEQ ID NO: 144) | YPEYMSNNFPCNVSCCFSLFPK DQNCFRNWRHI (SEQ ID NO: 145) |
| BCAS4_Exon1_BCAS3_Exon24 | NM_001010974.1 | NM_001099432.1 | MQRTGGGAPRPGRNHGLPGS LRQPDPVALLMLLVDADQPE PMRSGARELALFLTPEPGAE (SEQ ID NO: 146) | VPLTGA (SEQ ID NO: 147) |
| C22orf39_Exon2_HIRA_Exon2 | NM_173793.3 | NM_003325.3 | MADGSGWQPPRPCEAYRAE WKLCRSARHFLHHYYVHGE RPACEQWQRDLASCRDWEE RRNAEAQ (SEQ ID NO: 148) | ASRFFQLIFTLTGPSSQLEDKGR ILGRL (SEQ ID NO: 149) |
| PMF1_Exon4_BGLAP_^Exon4 | NM_007221.2 | NM_199173.3 | MAEASSANLGSGCEEKRHEG SSSESVPPGTTISRVKLLDTM VDTFLQKLVAAGSYQRFTDC YKCFYQLQPAMTQQIYDKFI AQLQTSIREEISDIKEEGNLEA VLNALDKIVEEGKVRKEPAW RPSGIPEKDLHSVMAPYFLQQ RDTLRRHVQKQEAENQQLAD AVLAGRRQVEELQLQVQAQ QQAWQ (SEQ ID NO: 150) | VRSPAVQSPAKVQPLCPSRRAA R (SEQ ID NO: 151) |
| SDHD_Exon3_TEX12_Exon3 | NM_003002.1 | NM_031275.4 | MAVLWRLSAVCGALGGRAL LLRTPVVRPAHISAFLQDRPIP EWCGVQHIHLSPSHHSGSKA ASLHWTSERVVSVLLLGLLP AAYLNPCSAMDYSLAAALTL HGH (SEQ ID NO: 152) | CLQCQIVHSCPLLENQIHLSLKF PDYFIKMKPWRKI (SEQ ID NO: 153) |
| PRR13_Exon3b_PCBP2_Exon2 | NM_001005354.2 | NM_001128914.1 | MWNPNAGGPPHPVPQPGYPG CQPLGPYPPPYPPPAPGIPPVN PLAPGMVGPAVIVDKKMQK KMKKAHKKMHKHQKHHKY HKHGK (SEQ ID NO: 154) | FLAFTPNQ (SEQ ID NO: 155) |
| RMND5A_Exon2_ANAPC1_ | NM_022780.2 | NM_022662.2 | MDQCVTVERELEKVLHKFSG YGQLCERGLEELIDYTGGLK HEILQSHGQDAELSGTLSLVL | DSL (SEQ ID NO: 157) |

TABLE 7-continued

| Trans-splicing ID | up-stream gene ACC# | down-stream gene ACC# | up WT sequence | down stream FS sequence |
|---|---|---|---|---|
| Exon25 | | | TQCCKRIKDTVQKLASDHKDI HSSVSRVGKAIDK (SEQ ID NO: 156) | |
| TYMP_ Exon9_ SCO2_ Exon2 | NM_ 001113756.1 | NM_ 005138.2 | MAALMTPGTGAPPAPGDFSG EGSQGLPDPSPEPKQLPELIR MKRDGGRLSEADIRGFVAAV VNGSAQGAQIGAMLMAIRLR GMDLEETSVLTQALAQSGQQ LEWPEAWRQQLVDKHSTGG VGDKVSLVLAPALAACGCKV PMISGRGLGHTGGTLDKLESI PGFNVIQSPEQMQVLLDQAG CCIVGQSEQLVPADGILYAAR DVTATVDSLPLITASILSKKLV EGLSALVVDVKFGGAAVFPN QEQARELAKTLVGVGASLGL RVAAALTAMDKPLGRCVGH ALEVEEALLCMDGAGPPDLR DLVTTLGGALLWLSGHAGTQ AQGAARVAAALDDGSALGR FERMLAAQGVDPGLARALCS GSPAERRQLLPRAREQEELLA PADGTVELVRALPLALVLHE LGAGRSRAGEPLRLGVGAEL LVDVGQRLRRG (SEQ ID NO: 158) | ASDPCCC (SEQ ID NO: 159) |
| NAIP_ Exon13_ OCLN_ Exon5 | NM_ 004536.2 | NM_ 002538.2 | MATQQKASDERISQFDHNLL PELSALLGLDAVQLAKELEEE EQKERAKMQKGYNSQMRSE AKRLKTFVTYEPYSSWIPQEM AAAGFYFTGVKSGIQCFCCSL ILFGAGLTRLPIEDHKRFHPDC GFLLNKDVGNIAKYDIRVKN LKSRLRGGKMRYQEEEARLA SFRNWPFYVQGISPCVLSEAG FVFTGKQDTVQCFSCGGCLG NWEEGDDPWKEHAKWFPKC EFLRSKKSSEEITQYIQSYKGF VDITGEHFVNSWVQRELPMA SAYCNDSIFAYEELRLDSFKD WPRESAVGVAALAKAGLFYT GIKDIVQCFSCGGCLEKWQE GDDPLDDHTRCFPNCPFLQN MKSSAEVTPDLQSRGELCELL ETTSESNLEDSIAVGPIVPEMA QGEAQWFQEAKNLNEQLRA AYTSASFRHMSLLDISSDLAT DHLLGCDLSIASKHISKPVQE PLVLPEVFGNLNSVMCVEGE AGSGKTVLLKKIAFLWASGC CPLLNRFQLVFYLSLSSTRPD EGLASIICDQLLEKEGSVTEM CVRNIIQQLKNQVLFLLDDYK EICSIPQVIGKLIQKNHLSRTC LLIAVRTNRARDIRRYLETILE IKAFPFYNTVCILRKLFSHNM TRLRKFMVYFGKNQSLQKIQ KTPLFVAAICAHWFQYPFDPS FDDVAVFKSYMERLSLRNKA TAEILKATVSSCGELALKGFF SCCFEFNDDDLAEAGVDEDE DLTMCLMSKFTAQRLRPFYR FLSPAFQEFLAGMRLIELLDS DRQEHQDLGLYHLKQINSPM MTVSAYNNFLNYVSSLPSTK AGPKIVSHLLHLVDNKESLEN ISENDDYLKHQPEISLQMQLL RGLWQICPQAYFSMVSEHLL VLALKTAYQSNTVAACSPFV LQFLQGRTLTLGALNLQYFFD HPESLSLLRSIHFPIRGNKTSP RAHFSVLETCFDKSQVPTIDQ DYASAFEPMNEWERNLAEKE | G (SEQ ID NO: 161) |

TABLE 7-continued

| Trans-splicing ID | up-stream gene ACC# | down-stream gene ACC# | up WT sequence | down stream FS sequence |
|---|---|---|---|---|
| | | | DNVKSYMDMQRRASPDLST GYWKLSPKQYKIPCLEVDVN DIDVVGQDMLEILMTVFSAS QRIELHLNHSRGFIESIRPALE LSKASVTKCSISKLELSAAEQ ELLLTLPSLESLEVSGTIQSQD QIFPNLDKFLCLKELSVDLEG NINVFSVIPEEFPNFHHMEKLL IQISAEYDPSKL (SEQ ID NO: 160) | |
| C1orf151_Exon1_NBL1_Exon3 | NM_001032363.1 | NM_182744.2 | MSESELGRKWDRCLADAVV KIG (SEQ ID NO: 162) | LWRPRA (SEQ ID NO: 163) |
| DDIT3_^Exon3_MARS_^Exon21 | NM_004083.4 | NM_004990.2 | MAAESLPFSFGTLSSWELEA WYEDLQEVLSSDENGGTYVS PP (SEQ ID NO: 164) | LPLGASGGFPSATANCFFRSKSF ATSAATSFLSAFCAFSSRTMFPC FVTSSISACICCGLAVVTVSTTA GFGDVFAWPPPKRCLKLSIWSF SNFWNKGLTVPIWCPAGKVHR KFVSRILQAGGGSCSWAWIVAL TVGM (SEQ ID NO: 165) |
| RIPK3_Exon9_ADCY4_Exon2 | NM_006871.3 | NM_139247.2 | MSCVKLWPSGAPAPLVSIEEL ENQELVGKGGFGTVFRAQHR KWGYDVAVKIVNSKAISREV KAMASLDNEFVLRLEGVIEK VNWDQDPKPALVTKFMENG SLSGLLQSQCPRPWPLLCRLL KEVVLGMFYLHDQNPVLLHR DLKPSNVLLDPELHVKLADF GLSTFQGGSQSGTGSGEPGGT LGYLAPELFVNVRKASTAS DVYSFGILMWAVLAGREVEL PTEPSLVYEAVCNRQNRPSLA ELPQAGPETPGLEGLKELMQL CWSSEPKDRPSFQECLPKTDE VFQMVENNMNAAVSTVKDF LSQLRSSNRRFSIPESGQGGTE MDGFRRTIENQHSRNDVMVS EWLNKLNLEEPPSSVPKKCPS LTKRSRAQEEQVPQAWTAGT SSDSMAQPPQTPETSTFRNQM PSPTSTGTPSPGPRGNQGAER QGMNWSCRTPEPNPVTG (SEQ ID NO: 166) | ADLRPELPDHCAVRAGRLLAA AGRPFPGAATAALDASPVRLG MGRAASARPRLVHRGRGERL GPGVLFSLRHLHGVCHAALGH AGRRRRGPRLLTLASAGPRAVS WATAGLTACTAAAVGSKRSAV PVRERGRSVPQGADGARPAGH VPGGTQLPALTPAAGHREEAPG TPSLVHPSCLPGPRDEGRDHGT AAGRTGVTAREH (SEQ ID NO: 167) |
| COMMD3_Exon1_BMI1_Exon2 | NM_012071.2 | NM_005180.5 | MELSESVQKGFQMLADPRSF DSNAFTLLLRAAFQSLLDAQ ADEAVL (SEQ ID NO: 168) | GFFIKQKCIEQRESRSLS (SEQ ID NO: 169) |
| MED8_Exon7c_ELOVL1_Exon2 | NM_052877.3 | NM_022821.2 | MQREEKQLEASLDALLSQVA DLKNSLGSFICKLENEYGRLT WPSVLDSFALLSGQLNTLNK VLKHEKTPLFRNQVIIPLVLSP DRDEDLMRQTEGRVPVFSHE VVPDHLRTKPDPEVEEQEKQ LTTDAARIGADAAQKQIQSLN KMCSNLLEKISKEERESESGG LRPNKQTFNPTDTNALVAAV AFGKGLSNWRPSGSSGPGQA GQPGAGTILAGTSGLQQVQM AGAPSQQQPMLSGVQMAQA GQPGKMPSGIKTNIKSASMHP YQR (SEQ ID NO: 170) | VLSQDGGCCELVPRGDEARRSP DPGLPSDGVPLANDLHSPDLRV LRSLTWASHHG (SEQ ID NO: 171) |
| POLR2J3-^Exon2_UPK38_^Exon7 | NM_001097615.1 | XM_001717094.1 | MNAPPAFESFLLFEGEKITINK DTKVPNACLFTMNKEDHTLG NIIKS (SEQ ID NO: 172) | RACFPPAFCRDCQFPEASPATLS VQPAEL (SEQ ID NO: 173) |
| BGLAP_^Exon2_PMF1_ | NM_199173.3 | NM_007221.2 | MAEASSANLGSGCEEKRHEG SSSESVPPGTTISRVKLLDTM VDTFLQKLVAAGSYQRFTDC | VRSPAVQSPAKVQPLCPSRRAA R (SEQ ID NO: 175) |

TABLE 7-continued

| Trans-splicing ID | up-stream gene ACC# | down-stream gene ACC# | up WT sequence | down stream FS sequence |
|---|---|---|---|---|
| ^Exon5 | | | YKCFYQLQPAMTQQIYDKFI AQLQTSIREEISDIKEEGNLEA VLNALDKIVEEGKVRKEPAW RPSGIPEKDLHSVMAPYFLQQ RDTLRRHVQKQEAENQQLAD AVLAGRRQVEELQLQVQAQ QQAWQ (SEQ ID NO: 174) | |
| TMEM199_ Exon5_ SARM1_ Exon2 | NM_ 152464.1 | NM_ 015077.2 | MASSLLAGERLVRALGPGGE LEPERLPRKLRAELEAALGKK HKGGDSSSGPQRLVSFRLIRD LHQHLRERDSKLYLHELLEGS EIYLPEVVKPPRNPELVARLE KIKIQLANEEYKRITRNVTCQ DTRHGGTLSDLGKQVRSLKA LVITIFNFIVTVVAAFVCTYLG SQYIFTEMASR (SEQ ID NO: 176) | PRGAHWAGRDPEPGEGTRTRR AGAERGRHLGAHVQAFGGDM PEAGGGRRPGRGAVLVPPHGP RAAAPLRAGAGQLRAARGPGG AATHGREARSRVALPARLLQG GRAASAARLPRSSGVGD (SEQ ID NO: 177) |
| C1QTNF6_ Exon2_ IL2RB_ Exon2 | NM_ 182486.1 | NM_ 000878.2 | MQWLRVRESPGEATGHRVT MGTAALGPVWAALLLFLLM CEIPMVELTFDRAVASGCQRC CDSEDPLDPAHVSSASSSGRP HALPEIRPYINITILKG (SEQ ID NO: 178) | LPSSAPPCGCNGGPCSVLASAPP HPPPAPGYLLGICSGEWHFPVH MLLQLESQHLLCLEPRWGSAG HFLPSPCLAGQTAVEPNL (SEQ ID NO: 179) |
| LOC100131434_ NA_ FLJ44451_ NA | XM_ 001713865.1 | XM_ 001714058.1 | MDPASRGCLGPTPAFRHRKE QSSASPRPSEATGARTMGSQA RRPPVIPFTKNETLFSLPGPDA RQPTRPRPGDLETGSLDEEPE GGKGTGGRKISRIDFITKFWV PASGVPDETKRLLVLHPRCYF QNSGLVVWSLHCSMSLLSNL ESSVFLPSVRCAYFSLEKLEE AGMLEM (SEQ ID NO: 180) | RPSTPCLHGAALHLHSGHSGS RLTNSSCFPGTRRLLALQFTQQ TGTVGHPTWQPVIR (SEQ ID NO: 181) |
| COX19_ Exon2_ CENTA1_ Exon2 | NM_ 001031617.2 | NM_ 006869.2 | MSTAMNFGTKSFQPRPPDKG SFPLDHLGECKSFKEKFMKCL HNNNFENALCRKESKEYLEC RMER (SEQ ID NO: 182) | SRLGLLHSGRLHLPELLGNPPE YPPGQQGEVRPPGRLGGGPSGV HGLPRERRRESQV (SEQ ID NO: 183) |
| ACSF2_ Exon10_ CHAD_ ^Exon4 | NM_ 025149.4 | NM_ 001267.2 | MAVYVGMLRLGRLCAGSSG VLGARAALSRSWQEARLQGV RFLSSREVDRMVSTPIGGLSY VQGCTKKHLNSKTVGQCLET TAQRVPEREALVVLHEDVRL TFAQLKEEVDKAASGLLSIGL CKGDRLGMWGPNSYAWVL MQLATAQAGIILVSVNPAYQ AMELEYVLKKVGCKALVFPK QFKTQQYYNVLKQICPEVEN AQPGALKSQRLPDLTTVISVD APLPGTLLLDEVVAAGSTRQ HLDQLQYNQQFLSCHDPINIQ FTSGTTGSPKGATLSHYNIVN NSNILGERLKLHEKTPEQLRM ILPNPLYHCLGSVAGTMMCL MYGATLILASPIFNGKKALEA IS RERGTFLYGTPTMFVDILN QPDFSSYDISTMCGGVIAGSP APPELIRAIINKINMKDLV (SEQ ID NO: 184) | RNLRKKLQHGKMDSKAPMSC (SEQ ID NO: 185) |
| TIMM23B_ NA_ LOC100132418_ NA | XM_ 928114.3 | XM_ 001719607.1 | MEGGGGSGNKTTGGLAGFFG AGGAGYSHADLAGVPLTGM NPLSPYLNVDPRYLVQDTEF ILPTGANKTRGRFELAFFTIGG CCMTGAAFGAMNGLRLGLK ETQNMAWSKPRNVQILNMV TRQGALWANTLGSLALLYSA FGVIIEKTRGAEDDLNTVAAG TMTGMLYKCT (SEQ ID NO: 186) | VSEMALDSPFCVLLSGS (SEQ ID NO: 187) |
| NDUFA13_ Exon4_ | NM_ 015965.5 | NM_ 198537.2 | MQEPRRVTPCLGKRGVKTPQ LQPGSAFLPRVRRQSFPARSD | GLGAAAPTCRHGKSGA (SEQ ID NO: 189) |

TABLE 7-continued

| Trans-splicing ID | up-stream gene ACC# | down-stream gene ACC# | up WT sequence | down stream FS sequence |
|---|---|---|---|---|
| YJEFN3_Exon2 | | | SYTTVRDFLAVPRTISSASATL IMAVAVSHFRPGPEVWDTAS MAASKVKQDMPPPGGYGPID YKRNLPRRGLSGYSMLAIGIG TLIYGHWSIMKWNRERRRLQ IEDFEARIALLPLLQAETDRRT LQMLRENLEEEAIIMKDVPD WK (SEQ ID NO: 188) | |
| ADHFE1_Exon13_C8orf46_NA | NM_144650.2 | NM_152765.3 | MAAAARARVAYLLRQLQRA ACQCPTHSHTYSQAPGLSPSG KTTDYAFEMAVSNIRYGAAV TKEVGMDLKNMGAKNVCLM TDKNLSKLPPVQVAMDSLVK NGIPFTVYDNVRVEPTDSSFM EAIEFAQKGAFDAYVAVGGG STMDTCKAANLYASSPHSDF LDYVSAPIGKGKPVSVPLKPL IAVPTTSGTGSETTGVAIFDYE HLKVKIGITSRAIKPTLGLIDP LHTLHMPARVVANSGFDVLC HALESYTTLPYHLRSPCPSNPI TRPAYQGSNPISDIWAIHALRI VAKYLKRAVRNPDDLEARSH MHLASAFAGIGFGNAGVHLC HGMSYPISGLVKMYKAKDY NVDHPLVPHGLSVVLTSPAVF TFTAQMFPERHLEMAEILGA DTRTARIQDAGLVLADTLRK FLFDLDVDDGLAAVGYSKAD IPALVKGTLPQ (SEQ ID NO: 190) | YPVQPEEEPKALSTS (SEQ ID NO: 191) |
| HPS4_Exon13_ASPHD2_^Exon4 | NM_022081.4 | NM_020437.4 | MATSTSTEAKSASWWNYFFL YDGSKVKEEGDPTRAGICYF YPSQTLLDQQELLCGQIAGVV RCVSDISDSPPTLVRLRKLKF AIKVDGDYLWVLGCAVELPD VSCKRFLDQLVGFFNFYNGP VSLAYENCS QEELSTEWDTFI EQILKNTSDLHKIFNSLWNLD QTKVEPLLLLKAARILQTCQR SPHILAGCILYKGLIVSTQLPP SLTAKVLLHRTAPQEQRLPTG EDAPQEHGAALPPNVQIIPVF VTKEEAISLHEFPVEQMTRSL ASPAGLQDGSAQHHPKGGST SALKENATGHVESMAWTTPD PTSPDEACPDGRKENGCLSGH DLESIRPAGLHNSARGEVLGL SSSLGKELVFLQEELDLSEIHI PEAQEVEMASGHFAFLHVPV PDGRAPYCKASLSASS SLEPT PPEDTAISSLRPPSAPEMLTQH GAQEQLEDHPGHSSQAPIPRA DPLPRRTRRPLLLPRLDPGQR GNKLPTGEQGLDEDVDGVCE SHAAPGLECSSGSANCQGAG PSADGISSRLTPAESCMGLVR MNLYTHCVKGLVLSLLAEEP LLGDSAAIEEVYHSSLASLNG LEVHLKETLPRDEAAS TS STY NFTHYDRIQSLLMANLPQVA TPQDRRFLQAVSLMHSEFAQ LPALYEMTV (SEQ ID NO: 192) | SNSCTS (SEQ ID NO: 193) |
| KIAA1267_Exon2_ARL17P1_Exon3 | NM_015443.2 | NM_001113738.1 | MAAMAPALTDAAAEAHHIRF KLAPPSSTLSPGSAENNGNAN ILIAANGTKRKAIAAEDPSLDF RNNPTKEDLGKLQPLVASYL CSDVTSVPSKESLKLQGVFSK QTVLKSHPLLSQSYELRAELL GRQPVLEFSLENLRTMNTSG QTALPQAPVNGLAKKLTKSS | VSVWRQ (SEQ ID NO: 195) |

TABLE 7-continued

| Trans-splicing ID | up-stream gene ACC# | down-stream gene ACC# | up WT sequence | down stream FS sequence |
|---|---|---|---|---|
| | | | THSDHDNSTSLNGGKRALTSS ALHGGEMGGSESGDLKGGM TNCTLPHRSLDVEHTTLYSNN STANKSSVNSMEQPALQGSS RLSPGTDSSSNLGGVKLEGKK SPLSSILFSALDSDTRITALLRR QADIESRARRLQKRLQVVQA KQVERHIQHQLGGFLEKTLSK LPNLESLRPRSQLMLTRKAEA ALRKAASETTTSEGLSNFLKS NSISEELERFTASGIANLRCSE QAFDSDVTDSSSGGESDIEEE ELTRADPEQRHVPLRRRSEW KWAADRAAIVSRWNWLQAH VSDLEYRIRQQTDIYKQIRAN K (SEQ ID NO: 194) | |
| LOC100129406_ NA_ CTTNBP2NL_ NA | XM_ 001722372.1 | NM_ 018704.2 | MAGRPGSQEQSKDRGTGSLP PPSQRPLGPSPEGAGPSPPPPG IPRGGGSSSSEGPHSYFLSLVD SQLLRRGFPLTPLIQRHLPPRT SALAERTH (SEQ ID NO: 196) | SIGHISTMLMAF (SEQ ID NO: 197) |
| RNF216_ Exon7_ RBAK_ Exon2 | NM_ 207116.1 | NM_ 021163.3 | MEEGNNNEEVIHLNNFHCHR GQEWINLRDGPITISDSSDEER IPMLVTPAPQQHEEEDLDDD VILTEDDSEDDYGEFLDLGPP GISEFTKPSGQTEREPKPGPSH NQAANDIVNPRSEQKVIILEE GSLLYTESDPLETQNQSSEDS ETELLSNLGESAALADDQAIE EDCWLDHPYFQSLNQQPREIT NQVVPQERQPEAELGRLLFQ HEFPGPAFPRPEPQQGGISGPS SPQPAHPLGEFEDQQLASDDE EPGPAFPMQESQEPNLENIWG QEAAEVDQELVELLVKETEA RFPDVANGFIEEIIHFKNYYDL NVLCNFLLENPDYPKREDRIII NPSSSLLASQDETKLPKIDFFD YSKLTPLDQRCFIQAADLLM ADFKVLSSQDIKWALHELKG HYAITRK (SEQ ID NO: 198) | VYQPQSLHVSKSSRK (SEQ ID NO: 199) |
| DEDD_ Exon4_ NIT1_Exon6 | NM_ 032998.2 | NM_ 005600.1 | MAGLKRRASQVWPEEHGEQ EHGLYSLHRMFDIVGTHLTH RDVRVLSFLFVDVIDDHERGL IRNGRDFLLALERQGRCDESN FRQVLQLLRIITRHDLLPYVTL KRRRA (SEQ ID NO: 200) | APSGLGL (SEQ ID NO: 201) |
| RAD54B_ Exon3_ LOC100128414_ NA | NM_ 012415.2 | XM_ 001722896.1 | MRRSAAPSQLQGNSFKKPKFI PPGRSNPGLNEEITKLNPDIKL FEGVAINNTFLPSQNDLRICSL NLPSEESTREINNRDNCSGKY CFEAPTLATLDPPHTV (SEQ ID NO: 202) | QTWMRRHRLVPVHYR (SEQ ID NO: 203) |
| TOPORS_ Exon2_ DDX58_ Exon2 | NM_ 005802.2 | NM_ 014314.3 | MGSQPPLGSPLSREEGEAPPP APASEGRRRSRRVLRLRGSCR HRPSFLGCRELAASAPARPAP ASSE (SEQ ID NO: 204) | KRCSIFRLRKTTRAQWRLPHFF SSSCWSSRRKAGSVAFWMP (SEQ ID NO: 205) |
| NDUFC2_ Exon2_ KCTD14_ Exon2 | NM_ 004549.4 | NM_ 023930.3 | MIARRNPEPLRFLPDEARSLPP PKLTDPRLLYIGFLGYCSGLID NLIRRRPIATAGLHRQLLYITA FFFAGYYLVKREDYLYAVRD REMFGYMKLHPEDFPEED (SEQ ID NO: 206) | VYCCGAERRG (SEQ ID NO: 207) |
| LRRC57_ ^Exon5_ SNAP23_ Exon8 | NM_ 153260.2 | NM_ 003825.2 | MGNSALRAHVETAQKTGVF QLKDRGLTEFPADLQKLTSNL RTIDLSNNKIESLPPLLIGKFTL LKSLSLNNNKLTVLPDEICNL KKLETLSLNNNHLRELPSTFG | SALSVIRFICGF (SEQ ID NO: 209) |

TABLE 7-continued

| Trans-splicing ID | up-stream gene ACC# | down-stream gene ACC# | up WT sequence | down stream FS sequence |
|---|---|---|---|---|
| | | | QLSALKTLSLSGNQLGALPPQ LCSLRHLDVMDLSKNQIRSIP DSVGELQVIELNLNQNQISQIS VKISCCPRLKILRL (SEQ ID NO: 208) | |
| IPO11_ NA_SLRN_ NA | NM_ 001134779.1 | NM_ 181506.4 | MVQPIIHLGYVVYSLLYLGY KPVQHVTALNTVSSCHKMVS MDLNSASTVVLQVLTQATSQ DTAVLKPAEEQKQWETQPG FYSVLLNIFTNHTLDINVRWL AVLYFKHGIDRYWRRVAPHA LSEEEKTTLRAGLITNFNEPIN QIATQIAVLIAKVARLDCPRQ WPELIPTLIESVKVQDDLRQH RALLTFYHVTKTLASKRLAA DRKLFYDLASGIYNFACSLW NHHTDTFLQEVSSGNEAAILS SLERTLLSLKVLRKLTVNGFV EPHKNMEVMGFLHGIFERLK QFLECSRSIGTDNVCRDRLEK TIILFTKVLLDFLDQHPFSFTP LIQRSLEFSVSYVFTEVGEGV TFERFIVQCMNLIKMIVKNYA YKPSKNFEDSSPETLEAHKIK MAFFTYPTLTEICRRLVSHYF LLTEEELTMWEEDPEGFTVEE TGGDSWKYSLRPCTEVLFIDI FHEYNQTLTPVLLEMMQTLQ GPTNVEDMNALLIKDAVYNA VGLAAYELFDSVDFDQWFKN QLLPELQVIHNRYKPLRRRVI WLIGQWISVKFKSDLRPMLY EAICNLLQDQDLVVRIETATT LKLTVDDFEFRTDQFLPYLET MFTLLFQLLQQVTECDTKMH VLHVLSCVIERVNMQIRPYVG CLVQYLPLLWKQSEEHNMLR CAILTTLIHLVQGLGADSKNL YPFLLPVIQLSTDVSQPPHVY LLEDGLELWLVTLENSPCITP ELLRIFQNMSPLLELSSENLRT CFKIINGYIFLSSTEFLQTYAV GLCQSFCELLKEITTEGQVQV LKVVENALKVNPILGPQMFQ PILPYVFKGIIEGERYPVVMST YLGVMGRVLLQNTSFFSSLL NEMAHKFNQEMDQLLGNMI EMWVDRMDNITQPERRKLSA LALLSLLPSDNS (SEQ ID NO: 210) | LASKGP (SEQ ID NO: 211) |
| SNRPF_ Exon2_ CCDC38_ ^Exon12 | NM_ 003095.2 | NM_ 182496.1 | MSLPLNPKPFLNGLTGKPVM VKLKWGMEYKGYLVSVDGY MNMQ (SEQ ID NO: 212) | QDFHLHLGNIETK (SEQ ID NO: 213) |
| RNF139_ Exon1_ NDUFB9_ Exon2 | NM_ 007218.3 | NM_ 005005.2 | MAAVGPPQQQVRMAHQQV WAALEVALRVPCLYIIDAIFN SYPDSSQSRFCIVLQIFLRLF (SEQ ID NO: 214) | ETNTDTLLV (SEQ ID NO: 215) |
| NDUFB8_ Exon4_ SEC31B_ ^Exon2 | NM_ 005004.2 | NM_ 015490.3 | MAVARAGVLGVQWLQRASR NVMPLGARTASHMTKDMFP GPYPRTPEERAAAAKKYNMR VEDYEPYPDDGMGYGDYPK LPDRSQHERDPWYSWDQPGL RLNWGEPMHWHLDMYNRN RVDTSPTPVSWHVMCMQLFG FLAFMIFMCWVGDVYPVYQP V (SEQ ID NO: 216) | DRP (SEQ ID NO: 217) |
| MIA_ Exon3_ RAB4B_Exon2 | NM_ 006533.2 | NM_ 016154.3 | MARSLVCLGVIILLSAFSGPG VRGGPMPKLADRKLCADQEC SHPISMAVALQDYMAPDCRF | TSSSNSW (SEQ ID NO: 219) |

TABLE 7-continued

| Trans-splicing ID | up-stream gene ACC# | down-stream gene ACC# | up WT sequence | down stream FS sequence |
|---|---|---|---|---|
| | | | LTIHRGQVVYVFSKLKGRGR LFWGGSVQGDYYGDLAARL GYFPSSIVREDQTLKPGKVDV KTD (SEQ ID NO: 218) | |
| THAP2_Exon2_TMEM19_Exon2 | NM_031435.2 | NM_018279.3 | MPTNCAAAGCATTYNKHINI SFHRFPLDPKRRKEWVRLVR RKNFVPGKHTFLCSKHFEASC FDLTGQTRRLKMDAVPTIFDF CTHIKSM (SEQ ID NO: 220) | VTYDLFLRGVGCFLLLFLF (SEQ ID NO: 221) |
| NIT1_Exon6_DEDD_Exon4 | NM_005600.1 | NM_032998.2 | MLGFITRPPHRFLSLLCPGLRI PQLSVLCAQPRPRAMAISSSS CELPLVAVCQVTSTPDKQQN FKTCAELVREAARLGACLAF LPEAFDFIARDPAETLHLSEPL GGKLLEEYTQLARECGLWLS LGGFHERGQDWEQTQKIYNC HVLLNSKGAVVATYRKTHLC DVEIPGQGPMCESNSTMPGPS LESPVSTPAGKIGLAVCYDMR FPELSLALAQAGAEILTYPSAF GSITGPAHWE (SEQ ID NO: 222) | QPVSS (SEQ ID NO: 223) |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of making an anti-cancer therapeutic composition, comprising:
   (a) contacting a biological sample obtained from a subject to a peptide array, the peptide array comprising a plurality of frameshift variant peptides, wherein the biological sample comprises antibodies, and wherein the plurality of frameshift peptides comprise one or more peptides having a sequence as set forth in any of SEQ ID NOs: 22-33, 35-54, 57-65, 67-68, 71-90, 92-94, 96-109, 111-117, 131, 133, 135, 137, 139, 141, 143, 145, 149, 151, 153, 165, 167, 169, 171, 173, 175, 177, 179, 181, 183, 185, 187, 189, 191, 197, 199, 203, 205, 207, 209, 213, or 221, wherein the plurality of frameshift peptides comprise peptides encoded by an mRNA having an RNA processing error, the RNA processing error comprising a mis-splicing or an insertion or a deletion during transcription, and wherein each frameshift peptide of the plurality of frameshift peptides comprises 10 amino acids or more;
   (b) detecting binding of the antibodies in the biological sample to at least one peptide in the peptide array; and
   (c) producing a composition comprising one or more immune reactive neoantigens corresponding to the at least one peptide bound by the antibodies.

2. The method of claim 1, wherein the plurality of frameshift variant peptides are fixed on a substrate.

3. The method of claim 2, wherein the substrate comprises glass, composite, resin, or combination thereof.

4. The method of claim 1, wherein the peptide array is configured to detect binding by at least one of fluorescence, luminescence, calorimetry, chromatography, radioactivity, Bio-Layer Interferometry, and surface plasmon resonance.

5. The method of claim 1, wherein the peptide array comprises at least about 25000, about 50000, about 75000, about 100000, about 125000, about 150000, about 175000, about 200000, about 225000, about 250000, about 275000, about 300000, about 325000, about 350000, about 375000, or about 400000 frameshift variant peptides.

6. The method of claim 1, wherein the biological sample comprises blood, serum, plasma, cerebrospinal fluid, saliva, urine, or combinations thereof.

7. The method of claim 1, wherein the subject is a human, a dog, a cat, a mouse, a rat, a rabbit, a horse, a cow, or a pig.

8. The method of claim 1, wherein the subject is suspected of having a cancer.

9. The method of claim 8, wherein the cancer is selected from the group consisting of acute lymphoblastic leukemia, acute monocytic leukemia, acute myeloid leukemia, acute promyelocytic leukemia, adenocarcinoma, adult T-cell leukemia, astrocytoma, bladder cancer, bone cancer, brain tumor, breast cancer, Burkitt's lymphoma, carcinoma, cervical cancer, chronic lymphocytic leukemia, chronic myelogenous leukemia, colon cancer, colorectal cancer, endometrial cancer, glioblastoma multiforme, glioma, hepatocellular carcinoma, Hodgkin's lymphoma, inflammatory breast cancer, kidney cancer, leukemia, lung cancer, lymphoma, malignant mesothelioma, medulloblastoma, melanoma, multiple myeloma, neuroblastoma, non-Hodgkin lymphoma, non-small cell lung cancer, ovarian cancer, pancreatic cancer, pituitary tumor, prostate cancer, retinoblastoma, skin cancer, small cell lung cancer, squamous cell carcinoma, stomach cancer, T-cell leukemia, T-cell lymphoma, thyroid cancer, and Wilms' tumor.

10. The method of claim 1, wherein the frameshift peptide comprises a peptide encoded by an mRNA having an RNA processing error comprising intron retention.

11. The method of claim 1, wherein the composition comprises an adjuvant.

12. The method of claim 11, wherein the adjuvant is selected from the group consisting of ABM2, AS01B, AS02, AS02A, Adjumer, Adjuvax, Algammulin, alum, aluminum phosphate, aluminum potassium sulfate, *Bordetella pertussis*, calcitriol, chitosan, cholera toxin, CpG, dibutyl phthalate, dimethyldioctadecylammonium bromide (DDA), Freund's adjuvant, Freund's complete, Freund's incomplete (IFA), GM-CSF, GMDP, gamma inulin, glycerol, HBSS (Hank's Balanced Salt Solution), polyinosinic-polycytidylic acid stabilized with polylysine and carboxymethylcellulose (poly-ICLC, also known as Hiltonol), IL-12, IL-2, imiquimod, interferon-gamma, ISCOM, lipid core peptide (LCP), lipofectin, lipopolysaccharide (LPS), liposomes, MF59, MLP+TDM, monophosphoryl lipid A, Montanide IMS-1313, Montanide ISA 206, Montanide ISA 720, Montanide ISA-51, Montanide ISA-50, nor-MDP, oil-in-water emulsion, P1005 (non-ionic copolymer), Pam3Cys (lipoprotein), pertussis toxin, poloxamer, QS21, RaLPS, Ribi, saponin, Seppic ISA 720, soybean oil, squalene, Syntex adjuvant formulation (SAF), synthetic polynucleotides (poly IC/poly AU), TiterMax tomatine, Vaxfectin, XtendIII, or Zymosan.

13. The method of claim 1, further comprising preparing a vector encoding the one or more immune reactive neoantigens.

14. The method of claim 1, wherein producing the composition comprises selecting immune reactive neoantigens with a high positive rate in a specific cancer type.

15. The method of claim 1, wherein producing the composition comprises selecting immune reactive neoantigens with a high positive rate across multiple cancer types.

16. A method of making an anti-cancer therapeutic composition, comprising:
(a) contacting a biological sample obtained from a subject to a peptide array, the peptide array comprising a plurality of frameshift variant peptides, wherein the biological sample comprises antibodies, and wherein the plurality of frameshift peptides comprise one or more peptides of SEQ ID NOs: 22-33, 35-54, 57-65, 67-68, 71-90, 92-94, 96-109, 111-117, 131, 133, 135, 137, 139, 141, 143, 145, 149, 151, 153, 165, 167, 169, 171, 173, 175, 177, 179, 181, 183, 185, 187, 189, 191, 197, 199, 203, 205, 207, 209, 213, or 221, wherein the plurality of frameshift peptides comprise peptides encoded by an mRNA having an RNA processing error, the RNA processing error comprising a mis-splicing or an insertion or a deletion during transcription, and wherein each frameshift peptide of the plurality of frameshift peptides comprises 10 amino acids or more;
(b) detecting binding of the antibodies in the biological sample to at least one peptide in the peptide array; and
(c) producing a composition comprising a nucleic acid encoding an immune reactive neoantigen corresponding to the at least one peptide bound by the antibodies.

* * * * *

SEQUENCE LISTING

```
<160> NUMBER OF SEQ ID NOS: 239

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 1
tgccatacct gtttttccc                                                  19

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
agttatctca ggtaggtgtt gc                                              22

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 3
```
aagggagtct gtggttga					18

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 4
caaagaggga agagagtgg					19

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
aaaggaaaag ctgaaagtgg aa				22

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
gcaacagcaa ggagaagaat ac				22

<210> SEQ ID NO 7
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 7
aagggagtct gtggttga					18

<210> SEQ ID NO 8
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 8
caaagaggga agagagtgg					19

<210> SEQ ID NO 9
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 9
ctgtcatggg tttcctg					17

<210> SEQ ID NO 10
<211> LENGTH: 17
<212> TYPE: DNA
<213> ORGANISM: Artificial Sequence

```
<220> FEATURE:
<223> OTHER INFORMATION: Synthetic Oligonucleotide

<400> SEQUENCE: 10
gagctgtcct ctccttg                                                      17

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
cctgaaactg attgagattg ag                                                22

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
tcttcagcct tcaccatttc                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
ccaaccgtga aaagatgacc                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
tgccaatagt gatgacctgg                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
ccaaccgcga gaagatgacc                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
tgccaatggt gatgacctgg                                                   20
```

```
<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
atcggtgatg tcggcgatat                                               20

<210> SEQ ID NO 18
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 18
gtaacacagg cagatgtagg a                                             21

<210> SEQ ID NO 19
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 19
caatggctct gggtgctgtg gaatc                                         25

<210> SEQ ID NO 20
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 20
gggtcgacag attatcggac c                                             21

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
gtcatactcc tgcgccagct                                               20

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 22

Ser Pro Ser Gln Ala Met Trp Ala Thr Arg Met
1               5                   10

<210> SEQ ID NO 23
<211> LENGTH: 28
<212> TYPE: PRT
<213> ORGANISM: Artificial Sequence
<220> FEATURE:
```

```
<223> OTHER INFORMATION: Synthetic Peptide

<400> SEQUENCE: 23

Gly Val Gly Gly Gly Ile Leu Pro Pro Glu Thr Pro Pro Val Ser Ala
1               5                   10                  15

Trp Gly Glu Leu Cys Pro Pro Ala Trp Leu His Leu
            20                  25

<210> SEQ ID NO 24
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 24

Arg His Glu Lys Cys Cys Asn Trp Lys Gln Gln Ala Glu Ser Gln Ser
1               5                   10                  15

His Cys Phe Arg Ser Cys Ser Lys Ile Val Val Leu Ala Ser Ala Arg
            20                  25                  30

Asn Leu Lys His Arg Ala Glu Asn
        35                  40

<210> SEQ ID NO 25
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 25

Thr Thr Asn Pro Ser Arg Ile Ser Leu Pro Ser Trp Val Trp Met Asn
1               5                   10                  15

Phe Leu Arg Lys Thr Ser
            20

<210> SEQ ID NO 26
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 26

Asp His Gly Gly Val Gly Arg Cys Ser Asn Val Leu Pro Trp Glu Glu
1               5                   10                  15

Gly Asp Ser Gln Arg His Lys Ala Arg Lys Ser Ala Leu Arg Ala Gln
            20                  25                  30

Gly Arg Ala Glu Asp Cys
        35

<210> SEQ ID NO 27
<211> LENGTH: 53
<212> TYPE: PRT
<213> ORGANISM: Artificial Sequence
<220> FEATURE:
<223> OTHER INFORMATION: Synthetic Peptide

<400> SEQUENCE: 27

Trp Ser Cys Ser Ser Ile Thr Gly Ala Ala Gly Asn Leu Asn Thr Thr
1               5                   10                  15

Ser Trp Ser Thr Arg Leu Trp Pro Asn Gly Arg Arg Lys Lys Leu Ser
            20                  25                  30
```

Ser Gly Trp Ser Ser Trp Ala Leu Gly His Leu Phe Thr Gly Lys Gly
        35                  40                  45

Phe Tyr Leu Asn Glu
    50

<210> SEQ ID NO 28
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 28

Phe Ser Leu Lys Met Ser Ser Tyr Pro Leu Leu Gly Leu Ile Met Lys
1               5                   10                  15

Gly Asn Ser Phe His Asn Val Ile Pro Val Asn Ala Leu Thr
            20                  25                  30

<210> SEQ ID NO 29
<211> LENGTH: 48
<212> TYPE: PRT
<213> ORGANISM: Artificial Sequence
<220> FEATURE:
<223> OTHER INFORMATION: Synthetic Peptide

<400> SEQUENCE: 29

Pro Cys Thr Gly Leu Ser Leu His Pro Met Ala Pro Arg Ile Trp Ser
1               5                   10                  15

Arg Trp Ser Phe Pro Ala Gly Arg Cys Gln Asp Arg Pro Asn Lys His
            20                  25                  30

Val Trp Pro Pro Gln Lys Lys Lys Lys Lys Lys Lys Lys Lys Lys Lys
        35                  40                  45

<210> SEQ ID NO 30
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 30

Gly Ser Ala Asp Arg Asp Asp Gly Lys Val
1               5                   10

<210> SEQ ID NO 31
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 31

Cys Tyr Gln His Pro Phe Pro Lys Lys Ser Gln Phe Pro Gly Ala Tyr
1               5                   10                  15

Trp Thr Ser Phe Glu Gly Glu Glu Glu Gly Ser Gly Gln Leu Thr Leu
            20                  25                  30

Pro Gly Pro
        35

<210> SEQ ID NO 32
<211> LENGTH: 28
<212> TYPE: PRT
<213> ORGANISM: Artificial Sequence

```
<220> FEATURE:
<223> OTHER INFORMATION: Synthetic Peptide

<400> SEQUENCE: 32

Gly Phe Ala Ala Ser Trp Leu Phe Lys Lys Pro Arg Pro Ser Glu Cys
1               5                   10                  15

His Thr Val Ile Phe Lys Glu Glu Ser Tyr Met Asn
            20                  25

<210> SEQ ID NO 33
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 33

Asp Ala Ala Phe Phe Met Ser Pro Lys Leu Ile Trp Trp Gln Glu Met
1               5                   10                  15

Ala Thr Glu Arg Gly Leu Phe Gly Leu Glu Ile Pro Ile Ile Leu Lys
            20                  25                  30

Glu Leu

<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 34

Cys Phe Thr Ser Ser Pro Leu Arg Trp
1               5

<210> SEQ ID NO 35
<211> LENGTH: 167
<212> TYPE: PRT
<213> ORGANISM: Artificial Sequence
<220> FEATURE:
<223> OTHER INFORMATION: Synthetic Peptide

<400> SEQUENCE: 35

Arg Val Gln Gly Thr Leu Val His Cys Pro Thr Arg His Leu Ser Gln
1               5                   10                  15

Arg Arg Gly Pro Gly Arg Gln Arg Gly Asn Ser Leu Pro Glu Pro Ser
            20                  25                  30

Ser Met Leu Thr Cys Pro Gln Pro His Arg Ala Thr Phe Pro Ala
            35                  40                  45

Ala Pro Gly Leu Gln Gly Cys Pro Arg Thr Gly Pro Ser Gln Pro Ser
50                  55                  60

Met Gln Leu Pro Ser Tyr Pro Glu Asp Gly Ser Gly Leu Ser Arg Gly
65                  70                  75                  80

His Lys Asp Val Arg Pro Gly Pro Pro Gly Gln Glu Arg Val Gln Val
            85                  90                  95

Leu Arg Ala Cys Ala Pro Gln Pro Gln His Gln Val Asp Cys Ser Ala
            100                 105                 110

Val Gly Gly Pro Val Ala Ala Arg Glu Lys Pro Pro Val Ser Arg Leu
            115                 120                 125

Gly Ser Ala His Gln Gly Leu Pro Thr Ser Ala Phe Glu Gly Ala Cys
            130                 135                 140
```

His Ala Leu Gly Asp Pro Gly Ile Phe Thr Gly Leu Glu Ala Gly Asp
145                 150                 155                 160

Arg Thr Val Ser Val Pro Gly
                165

<210> SEQ ID NO 36
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 36

Cys Leu Gln Lys His Leu Pro Val Ala Leu Ser Thr Ser Leu Cys
1               5                   10                  15

<210> SEQ ID NO 37
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 37

Met Thr Ser Leu Leu Ser Ser His His Pro Leu Lys Arg Arg Asn Leu
1               5                   10                  15

Glu Pro

<210> SEQ ID NO 38
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 38

Leu Leu Ser Ser His His Pro Leu Lys Arg Arg Asn Leu Glu Pro
1               5                   10                  15

<210> SEQ ID NO 39
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 39

Thr Ser Ala Ser Gln Ile Gln Ala Ile Leu Val Pro
1               5                   10

<210> SEQ ID NO 40
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 40

Leu Leu Leu Gln Leu Arg Pro Gly Ser Arg Pro Phe Pro Val Thr Tyr
1               5                   10                  15

Val Ser Val Thr Gly Arg Gln Pro Tyr Lys Ser Trp
                20                  25

<210> SEQ ID NO 41
<211> LENGTH: 26

```
<212> TYPE: PRT
<213> ORGANISM: Artificial Sequence
<220> FEATURE:
<223> OTHER INFORMATION: Synthetic Peptide

<400> SEQUENCE: 41

Ala Ala Ala Ala Ala His His His Ser Pro Arg Pro Ala Ala Leu Arg
1               5                   10                  15

His Pro Gln Glu Glu Thr Gly Cys Val Pro
            20                  25

<210> SEQ ID NO 42
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 42

Leu Leu Gln Pro Pro Phe Val Phe Ile Pro Pro Gly Cys Val Met Leu
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 43

Ser Pro Lys Leu Pro Leu Val Arg Arg Trp Met Gln
1               5                   10

<210> SEQ ID NO 44
<211> LENGTH: 61
<212> TYPE: PRT
<213> ORGANISM: Artificial Sequence
<220> FEATURE:
<223> OTHER INFORMATION: Synthetic Peptide

<400> SEQUENCE: 44

Leu Pro Cys Ser Ser Leu Thr Ser Tyr Trp Glu Met Leu Trp Leu Trp
1               5                   10                  15

Leu His Asp Trp Arg Arg Arg Gln Gly Gln Arg Cys Ser Phe Trp Val
            20                  25                  30

Thr Gln Pro Thr Ala Ala Ala Trp Met Cys Trp Val Leu Ser Lys
        35                  40                  45

Leu Glu Leu Arg Leu Ser Tyr Ile Leu Ala Leu Pro Ala
    50                  55                  60

<210> SEQ ID NO 45
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 45

His Phe Pro Ala Cys Gln Leu Leu Pro Leu Cys Asp Leu Ile Ser Ser
1               5                   10                  15

Ala Leu Pro Tyr Val Glu
            20

<210> SEQ ID NO 46
```

```
<211> LENGTH: 44
<212> TYPE: PRT
<213> ORGANISM: Artificial Sequence
<220> FEATURE:
<223> OTHER INFORMATION: Synthetic Peptide

<400> SEQUENCE: 46

Cys Leu Gln Asn Trp Trp Tyr Trp Tyr Cys Ser Cys Trp Pro Ser Gly
1               5                   10                  15

Asp Trp Cys Ser Gln Thr Arg Tyr Gly Gly His Leu Cys Ser Ser Gln
            20                  25                  30

Arg Tyr Asn Gly Ser Lys Ile Cys Arg Asn Ala Pro
        35                  40

<210> SEQ ID NO 47
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 47

Gly Phe Trp Ser Arg Phe Pro Pro Pro Trp
1               5                   10

<210> SEQ ID NO 48
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 48

Val Ser Pro Gly Val Ser Glu Leu Arg Arg Asn Ser Lys Lys Tyr Gly
1               5                   10                  15

Lys Ala Gly Glu Ala Val Trp Phe Ser Ser Asp Pro Pro Val Leu Phe
            20                  25                  30

Phe His Phe Leu Arg Thr Glu
        35

<210> SEQ ID NO 49
<211> LENGTH: 101
<212> TYPE: PRT
<213> ORGANISM: Artificial Sequence
<220> FEATURE:
<223> OTHER INFORMATION: Synthetic Peptide

<400> SEQUENCE: 49

Val Leu Gly Ser Gln Arg His Pro Gly Gln Gly Ser Cys Gly Ser Cys
1               5                   10                  15

Pro Trp His Leu Cys Ser Ser Pro His Pro Thr Cys Gly Ser Gly Phe
            20                  25                  30

Gly Thr Arg Ser Gly Arg Ala Gly Arg Cys Cys Gly Ala Gly Pro
        35                  40                  45

Ser Pro Gly Thr Trp Thr Val Arg Thr Pro Ala Ala Arg Arg Pro
    50                  55                  60

Ala Cys Ala Gly Ser Ala Arg Cys Arg Ala Ala Gly Arg Ala
65                  70                  75                  80

Val Ala Pro Arg Phe Glu Ser Cys Ser Ser Met Leu Pro Gly Thr Gly
                85                  90                  95

Thr Arg Arg Pro Cys
                100
```

<210> SEQ ID NO 50
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 50

Gly Trp Pro Gly His Val Met Gly Ser Gln Arg Arg Gln Thr Pro Leu
1               5                   10                  15

His Ala Arg Trp Trp Gly His His Gln Arg Pro Val Leu Gln Pro
            20                  25                  30

<210> SEQ ID NO 51
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 51

Gly Pro Arg Gly His Ala Gly Glu Gly Gly Arg Gln Ser Cys Gly Arg
1               5                   10                  15

Pro Val Leu Arg Gly Arg
            20

<210> SEQ ID NO 52
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 52

Val Gln Met Lys Met Met Lys Ser Ser Ser Asp Pro Leu Asp Ile Lys
1               5                   10                  15

Lys Asp Val Leu Leu Pro Ala Trp Asn
            20                  25

<210> SEQ ID NO 53
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 53

Glu Gly Val Leu Leu Gln Val Thr Asn Glu Glu Val Val Asn His Arg
1               5                   10                  15

Val Phe Lys Lys
            20

<210> SEQ ID NO 54
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 54

Lys Glu Gly Val Leu Leu Gln Val Thr Asn Glu Glu Val Val Asn His
1               5                   10                  15

Arg Val Phe Lys Lys

-continued

```
                20

<210> SEQ ID NO 55
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 55

Asp Ser Cys Gly Ile Val Asn Ser Tyr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 56

Asp Ser Cys Gly Ile Val Asn Ser Tyr
1               5

<210> SEQ ID NO 57
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 57

Asn Cys Pro Val Trp Arg His Asn Pro Cys Leu Ala Ser Trp Met Ser
1               5                   10                  15

Trp Arg Cys Trp Lys Ser
            20

<210> SEQ ID NO 58
<211> LENGTH: 64
<212> TYPE: PRT
<213> ORGANISM: Artificial Sequence
<220> FEATURE:
<223> OTHER INFORMATION: Synthetic Peptide

<400> SEQUENCE: 58

Ile Val Gly Pro Gly Pro Lys Pro Glu Ala Ser Ala Lys Leu Pro Ser
1               5                   10                  15

Arg Pro Ala Asp Asn Tyr Asp Asn Phe Val Leu Pro Glu Leu Pro Ser
            20                  25                  30

Val Pro Asp Thr Leu Pro Thr Ala Ser Ala Gly Ala Ser Thr Ser Ala
        35                  40                  45

Ser Glu Asp Ile Asp Phe Asp Leu Ser Arg Arg Phe Glu Glu Leu
    50                  55                  60

<210> SEQ ID NO 59
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 59

Val Gly Ser Met Pro Lys Glu Leu Leu Gly Glu Ser Ser Ser Ser Met
1               5                   10                  15
```

```
Ile Phe Glu Glu Arg Gly
            20
```

<210> SEQ ID NO 60
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 60

```
His Arg Asp Ser Arg Gly Ser Gly Arg Asn Gly Arg His Pro Glu Arg
1               5                   10                  15

Glu Gly Asp His Ala Lys Pro Glu Arg Pro Pro Gly Leu Leu Pro Gly
            20                  25                  30

Gln Ser Glu Glu Pro Gly Asp Arg Glu Pro Glu Ala Gly Glu Gln Asn
        35                  40                  45

Pro Gly Ala Leu Gly Glu Glu Gly Thr Pro Gly Gln Arg Leu Glu Pro
    50                  55                  60

Leu Leu Gln Asp His Arg Gly Pro Glu Gly Ser Asp Leu Arg Lys Tyr
65              70                  75                  80

Cys Gly Gln Cys Pro His Arg Ser Ala Asp
                85                  90
```

<210> SEQ ID NO 61
<211> LENGTH: 50
<212> TYPE: PRT
<213> ORGANISM: Artificial Sequence
<220> FEATURE:
<223> OTHER INFORMATION: Synthetic Peptide

<400> SEQUENCE: 61

```
Leu Leu Arg Ser Arg His Ser Thr Arg Ile Leu Pro Thr Ala Ala Gly
1               5                   10                  15

Leu Arg Leu Arg Ala Cys Thr Arg Ser Ser Met Arg Ser Cys Arg Ala
            20                  25                  30

Trp Leu Gly Ser Thr Gly Met Thr Cys Gly Ala Gln Arg Leu Arg Ser
        35                  40                  45

Leu Arg
    50
```

<210> SEQ ID NO 62
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 62

```
Arg Cys Gln Pro Asp Arg His Ser His Ile Trp Ala Leu Arg Trp Pro
1               5                   10                  15

Trp Trp Ser Trp Cys Gln His Gly Trp Gln Leu Trp Cys Leu Trp Phe
            20                  25                  30

Leu Leu Gln Val
        35
```

<210> SEQ ID NO 63
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 63

Glu Thr Pro Ser Asp Ser Asp His Lys Lys Lys Lys Lys Lys Glu
1               5                   10                  15

Glu Asp Pro Glu Arg Lys Arg Lys Lys Glu Lys Lys Lys Lys
            20                  25                  30

Val Glu

<210> SEQ ID NO 64
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 64

Ala Gly Asn Val Arg Ser Asn Ser Arg Pro Ser Ile Gln Arg
1               5                   10

<210> SEQ ID NO 65
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 65

Pro Ala Ser Gly Gly Ser Asp Leu Val Asn His Ser Phe Leu Cys Lys
1               5                   10                  15

Trp His Pro

<210> SEQ ID NO 66
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 66

Cys Leu Leu Leu Gly Ala Val Thr Leu
1               5

<210> SEQ ID NO 67
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 67

Glu Ile Pro Glu Arg Asn Gln Gly Pro Val Ala Ala Ile Arg Ser
1               5                   10                  15

<210> SEQ ID NO 68
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 68

Leu His Trp Gly Ser Thr Lys Val His Leu Leu Leu Ile
1               5                   10

```
<210> SEQ ID NO 69
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 69

Gly Gly Pro Arg Arg Ile Trp Ser
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 70

Gly Gly Pro Arg Arg Ile Trp Ser
1               5

<210> SEQ ID NO 71
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 71

Arg Ser Val Lys Trp Ser Pro Asn Thr Met Gln Met Gly Arg Thr Pro
1               5                   10                  15

Met Pro

<210> SEQ ID NO 72
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 72

Val Pro Thr Ala Cys Cys Arg Cys Cys Phe Cys Trp Asp Val
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 73

Ser Gly Lys Thr Ser Ser Ile Leu Cys Arg Arg Gly Arg Trp Arg Trp
1               5                   10                  15

Ser

<210> SEQ ID NO 74
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 74

Ala Gly Asp Ala Val Leu Gly Ala His Thr Gln Arg Pro Cys Val Val
```

```
Gly Gly Ser Gly
            20
```

<210> SEQ ID NO 75
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 75

```
Gly Ala Lys Pro Gly Gly Leu Ala Leu Gly Ala Val
1               5                   10
```

<210> SEQ ID NO 76
<211> LENGTH: 100
<212> TYPE: PRT
<213> ORGANISM: Artificial Sequence
<220> FEATURE:
<223> OTHER INFORMATION: Synthetic Peptide

<400> SEQUENCE: 76

```
Asp Glu Val Phe Ala Leu Pro Leu Ala His Leu Leu Gln Thr Gln Asn
1               5                   10                  15

Gln Gly Tyr Thr His Phe Cys Arg Gly Gly His Phe Arg Tyr Thr Leu
            20                  25                  30

Pro Val Phe Leu His Gly Pro His Arg Val Trp Gly Leu Thr Ala Val
        35                  40                  45

Ile Thr Glu Phe Ala Leu Gln Leu Leu Ala Pro Gly Thr Tyr Gln Pro
50                  55                  60

Arg Leu Ala Gly Leu Thr Cys Ser Gly Ala Glu Gly Leu Ala Arg Pro
65                  70                  75                  80

Lys Gln Pro Leu Ala Ser Pro Cys Gln Ala Ser Ser Thr Pro Gly Leu
                85                  90                  95

Asn Lys Gly Leu
            100
```

<210> SEQ ID NO 77
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 77

```
Gln Glu Asn Cys Ser Asn Pro Gly Gly Arg Gly Cys Ser Asp Pro Arg
1               5                   10                  15

Ser Cys His Phe Thr Pro Ala Trp Ala Lys Glu Gln Asn Ala Ile Ser
            20                  25                  30

Lys Asn Ile His Ile
            35
```

<210> SEQ ID NO 78
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 78

```
Ala Lys Phe Cys Pro Thr Phe Asn Lys Ser Met Glu Glu Gln Gly Lys
1               5                   10                  15
```

```
<210> SEQ ID NO 79
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 79

Gly Leu Trp Leu Phe Arg Pro Gln Asn Val Leu Gln Met Pro Gln Ser
1               5                   10                  15

Ile Leu Leu Gln Gln Gly Ala Ser Asp Pro Arg Leu Glu Ile Gly Thr
            20                  25                  30

<210> SEQ ID NO 80
<211> LENGTH: 49
<212> TYPE: PRT
<213> ORGANISM: Artificial Sequence
<220> FEATURE:
<223> OTHER INFORMATION: Synthetic Peptide

<400> SEQUENCE: 80

Asp Tyr Arg Arg Leu Pro Pro Gly Pro Ala Asn Phe Phe Cys Ile Phe
1               5                   10                  15

Ser Arg Asp Gly Val Ser Pro Cys Tyr Pro Gly Trp Ser Pro Ser Pro
            20                  25                  30

Asp Leu Val Met Ser Pro Leu Arg Ser Pro Lys Val Leu Gly Leu Gln
        35                  40                  45

Ala

<210> SEQ ID NO 81
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 81

Pro Leu Arg Arg Pro Cys Thr Arg Ser Cys Trp Gly Gln Gly Ser
1               5                   10                  15

<210> SEQ ID NO 82
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 82

Cys Asp Leu Asn Ser Leu Cys Ile Phe Val Ala Ile Phe His Thr Lys
1               5                   10                  15

Cys Phe Lys Cys Gly Glu Ser Ile Lys His Leu Tyr Ser
            20                  25

<210> SEQ ID NO 83
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 83

Gly Thr Ile Val Val Gln Trp Gly Pro Ser Trp Cys Leu Thr
```

<210> SEQ ID NO 84
<211> LENGTH: 88
<212> TYPE: PRT
<213> ORGANISM: Artificial Sequence
<220> FEATURE:
<223> OTHER INFORMATION: Synthetic Peptide

<400> SEQUENCE: 84

```
Gly Leu Trp Met Val Val Arg Ser Val Trp Ile Met Gln Ala Ser Leu
1               5                   10                  15

Leu Gly Glu Pro Glu Glu Val Ala Leu Gly Pro Met Gly Val Val Ala
            20                  25                  30

Ala Thr Leu Glu Val Val Gly Thr Arg Ala Met Gly Val Ala Gly Ile
        35                  40                  45

Met Thr Val Asp Leu Glu Gly Met Asp Met Asp Met Asp Val Pro Glu
    50                  55                  60

Thr Ile Met Ala Glu Thr Arg Val Val Met Thr Ala Thr Gln Glu Glu
65                  70                  75                  80

Ile Thr Glu Thr Ile Met Thr Thr
                85
```

<210> SEQ ID NO 85
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 85

```
Ser Leu Pro Pro Asn Pro Ser Ala Ala Arg Glu Thr Lys Gly Ile Ser
1               5                   10                  15

Pro Ile Lys Asp Ser Lys Cys Val Phe Pro Arg Thr Ser Pro Gly Lys
            20                  25                  30

Asp Pro Leu Pro
        35
```

<210> SEQ ID NO 86
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 86

```
Gly Leu Phe Val Phe Pro Ile Tyr Cys Leu Cys
1               5                   10
```

<210> SEQ ID NO 87
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 87

```
Glu Val Trp Arg His Leu Leu Gly Arg Pro His Ser
1               5                   10
```

<210> SEQ ID NO 88
<211> LENGTH: 12
<212> TYPE: PRT

```
<213> ORGANISM: Artificial Sequence
<220> FEATURE:
<223> OTHER INFORMATION: Synthetic Peptide

<400> SEQUENCE: 88

Ile Arg Glu Leu Cys His Arg Tyr Leu Pro Gln Pro
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 89

Gly Val Arg Gln Trp Gln His Leu Gln Pro
1               5                   10

<210> SEQ ID NO 90
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 90

Gly Leu Leu Trp Cys Ala Ala Val His His Gly Glu Trp Gly Gln Arg
1               5                   10                  15

Leu Arg Gly Cys Gly Val Trp Glu Thr Pro Arg Thr Glu Gly
            20                  25                  30

<210> SEQ ID NO 91
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 91

Phe Gly Lys Ala His Gly Ala Ser Trp
1               5

<210> SEQ ID NO 92
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 92

Gly Asp Gly Gly Ser Gly Ser Lys Gly Arg Pro Val Glu Gln Thr Glu
1               5                   10                  15

Val Phe Leu Cys Ile Ser Lys Pro Ser Ser Phe Leu
            20                  25

<210> SEQ ID NO 93
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 93

Leu His Ala Arg Ala Pro Gly Pro Arg Gly Pro Pro Leu Leu Cys Pro
1               5                   10                  15
```

```
Cys Cys Leu Arg Val Ser His
            20
```

<210> SEQ ID NO 94
<211> LENGTH: 62
<212> TYPE: PRT
<213> ORGANISM: Artificial Sequence
<220> FEATURE:
<223> OTHER INFORMATION: Synthetic Peptide

<400> SEQUENCE: 94

```
Leu Pro Gln Gln Asp Leu Trp His Leu Gln Phe His Gln Gly Leu Pro
1               5                   10                  15

Arg Arg Cys His Pro Val Cys Ala Glu Pro Pro His Val Gln Leu
            20                  25                  30

Cys Pro Ala His Trp Gly Ala Pro Ser Phe Pro Thr Ser Trp Ser Gln
            35                  40                  45

Leu His Leu His Ser Asn Cys Arg Gly Pro Gly Cys Ser Arg
        50                  55                  60
```

<210> SEQ ID NO 95
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 95

```
Gly Ile Phe Glu Leu Phe Ile Leu
1               5
```

<210> SEQ ID NO 96
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 96

```
Gly Ile Gly Ala Val Cys Met Asp Trp Trp Ala Ala Ala Pro Pro Gly
1               5                   10                  15

Glu Cys Ala Pro Arg Pro Gly Cys Ala Ala His His Cys Gly His Arg
            20                  25                  30

Leu Leu His
        35
```

<210> SEQ ID NO 97
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 97

```
Ser Pro Cys Pro Ser Ser Pro Pro Ser Gln Pro Trp
1               5                   10
```

<210> SEQ ID NO 98
<211> LENGTH: 25
<212> TYPE: PRT
<213> ORGANISM: Artificial Sequence
<220> FEATURE:
<223> OTHER INFORMATION: Synthetic Peptide

```
<400> SEQUENCE: 98

Val Leu Ser Asp Leu Gly Cys Ala Ala Gly Lys Ser Asp Asp Pro Gln
1               5                   10                  15

Leu Trp Gly His Ser His Ile Thr Gly
            20                  25

<210> SEQ ID NO 99
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 99

Cys Cys Gly Ile Tyr Cys His Glu Glu Pro Gln Arg Glu Asp Ser Ser
1               5                   10                  15

Ile

<210> SEQ ID NO 100
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 100

His Phe Pro Asp Gly Glu Val Thr Ala Glu Arg Cys Gly His Leu Ala
1               5                   10                  15

Phe Pro Tyr Pro Leu Pro Phe Pro Ser Pro Pro Ser Tyr Ser Phe
            20                  25                  30

His Val Pro Phe Gln Thr Glu
        35

<210> SEQ ID NO 101
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 101

Ile Ser Val Ser Ile Met Trp Thr Gln Arg Arg Lys Leu
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 102

Val Lys Gly Val Leu His Ser Leu Thr Ala Ala Gly Gln Thr His
1               5                   10                  15

<210> SEQ ID NO 103
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 103

Lys His Gln Ala Met Asp His His Gly Val Pro Gly Arg Arg Leu Ser
```

```
1               5                   10                  15
Thr Gly Leu Ala
        20
```

<210> SEQ ID NO 104
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 104

```
Gly Asp Gln Gln Pro Asp Arg Thr Gln Ala Gly Leu Lys Ser Val Ser
1               5                   10                  15

Gln Val Glu Asp Val Phe Arg Glu Leu Ile Gly Thr Gln Lys Thr Arg
            20                  25                  30

Thr Gly Cys Phe Pro Pro Ser Gly Ser
        35                  40
```

<210> SEQ ID NO 105
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 105

```
Cys Ser Ala Gln Ala Arg Asn Arg Ser Glu Asp Glu Thr Gln Pro Leu
1               5                   10                  15

Pro Leu Gly Thr Leu Leu Ala Phe
            20
```

<210> SEQ ID NO 106
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 106

```
His Gln Ala Leu Gly Ala Val Pro Ser Cys Glu Gly Val
1               5                   10
```

<210> SEQ ID NO 107
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 107

```
Gln Phe Arg Thr Pro Gly Trp Pro Leu Lys Ala Leu Ala Gly Arg Gly
1               5                   10                  15

Trp Pro Glu Asp Ala Ser Pro Gly Gln Glu Pro Ser Lys Gly Ala Gly
            20                  25                  30

Arg Gly Trp Ala
        35
```

<210> SEQ ID NO 108
<211> LENGTH: 64
<212> TYPE: PRT
<213> ORGANISM: Artificial Sequence
<220> FEATURE:
<223> OTHER INFORMATION: Synthetic Peptide

<400> SEQUENCE: 108

Pro Arg Ala Ala Val Ser Gly Ile Gln Gln Trp Trp Asn Gly Arg Gln
1               5                   10                  15

Asn Trp Lys Arg Lys Glu Lys Met Ser Ser Arg Leu Ala Gly Ala
            20                  25                  30

Phe Arg Val Leu Trp Arg Ala Val Ser Thr Ala Ser Ile Arg Arg His
        35                  40                  45

Ile Gln Val Ala Pro Arg Pro Leu Gln Ala Gly Pro Ala Met Gly Pro
    50                  55                  60

<210> SEQ ID NO 109
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 109

Leu Ile Val Gly Gly Gly Ala Pro Asp Arg Lys Gly Phe Gln
1               5                   10

<210> SEQ ID NO 110
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 110

Cys Gln Arg Cys Pro Leu Cys Trp Pro
1               5

<210> SEQ ID NO 111
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 111

Gly Val Arg Cys Leu Ile His Ser Ile His Gly Phe Leu
1               5                   10

<210> SEQ ID NO 112
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 112

Trp Pro Gln Leu Leu Leu Glu Pro Asn Ser Gly Lys Ser Ala Ser Arg
1               5                   10                  15

Arg Arg Pro Gln Gly Gly Pro Gln Pro Pro Lys Leu Arg Val Val Glu
            20                  25                  30

Ala Glu Val Gly Asp Ser Trp Lys Arg
        35                  40

<210> SEQ ID NO 113
<211> LENGTH: 72
<212> TYPE: PRT
<213> ORGANISM: Artificial Sequence
<220> FEATURE:

<223> OTHER INFORMATION: Synthetic Peptide

<400> SEQUENCE: 113

Val Ala Ala Arg Ala Trp Ala Gln Pro Pro Leu Pro Gly Ala Glu Cys
1               5                   10                  15

Gly His Arg Arg Glu Gly Ala Thr Leu Ala Gly His Arg Gly Arg Pro
            20                  25                  30

Ala Ala Ala His Arg Gly Leu Arg Pro Gly His Ala Ala Ala Ala Thr
        35                  40                  45

Glu His Gln Ala Gln Glu Ala Ser Pro Arg Gly Asp Arg Gly Gly Arg
    50                  55                  60

His Gly Ser Gly Leu Leu Gln Leu
65                  70

<210> SEQ ID NO 114
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 114

Arg Tyr Gly Arg Cys Val His Cys Arg Glu Ile Val Leu Gln Gln Pro
1               5                   10                  15

Ser Gly His Arg Gln Pro
            20

<210> SEQ ID NO 115
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 115

Gly Leu Met Ala Ser Asp Tyr Ser Glu Glu Val Ala Thr Ser Glu Lys
1               5                   10                  15

Phe Pro Phe

<210> SEQ ID NO 116
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 116

Asp Arg Lys Arg Gly Cys Cys Pro Thr Ser Ser Ser Leu Pro Ile Ser
1               5                   10                  15

Leu Arg Val Arg Leu Ser
            20

<210> SEQ ID NO 117
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 117

Ser His Ser Gln Ser Gly Gly Pro Arg His Pro Gly Gly Thr Arg Arg
1               5                   10                  15

```
Lys Ala Met Gly Ser Gln Cys Pro Glu Leu Gln Gly Gly Pro Glu Pro
            20                  25                  30

Gln Arg Pro Ser Ser Arg Arg Glu Ile
        35                  40
```

<210> SEQ ID NO 118
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 118

```
Ala Val Leu Leu Met Cys Gln Leu Tyr Gln Pro Trp Met Cys Lys Glu
1               5                   10                  15

Tyr Tyr Arg Leu Leu
            20
```

<210> SEQ ID NO 119
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 119

```
Ile Pro Arg Met Gln Pro Gln Ala Ser Ala Asn His Cys Gln Leu Leu
1               5                   10                  15

Lys Val Met Val Ala
            20
```

<210> SEQ ID NO 120
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 120

```
Thr Ala Ile Ile Gly Pro Asn Gly Ser Gly Cys Ser Gly Val Tyr Cys
1               5                   10                  15

His Glu Glu Pro Gln Gly Glu Asp Ser Ser Val
            20                  25
```

<210> SEQ ID NO 121
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 121

```
Gly Arg Val Ile Glu Cys Asp Val Val Lys Gly Ser Cys Gln Asp Gly
1               5                   10                  15

Glu Ala Val His Trp Lys Ser Ala Pro Gly Gly His Arg Ala Gly Asp
            20                  25                  30

Pro Leu Thr Leu Arg Ala Val Arg Glu Gly Ala Gly Met
        35                  40                  45
```

<210> SEQ ID NO 122
<211> LENGTH: 33
<212> TYPE: PRT
<213> ORGANISM: Artificial Sequence
<220> FEATURE:

<223> OTHER INFORMATION: Synthetic Peptide

<400> SEQUENCE: 122

Ile Cys Met Ser Pro Leu Leu Trp Ala Thr Leu Gln Ala Pro Glu
1               5                   10                  15

Thr Thr Ser Ala Ala Cys Lys Ala Ser Tyr Arg Pro Glu Gly Leu Tyr
            20                  25                  30

Leu

<210> SEQ ID NO 123
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 123

Tyr Phe Ser Cys Asp Lys Arg Cys Ile Lys His Tyr Ala Gly Asn Lys
1               5                   10                  15

Ser Leu Leu Thr Phe Ser Gly Tyr
            20

<210> SEQ ID NO 124
<211> LENGTH: 59
<212> TYPE: PRT
<213> ORGANISM: Artificial Sequence
<220> FEATURE:
<223> OTHER INFORMATION: Synthetic Peptide

<400> SEQUENCE: 124

Thr Leu Cys Met Glu Val Met Leu Arg Trp Asn Thr Arg Glu Leu Gly
1               5                   10                  15

Tyr Leu Tyr Leu Gln Leu Cys Phe Leu Asn Thr His Phe Leu His Thr
            20                  25                  30

Ser Gln Glu Glu Lys Leu Leu Thr Leu Gly Arg Phe Leu Thr Trp Thr
        35                  40                  45

Ser Arg Cys Gly Ser Phe Val Ile Arg Pro Leu
    50                  55

<210> SEQ ID NO 125
<211> LENGTH: 1260
<212> TYPE: DNA
<213> ORGANISM: Artificial Sequence
<220> FEATURE:
<223> OTHER INFORMATION: Synthetic oligonucleotide

<400> SEQUENCE: 125
atggcggagc gcaggagaca caagaagcgg atccaggaag ttggtgaacc atctaaagaa    60
gagaaggctg tagccaagta tcttcgattt aactgtccaa caaagtctac caatatgatg   120
gggcaccgag ttgattattt cattgcttca aaagcagtgg attgcctttt ggattcaaag   180
tgggcaaagg ccaagaaagg agaggaagct ttatttacaa caagggagtc tgtggttgac   240
tactgcaaca ggcttttaaa gaagcagttt tttcaccggg cactaaaagt aatgaaaatg   300
aagtatgata agacataaa aaagaaaaa gagaaggaa aggccgaaag tggaaaagaa   360
gaagataaaa agagcaggaa agaaaatcta aggatgaaa agacgaaaaa ggagaaagaa   420 aaaaaaaaa gatggggaaa aggaagagga ttacaaggac gacgacgaca agtgaaattc   480
atggtgagca agggcgagga gctgttcacc ggggtggtgc ccatcctggt cgagctggac   540
ggcgacgtaa acggccacaa gttcagcgtg tccggcgagg gcgagggcga tgccacctac   600

```
ggcaagctga ccctgaagtt catctgcacc accggcaagc tgcccgtgcc ctggcccacc    660
ctcgtgacca ccctgaccta cggcgtgcag tgcttcagcc actacccga ccacatgaag    720 cagcacgact tcttcaagtc cgccatgccc gaaggctacg tccaggagcg caccatcttc    780
ttcaaggacg acggcaacta caagacccgc gccgaggtga agttcgaggg cgacaccctg    840
gtgaaccgca tcgagctgaa gggcatcgac ttcaaggagg acggcaacat cctggggcac    900
aagctggagt acaactacaa cagccacaac gtctatatca tggccgacaa gcagaagaac    960
ggcatcaagg tgaacttcaa gatccgccac aacatcgagg acggcagcgt gcagctcgcc   1020
gaccactacc agcagaacac ccccatcggc gacggccccg tgctgctgcc cgacaaccac   1080
tacctgagca cccagtccgc cctgagcaaa gaccccaacg agaagcgcga tcacatggtc   1140
ctgctggagt tcgtgaccgc cgccgggatc actctcggca tggacgagct gtacaagaga   1200
tctggtacca cgcgtatcga taagcttgca tgcctgcagg tcgactctag aggatcgtga   1260

<210> SEQ ID NO 126
<211> LENGTH: 1260
<212> TYPE: DNA
<213> ORGANISM: Artificial Sequence
<220> FEATURE:
<223> OTHER INFORMATION: Synthetic oligonucleotide

<400> SEQUENCE: 126
atggcggagc gcaggagaca caagaagcgg atccaggaag ttggtgaacc atctaaagaa     60
gagaaggctg tagccaagta tcttcgattt aactgtccaa caaagtctac caatatgatg    120
gggcaccgag ttgattattt cattgcttca aaagcagtgg attgccttt ggattcaaag     180 tgggcaaagg ccaagaaagg agaggaagct ttatttacaa caaggagtc tgtggttgac    240 tactgcaaca ggcttttaaa gaagcagttt tttcaccggg cactaaaagt aatgaaaatg    300
aagtatgata agacataaa aaagaaaaa gagaaaggaa aggccgaaag tggaaaagaa     360
gaagataaaa agagcaggaa agaaaatcta aaggatgaaa agacgaaaaa ggagaaagaa    420
aaaaaaaaaa gatggggaaa aggaagagga ttacaaggac gacgacgaca agtgaaattc    480
atggtgagca agggcgagga gctgttcacc ggggtggtgc ccatcctggt cgagctggac    540
ggcgacgtaa acggccacaa gttcagcgtg tccggcgagg gcgagggcga tgccacctac    600
ggcaagctga ccctgaagtt catctgcacc accggcaagc tgcccgtgcc ctggcccacc    660
ctcgtgacca ccctgaccta cggcgtgcag tgcttcagcc actacccga ccacatgaag    720 cagcacgact tcttcaagtc cgccatgccc gaaggctacg tccaggagcg caccatcttc    780
ttcaaggacg acggcaacta caagacccgc gccgaggtga agttcgaggg cgacaccctg    840
gtgaaccgca tcgagctgaa gggcatcgac ttcaaggagg acggcaacat cctggggcac    900
aagctggagt acaactacaa cagccacaac gtctatatca tggccgacaa gcagaagaac    960
ggcatcaagg tgaacttcaa gatccgccac aacatcgagg acggcagcgt gcagctcgcc   1020
gaccactacc agcagaacac ccccatcggc gacggccccg tgctgctgcc cgacaaccac   1080
tacctgagca cccagtccgc cctgagcaaa gaccccaacg agaagcgcga tcacatggtc   1140
ctgctggagt tcgtgaccgc cgccgggatc actctcggca tggacgagct gtacaagaga   1200
tctggtacca cgcgtatcga taagcttgca tgcctgcagg tcgactctag aggatcgtga   1260

<210> SEQ ID NO 127
<211> LENGTH: 1259
<212> TYPE: DNA
```

<213> ORGANISM: Artificial Sequence
<220> FEATURE:
<223> OTHER INFORMATION: Synthetic oligonucleotide

<400> SEQUENCE: 127

```
atggcggagc gcaggagaca caagaagcgg atccaggaag ttggtgaacc atctaaagaa    60
gagaaggctg tagccaagta tcttcgattt aactgtccaa caaagtctac caatatgatg   120
gggcaccgag ttgattattt cattgcttca aaagcagtgg attgcctttt ggattcaaag   180
tgggcaaagg ccaagaaagg agaggaagct ttatttacaa caagggagtc tgtggttgac   240
tactgcaaca ggcttttaaa gaagcagttt tttcaccggg cactaaaagt aatgaaaatg   300
aagtatgata agacataaa aaaagaaaaa gagaaaggaa aggccgaaag tggaaaagaa   360
gaagataaaa agagcaggaa agaaaatcta aaggatgaaa agacgaaaaa ggagaaagag   420
aggaagagag atggggaaaa ggaagaggat tacaaggacg acgacgacaa gtgaaattca   480
tggtgagcaa gggcgaggag ctgttcaccg gggtggtgcc catcctggtc gagctggacg   540
gcgacgtaaa cggccacaag ttcagcgtgt ccggcgaggg cgagggcgat gccacctacg   600
gcaagctgac cctgaagttc atctgcacca ccggcaagct gcccgtgccc tggcccaccc   660
tcgtgaccac cctgacctac ggcgtgcagt gcttcagcca ctaccccgac cacatgaagc   720
agcacgactt cttcaagtcc gccatgcccg aaggctacgt ccaggagcgc accatcttct   780
tcaaggacga cggcaactac aagacccgcg ccgaggtgaa gttcgagggc gacaccctgg   840
tgaaccgcat cgagctgaag ggcatcgact tcaaggagga cggcaacatc ctggggcaca   900
agctggagta caactacaac agccacaacg tctatatcat ggccgacaag cagaagaacg   960
gcatcaaggt gaacttcaag atccgccaca acatcgagga cggcagcgtg cagctcgccg  1020
accactacca gcagaacacc cccatcggcg acggccccgt gctgctgccc gacaaccact  1080
acctgagcac ccagtccgcc ctgagcaaag accccaacga agcgcgat cacatggtcc   1140
tgctggagtt cgtgaccgcc gccgggatca ctctcggcat ggacgagctg tacaagagat  1200
ctggtaccac gcgtatcgat aagcttgcat gcctgcaggt cgactctaga ggatcgtga  1259
```

<210> SEQ ID NO 128
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 128

```
Met Ala Ser Ala Lys Ser Leu Asp Arg Trp Lys Ala Arg Leu Leu Glu
1               5                   10                  15

Gly Gly Ser Thr Ala Leu Thr Tyr Ala Leu Val Arg Ala Glu Val Ser
            20                  25                  30

Phe Pro Ala Glu Val Ala Pro Val Arg Gln Gln Gly Ser Val Ala Gly
        35                  40                  45

Ala Arg Ala Gly Val Val Ser Leu Leu Gly Cys Arg Ser Ser Trp Thr
    50                  55                  60

Ala Ala Met Glu Leu Ser Ala Glu Tyr Leu Arg Glu Lys Leu Gln Arg
65                  70                  75                  80

Asp Leu Glu Ala Glu His Val Glu Val Glu Asp Thr Thr Leu Asn Arg
                85                  90                  95

Cys Ser Cys Ser Phe Arg Val Leu Val Val Ser Ala Lys Phe Glu Gly
            100                 105                 110
```

Lys Pro Leu Leu Gln Arg His Arg
            115                 120

<210> SEQ ID NO 129
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 129

Leu Leu Asn Arg
1

<210> SEQ ID NO 130
<211> LENGTH: 84
<212> TYPE: PRT
<213> ORGANISM: Artificial Sequence
<220> FEATURE:
<223> OTHER INFORMATION: Synthetic Peptide

<400> SEQUENCE: 130

Met Leu Pro Gly Val Gly Val Phe Gly Thr Ser Leu Thr Ala Arg Val
1               5                   10                  15

Ile Ile Pro Leu Leu Lys Asp Glu Gly Phe Ala Val Lys Ala Leu Trp
                20                  25                  30

Gly Arg Thr Gln Glu Glu Ala Glu Leu Ala Lys Glu Met Ser Val
            35                  40                  45

Pro Phe Tyr Thr Ser Arg Ile Asp Glu Val Leu Leu His Gln Asp Val
    50                  55                  60

Asp Leu Val Cys Ile Asn Leu Pro Pro Leu Thr Arg Gln Ile Ala
65                  70                  75                  80

Val Lys Thr Leu

<210> SEQ ID NO 131
<211> LENGTH: 64
<212> TYPE: PRT
<213> ORGANISM: Artificial Sequence
<220> FEATURE:
<223> OTHER INFORMATION: Synthetic Peptide

<400> SEQUENCE: 131

Glu Pro Gly His Gln Arg Lys Lys Ile Ser Arg Gln Lys Asn Thr Gly
1               5                   10                  15

Glu Lys Lys Met Pro Arg Gly Ser Val Gln Leu Ser Phe Cys Ser Leu
                20                  25                  30

Gln His Pro His Met Gly His Leu Phe Thr Pro His Asp Ala Ala Leu
            35                  40                  45

Gly Glu Ser Gln Gly Thr Gly Phe Lys Pro Leu Gly Met Gln Pro Val
    50                  55                  60

<210> SEQ ID NO 132
<211> LENGTH: 125
<212> TYPE: PRT
<213> ORGANISM: Artificial Sequence
<220> FEATURE:
<223> OTHER INFORMATION: Synthetic Peptide

<400> SEQUENCE: 132

Met Arg Ser Lys Gly Arg Ala Arg Lys Leu Ala Thr Asn Asn Glu Cys
1               5                   10                  15

Val Tyr Gly Asn Tyr Pro Glu Ile Pro Leu Glu Glu Met Pro Asp Ala

```
                    20                  25                  30
Asp Gly Val Ala Ser Thr Pro Ser Leu Asn Ile Gln Glu Pro Cys Ser
                35                  40                  45

Pro Ala Thr Ser Ser Glu Ala Phe Thr Pro Lys Glu Gly Ser Pro Tyr
            50                  55                  60

Lys Ala Pro Ile Tyr Ile Pro Asp Asp Ile Pro Ile Pro Ala Glu Phe
 65                  70                  75                  80

Glu Leu Arg Glu Ser Asn Met Pro Gly Ala Gly Leu Gly Ile Trp Thr
                    85                  90                  95

Lys Arg Lys Ile Glu Val Gly Glu Lys Phe Gly Pro Tyr Val Gly Glu
                100                 105                 110

Gln Arg Ser Asn Leu Lys Asp Pro Ser Tyr Gly Trp Glu
                115                 120                 125

<210> SEQ ID NO 133
<211> LENGTH: 255
<212> TYPE: PRT
<213> ORGANISM: Artificial Sequence
<220> FEATURE:
<223> OTHER INFORMATION: Synthetic Peptide

<400> SEQUENCE: 133

Ile Leu Asp Glu Phe Tyr Asn Val Lys Phe Cys Ile Asp Ala Ser Gln
  1               5                  10                  15

Pro Asp Val Gly Ser Trp Leu Lys Tyr Ile Arg Phe Ala Gly Cys Tyr
                20                  25                  30

Asp Gln His Asn Leu Val Ala Cys Gln Ile Asn Asp Gln Ile Phe Tyr
                35                  40                  45

Arg Val Val Ala Asp Ile Ala Pro Gly Glu Glu Leu Leu Leu Phe Met
            50                  55                  60

Lys Ser Glu Asp Tyr Pro His Glu Thr Met Ala Pro Asp Ile His Glu
 65                  70                  75                  80

Glu Arg Gln Tyr Arg Cys Glu Asp Cys Asp Gln Leu Phe Glu Ser Lys
                    85                  90                  95

Ala Glu Leu Ala Asp His Gln Lys Phe Pro Cys Ser Thr Pro His Ser
                100                 105                 110

Ala Phe Ser Met Val Glu Glu Asp Phe Gln Gln Lys Leu Glu Ser Glu
                115                 120                 125

Asn Asp Leu Gln Glu Ile His Thr Ile Gln Glu Cys Lys Glu Cys Asp
            130                 135                 140

Gln Val Phe Pro Asp Leu Gln Ser Leu Glu Lys His Met Leu Ser His
145                 150                 155                 160

Thr Glu Glu Arg Glu Tyr Lys Cys Asp Gln Cys Pro Lys Ala Phe Asn
                    165                 170                 175

Trp Lys Ser Asn Leu Ile Arg His Gln Met Ser His Asp Ser Gly Lys
                180                 185                 190

His Tyr Glu Cys Glu Asn Cys Ala Lys Val Phe Thr Asp Pro Ser Asn
                195                 200                 205

Leu Gln Arg His Ile Arg Ser Gln His Val Gly Ala Arg Ala His Ala
            210                 215                 220

Cys Pro Glu Cys Gly Lys Thr Phe Ala Thr Ser Ser Gly Leu Lys Gln
225                 230                 235                 240

His Lys His Ile His Ser Ser Val Lys Pro Phe Ile Cys Glu Val
                    245                 250                 255
```

```
<210> SEQ ID NO 134
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 134

Met Ala Val Ser Thr Val Phe Ser Thr Ser Ser Leu Met Leu Ala Leu
1               5                   10                  15

Ser Arg His Ser Leu Leu Ser Pro Leu Ser Val Thr Ser Phe Arg
                20                  25                  30

Arg Phe Tyr Arg Gly Asp Ser Pro Thr Asp Ser Gln Lys Asp Met Ile
            35                  40                  45

Glu Ile Pro Leu Pro Pro Trp Gln Glu Arg Thr Asp Glu Ser Ile Glu
    50                  55                  60

Thr Lys Arg Ala Arg Leu Leu Tyr Glu Ser Arg Lys Arg Gly Met Leu
65                  70                  75                  80

Glu Asn Cys Ile Leu Leu Ser Leu Phe Ala Lys Glu His Leu Gln His
                85                  90                  95

Met Thr Glu Lys Gln Leu Asn Leu Tyr Asp Arg Leu Ile Asn Glu Pro
            100                 105                 110

Ser Asn Asp Trp Asp Ile Tyr Tyr Trp Ala Thr
            115                 120

<210> SEQ ID NO 135
<211> LENGTH: 124
<212> TYPE: PRT
<213> ORGANISM: Artificial Sequence
<220> FEATURE:
<223> OTHER INFORMATION: Synthetic Peptide

<400> SEQUENCE: 135

Gly Pro Glu Gly Pro Phe Arg His Pro Gly Ala Arg Ala Ser Gly His
1               5                   10                  15

His Gly Ala Gly Ala Gln Gly Ser Ala Ser Ala Pro Pro Ala Ala Gly
                20                  25                  30

Pro Gly Pro Ala Gly Ala Gly Glu Leu Pro Thr Trp Pro Thr Leu His
            35                  40                  45

Asp Val Gly Val Gln Phe Gln Val Ser Gln Gly Pro Ser Arg Pro Ala
    50                  55                  60

Arg Phe Leu Ala Glu Glu Ile Asp Arg Arg Lys Gly Gly Glu Trp Leu
65                  70                  75                  80

His Gln Thr Val Pro Pro Glu Pro His Cys Leu Pro Thr Ala Leu Thr
                85                  90                  95

Gly Pro Pro Trp Gly Pro Cys Pro Pro Arg Pro Glu Cys His Gln
            100                 105                 110

Val Arg Leu Pro Pro Gln Asp Ser Pro Thr Trp Arg
        115                 120

<210> SEQ ID NO 136
<211> LENGTH: 132
<212> TYPE: PRT
<213> ORGANISM: Artificial Sequence
<220> FEATURE:
<223> OTHER INFORMATION: Synthetic Peptide

<400> SEQUENCE: 136

Met Val Gly Ala Leu Cys Gly Cys Trp Phe Arg Leu Gly Gly Ala Arg
1               5                   10                  15
```

```
Pro Leu Ile Pro Leu Gly Pro Thr Val Gln Thr Ser Met Ser Gln
            20                  25                  30

Ser Gln Val Ala Leu Leu Gly Leu Ser Leu Leu Leu Met Leu Leu Leu
        35                  40                  45

Tyr Val Gly Leu Pro Gly Pro Pro Glu Gln Thr Ser Cys Leu Trp Gly
50                  55                  60

Asp Pro Asn Val Thr Val Leu Ala Gly Leu Thr Pro Gly Asn Ser Pro
65                  70                  75                  80

Ile Phe Tyr Arg Glu Val Leu Pro Leu Asn Gln Ala His Arg Val Glu
                85                  90                  95

Val Val Leu Leu His Gly Lys Ala Phe Asn Ser His Thr Trp Glu Gln
            100                 105                 110

Leu Gly Thr Leu Gln Leu Leu Ser Gln Arg Gly Tyr Arg Ala Val Ala
            115                 120                 125

Leu Asp Leu Pro
        130
```

```
<210> SEQ ID NO 137
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 137

Ala His His Ala Gln Arg His Asp Gln Gln Gly Ser Arg Gly Gly Ala
1               5                   10                  15

Pro Ile Gly Asp Ala Leu Pro Pro Val Pro Ala Tyr Pro His Cys Pro
                20                  25                  30

Ala Gln Ala
        35
```

```
<210> SEQ ID NO 138
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 138

Met Lys Ile Phe Val Gly Asn Val Asp Gly Ala Asp Thr Thr Pro Glu
1               5                   10                  15

Glu Leu Ala Ala Leu Phe Ala Pro Tyr Gly Thr Val Met Ser Cys Ala
                20                  25                  30

Val Met Lys Gln Phe Ala Phe Val His Met Arg Glu Asn Ala Gly Ala
            35                  40                  45

Leu Arg Ala Ile Glu Ala Leu His Gly His Glu Leu Arg Pro Gly Arg
        50                  55                  60

Ala Leu Val Val Glu Met Ser Arg Pro Arg Pro Leu Asn Thr Trp Lys
65                  70                  75                  80

Ile Phe Val Gly Asn Val Ser Ala Ala Cys Thr Ser Gln Glu Leu Arg
                85                  90                  95

Ser Leu Phe Glu Arg Arg Gly Arg Val Ile Glu Cys Asp Val Val Lys
            100                 105                 110
```

```
<210> SEQ ID NO 139
<211> LENGTH: 35
<212> TYPE: PRT
```

<213> ORGANISM: Artificial Sequence
<220> FEATURE:
<223> OTHER INFORMATION: Synthetic Peptide

<400> SEQUENCE: 139

Gly Ser Cys Gln Asp Gly Glu Ala Val His Arg Lys Pro Ala Pro Gly
1               5                   10                  15

Gly Tyr Arg Ala Gly Asp Ser Leu Thr Leu Arg Ala Val Trp Glu Gly
            20                  25                  30

Ala Gly Met
        35

<210> SEQ ID NO 140
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 140

Met Val His Ala Phe Leu Ile His Thr Leu Arg Ala Pro Asn Thr Glu
1               5                   10                  15

Asp Thr Gly Leu Cys Arg Val Leu Tyr Ser Cys Val Phe Gly Ala Glu
            20                  25                  30

Lys Ser Pro Asp Asp Pro Arg Pro His Gly Ala Glu Arg Asp Arg Leu
        35                  40                  45

Leu Arg Lys Glu Gln Ile Leu Ala Val Ala
    50                  55

<210> SEQ ID NO 141
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 141

Ser Leu Val Ser Ser Gln Ser Ile His Pro Ser Trp Gly Gln Ser Pro
1               5                   10                  15

Leu Ser Arg Ile
            20

<210> SEQ ID NO 142
<211> LENGTH: 340
<212> TYPE: PRT
<213> ORGANISM: Artificial Sequence
<220> FEATURE:
<223> OTHER INFORMATION: Synthetic Peptide

<400> SEQUENCE: 142

Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Lys Glu Asn
            20                  25                  30

Thr Pro Pro Ala Leu Ser Gly Thr Arg Val Leu Ala Ser Lys Thr Ala
        35                  40                  45

Arg Arg Ile Phe Gln Glu Pro Thr Glu Pro Lys Thr Lys Ala Ala Ala
    50                  55                  60

Pro Gly Val Glu Asp Glu Pro Leu Leu Arg Glu Asn Pro Arg Arg Phe
65                  70                  75                  80

Val Ile Phe Pro Ile Glu Tyr His Asp Ile Trp Gln Met Tyr Lys Lys

```
            85                  90                  95
Ala Glu Ala Ser Phe Trp Thr Ala Glu Val Asp Leu Ser Lys Asp
            100                 105                 110

Ile Gln His Trp Glu Ser Leu Lys Pro Glu Glu Arg Tyr Phe Ile Ser
            115                 120                 125

His Val Leu Ala Phe Phe Ala Ala Ser Asp Gly Ile Val Asn Glu Asn
            130                 135                 140

Leu Val Glu Arg Phe Ser Gln Glu Val Gln Ile Thr Glu Ala Arg Cys
145                 150                 155                 160

Phe Tyr Gly Phe Gln Ile Ala Met Glu Asn Ile His Ser Glu Met Tyr
                    165                 170                 175

Ser Leu Leu Ile Asp Thr Tyr Ile Lys Asp Pro Lys Glu Arg Glu Phe
                180                 185                 190

Leu Phe Asn Ala Ile Glu Thr Met Pro Cys Val Lys Lys Lys Ala Asp
                195                 200                 205

Trp Ala Leu Arg Trp Ile Gly Asp Lys Glu Ala Thr Tyr Gly Glu Arg
210                 215                 220

Val Val Ala Phe Ala Ala Val Glu Gly Ile Phe Phe Ser Gly Ser Phe
225                 230                 235                 240

Ala Ser Ile Phe Trp Leu Lys Lys Arg Gly Leu Met Pro Gly Leu Thr
                    245                 250                 255

Phe Ser Asn Glu Leu Ile Ser Arg Asp Glu Gly Leu His Cys Asp Phe
                260                 265                 270

Ala Cys Leu Met Phe Lys His Leu Val His Lys Pro Ser Glu Glu Arg
                275                 280                 285

Val Arg Glu Ile Ile Ile Asn Ala Val Arg Ile Glu Gln Glu Phe Leu
                290                 295                 300

Thr Glu Ala Leu Pro Val Lys Leu Ile Gly Met Asn Cys Thr Leu Met
305                 310                 315                 320

Lys Gln Tyr Ile Glu Phe Val Ala Asp Arg Leu Met Leu Glu Leu Gly
                    325                 330                 335

Phe Ser Lys Val
            340

<210> SEQ ID NO 143
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 143

Leu Gly Asp Arg Glu Val Gln Ser Arg Trp Ser Pro Gly Pro Arg Gly
1               5                   10                  15

Asp Ser Thr Pro Val Arg Glu Met Glu Thr Asn His Pro Pro Ser Val
                20                  25                  30

Arg Gly

<210> SEQ ID NO 144
<211> LENGTH: 53
<212> TYPE: PRT
<213> ORGANISM: Artificial Sequence
<220> FEATURE:
<223> OTHER INFORMATION: Synthetic Peptide

<400> SEQUENCE: 144

Met Ser Met Asp Val Thr Phe Leu Gly Thr Gly Ala Ala Tyr Pro Ser
```

```
                 1               5                  10                 15
Pro Thr Arg Gly Ala Ser Ala Val Val Leu Arg Cys Glu Gly Glu Cys
                        20                  25                  30

Trp Leu Phe Asp Cys Gly Glu Gly Thr Gln Thr Gln Leu Met Lys Ser
            35                  40                  45

Gln Leu Lys Ala Gly
    50

<210> SEQ ID NO 145
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 145

Tyr Pro Glu Tyr Met Ser Asn Asn Phe Pro Cys Asn Val Ser Cys Cys
1               5                   10                  15

Phe Ser Leu Phe Pro Lys Asp Gln Asn Cys Phe Arg Asn Trp Arg His
            20                  25                  30

Ile

<210> SEQ ID NO 146
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 146

Met Gln Arg Thr Gly Gly Gly Ala Pro Arg Pro Gly Arg Asn His Gly
1               5                   10                  15

Leu Pro Gly Ser Leu Arg Gln Pro Asp Pro Val Ala Leu Leu Met Leu
            20                  25                  30

Leu Val Asp Ala Asp Gln Pro Glu Pro Met Arg Ser Gly Ala Arg Glu
        35                  40                  45

Leu Ala Leu Phe Leu Thr Pro Glu Pro Gly Ala Glu
    50                  55                  60

<210> SEQ ID NO 147
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 147

Val Pro Leu Thr Gly Ala
1               5

<210> SEQ ID NO 148
<211> LENGTH: 64
<212> TYPE: PRT
<213> ORGANISM: Artificial Sequence
<220> FEATURE:
<223> OTHER INFORMATION: Synthetic Peptide

<400> SEQUENCE: 148

Met Ala Asp Gly Ser Gly Trp Gln Pro Pro Arg Pro Cys Glu Ala Tyr
1               5                   10                  15

Arg Ala Glu Trp Lys Leu Cys Arg Ser Ala Arg His Phe Leu His His
            20                  25                  30
```

Tyr Tyr Val His Gly Glu Arg Pro Ala Cys Glu Gln Trp Gln Arg Asp
            35                  40                  45

Leu Ala Ser Cys Arg Asp Trp Glu Glu Arg Arg Asn Ala Glu Ala Gln
        50                  55                  60

<210> SEQ ID NO 149
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 149

Ala Ser Arg Phe Phe Gln Leu Ile Phe Thr Leu Thr Gly Pro Ser Ser
1               5                   10                  15

Gln Leu Glu Asp Lys Gly Arg Ile Leu Gly Arg Leu
            20                  25

<210> SEQ ID NO 150
<211> LENGTH: 188
<212> TYPE: PRT
<213> ORGANISM: Artificial Sequence
<220> FEATURE:
<223> OTHER INFORMATION: Synthetic Peptide

<400> SEQUENCE: 150

Met Ala Glu Ala Ser Ser Ala Asn Leu Gly Ser Gly Cys Glu Glu Lys
1               5                   10                  15

Arg His Glu Gly Ser Ser Ser Glu Ser Val Pro Pro Gly Thr Thr Ile
            20                  25                  30

Ser Arg Val Lys Leu Leu Asp Thr Met Val Asp Thr Phe Leu Gln Lys
        35                  40                  45

Leu Val Ala Ala Gly Ser Tyr Gln Arg Phe Thr Asp Cys Tyr Lys Cys
    50                  55                  60

Phe Tyr Gln Leu Gln Pro Ala Met Thr Gln Gln Ile Tyr Asp Lys Phe
65                  70                  75                  80

Ile Ala Gln Leu Gln Thr Ser Ile Arg Glu Glu Ile Ser Asp Ile Lys
                85                  90                  95

Glu Glu Gly Asn Leu Glu Ala Val Leu Asn Ala Leu Asp Lys Ile Val
            100                 105                 110

Glu Glu Gly Lys Val Arg Lys Glu Pro Ala Trp Arg Pro Ser Gly Ile
        115                 120                 125

Pro Glu Lys Asp Leu His Ser Val Met Ala Pro Tyr Phe Leu Gln Gln
    130                 135                 140

Arg Asp Thr Leu Arg Arg His Val Gln Lys Gln Glu Ala Glu Asn Gln
145                 150                 155                 160

Gln Leu Ala Asp Ala Val Leu Ala Gly Arg Arg Gln Val Glu Glu Leu
                165                 170                 175

Gln Leu Gln Val Gln Ala Gln Gln Gln Ala Trp Gln
            180                 185

<210> SEQ ID NO 151
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 151

Val Arg Ser Pro Ala Val Gln Ser Pro Ala Lys Val Gln Pro Leu Cys
1               5                   10                  15

Pro Ser Arg Arg Ala Ala Arg
            20

<210> SEQ ID NO 152
<211> LENGTH: 104
<212> TYPE: PRT
<213> ORGANISM: Artificial Sequence
<220> FEATURE:
<223> OTHER INFORMATION: Synthetic Peptide

<400> SEQUENCE: 152

Met Ala Val Leu Trp Arg Leu Ser Ala Val Cys Gly Ala Leu Gly Gly
1               5                   10                  15

Arg Ala Leu Leu Leu Arg Thr Pro Val Val Arg Pro Ala His Ile Ser
            20                  25                  30

Ala Phe Leu Gln Asp Arg Pro Ile Pro Glu Trp Cys Gly Val Gln His
        35                  40                  45

Ile His Leu Ser Pro Ser His His Ser Gly Ser Lys Ala Ala Ser Leu
    50                  55                  60

His Trp Thr Ser Glu Arg Val Val Ser Val Leu Leu Gly Leu Leu
65                  70                  75                  80

Pro Ala Ala Tyr Leu Asn Pro Cys Ser Ala Met Asp Tyr Ser Leu Ala
                85                  90                  95

Ala Ala Leu Thr Leu His Gly His
            100

<210> SEQ ID NO 153
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 153

Cys Leu Gln Cys Gln Ile Val His Ser Cys Pro Leu Leu Glu Asn Gln
1               5                   10                  15

Ile His Leu Ser Leu Lys Phe Pro Asp Tyr Phe Ile Lys Met Lys Pro
            20                  25                  30

Trp Arg Lys Ile
            35

<210> SEQ ID NO 154
<211> LENGTH: 84
<212> TYPE: PRT
<213> ORGANISM: Artificial Sequence
<220> FEATURE:
<223> OTHER INFORMATION: Synthetic Peptide

<400> SEQUENCE: 154

Met Trp Asn Pro Asn Ala Gly Gly Pro Pro His Pro Val Pro Gln Pro
1               5                   10                  15

Gly Tyr Pro Gly Cys Gln Pro Leu Gly Pro Tyr Pro Pro Tyr Pro
            20                  25                  30

Pro Pro Ala Pro Gly Ile Pro Pro Val Asn Pro Leu Ala Pro Gly Met
        35                  40                  45

Val Gly Pro Ala Val Ile Val Asp Lys Lys Met Gln Lys Lys Met Lys
    50                  55                  60

Lys Ala His Lys Lys Met His Lys His Gln Lys His His Lys Tyr His

```
                65                  70                  75                  80
Lys His Gly Lys

<210> SEQ ID NO 155
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 155

Phe Leu Ala Phe Thr Pro Asn Gln
1               5

<210> SEQ ID NO 156
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 156

Met Asp Gln Cys Val Thr Val Glu Arg Glu Leu Glu Lys Val Leu His
1               5                   10                  15

Lys Phe Ser Gly Tyr Gly Gln Leu Cys Glu Arg Gly Leu Glu Glu Leu
            20                  25                  30

Ile Asp Tyr Thr Gly Gly Leu Lys His Glu Ile Leu Gln Ser His Gly
        35                  40                  45

Gln Asp Ala Glu Leu Ser Gly Thr Leu Ser Leu Val Leu Thr Gln Cys
    50                  55                  60

Cys Lys Arg Ile Lys Asp Thr Val Gln Lys Leu Ala Ser Asp His Lys
65                  70                  75                  80

Asp Ile His Ser Ser Val Ser Arg Val Gly Lys Ala Ile Asp Lys
                85                  90                  95

<210> SEQ ID NO 157
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 157

Asp Ser Leu
1

<210> SEQ ID NO 158
<211> LENGTH: 434
<212> TYPE: PRT
<213> ORGANISM: Artificial Sequence
<220> FEATURE:
<223> OTHER INFORMATION: Synthetic Peptide

<400> SEQUENCE: 158

Met Ala Ala Leu Met Thr Pro Gly Thr Gly Ala Pro Ala Pro Gly
1               5                   10                  15

Asp Phe Ser Gly Glu Gly Ser Gln Gly Leu Pro Asp Pro Ser Pro Glu
            20                  25                  30

Pro Lys Gln Leu Pro Glu Leu Ile Arg Met Lys Arg Asp Gly Gly Arg
        35                  40                  45

Leu Ser Glu Ala Asp Ile Arg Gly Phe Val Ala Ala Val Val Asn Gly
    50                  55                  60
```

```
Ser Ala Gln Gly Ala Gln Ile Gly Ala Met Leu Met Ala Ile Arg Leu
 65                  70                  75                  80

Arg Gly Met Asp Leu Glu Thr Ser Val Leu Thr Gln Ala Leu Ala
             85                  90                  95

Gln Ser Gly Gln Gln Leu Glu Trp Pro Glu Ala Trp Arg Gln Leu
            100                 105                 110

Val Asp Lys His Ser Thr Gly Val Gly Asp Lys Val Ser Leu Val
            115                 120                 125

Leu Ala Pro Ala Leu Ala Ala Cys Gly Cys Lys Val Pro Met Ile Ser
130                 135                 140

Gly Arg Gly Leu Gly His Thr Gly Gly Thr Leu Asp Lys Leu Glu Ser
145                 150                 155                 160

Ile Pro Gly Phe Asn Val Ile Gln Ser Pro Glu Gln Met Gln Val Leu
            165                 170                 175

Leu Asp Gln Ala Gly Cys Cys Ile Val Gly Gln Ser Glu Gln Leu Val
            180                 185                 190

Pro Ala Asp Gly Ile Leu Tyr Ala Ala Arg Asp Val Thr Ala Thr Val
            195                 200                 205

Asp Ser Leu Pro Leu Ile Thr Ala Ser Ile Leu Ser Lys Lys Leu Val
210                 215                 220

Glu Gly Leu Ser Ala Leu Val Val Asp Val Lys Phe Gly Gly Ala Ala
225                 230                 235                 240

Val Phe Pro Asn Gln Glu Gln Ala Arg Glu Leu Ala Lys Thr Leu Val
            245                 250                 255

Gly Val Gly Ala Ser Leu Gly Leu Arg Val Ala Ala Ala Leu Thr Ala
            260                 265                 270

Met Asp Lys Pro Leu Gly Arg Cys Val Gly His Ala Leu Glu Val Glu
            275                 280                 285

Glu Ala Leu Leu Cys Met Asp Gly Ala Gly Pro Pro Asp Leu Arg Asp
290                 295                 300

Leu Val Thr Thr Leu Gly Gly Ala Leu Leu Trp Leu Ser Gly His Ala
305                 310                 315                 320

Gly Thr Gln Ala Gln Gly Ala Ala Arg Val Ala Ala Leu Asp Asp
            325                 330                 335

Gly Ser Ala Leu Gly Arg Phe Glu Arg Met Leu Ala Ala Gln Gly Val
            340                 345                 350

Asp Pro Gly Leu Ala Arg Ala Leu Cys Ser Gly Ser Pro Ala Glu Arg
            355                 360                 365

Arg Gln Leu Leu Pro Arg Ala Arg Glu Gln Glu Leu Leu Ala Pro
            370                 375                 380

Ala Asp Gly Thr Val Glu Leu Val Arg Ala Leu Pro Leu Ala Leu Val
385                 390                 395                 400

Leu His Glu Leu Gly Ala Gly Arg Ser Arg Ala Gly Glu Pro Leu Arg
            405                 410                 415

Leu Gly Val Gly Ala Glu Leu Leu Val Asp Val Gly Gln Arg Leu Arg
            420                 425                 430

Arg Gly
```

<210> SEQ ID NO 159
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 159

Ala Ser Asp Pro Cys Cys Cys
1               5

<210> SEQ ID NO 160
<211> LENGTH: 1147
<212> TYPE: PRT
<213> ORGANISM: Artificial Sequence
<220> FEATURE:
<223> OTHER INFORMATION: Synthetic Peptide

<400> SEQUENCE: 160

Met Ala Thr Gln Gln Lys Ala Ser Asp Glu Arg Ile Ser Gln Phe Asp
1               5                   10                  15

His Asn Leu Leu Pro Glu Leu Ser Ala Leu Leu Gly Leu Asp Ala Val
            20                  25                  30

Gln Leu Ala Lys Glu Leu Glu Glu Glu Gln Lys Glu Arg Ala Lys
        35                  40                  45

Met Gln Lys Gly Tyr Asn Ser Gln Met Arg Ser Glu Ala Lys Arg Leu
50                  55                  60

Lys Thr Phe Val Thr Tyr Glu Pro Tyr Ser Ser Trp Ile Pro Gln Glu
65                  70                  75                  80

Met Ala Ala Gly Phe Tyr Phe Thr Gly Val Lys Ser Gly Ile Gln
            85                  90                  95

Cys Phe Cys Cys Ser Leu Ile Leu Phe Gly Ala Gly Leu Thr Arg Leu
            100                 105                 110

Pro Ile Glu Asp His Lys Arg Phe His Pro Asp Cys Gly Phe Leu Leu
            115                 120                 125

Asn Lys Asp Val Gly Asn Ile Ala Lys Tyr Asp Ile Arg Val Lys Asn
130                 135                 140

Leu Lys Ser Arg Leu Arg Gly Lys Met Arg Tyr Gln Glu Glu Glu
145                 150                 155                 160

Ala Arg Leu Ala Ser Phe Arg Asn Trp Pro Phe Tyr Val Gln Gly Ile
            165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
            195                 200                 205

Glu Gly Asp Asp Pro Trp Lys Glu His Ala Lys Trp Phe Pro Lys Cys
210                 215                 220

Glu Phe Leu Arg Ser Lys Lys Ser Ser Glu Ile Thr Gln Tyr Ile
225                 230                 235                 240

Gln Ser Tyr Lys Gly Phe Val Asp Ile Thr Gly Glu His Phe Val Asn
            245                 250                 255

Ser Trp Val Gln Arg Glu Leu Pro Met Ala Ser Ala Tyr Cys Asn Asp
            260                 265                 270

Ser Ile Phe Ala Tyr Glu Glu Leu Arg Leu Asp Ser Phe Lys Asp Trp
            275                 280                 285

Pro Arg Glu Ser Ala Val Gly Val Ala Ala Leu Ala Lys Ala Gly Leu
            290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
            325                 330                 335

-continued

```
Arg Cys Phe Pro Asn Cys Pro Phe Leu Gln Asn Met Lys Ser Ser Ala
            340                 345                 350
Glu Val Thr Pro Asp Leu Gln Ser Arg Gly Glu Leu Cys Glu Leu Leu
            355                 360                 365
Glu Thr Thr Ser Glu Ser Asn Leu Glu Asp Ser Ile Ala Val Gly Pro
        370                 375                 380
Ile Val Pro Glu Met Ala Gln Gly Glu Ala Gln Trp Phe Gln Glu Ala
385                 390                 395                 400
Lys Asn Leu Asn Glu Gln Leu Arg Ala Ala Tyr Thr Ser Ala Ser Phe
                405                 410                 415
Arg His Met Ser Leu Leu Asp Ile Ser Ser Asp Leu Ala Thr Asp His
            420                 425                 430
Leu Leu Gly Cys Asp Leu Ser Ile Ala Ser Lys His Ile Ser Lys Pro
            435                 440                 445
Val Gln Glu Pro Leu Val Leu Pro Glu Val Phe Gly Asn Leu Asn Ser
        450                 455                 460
Val Met Cys Val Glu Gly Glu Ala Gly Ser Gly Lys Thr Val Leu Leu
465                 470                 475                 480
Lys Lys Ile Ala Phe Leu Trp Ala Ser Gly Cys Cys Pro Leu Leu Asn
                485                 490                 495
Arg Phe Gln Leu Val Phe Tyr Leu Ser Leu Ser Ser Thr Arg Pro Asp
            500                 505                 510
Glu Gly Leu Ala Ser Ile Ile Cys Asp Gln Leu Leu Glu Lys Glu Gly
            515                 520                 525
Ser Val Thr Glu Met Cys Val Arg Asn Ile Ile Gln Gln Leu Lys Asn
        530                 535                 540
Gln Val Leu Phe Leu Leu Asp Asp Tyr Lys Glu Ile Cys Ser Ile Pro
545                 550                 555                 560
Gln Val Ile Gly Lys Leu Ile Gln Lys Asn His Leu Ser Arg Thr Cys
                565                 570                 575
Leu Leu Ile Ala Val Arg Thr Asn Arg Ala Arg Asp Ile Arg Arg Tyr
            580                 585                 590
Leu Glu Thr Ile Leu Glu Ile Lys Ala Phe Pro Phe Tyr Asn Thr Val
            595                 600                 605
Cys Ile Leu Arg Lys Leu Phe Ser His Asn Met Thr Arg Leu Arg Lys
        610                 615                 620
Phe Met Val Tyr Phe Gly Lys Asn Gln Ser Leu Gln Lys Ile Gln Lys
625                 630                 635                 640
Thr Pro Leu Phe Val Ala Ala Ile Cys Ala His Trp Phe Gln Tyr Pro
                645                 650                 655
Phe Asp Pro Ser Phe Asp Asp Val Ala Val Phe Lys Ser Tyr Met Glu
            660                 665                 670
Arg Leu Ser Leu Arg Asn Lys Ala Thr Ala Glu Ile Leu Lys Ala Thr
            675                 680                 685
Val Ser Ser Cys Gly Glu Leu Ala Leu Lys Gly Phe Phe Ser Cys Cys
        690                 695                 700
Phe Glu Phe Asn Asp Asp Leu Ala Glu Ala Gly Val Asp Glu Asp
705                 710                 715                 720
Glu Asp Leu Thr Met Cys Leu Met Ser Lys Phe Thr Ala Gln Arg Leu
                725                 730                 735
Arg Pro Phe Tyr Arg Phe Leu Ser Pro Ala Phe Gln Glu Phe Leu Ala
            740                 745                 750
Gly Met Arg Leu Ile Glu Leu Leu Asp Ser Asp Arg Gln Glu His Gln
```

-continued

```
                755                 760                 765
Asp Leu Gly Leu Tyr His Leu Lys Gln Ile Asn Ser Pro Met Met Thr
770                 775                 780

Val Ser Ala Tyr Asn Asn Phe Leu Asn Tyr Val Ser Ser Leu Pro Ser
785                 790                 795                 800

Thr Lys Ala Gly Pro Lys Ile Val Ser His Leu Leu His Leu Val Asp
                805                 810                 815

Asn Lys Glu Ser Leu Glu Asn Ile Ser Glu Asn Asp Asp Tyr Leu Lys
                820                 825                 830

His Gln Pro Glu Ile Ser Leu Gln Met Gln Leu Leu Arg Gly Leu Trp
                835                 840                 845

Gln Ile Cys Pro Gln Ala Tyr Phe Ser Met Val Ser Glu His Leu Leu
850                 855                 860

Val Leu Ala Leu Lys Thr Ala Tyr Gln Ser Asn Thr Val Ala Ala Cys
865                 870                 875                 880

Ser Pro Phe Val Leu Gln Phe Leu Gln Gly Arg Thr Leu Thr Leu Gly
                885                 890                 895

Ala Leu Asn Leu Gln Tyr Phe Phe Asp His Pro Glu Ser Leu Ser Leu
                900                 905                 910

Leu Arg Ser Ile His Phe Pro Ile Arg Gly Asn Lys Thr Ser Pro Arg
                915                 920                 925

Ala His Phe Ser Val Leu Glu Thr Cys Phe Asp Lys Ser Gln Val Pro
930                 935                 940

Thr Ile Asp Gln Asp Tyr Ala Ser Ala Phe Glu Pro Met Asn Glu Trp
945                 950                 955                 960

Glu Arg Asn Leu Ala Glu Lys Glu Asp Asn Val Lys Ser Tyr Met Asp
                965                 970                 975

Met Gln Arg Arg Ala Ser Pro Asp Leu Ser Thr Gly Tyr Trp Lys Leu
                980                 985                 990

Ser Pro Lys Gln Tyr Lys Ile Pro Cys Leu Glu Val Asp Val Asn Asp
                995                 1000                1005

Ile Asp Val Val Gly Gln Asp Met Leu Glu Ile Leu Met Thr Val Phe
1010                1015                1020

Ser Ala Ser Gln Arg Ile Glu Leu His Leu Asn His Ser Arg Gly Phe
1025                1030                1035                1040

Ile Glu Ser Ile Arg Pro Ala Leu Glu Leu Ser Lys Ala Ser Val Thr
                1045                1050                1055

Lys Cys Ser Ile Ser Lys Leu Glu Leu Ser Ala Ala Glu Gln Glu Leu
                1060                1065                1070

Leu Leu Thr Leu Pro Ser Leu Glu Ser Leu Glu Val Ser Gly Thr Ile
                1075                1080                1085

Gln Ser Gln Asp Gln Ile Phe Pro Asn Leu Asp Lys Phe Leu Cys Leu
                1090                1095                1100

Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
                1125                1130                1135

Gln Ile Ser Ala Glu Tyr Asp Pro Ser Lys Leu
                1140                1145

<210> SEQ ID NO 161
<211> LENGTH: 1
<212> TYPE: PRT
<213> ORGANISM: Artificial Sequence
```

-continued

```
<220> FEATURE:
<223> OTHER INFORMATION: Synthetic Peptide

<400> SEQUENCE: 161

Gly
1

<210> SEQ ID NO 162
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 162

Met Ser Glu Ser Glu Leu Gly Arg Lys Trp Asp Arg Cys Leu Ala Asp
1               5                   10                  15

Ala Val Val Lys Ile Gly
            20

<210> SEQ ID NO 163
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 163

Leu Trp Arg Pro Arg Ala
1               5

<210> SEQ ID NO 164
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 164

Met Ala Ala Glu Ser Leu Pro Phe Ser Phe Gly Thr Leu Ser Ser Trp
1               5                   10                  15

Glu Leu Glu Ala Trp Tyr Glu Asp Leu Gln Glu Val Leu Ser Ser Asp
            20                  25                  30

Glu Asn Gly Gly Thr Tyr Val Ser Pro Pro
            35                  40

<210> SEQ ID NO 165
<211> LENGTH: 138
<212> TYPE: PRT
<213> ORGANISM: Artificial Sequence
<220> FEATURE:
<223> OTHER INFORMATION: Synthetic Peptide

<400> SEQUENCE: 165

Leu Pro Leu Gly Ala Ser Gly Gly Phe Pro Ser Ala Thr Ala Asn Cys
1               5                   10                  15

Phe Phe Arg Ser Lys Ser Phe Ala Thr Ser Ala Thr Ser Phe Leu
            20                  25                  30

Ser Ala Phe Cys Ala Phe Ser Arg Thr Met Phe Pro Cys Phe Val
            35                  40                  45

Thr Ser Ser Ile Ser Ala Cys Ile Cys Cys Gly Leu Ala Val Val Thr
            50                  55                  60

Val Ser Thr Thr Ala Gly Phe Gly Asp Val Phe Ala Trp Pro Pro Pro
```

```
                65                  70                  75                  80
Lys Arg Cys Leu Lys Leu Ser Ile Trp Ser Phe Ser Asn Phe Trp Asn
                    85                  90                  95
Lys Gly Leu Thr Val Pro Ile Trp Cys Pro Ala Gly Lys Val His Arg
                    100                 105                 110
Lys Phe Val Ser Arg Ile Leu Gln Ala Gly Gly Ser Cys Ser Trp
                    115                 120                 125
Ala Trp Ile Val Ala Leu Thr Val Gly Met
                    130                 135

<210> SEQ ID NO 166
<211> LENGTH: 446
<212> TYPE: PRT
<213> ORGANISM: Artificial Sequence
<220> FEATURE:
<223> OTHER INFORMATION: Synthetic Peptide

<400> SEQUENCE: 166

Met Ser Cys Val Lys Leu Trp Pro Ser Gly Ala Pro Ala Pro Leu Val
1               5                   10                  15
Ser Ile Glu Glu Leu Glu Asn Gln Glu Leu Val Gly Lys Gly Gly Phe
                20                  25                  30
Gly Thr Val Phe Arg Ala Gln His Arg Lys Trp Gly Tyr Asp Val Ala
                35                  40                  45
Val Lys Ile Val Asn Ser Lys Ala Ile Ser Arg Glu Val Lys Ala Met
            50                  55                  60
Ala Ser Leu Asp Asn Glu Phe Val Leu Arg Leu Glu Gly Val Ile Glu
65                  70                  75                  80
Lys Val Asn Trp Asp Gln Asp Pro Lys Pro Ala Leu Val Thr Lys Phe
                85                  90                  95
Met Glu Asn Gly Ser Leu Ser Gly Leu Leu Gln Ser Gln Cys Pro Arg
                100                 105                 110
Pro Trp Pro Leu Leu Cys Arg Leu Leu Lys Glu Val Val Leu Gly Met
                115                 120                 125
Phe Tyr Leu His Asp Gln Asn Pro Val Leu Leu His Arg Asp Leu Lys
                130                 135                 140
Pro Ser Asn Val Leu Leu Asp Pro Glu Leu His Val Lys Leu Ala Asp
145                 150                 155                 160
Phe Gly Leu Ser Thr Phe Gln Gly Gly Ser Gln Ser Gly Thr Gly Ser
                165                 170                 175
Gly Glu Pro Gly Gly Thr Leu Gly Tyr Leu Ala Pro Glu Leu Phe Val
                180                 185                 190
Asn Val Asn Arg Lys Ala Ser Thr Ala Ser Asp Val Tyr Ser Phe Gly
                195                 200                 205
Ile Leu Met Trp Ala Val Leu Ala Gly Arg Glu Val Glu Leu Pro Thr
                210                 215                 220
Glu Pro Ser Leu Val Tyr Glu Ala Val Cys Asn Arg Gln Asn Arg Pro
225                 230                 235                 240
Ser Leu Ala Glu Leu Pro Gln Ala Gly Pro Glu Thr Pro Gly Leu Glu
                245                 250                 255
Gly Leu Lys Glu Leu Met Gln Leu Cys Trp Ser Ser Glu Pro Lys Asp
                260                 265                 270
Arg Pro Ser Phe Gln Glu Cys Leu Pro Lys Thr Asp Glu Val Phe Gln
                275                 280                 285
Met Val Glu Asn Asn Met Asn Ala Ala Val Ser Thr Val Lys Asp Phe
```

```
           290                 295                 300

Leu Ser Gln Leu Arg Ser Ser Asn Arg Arg Phe Ser Ile Pro Glu Ser
305                 310                 315                 320

Gly Gln Gly Gly Thr Glu Met Asp Gly Phe Arg Arg Thr Ile Glu Asn
                325                 330                 335

Gln His Ser Arg Asn Asp Val Met Val Ser Glu Trp Leu Asn Lys Leu
                340                 345                 350

Asn Leu Glu Glu Pro Pro Ser Ser Val Pro Lys Lys Cys Pro Ser Leu
            355                 360                 365

Thr Lys Arg Ser Arg Ala Gln Glu Glu Gln Val Pro Gln Ala Trp Thr
        370                 375                 380

Ala Gly Thr Ser Ser Asp Ser Met Ala Gln Pro Pro Gln Thr Pro Glu
385                 390                 395                 400

Thr Ser Thr Phe Arg Asn Gln Met Pro Ser Pro Thr Ser Thr Gly Thr
                405                 410                 415

Pro Ser Pro Gly Pro Arg Gly Asn Gln Gly Ala Glu Arg Gln Gly Met
            420                 425                 430

Asn Trp Ser Cys Arg Thr Pro Glu Pro Asn Pro Val Thr Gly
        435                 440                 445

<210> SEQ ID NO 167
<211> LENGTH: 203
<212> TYPE: PRT
<213> ORGANISM: Artificial Sequence
<220> FEATURE:
<223> OTHER INFORMATION: Synthetic Peptide

<400> SEQUENCE: 167

Asp Leu Arg Pro Glu Leu Pro Asp His Cys Ala Val Arg Ala Gly Arg
1               5                   10                  15

Leu Leu Ala Ala Ala Gly Pro Arg Phe Pro Gly Ala Ala Thr Ala Ala
            20                  25                  30

Leu Asp Ala Ser Pro Val Arg Leu Gly Met Gly Arg Ala Ala Ser Ala
        35                  40                  45

Arg Pro Arg Leu Pro Val His Arg Gly Arg Gly Glu Arg Leu Gly Pro
    50                  55                  60

Gly Val Leu Phe Ser Leu Arg His Leu His Gly Val Cys His Ala Ala
65              70                  75                  80

Leu Gly His Ala Gly Arg Arg Arg Gly Pro Arg Leu Leu Thr Leu
            85                  90                  95

Ala Ser Ala Gly Pro Arg Ala Val Ser Trp Ala Thr Ala Gly Leu Thr
            100                 105                 110

Ala Cys Thr Ala Ala Val Gly Ser Lys Arg Ser Ala Val Pro Val
        115                 120                 125

Arg Glu Arg Gly Arg Ser Val Pro Gln Gly Ala Asp Gly Ala Arg Pro
    130                 135                 140

Ala Gly His Val Pro Gly Gly Thr Gln Leu Pro Ala Leu Thr Pro Ala
145                 150                 155                 160

Ala Gly His Arg Glu Glu Ala Pro Gly Thr Pro Ser Leu Val His Pro
                165                 170                 175

Ser Cys Leu Pro Gly Pro Arg Asp Glu Gly Arg Asp His Gly Thr Ala
            180                 185                 190

Ala Gly Arg Thr Gly Val Thr Ala Arg Glu His
        195                 200
```

<210> SEQ ID NO 168
<211> LENGTH: 46
<212> TYPE: PRT
<213> ORGANISM: Artificial Sequence
<220> FEATURE:
<223> OTHER INFORMATION: Synthetic Peptide

<400> SEQUENCE: 168

```
Met Glu Leu Ser Glu Ser Val Gln Lys Gly Phe Gln Met Leu Ala Asp
1               5                   10                  15

Pro Arg Ser Phe Asp Ser Asn Ala Phe Thr Leu Leu Arg Ala Ala
            20                  25                  30

Phe Gln Ser Leu Leu Asp Ala Gln Ala Asp Glu Ala Val Leu
        35                  40                  45
```

<210> SEQ ID NO 169
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 169

```
Gly Phe Phe Ile Lys Gln Lys Cys Ile Glu Gln Arg Glu Ser Arg Ser
1               5                   10                  15

Leu Ser
```

<210> SEQ ID NO 170
<211> LENGTH: 274
<212> TYPE: PRT
<213> ORGANISM: Artificial Sequence
<220> FEATURE:
<223> OTHER INFORMATION: Synthetic Peptide

<400> SEQUENCE: 170

```
Met Gln Arg Glu Glu Lys Gln Leu Glu Ala Ser Leu Asp Ala Leu Leu
1               5                   10                  15

Ser Gln Val Ala Asp Leu Lys Asn Ser Leu Gly Ser Phe Ile Cys Lys
            20                  25                  30

Leu Glu Asn Glu Tyr Gly Arg Leu Thr Trp Pro Ser Val Leu Asp Ser
        35                  40                  45

Phe Ala Leu Leu Ser Gly Gln Leu Asn Thr Leu Asn Lys Val Leu Lys
    50                  55                  60

His Glu Lys Thr Pro Leu Phe Arg Asn Gln Val Ile Ile Pro Leu Val
65                  70                  75                  80

Leu Ser Pro Asp Arg Asp Glu Asp Leu Met Arg Gln Thr Glu Gly Arg
                85                  90                  95

Val Pro Val Phe Ser His Glu Val Val Pro Asp His Leu Arg Thr Lys
            100                 105                 110

Pro Asp Pro Glu Val Glu Glu Gln Lys Gln Leu Thr Thr Asp Ala
        115                 120                 125

Ala Arg Ile Gly Ala Asp Ala Ala Gln Lys Gln Ile Gln Ser Leu Asn
    130                 135                 140

Lys Met Cys Ser Asn Leu Leu Glu Lys Ile Ser Lys Glu Glu Arg Glu
145                 150                 155                 160

Ser Glu Ser Gly Gly Leu Arg Pro Asn Lys Gln Thr Phe Asn Pro Thr
                165                 170                 175

Asp Thr Asn Ala Leu Val Ala Val Ala Phe Gly Lys Gly Leu Ser
            180                 185                 190
```

```
Asn Trp Arg Pro Ser Gly Ser Ser Gly Pro Gly Gln Ala Gly Gln Pro
            195                 200                 205

Gly Ala Gly Thr Ile Leu Ala Gly Thr Ser Gly Leu Gln Gln Val Gln
    210                 215                 220

Met Ala Gly Ala Pro Ser Gln Gln Gln Pro Met Leu Ser Gly Val Gln
225                 230                 235                 240

Met Ala Gln Ala Gly Gln Pro Gly Lys Met Pro Ser Gly Ile Lys Thr
                245                 250                 255

Asn Ile Lys Ser Ala Ser Met His Pro Tyr Gln Arg Ser Glu Gln Ile
            260                 265                 270

Asp Asn

<210> SEQ ID NO 171
<211> LENGTH: 55
<212> TYPE: PRT
<213> ORGANISM: Artificial Sequence
<220> FEATURE:
<223> OTHER INFORMATION: Synthetic Peptide

<400> SEQUENCE: 171

Val Leu Ser Gln Asp Gly Gly Cys Cys Glu Leu Val Pro Arg Gly Asp
1               5                   10                  15

Glu Ala Arg Arg Ser Pro Asp Pro Gly Leu Pro Ser Asp Gly Val Pro
            20                  25                  30

Leu Ala Asn Asp Leu His Ser Pro Asp Leu Arg Val Leu Arg Ser Leu
        35                  40                  45

Thr Trp Ala Ser His His Gly
    50                  55

<210> SEQ ID NO 172
<211> LENGTH: 47
<212> TYPE: PRT
<213> ORGANISM: Artificial Sequence
<220> FEATURE:
<223> OTHER INFORMATION: Synthetic Peptide

<400> SEQUENCE: 172

Met Asn Ala Pro Pro Ala Phe Glu Ser Phe Leu Leu Phe Glu Gly Glu
1               5                   10                  15

Lys Ile Thr Ile Asn Lys Asp Thr Lys Val Pro Asn Ala Cys Leu Phe
            20                  25                  30

Thr Met Asn Lys Glu Asp His Thr Leu Gly Asn Ile Ile Lys Ser
        35                  40                  45

<210> SEQ ID NO 173
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 173

Arg Ala Cys Phe Pro Phe Ala Phe Cys Arg Asp Cys Gln Phe Pro Glu
1               5                   10                  15

Ala Ser Pro Ala Thr Leu Ser Val Gln Pro Ala Glu Leu
            20                  25

<210> SEQ ID NO 174
<211> LENGTH: 188
<212> TYPE: PRT
<213> ORGANISM: Artificial Sequence
```

-continued

```
<220> FEATURE:
<223> OTHER INFORMATION: Synthetic Peptide

<400> SEQUENCE: 174

Met Ala Glu Ala Ser Ser Ala Asn Leu Gly Ser Gly Cys Glu Glu Lys
1               5                   10                  15

Arg His Glu Gly Ser Ser Ser Glu Ser Val Pro Pro Gly Thr Thr Ile
            20                  25                  30

Ser Arg Val Lys Leu Leu Asp Thr Met Val Asp Thr Phe Leu Gln Lys
        35                  40                  45

Leu Val Ala Ala Gly Ser Tyr Gln Arg Phe Thr Asp Cys Tyr Lys Cys
    50                  55                  60

Phe Tyr Gln Leu Gln Pro Ala Met Thr Gln Gln Ile Tyr Asp Lys Phe
65                  70                  75                  80

Ile Ala Gln Leu Gln Thr Ser Ile Arg Glu Glu Ile Ser Asp Ile Lys
                85                  90                  95

Glu Glu Gly Asn Leu Glu Ala Val Leu Asn Ala Leu Asp Lys Ile Val
            100                 105                 110

Glu Glu Gly Lys Val Arg Lys Glu Pro Ala Trp Arg Pro Ser Gly Ile
        115                 120                 125

Pro Glu Lys Asp Leu His Ser Val Met Ala Pro Tyr Phe Leu Gln Gln
    130                 135                 140

Arg Asp Thr Leu Arg Arg His Val Gln Lys Gln Glu Ala Glu Asn Gln
145                 150                 155                 160

Gln Leu Ala Asp Ala Val Leu Ala Gly Arg Arg Gln Val Glu Glu Leu
                165                 170                 175

Gln Leu Gln Val Gln Ala Gln Gln Gln Ala Trp Gln
            180                 185

<210> SEQ ID NO 175
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 175

Val Arg Ser Pro Ala Val Gln Ser Pro Ala Lys Val Gln Pro Leu Cys
1               5                   10                  15

Pro Ser Arg Arg Ala Ala Arg
            20

<210> SEQ ID NO 176
<211> LENGTH: 178
<212> TYPE: PRT
<213> ORGANISM: Artificial Sequence
<220> FEATURE:
<223> OTHER INFORMATION: Synthetic Peptide

<400> SEQUENCE: 176

Met Ala Ser Ser Leu Leu Ala Gly Glu Arg Leu Val Arg Ala Leu Gly
1               5                   10                  15

Pro Gly Gly Glu Leu Glu Pro Glu Arg Leu Pro Arg Lys Leu Arg Ala
            20                  25                  30

Glu Leu Glu Ala Ala Leu Gly Lys Lys His Lys Gly Gly Asp Ser Ser
        35                  40                  45

Ser Gly Pro Gln Arg Leu Val Ser Phe Arg Leu Ile Arg Asp Leu His
    50                  55                  60
```

Gln His Leu Arg Glu Arg Asp Ser Lys Leu Tyr Leu His Glu Leu Leu
65                  70                  75                  80

Glu Gly Ser Glu Ile Tyr Leu Pro Glu Val Val Lys Pro Pro Arg Asn
                85                  90                  95

Pro Glu Leu Val Ala Arg Leu Glu Lys Ile Lys Ile Gln Leu Ala Asn
            100                 105                 110

Glu Glu Tyr Lys Arg Ile Thr Arg Asn Val Thr Cys Gln Asp Thr Arg
            115                 120                 125

His Gly Gly Thr Leu Ser Asp Leu Gly Lys Gln Val Arg Ser Leu Lys
130                 135                 140

Ala Leu Val Ile Thr Ile Phe Asn Phe Ile Val Thr Val Val Ala Ala
145                 150                 155                 160

Phe Val Cys Thr Tyr Leu Gly Ser Gln Tyr Ile Phe Thr Glu Met Ala
                165                 170                 175

Ser Arg

<210> SEQ ID NO 177
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 177

Pro Arg Gly Ala His Trp Ala Gly Arg Asp Pro Glu Pro Gly Glu Gly
1               5                   10                  15

Thr Arg Thr Arg Arg Ala Gly Ala Glu Arg Gly Arg His Leu Gly Ala
            20                  25                  30

His Val Gln Ala Phe Gly Gly Asp Met Pro Glu Ala Gly Gly Gly Arg
        35                  40                  45

Arg Pro Gly Arg Gly Ala Val Leu Val Pro Pro His Gly Pro Arg Ala
50                  55                  60

Ala Ala Pro Leu Arg Ala Gly Ala Gly Gln Leu Arg Ala Ala Arg Gly
65                  70                  75                  80

Pro Gly Gly Ala Ala Thr His Gly Arg Glu Ala Arg Ser Arg Val Ala
                85                  90                  95

Leu Pro Ala Arg Leu Leu Gln Gly Gly Arg Ala Ala Ser Ala Ala Arg
            100                 105                 110

Leu Pro Arg Ser Ser Gly Val Gly Asp
            115                 120

<210> SEQ ID NO 178
<211> LENGTH: 97
<212> TYPE: PRT
<213> ORGANISM: Artificial Sequence
<220> FEATURE:
<223> OTHER INFORMATION: Synthetic Peptide

<400> SEQUENCE: 178

Met Gln Trp Leu Arg Val Arg Glu Ser Pro Gly Glu Ala Thr Gly His
1               5                   10                  15

Arg Val Thr Met Gly Thr Ala Ala Leu Gly Pro Val Trp Ala Ala Leu
            20                  25                  30

Leu Leu Phe Leu Leu Met Cys Glu Ile Pro Met Val Glu Leu Thr Phe
        35                  40                  45

Asp Arg Ala Val Ala Ser Gly Cys Gln Arg Cys Cys Asp Ser Glu Asp
50                  55                  60

```
Pro Leu Asp Pro Ala His Val Ser Ser Ala Ser Ser Gly Arg Pro
 65                  70                  75                  80

His Ala Leu Pro Glu Ile Arg Pro Tyr Ile Asn Ile Thr Ile Leu Lys
                 85                  90                  95

Gly
```

<210> SEQ ID NO 179
<211> LENGTH: 84
<212> TYPE: PRT
<213> ORGANISM: Artificial Sequence
<220> FEATURE:
<223> OTHER INFORMATION: Synthetic Peptide

<400> SEQUENCE: 179

```
Leu Pro Ser Ser Ala Pro Pro Cys Gly Cys Asn Gly Gly Pro Cys Ser
 1               5                  10                  15

Val Leu Ala Ser Ala Pro Pro His Pro Pro Ala Pro Gly Tyr Leu
                 20                  25                  30

Leu Gly Ile Cys Ser Gly Glu Trp His Phe Pro Val His Met Leu Leu
             35                  40                  45

Gln Leu Glu Ser Gln His Leu Leu Cys Leu Glu Pro Arg Trp Gly Ser
 50                  55                  60

Ala Gly His Phe Leu Pro Ser Pro Cys Leu Ala Gly Gln Thr Ala Val
 65                  70                  75                  80

Glu Pro Asn Leu
```

<210> SEQ ID NO 180
<211> LENGTH: 173
<212> TYPE: PRT
<213> ORGANISM: Artificial Sequence
<220> FEATURE:
<223> OTHER INFORMATION: Synthetic Peptide

<400> SEQUENCE: 180

```
Met Asp Pro Ala Ser Arg Gly Cys Leu Gly Pro Thr Pro Ala Phe Arg
 1               5                  10                  15

His Arg Lys Glu Gln Ser Ser Ala Ser Pro Arg Pro Ser Glu Ala Thr
                 20                  25                  30

Gly Ala Arg Thr Met Gly Ser Gln Ala Arg Arg Pro Pro Val Ile Pro
             35                  40                  45

Phe Thr Lys Asn Glu Thr Leu Phe Ser Leu Pro Gly Pro Asp Ala Arg
 50                  55                  60

Gln Pro Thr Arg Pro Arg Pro Gly Asp Leu Glu Thr Gly Ser Leu Asp
 65                  70                  75                  80

Glu Glu Pro Glu Gly Gly Lys Gly Thr Gly Gly Arg Lys Ile Ser Arg
                 85                  90                  95

Ile Asp Phe Ile Thr Lys Phe Trp Val Pro Ala Ser Gly Val Pro Asp
             100                 105                 110

Glu Thr Lys Arg Leu Leu Val Leu His Pro Arg Cys Tyr Phe Gln Asn
             115                 120                 125

Ser Gly Leu Val Val Trp Ser Leu His Cys Ser Met Ser Leu Leu Ser
 130                 135                 140

Asn Leu Glu Ser Ser Val Phe Leu Pro Ser Val Arg Cys Ala Tyr Phe
 145                 150                 155                 160

Ser Leu Glu Lys Leu Glu Glu Ala Gly Met Leu Glu Met
                 165                 170
```

-continued

```
<210> SEQ ID NO 181
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 181

Arg Pro Ser Thr Pro Cys Leu His Gly Ala Ala Leu His Leu His Ser
1               5                   10                  15

Gly His Gly Ser Gly Ser Arg Leu Thr Asn Ser Ser Cys Phe Pro Gly
            20                  25                  30

Thr Arg Arg Leu Leu Ala Leu Gln Phe Thr Gln Gln Thr Gly Thr Val
        35                  40                  45

Gly His Pro Thr Trp Gln Pro Val Ile Arg
    50                  55

<210> SEQ ID NO 182
<211> LENGTH: 65
<212> TYPE: PRT
<213> ORGANISM: Artificial Sequence
<220> FEATURE:
<223> OTHER INFORMATION: Synthetic Peptide

<400> SEQUENCE: 182

Met Ser Thr Ala Met Asn Phe Gly Thr Lys Ser Phe Gln Pro Arg Pro
1               5                   10                  15

Pro Asp Lys Gly Ser Phe Pro Leu Asp His Leu Gly Glu Cys Lys Ser
            20                  25                  30

Phe Lys Glu Lys Phe Met Lys Cys Leu His Asn Asn Asn Phe Glu Asn
        35                  40                  45

Ala Leu Cys Arg Lys Glu Ser Lys Glu Tyr Leu Glu Cys Arg Met Glu
    50                  55                  60

Arg
65

<210> SEQ ID NO 183
<211> LENGTH: 57
<212> TYPE: PRT
<213> ORGANISM: Artificial Sequence
<220> FEATURE:
<223> OTHER INFORMATION: Synthetic Peptide

<400> SEQUENCE: 183

Ser Arg Leu Gly Leu Leu His Ser Gly Arg Leu His Leu Pro Glu Leu
1               5                   10                  15

Leu Gly Asn Pro Pro Glu Tyr Pro Pro Gly Gln Gln Gly Glu Val Arg
            20                  25                  30

Pro Pro Gly Arg Leu Gly Gly Pro Ser Gly Val His Gly Leu Pro
        35                  40                  45

Arg Glu Arg Arg Arg Glu Ser Gln Val
    50                  55

<210> SEQ ID NO 184
<211> LENGTH: 405
<212> TYPE: PRT
<213> ORGANISM: Artificial Sequence
<220> FEATURE:
<223> OTHER INFORMATION: Synthetic Peptide

<400> SEQUENCE: 184

Met Ala Val Tyr Val Gly Met Leu Arg Leu Gly Arg Leu Cys Ala Gly
```

```
1               5                   10                  15
Ser Ser Gly Val Leu Gly Ala Arg Ala Ala Leu Ser Arg Ser Trp Gln
            20                  25                  30

Glu Ala Arg Leu Gln Gly Val Arg Phe Leu Ser Ser Arg Glu Val Asp
            35                  40                  45

Arg Met Val Ser Thr Pro Ile Gly Gly Leu Ser Tyr Val Gln Gly Cys
50                  55                  60

Thr Lys Lys His Leu Asn Ser Lys Thr Val Gly Gln Cys Leu Glu Thr
65                  70                  75                  80

Thr Ala Gln Arg Val Pro Glu Arg Glu Ala Leu Val Val Leu His Glu
            85                  90                  95

Asp Val Arg Leu Thr Phe Ala Gln Leu Lys Glu Val Asp Lys Ala
            100                 105                 110

Ala Ser Gly Leu Leu Ser Ile Gly Leu Cys Lys Gly Asp Arg Leu Gly
            115                 120                 125

Met Trp Gly Pro Asn Ser Tyr Ala Trp Val Leu Met Gln Leu Ala Thr
130                 135                 140

Ala Gln Ala Gly Ile Ile Leu Val Ser Val Asn Pro Ala Tyr Gln Ala
145                 150                 155                 160

Met Glu Leu Glu Tyr Val Leu Lys Lys Val Gly Cys Lys Ala Leu Val
            165                 170                 175

Phe Pro Lys Gln Phe Lys Thr Gln Gln Tyr Tyr Asn Val Leu Lys Gln
            180                 185                 190

Ile Cys Pro Glu Val Glu Asn Ala Gln Pro Gly Ala Leu Lys Ser Gln
            195                 200                 205

Arg Leu Pro Asp Leu Thr Thr Val Ile Ser Val Asp Ala Pro Leu Pro
210                 215                 220

Gly Thr Leu Leu Leu Asp Glu Val Val Ala Ala Gly Ser Thr Arg Gln
225                 230                 235                 240

His Leu Asp Gln Leu Gln Tyr Asn Gln Gln Phe Leu Ser Cys His Asp
            245                 250                 255

Pro Ile Asn Ile Gln Phe Thr Ser Gly Thr Thr Gly Ser Pro Lys Gly
            260                 265                 270

Ala Thr Leu Ser His Tyr Asn Ile Val Asn Asn Ser Asn Ile Leu Gly
            275                 280                 285

Glu Arg Leu Lys Leu His Glu Lys Thr Pro Glu Gln Leu Arg Met Ile
            290                 295                 300

Leu Pro Asn Pro Leu Tyr His Cys Leu Gly Ser Val Ala Gly Thr Met
305                 310                 315                 320

Met Cys Leu Met Tyr Gly Ala Thr Leu Ile Leu Ala Ser Pro Ile Phe
            325                 330                 335

Asn Gly Lys Lys Ala Leu Glu Ala Ile Ser Arg Glu Arg Gly Thr Phe
            340                 345                 350

Leu Tyr Gly Thr Pro Thr Met Phe Val Asp Ile Leu Asn Gln Pro Asp
            355                 360                 365

Phe Ser Ser Tyr Asp Ile Ser Thr Met Cys Gly Gly Val Ile Ala Gly
            370                 375                 380

Ser Pro Ala Pro Pro Glu Leu Ile Arg Ala Ile Ile Asn Lys Ile Asn
385                 390                 395                 400

Met Lys Asp Leu Val
            405

<210> SEQ ID NO 185
```

```
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 185

Arg Asn Leu Arg Lys Lys Leu Gln His Gly Lys Met Asp Ser Lys Ala
1               5                   10                  15

Pro Met Ser Cys
            20

<210> SEQ ID NO 186
<211> LENGTH: 171
<212> TYPE: PRT
<213> ORGANISM: Artificial Sequence
<220> FEATURE:
<223> OTHER INFORMATION: Synthetic Peptide

<400> SEQUENCE: 186

Met Glu Gly Gly Gly Gly Ser Gly Asn Lys Thr Thr Gly Gly Leu Ala
1               5                   10                  15

Gly Phe Phe Gly Ala Gly Gly Ala Gly Tyr Ser His Ala Asp Leu Ala
            20                  25                  30

Gly Val Pro Leu Thr Gly Met Asn Pro Leu Ser Pro Tyr Leu Asn Val
        35                  40                  45

Asp Pro Arg Tyr Leu Val Gln Asp Thr Asp Glu Phe Ile Leu Pro Thr
    50                  55                  60

Gly Ala Asn Lys Thr Arg Gly Arg Phe Glu Leu Ala Phe Phe Thr Ile
65                  70                  75                  80

Gly Gly Cys Cys Met Thr Gly Ala Ala Phe Gly Ala Met Asn Gly Leu
                85                  90                  95

Arg Leu Gly Leu Lys Glu Thr Gln Asn Met Ala Trp Ser Lys Pro Arg
            100                 105                 110

Asn Val Gln Ile Leu Asn Met Val Thr Arg Gln Gly Ala Leu Trp Ala
        115                 120                 125

Asn Thr Leu Gly Ser Leu Ala Leu Leu Tyr Ser Ala Phe Gly Val Ile
    130                 135                 140

Ile Glu Lys Thr Arg Gly Ala Glu Asp Asp Leu Asn Thr Val Ala Ala
145                 150                 155                 160

Gly Thr Met Thr Gly Met Leu Tyr Lys Cys Thr
                165                 170

<210> SEQ ID NO 187
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 187

Val Ser Glu Met Ala Leu Asp Ser Pro Phe Cys Val Leu Leu Ser Gly
1               5                   10                  15

Ser

<210> SEQ ID NO 188
<211> LENGTH: 188
<212> TYPE: PRT
<213> ORGANISM: Artificial Sequence
<220> FEATURE:
<223> OTHER INFORMATION: Synthetic Peptide
```

```
<400> SEQUENCE: 188

Met Gln Glu Pro Arg Arg Val Thr Pro Cys Leu Gly Lys Arg Gly Val
1               5                   10                  15

Lys Thr Pro Gln Leu Gln Pro Gly Ser Ala Phe Leu Pro Arg Val Arg
            20                  25                  30

Arg Gln Ser Phe Pro Ala Arg Ser Asp Ser Tyr Thr Thr Val Arg Asp
                35                  40                  45

Phe Leu Ala Val Pro Arg Thr Ile Ser Ser Ala Ser Ala Thr Leu Ile
    50                  55                  60

Met Ala Val Ala Val Ser His Phe Arg Pro Gly Pro Glu Val Trp Asp
65                  70                  75                  80

Thr Ala Ser Met Ala Ala Ser Lys Val Lys Gln Asp Met Pro Pro Pro
                85                  90                  95

Gly Gly Tyr Gly Pro Ile Asp Tyr Lys Arg Asn Leu Pro Arg Arg Gly
                100                 105                 110

Leu Ser Gly Tyr Ser Met Leu Ala Ile Gly Ile Gly Thr Leu Ile Tyr
                115                 120                 125

Gly His Trp Ser Ile Met Lys Trp Asn Arg Glu Arg Arg Leu Gln
130                 135                 140

Ile Glu Asp Phe Glu Ala Arg Ile Ala Leu Leu Pro Leu Leu Gln Ala
145                 150                 155                 160

Glu Thr Asp Arg Arg Thr Leu Gln Met Leu Arg Glu Asn Leu Glu Glu
                165                 170                 175

Glu Ala Ile Ile Met Lys Asp Val Pro Asp Trp Lys
                180                 185

<210> SEQ ID NO 189
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 189

Gly Leu Gly Ala Ala Ala Pro Thr Cys Arg His Gly Lys Ser Gly Ala
1               5                   10                  15

<210> SEQ ID NO 190
<211> LENGTH: 440
<212> TYPE: PRT
<213> ORGANISM: Artificial Sequence
<220> FEATURE:
<223> OTHER INFORMATION: Synthetic Peptide

<400> SEQUENCE: 190

Met Ala Ala Ala Ala Arg Ala Arg Val Ala Tyr Leu Leu Arg Gln Leu
1               5                   10                  15

Gln Arg Ala Ala Cys Gln Cys Pro Thr His Ser His Thr Tyr Ser Gln
            20                  25                  30

Ala Pro Gly Leu Ser Pro Ser Gly Lys Thr Thr Asp Tyr Ala Phe Glu
                35                  40                  45

Met Ala Val Ser Asn Ile Arg Tyr Gly Ala Ala Val Thr Lys Glu Val
    50                  55                  60

Gly Met Asp Leu Lys Asn Met Gly Ala Lys Asn Val Cys Leu Met Thr
65                  70                  75                  80

Asp Lys Asn Leu Ser Lys Leu Pro Pro Val Gln Val Ala Met Asp Ser
                85                  90                  95
```

Leu Val Lys Asn Gly Ile Pro Phe Thr Val Tyr Asp Asn Val Arg Val
            100                 105                 110

Glu Pro Thr Asp Ser Ser Phe Met Glu Ala Ile Glu Phe Ala Gln Lys
            115                 120                 125

Gly Ala Phe Asp Ala Tyr Val Ala Val Gly Gly Ser Thr Met Asp
            130                 135                 140

Thr Cys Lys Ala Ala Asn Leu Tyr Ala Ser Pro His Ser Asp Phe
145                 150                 155                 160

Leu Asp Tyr Val Ser Ala Pro Ile Gly Lys Gly Lys Pro Val Ser Val
            165                 170                 175

Pro Leu Lys Pro Leu Ile Ala Val Pro Thr Thr Ser Gly Thr Gly Ser
            180                 185                 190

Glu Thr Thr Gly Val Ala Ile Phe Asp Tyr Glu His Leu Lys Val Lys
            195                 200                 205

Ile Gly Ile Thr Ser Arg Ala Ile Lys Pro Thr Leu Gly Leu Ile Asp
            210                 215                 220

Pro Leu His Thr Leu His Met Pro Ala Arg Val Val Ala Asn Ser Gly
225                 230                 235                 240

Phe Asp Val Leu Cys His Ala Leu Glu Ser Tyr Thr Thr Leu Pro Tyr
            245                 250                 255

His Leu Arg Ser Pro Cys Pro Ser Asn Pro Ile Thr Arg Pro Ala Tyr
            260                 265                 270

Gln Gly Ser Asn Pro Ile Ser Asp Ile Trp Ala Ile His Ala Leu Arg
            275                 280                 285

Ile Val Ala Lys Tyr Leu Lys Arg Ala Val Arg Asn Pro Asp Asp Leu
            290                 295                 300

Glu Ala Arg Ser His Met His Leu Ala Ser Ala Phe Ala Gly Ile Gly
305                 310                 315                 320

Phe Gly Asn Ala Gly Val His Leu Cys His Gly Met Ser Tyr Pro Ile
            325                 330                 335

Ser Gly Leu Val Lys Met Tyr Lys Ala Lys Asp Tyr Asn Val Asp His
            340                 345                 350

Pro Leu Val Pro His Gly Leu Ser Val Val Leu Thr Ser Pro Ala Val
            355                 360                 365

Phe Thr Phe Thr Ala Gln Met Phe Pro Glu Arg His Leu Glu Met Ala
            370                 375                 380

Glu Ile Leu Gly Ala Asp Thr Arg Thr Ala Arg Ile Gln Asp Ala Gly
385                 390                 395                 400

Leu Val Leu Ala Asp Thr Leu Arg Lys Phe Leu Phe Asp Leu Asp Val
            405                 410                 415

Asp Asp Gly Leu Ala Ala Val Gly Tyr Ser Lys Ala Asp Ile Pro Ala
            420                 425                 430

Leu Val Lys Gly Thr Leu Pro Gln
            435                 440

<210> SEQ ID NO 191
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 191

Tyr Pro Val Gln Pro Glu Glu Pro Lys Ala Leu Ser Thr Ser
1               5                   10                  15

<210> SEQ ID NO 192
<211> LENGTH: 651
<212> TYPE: PRT
<213> ORGANISM: Artificial Sequence
<220> FEATURE:
<223> OTHER INFORMATION: Synthetic Peptide

<400> SEQUENCE: 192

```
Met Ala Thr Ser Thr Ser Thr Glu Ala Lys Ser Ala Ser Trp Trp Asn
1               5                   10                  15

Tyr Phe Phe Leu Tyr Asp Gly Ser Lys Val Lys Glu Glu Gly Asp Pro
                20                  25                  30

Thr Arg Ala Gly Ile Cys Tyr Phe Tyr Pro Ser Gln Thr Leu Leu Asp
            35                  40                  45

Gln Gln Glu Leu Leu Cys Gly Gln Ile Ala Gly Val Val Arg Cys Val
50                  55                  60

Ser Asp Ile Ser Asp Ser Pro Pro Thr Leu Val Arg Leu Arg Lys Leu
65                  70                  75                  80

Lys Phe Ala Ile Lys Val Asp Gly Asp Tyr Leu Trp Val Leu Gly Cys
                85                  90                  95

Ala Val Glu Leu Pro Asp Val Ser Cys Lys Arg Phe Leu Asp Gln Leu
                100                 105                 110

Val Gly Phe Phe Asn Phe Tyr Asn Gly Pro Val Ser Leu Ala Tyr Glu
            115                 120                 125

Asn Cys Ser Gln Glu Glu Leu Ser Thr Glu Trp Asp Thr Phe Ile Glu
130                 135                 140

Gln Ile Leu Lys Asn Thr Ser Asp Leu His Lys Ile Phe Asn Ser Leu
145                 150                 155                 160

Trp Asn Leu Asp Gln Thr Lys Val Glu Pro Leu Leu Leu Leu Lys Ala
                165                 170                 175

Ala Arg Ile Leu Gln Thr Cys Gln Arg Ser Pro His Ile Leu Ala Gly
                180                 185                 190

Cys Ile Leu Tyr Lys Gly Leu Ile Val Ser Thr Gln Leu Pro Pro Ser
            195                 200                 205

Leu Thr Ala Lys Val Leu Leu His Arg Thr Ala Pro Gln Glu Gln Arg
210                 215                 220

Leu Pro Thr Gly Glu Asp Ala Pro Gln Glu His Gly Ala Ala Leu Pro
225                 230                 235                 240

Pro Asn Val Gln Ile Ile Pro Val Phe Val Thr Lys Glu Glu Ala Ile
                245                 250                 255

Ser Leu His Glu Phe Pro Val Glu Gln Met Thr Arg Ser Leu Ala Ser
                260                 265                 270

Pro Ala Gly Leu Gln Asp Gly Ser Ala Gln His Pro Lys Gly Gly
            275                 280                 285

Ser Thr Ser Ala Leu Lys Glu Asn Ala Thr Gly His Val Glu Ser Met
            290                 295                 300

Ala Trp Thr Thr Pro Asp Pro Thr Ser Pro Asp Glu Ala Cys Pro Asp
305                 310                 315                 320

Gly Arg Lys Glu Asn Gly Cys Leu Ser Gly His Asp Leu Glu Ser Ile
                325                 330                 335

Arg Pro Ala Gly Leu His Asn Ser Ala Arg Gly Glu Val Leu Gly Leu
            340                 345                 350

Ser Ser Ser Leu Gly Lys Glu Leu Val Phe Leu Gln Glu Glu Leu Asp
            355                 360                 365
```

```
Leu Ser Glu Ile His Ile Pro Glu Ala Gln Glu Val Glu Met Ala Ser
        370                 375                 380

Gly His Phe Ala Phe Leu His Val Pro Val Pro Asp Gly Arg Ala Pro
385                 390                 395                 400

Tyr Cys Lys Ala Ser Leu Ser Ala Ser Ser Leu Glu Pro Thr Pro
                405                 410                 415

Pro Glu Asp Thr Ala Ile Ser Ser Leu Arg Pro Pro Ser Ala Pro Glu
            420                 425                 430

Met Leu Thr Gln His Gly Ala Gln Glu Gln Leu Glu Asp His Pro Gly
                435                 440                 445

His Ser Ser Gln Ala Pro Ile Pro Arg Ala Asp Pro Leu Pro Arg Arg
    450                 455                 460

Thr Arg Arg Pro Leu Leu Leu Pro Arg Leu Asp Pro Gly Gln Arg Gly
465                 470                 475                 480

Asn Lys Leu Pro Thr Gly Glu Gln Gly Leu Asp Glu Val Asp Gly
                485                 490                 495

Val Cys Glu Ser His Ala Ala Pro Gly Leu Glu Cys Ser Ser Gly Ser
                500                 505                 510

Ala Asn Cys Gln Gly Ala Gly Pro Ser Ala Asp Gly Ile Ser Ser Arg
                515                 520                 525

Leu Thr Pro Ala Glu Ser Cys Met Gly Leu Val Arg Met Asn Leu Tyr
        530                 535                 540

Thr His Cys Val Lys Gly Leu Val Leu Ser Leu Leu Ala Glu Glu Pro
545                 550                 555                 560

Leu Leu Gly Asp Ser Ala Ala Ile Glu Glu Val Tyr His Ser Ser Leu
                565                 570                 575

Ala Ser Leu Asn Gly Leu Glu Val His Leu Lys Glu Thr Leu Pro Arg
                580                 585                 590

Asp Glu Ala Ala Ser Thr Ser Ser Thr Tyr Asn Phe Thr His Tyr Asp
                595                 600                 605

Arg Ile Gln Ser Leu Leu Met Ala Asn Leu Pro Gln Val Ala Thr Pro
        610                 615                 620

Gln Asp Arg Arg Phe Leu Gln Ala Val Ser Leu Met His Ser Glu Phe
625                 630                 635                 640

Ala Gln Leu Pro Ala Leu Tyr Glu Met Thr Val
                645                 650

<210> SEQ ID NO 193
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 193

Ser Asn Ser Cys Thr Ser
1               5

<210> SEQ ID NO 194
<211> LENGTH: 477
<212> TYPE: PRT
<213> ORGANISM: Artificial Sequence
<220> FEATURE:
<223> OTHER INFORMATION: Synthetic Peptide

<400> SEQUENCE: 194

Met Ala Ala Met Ala Pro Ala Leu Thr Asp Ala Ala Ala Glu Ala His
```

-continued

```
1               5                   10                  15
His Ile Arg Phe Lys Leu Ala Pro Pro Ser Ser Thr Leu Ser Pro Gly
                20                  25                  30

Ser Ala Glu Asn Asn Gly Asn Ala Asn Ile Leu Ile Ala Ala Asn Gly
                35                  40                  45

Thr Lys Arg Lys Ala Ile Ala Ala Glu Asp Pro Ser Leu Asp Phe Arg
                50                  55                  60

Asn Asn Pro Thr Lys Glu Asp Leu Gly Lys Leu Gln Pro Leu Val Ala
 65                  70                  75                  80

Ser Tyr Leu Cys Ser Asp Val Thr Ser Val Pro Ser Lys Glu Ser Leu
                    85                  90                  95

Lys Leu Gln Gly Val Phe Ser Lys Gln Thr Val Leu Lys Ser His Pro
                100                 105                 110

Leu Leu Ser Gln Ser Tyr Glu Leu Arg Ala Glu Leu Leu Gly Arg Gln
                115                 120                 125

Pro Val Leu Glu Phe Ser Leu Glu Asn Leu Arg Thr Met Asn Thr Ser
                130                 135                 140

Gly Gln Thr Ala Leu Pro Gln Ala Pro Val Asn Gly Leu Ala Lys Lys
145                 150                 155                 160

Leu Thr Lys Ser Ser Thr His Ser Asp His Asp Asn Ser Thr Ser Leu
                    165                 170                 175

Asn Gly Gly Lys Arg Ala Leu Thr Ser Ser Ala Leu His Gly Gly Glu
                180                 185                 190

Met Gly Gly Ser Glu Ser Gly Asp Leu Lys Gly Gly Met Thr Asn Cys
                    195                 200                 205

Thr Leu Pro His Arg Ser Leu Asp Val Glu His Thr Thr Leu Tyr Ser
                210                 215                 220

Asn Asn Ser Thr Ala Asn Lys Ser Ser Val Asn Ser Met Glu Gln Pro
225                 230                 235                 240

Ala Leu Gln Gly Ser Ser Arg Leu Ser Pro Gly Thr Asp Ser Ser Ser
                    245                 250                 255

Asn Leu Gly Gly Val Lys Leu Glu Gly Lys Lys Ser Pro Leu Ser Ser
                    260                 265                 270

Ile Leu Phe Ser Ala Leu Asp Ser Asp Thr Arg Ile Thr Ala Leu Leu
                275                 280                 285

Arg Arg Gln Ala Asp Ile Glu Ser Arg Ala Arg Leu Gln Lys Arg
                290                 295                 300

Leu Gln Val Val Gln Ala Lys Gln Val Glu Arg His Ile Gln His Gln
305                 310                 315                 320

Leu Gly Gly Phe Leu Glu Lys Thr Leu Ser Lys Leu Pro Asn Leu Glu
                    325                 330                 335

Ser Leu Arg Pro Arg Ser Gln Leu Met Leu Thr Arg Lys Ala Glu Ala
                340                 345                 350

Ala Leu Arg Lys Ala Ala Ser Glu Thr Thr Thr Ser Glu Gly Leu Ser
                    355                 360                 365

Asn Phe Leu Lys Ser Asn Ser Ile Ser Glu Glu Leu Glu Arg Phe Thr
                370                 375                 380

Ala Ser Gly Ile Ala Asn Leu Arg Cys Ser Glu Gln Ala Phe Asp Ser
385                 390                 395                 400

Asp Val Thr Asp Ser Ser Ser Gly Gly Glu Ser Asp Ile Glu Glu Glu
                    405                 410                 415

Glu Leu Thr Arg Ala Asp Pro Glu Gln Arg His Val Pro Leu Arg Arg
                420                 425                 430
```

```
Arg Ser Glu Trp Lys Trp Ala Ala Asp Arg Ala Ala Ile Val Ser Arg
            435                 440                 445

Trp Asn Trp Leu Gln Ala His Val Ser Asp Leu Glu Tyr Arg Ile Arg
    450                 455                 460

Gln Gln Thr Asp Ile Tyr Lys Gln Ile Arg Ala Asn Lys
465                 470                 475

<210> SEQ ID NO 195
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 195

Val Ser Val Trp Arg Gln
1               5

<210> SEQ ID NO 196
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 196

Met Ala Gly Arg Pro Gly Ser Gln Glu Gln Ser Lys Asp Arg Gly Thr
1               5                   10                  15

Gly Ser Leu Pro Pro Pro Ser Gln Arg Pro Leu Gly Pro Ser Pro Glu
            20                  25                  30

Gly Ala Gly Pro Ser Pro Pro Pro Gly Ile Pro Arg Gly Gly Gly
        35                  40                  45

Ser Ser Ser Ser Glu Gly Pro His Ser Tyr Phe Leu Ser Leu Val Asp
    50                  55                  60

Ser Gln Leu Leu Arg Arg Gly Phe Pro Leu Thr Pro Leu Ile Gln Arg
65                  70                  75                  80

His Leu Pro Pro Arg Thr Ser Ala Leu Ala Glu Arg Thr His
                85                  90

<210> SEQ ID NO 197
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 197

Ser Ile Gly His Ile Ser Thr Met Leu Met Ala Phe
1               5                   10

<210> SEQ ID NO 198
<211> LENGTH: 406
<212> TYPE: PRT
<213> ORGANISM: Artificial Sequence
<220> FEATURE:
<223> OTHER INFORMATION: Synthetic Peptide

<400> SEQUENCE: 198

Met Glu Glu Gly Asn Asn Asn Glu Val Ile His Leu Asn Asn Phe
1               5                   10                  15

His Cys His Arg Gly Gln Glu Trp Ile Asn Leu Arg Asp Gly Pro Ile
            20                  25                  30
```

Thr Ile Ser Asp Ser Ser Asp Glu Glu Arg Ile Pro Met Leu Val Thr
          35                  40                  45

Pro Ala Pro Gln Gln His Glu Glu Asp Leu Asp Asp Asp Val Ile
 50                  55                  60

Leu Thr Glu Asp Asp Ser Glu Asp Asp Tyr Gly Glu Phe Leu Asp Leu
 65                  70                  75                  80

Gly Pro Pro Gly Ile Ser Glu Phe Thr Lys Pro Ser Gly Gln Thr Glu
                 85                  90                  95

Arg Glu Pro Lys Pro Gly Pro Ser His Asn Gln Ala Ala Asn Asp Ile
                100                 105                 110

Val Asn Pro Arg Ser Glu Gln Lys Val Ile Ile Leu Glu Glu Gly Ser
                115                 120                 125

Leu Leu Tyr Thr Glu Ser Asp Pro Leu Glu Thr Gln Asn Gln Ser Ser
        130                 135                 140

Glu Asp Ser Glu Thr Glu Leu Leu Ser Asn Leu Gly Glu Ser Ala Ala
145                 150                 155                 160

Leu Ala Asp Asp Gln Ala Ile Glu Glu Asp Cys Trp Leu Asp His Pro
                165                 170                 175

Tyr Phe Gln Ser Leu Asn Gln Gln Pro Arg Glu Ile Thr Asn Gln Val
                180                 185                 190

Val Pro Gln Glu Arg Gln Pro Glu Ala Glu Leu Gly Arg Leu Leu Phe
                195                 200                 205

Gln His Glu Phe Pro Gly Pro Ala Phe Pro Arg Pro Glu Pro Gln Gln
        210                 215                 220

Gly Gly Ile Ser Gly Pro Ser Ser Pro Gln Pro Ala His Pro Leu Gly
225                 230                 235                 240

Glu Phe Glu Asp Gln Gln Leu Ala Ser Asp Asp Glu Glu Pro Gly Pro
                245                 250                 255

Ala Phe Pro Met Gln Glu Ser Gln Glu Pro Asn Leu Glu Asn Ile Trp
                260                 265                 270

Gly Gln Glu Ala Ala Glu Val Asp Gln Glu Leu Val Glu Leu Leu Val
        275                 280                 285

Lys Glu Thr Glu Ala Arg Phe Pro Asp Val Ala Asn Gly Phe Ile Glu
290                 295                 300

Glu Ile Ile His Phe Lys Asn Tyr Tyr Asp Leu Asn Val Leu Cys Asn
305                 310                 315                 320

Phe Leu Leu Glu Asn Pro Asp Tyr Pro Lys Arg Glu Asp Arg Ile Ile
                325                 330                 335

Ile Asn Pro Ser Ser Ser Leu Leu Ala Ser Gln Asp Glu Thr Lys Leu
                340                 345                 350

Pro Lys Ile Asp Phe Phe Asp Tyr Ser Lys Leu Thr Pro Leu Asp Gln
                355                 360                 365

Arg Cys Phe Ile Gln Ala Ala Asp Leu Leu Met Ala Asp Phe Lys Val
        370                 375                 380

Leu Ser Ser Gln Asp Ile Lys Trp Ala Leu His Glu Leu Lys Gly His
385                 390                 395                 400

Tyr Ala Ile Thr Arg Lys
                405

<210> SEQ ID NO 199
<211> LENGTH: 15
<212> TYPE: PRT
<213> ORGANISM: Artificial Sequence
<220> FEATURE:

<223> OTHER INFORMATION: Synthetic Peptide

<400> SEQUENCE: 199

Val Tyr Gln Pro Gln Ser Leu His Val Ser Lys Ser Ser Arg Lys
1               5                   10                  15

<210> SEQ ID NO 200
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 200

Met Ala Gly Leu Lys Arg Arg Ala Ser Gln Val Trp Pro Glu Glu His
1               5                   10                  15

Gly Glu Gln Glu His Gly Leu Tyr Ser Leu His Arg Met Phe Asp Ile
                20                  25                  30

Val Gly Thr His Leu Thr His Arg Asp Val Arg Val Leu Ser Phe Leu
            35                  40                  45

Phe Val Asp Val Ile Asp Asp His Glu Arg Gly Leu Ile Arg Asn Gly
        50                  55                  60

Arg Asp Phe Leu Leu Ala Leu Glu Arg Gln Gly Arg Cys Asp Glu Ser
65                  70                  75                  80

Asn Phe Arg Gln Val Leu Gln Leu Leu Arg Ile Ile Thr Arg His Asp
                85                  90                  95

Leu Leu Pro Tyr Val Thr Leu Lys Arg Arg Ala
                100                 105

<210> SEQ ID NO 201
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 201

Ala Pro Ser Gly Leu Gly Leu
1               5

<210> SEQ ID NO 202
<211> LENGTH: 102
<212> TYPE: PRT
<213> ORGANISM: Artificial Sequence
<220> FEATURE:
<223> OTHER INFORMATION: Synthetic Peptide

<400> SEQUENCE: 202

Met Arg Arg Ser Ala Ala Pro Ser Gln Leu Gln Gly Asn Ser Phe Lys
1               5                   10                  15

Lys Pro Lys Phe Ile Pro Pro Gly Arg Ser Asn Pro Gly Leu Asn Glu
                20                  25                  30

Glu Ile Thr Lys Leu Asn Pro Asp Ile Lys Leu Phe Glu Gly Val Ala
            35                  40                  45

Ile Asn Asn Thr Phe Leu Pro Ser Gln Asn Asp Leu Arg Ile Cys Ser
        50                  55                  60

Leu Asn Leu Pro Ser Glu Glu Ser Thr Arg Glu Ile Asn Asn Arg Asp
65                  70                  75                  80

Asn Cys Ser Gly Lys Tyr Cys Phe Glu Ala Pro Thr Leu Ala Thr Leu
                85                  90                  95

```
Asp Pro Pro His Thr Val
            100

<210> SEQ ID NO 203
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 203

Gln Thr Trp Met Arg Arg His Arg Leu Val Pro Val His Tyr Arg
1               5                   10                  15

<210> SEQ ID NO 204
<211> LENGTH: 66
<212> TYPE: PRT
<213> ORGANISM: Artificial Sequence
<220> FEATURE:
<223> OTHER INFORMATION: Synthetic Peptide

<400> SEQUENCE: 204

Met Gly Ser Gln Pro Pro Leu Gly Ser Pro Leu Ser Arg Glu Glu Gly
1               5                   10                  15

Glu Ala Pro Pro Pro Ala Pro Ala Ser Glu Gly Arg Arg Ser Arg
            20                  25                  30

Arg Val Arg Leu Arg Gly Ser Cys Arg His Arg Pro Ser Phe Leu Gly
        35                  40                  45

Cys Arg Glu Leu Ala Ala Ser Ala Pro Ala Arg Pro Ala Pro Ala Ser
    50                  55                  60

Ser Glu
65

<210> SEQ ID NO 205
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 205

Lys Arg Cys Ser Ile Phe Arg Leu Arg Lys Thr Thr Arg Ala Gln Trp
1               5                   10                  15

Arg Leu Pro His Phe Phe Ser Ser Cys Trp Ser Ser Arg Arg Lys
            20                  25                  30

Ala Gly Ser Val Ala Phe Trp Met Pro
        35                  40

<210> SEQ ID NO 206
<211> LENGTH: 104
<212> TYPE: PRT
<213> ORGANISM: Artificial Sequence
<220> FEATURE:
<223> OTHER INFORMATION: Synthetic Peptide

<400> SEQUENCE: 206

Met Ile Ala Arg Arg Asn Pro Glu Pro Leu Arg Phe Leu Pro Asp Glu
1               5                   10                  15

Ala Arg Ser Leu Pro Pro Pro Lys Leu Thr Asp Pro Arg Leu Leu Tyr
            20                  25                  30

Ile Gly Phe Leu Gly Tyr Cys Ser Gly Leu Ile Asp Asn Leu Ile Arg
        35                  40                  45
```

Arg Arg Pro Ile Ala Thr Ala Gly Leu His Arg Gln Leu Leu Tyr Ile
            50                  55                  60

Thr Ala Phe Phe Phe Ala Gly Tyr Tyr Leu Val Lys Arg Glu Asp Tyr
 65                  70                  75                  80

Leu Tyr Ala Val Arg Asp Arg Glu Met Phe Gly Tyr Met Lys Leu His
                85                  90                  95

Pro Glu Asp Phe Pro Glu Glu Asp
            100

<210> SEQ ID NO 207
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 207

Val Tyr Cys Cys Gly Ala Glu Arg Arg Gly
 1               5                  10

<210> SEQ ID NO 208
<211> LENGTH: 183
<212> TYPE: PRT
<213> ORGANISM: Artificial Sequence
<220> FEATURE:
<223> OTHER INFORMATION: Synthetic Peptide

<400> SEQUENCE: 208

Met Gly Asn Ser Ala Leu Arg Ala His Val Glu Thr Ala Gln Lys Thr
 1               5                  10                  15

Gly Val Phe Gln Leu Lys Asp Arg Gly Leu Thr Glu Phe Pro Ala Asp
                20                  25                  30

Leu Gln Lys Leu Thr Ser Asn Leu Arg Thr Ile Asp Leu Ser Asn Asn
            35                  40                  45

Lys Ile Glu Ser Leu Pro Pro Leu Leu Ile Gly Lys Phe Thr Leu Leu
 50                  55                  60

Lys Ser Leu Ser Leu Asn Asn Asn Lys Leu Thr Val Leu Pro Asp Glu
 65                  70                  75                  80

Ile Cys Asn Leu Lys Lys Leu Glu Thr Leu Ser Leu Asn Asn Asn His
                85                  90                  95

Leu Arg Glu Leu Pro Ser Thr Phe Gly Gln Leu Ser Ala Leu Lys Thr
            100                 105                 110

Leu Ser Leu Ser Gly Asn Gln Leu Gly Ala Leu Pro Pro Gln Leu Cys
            115                 120                 125

Ser Leu Arg His Leu Asp Val Met Asp Leu Ser Lys Asn Gln Ile Arg
    130                 135                 140

Ser Ile Pro Asp Ser Val Gly Glu Leu Gln Val Ile Glu Leu Asn Leu
145                 150                 155                 160

Asn Gln Asn Gln Ile Ser Gln Ile Ser Val Lys Ile Ser Cys Cys Pro
                165                 170                 175

Arg Leu Lys Ile Leu Arg Leu
            180

<210> SEQ ID NO 209
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 209

Ser Ala Leu Ser Val Ile Arg Phe Ile Cys Gly Phe
1               5                   10

<210> SEQ ID NO 210
<211> LENGTH: 901
<212> TYPE: PRT
<213> ORGANISM: Artificial Sequence
<220> FEATURE:
<223> OTHER INFORMATION: Synthetic Peptide

<400> SEQUENCE: 210

Met Val Gln Pro Ile Ile His Leu Gly Tyr Val Val Tyr Ser Leu Leu
1               5                   10                  15

Tyr Leu Gly Tyr Lys Pro Val Gln His Val Thr Ala Leu Asn Thr Val
                20                  25                  30

Ser Ser Cys His Lys Met Val Ser Met Asp Leu Asn Ser Ala Ser Thr
            35                  40                  45

Val Val Leu Gln Val Leu Thr Gln Ala Thr Ser Gln Asp Thr Ala Val
        50                  55                  60

Leu Lys Pro Ala Glu Glu Gln Leu Lys Gln Trp Glu Thr Gln Pro Gly
65                  70                  75                  80

Phe Tyr Ser Val Leu Leu Asn Ile Phe Thr Asn His Thr Leu Asp Ile
                85                  90                  95

Asn Val Arg Trp Leu Ala Val Leu Tyr Phe Lys His Gly Ile Asp Arg
            100                 105                 110

Tyr Trp Arg Arg Val Ala Pro His Ala Leu Ser Glu Glu Lys Thr
        115                 120                 125

Thr Leu Arg Ala Gly Leu Ile Thr Asn Phe Asn Glu Pro Ile Asn Gln
130                 135                 140

Ile Ala Thr Gln Ile Ala Val Leu Ile Ala Lys Val Ala Arg Leu Asp
145                 150                 155                 160

Cys Pro Arg Gln Trp Pro Glu Leu Ile Pro Thr Leu Ile Glu Ser Val
                165                 170                 175

Lys Val Gln Asp Asp Leu Arg Gln His Arg Ala Leu Leu Thr Phe Tyr
            180                 185                 190

His Val Thr Lys Thr Leu Ala Ser Lys Arg Leu Ala Ala Asp Arg Lys
        195                 200                 205

Leu Phe Tyr Asp Leu Ala Ser Gly Ile Tyr Asn Phe Ala Cys Ser Leu
210                 215                 220

Trp Asn His His Thr Asp Thr Phe Leu Gln Glu Val Ser Ser Gly Asn
225                 230                 235                 240

Glu Ala Ala Ile Leu Ser Ser Leu Glu Arg Thr Leu Leu Ser Leu Lys
                245                 250                 255

Val Leu Arg Lys Leu Thr Val Asn Gly Phe Val Glu Pro His Lys Asn
            260                 265                 270

Met Glu Val Met Gly Phe Leu His Gly Ile Phe Glu Arg Leu Lys Gln
        275                 280                 285

Phe Leu Glu Cys Ser Arg Ser Ile Gly Thr Asp Asn Val Cys Arg Asp
290                 295                 300

Arg Leu Glu Lys Thr Ile Ile Leu Phe Thr Lys Val Leu Leu Asp Phe
305                 310                 315                 320

Leu Asp Gln His Pro Phe Ser Phe Thr Pro Leu Ile Gln Arg Ser Leu
                325                 330                 335

Glu Phe Ser Val Ser Tyr Val Phe Thr Glu Val Gly Glu Gly Val Thr

```
                340             345             350
Phe Glu Arg Phe Ile Val Gln Cys Met Asn Leu Ile Lys Met Ile Val
            355             360             365
Lys Asn Tyr Ala Tyr Lys Pro Ser Lys Asn Phe Glu Asp Ser Ser Pro
        370             375             380
Glu Thr Leu Glu Ala His Lys Ile Lys Met Ala Phe Phe Thr Tyr Pro
385             390             395             400
Thr Leu Thr Glu Ile Cys Arg Arg Leu Val Ser His Tyr Phe Leu Leu
                405             410             415
Thr Glu Glu Glu Leu Thr Met Trp Glu Glu Asp Pro Glu Gly Phe Thr
            420             425             430
Val Glu Glu Thr Gly Gly Asp Ser Trp Lys Tyr Ser Leu Arg Pro Cys
            435             440             445
Thr Glu Val Leu Phe Ile Asp Ile Phe His Glu Tyr Asn Gln Thr Leu
            450             455             460
Thr Pro Val Leu Leu Glu Met Met Gln Thr Leu Gln Gly Pro Thr Asn
465             470             475             480
Val Glu Asp Met Asn Ala Leu Leu Ile Lys Asp Ala Val Tyr Asn Ala
            485             490             495
Val Gly Leu Ala Ala Tyr Glu Leu Phe Asp Ser Val Asp Phe Asp Gln
            500             505             510
Trp Phe Lys Asn Gln Leu Leu Pro Glu Leu Gln Val Ile His Asn Arg
            515             520             525
Tyr Lys Pro Leu Arg Arg Val Ile Trp Leu Ile Gly Gln Trp Ile
            530             535             540
Ser Val Lys Phe Lys Ser Asp Leu Arg Pro Met Leu Tyr Glu Ala Ile
545             550             555             560
Cys Asn Leu Leu Gln Asp Gln Asp Leu Val Val Arg Ile Glu Thr Ala
            565             570             575
Thr Thr Leu Lys Leu Thr Val Asp Asp Phe Glu Phe Arg Thr Asp Gln
            580             585             590
Phe Leu Pro Tyr Leu Glu Thr Met Phe Thr Leu Leu Phe Gln Leu Leu
            595             600             605
Gln Gln Val Thr Glu Cys Asp Thr Lys Met His Val Leu His Val Leu
    610             615             620
Ser Cys Val Ile Glu Arg Val Asn Met Gln Ile Arg Pro Tyr Val Gly
625             630             635             640
Cys Leu Val Gln Tyr Leu Pro Leu Leu Trp Lys Gln Ser Glu Glu His
                645             650             655
Asn Met Leu Arg Cys Ala Ile Leu Thr Thr Leu Ile His Leu Val Gln
            660             665             670
Gly Leu Gly Ala Asp Ser Lys Asn Leu Tyr Pro Phe Leu Leu Pro Val
        675             680             685
Ile Gln Leu Ser Thr Asp Val Ser Gln Pro Pro His Val Tyr Leu Leu
        690             695             700
Glu Asp Gly Leu Glu Leu Trp Leu Val Thr Leu Glu Asn Ser Pro Cys
705             710             715             720
Ile Thr Pro Glu Leu Leu Arg Ile Phe Gln Asn Met Ser Pro Leu Leu
            725             730             735
Glu Leu Ser Ser Glu Asn Leu Arg Thr Cys Phe Lys Ile Ile Asn Gly
            740             745             750
Tyr Ile Phe Leu Ser Ser Thr Glu Phe Leu Gln Thr Tyr Ala Val Gly
        755             760             765
```

-continued

```
Leu Cys Gln Ser Phe Cys Glu Leu Leu Lys Glu Ile Thr Thr Glu Gly
        770                 775                 780

Gln Val Gln Val Leu Lys Val Val Glu Asn Ala Leu Lys Val Asn Pro
785                 790                 795                 800

Ile Leu Gly Pro Gln Met Phe Gln Pro Ile Leu Pro Tyr Val Phe Lys
                805                 810                 815

Gly Ile Ile Glu Gly Glu Arg Tyr Pro Val Val Met Ser Thr Tyr Leu
                820                 825                 830

Gly Val Met Gly Arg Val Leu Leu Gln Asn Thr Ser Phe Phe Ser Ser
            835                 840                 845

Leu Leu Asn Glu Met Ala His Lys Phe Asn Gln Glu Met Asp Gln Leu
        850                 855                 860

Leu Gly Asn Met Ile Glu Met Trp Val Asp Arg Met Asp Asn Ile Thr
865                 870                 875                 880

Gln Pro Glu Arg Arg Lys Leu Ser Ala Leu Ala Leu Leu Ser Leu Leu
                885                 890                 895

Pro Ser Asp Asn Ser
            900

<210> SEQ ID NO 211
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 211

Leu Ala Ser Lys Gly Pro
1               5

<210> SEQ ID NO 212
<211> LENGTH: 43
<212> TYPE: PRT
<213> ORGANISM: Artificial Sequence
<220> FEATURE:
<223> OTHER INFORMATION: Synthetic Peptide

<400> SEQUENCE: 212

Met Ser Leu Pro Leu Asn Pro Lys Pro Phe Leu Asn Gly Leu Thr Gly
1               5                   10                  15

Lys Pro Val Met Val Lys Leu Lys Trp Gly Met Glu Tyr Lys Gly Tyr
                20                  25                  30

Leu Val Ser Val Asp Gly Tyr Met Asn Met Gln
            35                  40

<210> SEQ ID NO 213
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 213

Gln Asp Phe His Leu His Leu Gly Asn Ile Glu Thr Lys
1               5                   10

<210> SEQ ID NO 214
<211> LENGTH: 60
<212> TYPE: PRT
<213> ORGANISM: Artificial Sequence
<220> FEATURE:
```

<223> OTHER INFORMATION: Synthetic Peptide

<400> SEQUENCE: 214

Met Ala Ala Val Gly Pro Pro Gln Gln Gln Val Arg Met Ala His Gln
1               5                   10                  15

Gln Val Trp Ala Ala Leu Glu Val Ala Leu Arg Val Pro Cys Leu Tyr
            20                  25                  30

Ile Ile Asp Ala Ile Phe Asn Ser Tyr Pro Asp Ser Ser Gln Ser Arg
        35                  40                  45

Phe Cys Ile Val Leu Gln Ile Phe Leu Arg Leu Phe
50                  55                  60

<210> SEQ ID NO 215
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 215

Glu Thr Asn Thr Asp Thr Leu Leu Val
1               5

<210> SEQ ID NO 216
<211> LENGTH: 156
<212> TYPE: PRT
<213> ORGANISM: Artificial Sequence
<220> FEATURE:
<223> OTHER INFORMATION: Synthetic Peptide

<400> SEQUENCE: 216

Met Ala Val Ala Arg Ala Gly Val Leu Gly Val Gln Trp Leu Gln Arg
1               5                   10                  15

Ala Ser Arg Asn Val Met Pro Leu Gly Ala Arg Thr Ala Ser His Met
            20                  25                  30

Thr Lys Asp Met Phe Pro Gly Pro Tyr Pro Arg Thr Pro Glu Glu Arg
        35                  40                  45

Ala Ala Ala Ala Lys Lys Tyr Asn Met Arg Val Glu Asp Tyr Glu Pro
    50                  55                  60

Tyr Pro Asp Asp Gly Met Gly Tyr Gly Asp Tyr Pro Lys Leu Pro Asp
65                  70                  75                  80

Arg Ser Gln His Glu Arg Asp Pro Trp Tyr Ser Trp Asp Gln Pro Gly
                85                  90                  95

Leu Arg Leu Asn Trp Gly Glu Pro Met His Trp His Leu Asp Met Tyr
            100                 105                 110

Asn Arg Asn Arg Val Asp Thr Ser Pro Thr Pro Val Ser Trp His Val
        115                 120                 125

Met Cys Met Gln Leu Phe Gly Phe Leu Ala Phe Met Ile Phe Met Cys
    130                 135                 140

Trp Val Gly Asp Val Tyr Pro Val Tyr Gln Pro Val
145                 150                 155

<210> SEQ ID NO 217
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 217

Asp Arg Pro
1

<210> SEQ ID NO 218
<211> LENGTH: 124
<212> TYPE: PRT
<213> ORGANISM: Artificial Sequence
<220> FEATURE:
<223> OTHER INFORMATION: Synthetic Peptide

<400> SEQUENCE: 218

Met Ala Arg Ser Leu Val Cys Leu Gly Val Ile Ile Leu Leu Ser Ala
1               5                   10                  15

Phe Ser Gly Pro Gly Val Arg Gly Gly Pro Met Pro Lys Leu Ala Asp
            20                  25                  30

Arg Lys Leu Cys Ala Asp Gln Glu Cys Ser His Pro Ile Ser Met Ala
        35                  40                  45

Val Ala Leu Gln Asp Tyr Met Ala Pro Asp Cys Arg Phe Leu Thr Ile
    50                  55                  60

His Arg Gly Gln Val Val Tyr Val Phe Ser Lys Leu Lys Gly Arg Gly
65                  70                  75                  80

Arg Leu Phe Trp Gly Gly Ser Val Gln Gly Asp Tyr Tyr Gly Asp Leu
                85                  90                  95

Ala Ala Arg Leu Gly Tyr Phe Pro Ser Ser Ile Val Arg Glu Asp Gln
            100                 105                 110

Thr Leu Lys Pro Gly Lys Val Asp Val Lys Thr Asp
        115                 120

<210> SEQ ID NO 219
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 219

Thr Ser Ser Ser Asn Ser Trp
1               5

<210> SEQ ID NO 220
<211> LENGTH: 89
<212> TYPE: PRT
<213> ORGANISM: Artificial Sequence
<220> FEATURE:
<223> OTHER INFORMATION: Synthetic Peptide

<400> SEQUENCE: 220

Met Pro Thr Asn Cys Ala Ala Gly Cys Ala Thr Thr Tyr Asn Lys
1               5                   10                  15

His Ile Asn Ile Ser Phe His Arg Phe Pro Leu Asp Pro Lys Arg Arg
            20                  25                  30

Lys Glu Trp Val Arg Leu Val Arg Lys Asn Phe Val Pro Gly Lys
        35                  40                  45

His Thr Phe Leu Cys Ser Lys His Phe Glu Ala Ser Cys Phe Asp Leu
    50                  55                  60

Thr Gly Gln Thr Arg Arg Leu Lys Met Asp Ala Val Pro Thr Ile Phe
65                  70                  75                  80

Asp Phe Cys Thr His Ile Lys Ser Met
                85

<210> SEQ ID NO 221
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 221

Val Thr Tyr Asp Leu Phe Leu Arg Gly Val Gly Cys Phe Leu Leu
1               5                   10                  15

Phe Leu Phe

<210> SEQ ID NO 222
<211> LENGTH: 239
<212> TYPE: PRT
<213> ORGANISM: Artificial Sequence
<220> FEATURE:
<223> OTHER INFORMATION: Synthetic Peptide

<400> SEQUENCE: 222

Met Leu Gly Phe Ile Thr Arg Pro Pro His Arg Phe Leu Ser Leu Leu
1               5                   10                  15

Cys Pro Gly Leu Arg Ile Pro Gln Leu Ser Val Leu Cys Ala Gln Pro
                20                  25                  30

Arg Pro Arg Ala Met Ala Ile Ser Ser Ser Cys Glu Leu Pro Leu
        35                  40                  45

Val Ala Val Cys Gln Val Thr Ser Thr Pro Asp Lys Gln Gln Asn Phe
    50                  55                  60

Lys Thr Cys Ala Glu Leu Val Arg Glu Ala Arg Leu Gly Ala Cys
65                  70                  75                  80

Leu Ala Phe Leu Pro Glu Ala Phe Asp Phe Ile Ala Arg Asp Pro Ala
                85                  90                  95

Glu Thr Leu His Leu Ser Glu Pro Leu Gly Gly Lys Leu Leu Glu Glu
            100                 105                 110

Tyr Thr Gln Leu Ala Arg Glu Cys Gly Leu Trp Leu Ser Leu Gly Gly
            115                 120                 125

Phe His Glu Arg Gly Gln Asp Trp Glu Gln Thr Gln Lys Ile Tyr Asn
130                 135                 140

Cys His Val Leu Leu Asn Ser Lys Gly Ala Val Val Ala Thr Tyr Arg
145                 150                 155                 160

Lys Thr His Leu Cys Asp Val Glu Ile Pro Gly Gln Gly Pro Met Cys
                165                 170                 175

Glu Ser Asn Ser Thr Met Pro Gly Pro Ser Leu Glu Ser Pro Val Ser
            180                 185                 190

Thr Pro Ala Gly Lys Ile Gly Leu Ala Val Cys Tyr Asp Met Arg Phe
            195                 200                 205

Pro Glu Leu Ser Leu Ala Leu Ala Gln Ala Gly Ala Glu Ile Leu Thr
        210                 215                 220

Tyr Pro Ser Ala Phe Gly Ser Ile Thr Gly Pro Ala His Trp Glu
225                 230                 235

<210> SEQ ID NO 223
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 223

Gln Pro Val Ser Ser
1               5

<210> SEQ ID NO 224
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 224 aaaaaaa                                                                 7

<210> SEQ ID NO 225
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 225
aaagaaaaaa aaaaagatgg ggaaaaggaa gagcctaaa                              39

<210> SEQ ID NO 226
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 226

Lys Glu Lys Lys Lys Asp Gly Glu Lys Glu Glu Pro Lys
1               5                   10

<210> SEQ ID NO 227
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 227
aaagaaaaaa aaaaaagatg gggaaaagga agagcctaa                              39

<210> SEQ ID NO 228
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 228

Lys Glu Lys Lys Lys Arg Trp Gly Lys Gly Arg Ala
1               5                   10

<210> SEQ ID NO 229
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 229
aaagaaaaaa aaagatggg gaaaggaag agcctaaaa                                39

<210> SEQ ID NO 230

```
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 230

Lys Glu Lys Lys Lys Met Gly Lys Arg Lys Ser Leu Lys
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 231

Cys Lys Gly Arg Thr Pro Asp Thr Ser Lys
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 232

Cys Thr Thr Ser Pro Arg Arg Ser Ser Pro
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 233

Cys Thr Thr Leu Ser Ser Gln Cys Arg Ser
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 234

Cys Thr Leu Arg Leu Pro Pro Val Arg Asn
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 235

Cys Asn Lys Tyr Leu Lys Arg Ser Gln Leu
1               5                   10

<210> SEQ ID NO 236
<211> LENGTH: 10
```

```
<212> TYPE: PRT
<213> ORGANISM: Artificial Sequence
<220> FEATURE:
<223> OTHER INFORMATION: Synthetic Peptide

<400> SEQUENCE: 236

Cys Thr His Trp Arg Val His Ser Leu Thr
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 237

Cys Lys Lys Pro Ser Gly Thr Trp Pro Leu
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 238

Cys Thr Pro Lys Gln Lys Asn Pro Arg Lys
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 239

Cys Lys Asn Ile Ala Ser Thr Ser Ile Phe
1               5                   10
```